United States Patent
Kim et al.

(10) Patent No.: US 9,882,143 B2
(45) Date of Patent: *Jan. 30, 2018

(54) AMINE-BASED COMPOUND AND ORGANIC LIGHT-EMITTING DIODE INCLUDING THE SAME

(71) Applicant: Samsung Display Co., Ltd., Yongin-si, Gyeonggi-Do (KR)

(72) Inventors: Youngkook Kim, Yongin-si (KR); Seokhwan Hwang, Yongin-si (KR); Hyejin Jung, Yongin-si (KR); Jino Lim, Yongin-si (KR); Sanghyun Han, Yongin-si (KR); Eunjae Jeong, Yongin-si (KR); Sooyon Kim, Yongin-si (KR); Junha Park, Yongin-si (KR); Eunyoung Lee, Yongin-si (KR); Jonghyuk Lee, Yongin-si (KR)

(73) Assignee: Samsung Display Co., Ltd., Yongin-si, Gyeonggi-Do (KR)

( * ) Notice: Subject to any disclaimer, the term of this patent is extended or adjusted under 35 U.S.C. 154(b) by 288 days.

This patent is subject to a terminal disclaimer.

(21) Appl. No.: 14/876,742

(22) Filed: Oct. 6, 2015

(65) Prior Publication Data

US 2016/0028015 A1 Jan. 28, 2016

Related U.S. Application Data

(63) Continuation-in-part of application No. 13/598,489, filed on Aug. 29, 2012, now Pat. No. 9,181,474.

(30) Foreign Application Priority Data

Feb. 7, 2012 (KR) .................. 10-2012-0012532
Jun. 8, 2012 (KR) .................. 10-2012-0061676

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/56* (2013.01); *C07C 211/59* (2013.01);
(Continued)

(58) Field of Classification Search
None
See application file for complete search history.

(56) References Cited

U.S. PATENT DOCUMENTS 5,645,948 A 7/1997 Shi et al.
5,935,721 A 8/1999 Shi et al.
(Continued)

FOREIGN PATENT DOCUMENTS

JP 10-017860 1/1998
JP 11-087067 3/1999
(Continued)

OTHER PUBLICATIONS

Office Action dated Jun. 13, 2016, in corresponding Taiwan Patent Application No. 102104287.
(Continued)

*Primary Examiner* — Gregory Clark
(74) *Attorney, Agent, or Firm* — Knobbe, Martens, Olson & Bear, LLP

(57) ABSTRACT

An amine-based compound and an organic light-emitting diode including the amine-based compound.

39 Claims, 1 Drawing Sheet

(51) Int. Cl.

| | | |
|---|---|---|
| *C07C 211/59* | (2006.01) | |
| *C09K 11/02* | (2006.01) | |
| *C09K 11/06* | (2006.01) | |
| *C07C 211/56* | (2006.01) | |
| *C07C 255/58* | (2006.01) | |
| *C07C 211/61* | (2006.01) | |
| *C07D 209/88* | (2006.01) | |
| *C07D 333/76* | (2006.01) | |
| *C07D 307/91* | (2006.01) | |
| *C07F 7/08* | (2006.01) | |
| *C07D 251/22* | (2006.01) | |
| *C07D 235/18* | (2006.01) | |
| *C07D 213/38* | (2006.01) | |
| *C07D 471/04* | (2006.01) | |
| *C07D 213/74* | (2006.01) | |
| *C07D 409/12* | (2006.01) | |
| *C07D 405/12* | (2006.01) | |
| *C07D 401/12* | (2006.01) | |
| *C07C 217/92* | (2006.01) | |
| *C07D 213/36* | (2006.01) | |
| *H05B 33/10* | (2006.01) | |
| *C07D 209/86* | (2006.01) | |

(52) U.S. Cl.
CPC .......... *C07C 211/61* (2013.01); *C07C 217/92* (2013.01); *C07C 255/58* (2013.01); *C07D 209/86* (2013.01); *C07D 209/88* (2013.01); *C07D 213/36* (2013.01); *C07D 213/38* (2013.01); *C07D 213/74* (2013.01); *C07D 235/18* (2013.01); *C07D 251/22* (2013.01); *C07D 307/91* (2013.01); *C07D 333/76* (2013.01); *C07D 401/12* (2013.01); *C07D 405/12* (2013.01); *C07D 409/12* (2013.01); *C07D 471/04* (2013.01); *C07F 7/0809* (2013.01); *C07F 7/0818* (2013.01); *C09K 11/025* (2013.01); *C09K 11/06* (2013.01); *H01L 51/0058* (2013.01); *H05B 33/10* (2013.01); *C07C 2603/18* (2017.05); *C07C 2603/24* (2017.05); *C07C 2603/26* (2017.05); *C07C 2603/50* (2017.05); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0061* (2013.01); *H01L 51/0067* (2013.01); *H01L 51/0072* (2013.01); *H01L 51/0077* (2013.01); *H01L 51/0081* (2013.01); *H01L 51/5012* (2013.01); *H01L 51/5072* (2013.01)

(56) References Cited

U.S. PATENT DOCUMENTS

| | | |
|---|---|---|
| 6,465,115 B2 | 10/2002 | Shi et al. |
| 6,596,415 B2 | 7/2003 | Shi et al. |
| 2003/0165715 A1 | 9/2003 | Yoon et al. |
| 2004/0265630 A1 | 12/2004 | Suh et al. |
| 2007/0205412 A1 | 9/2007 | Bae et al. |
| 2010/0044681 A1 | 2/2010 | Kim et al. |
| 2010/0164371 A1 | 7/2010 | Jeong et al. |
| 2011/0114930 A1 | 5/2011 | Kim et al. |
| 2011/0114934 A1 | 5/2011 | Kim et al. |

FOREIGN PATENT DOCUMENTS

| | | |
|---|---|---|
| KR | 10-0691543 | 3/2007 |
| KR | 10-2007-0104086 A | 10/2007 |
| KR | 10-2010-0006979 | 1/2010 |
| KR | 10-2010-00007143 A | 1/2010 |
| KR | 10-2010-0071726 A | 6/2010 |
| KR | 10-2011-0018195 A | 2/2011 |

OTHER PUBLICATIONS

Y.T. Tao, E. Balasubramaniam, A. Danel, B. Jarosz and P. Tomasik, Sharp green electroluminescence from 1H-pyrazolo[3,4-b]quinoline-based light-emitting diodes, Applied Physical Letters, (2000), pp. 1575-1577, vol. 77, American Institute of Physics.

Youichi Sakamoto, Toshiyasu Suzoki, Atsushi Miura, Hisayoshi Fujikawa, Shizuo Tokito, and Yasunori Taga, Synthesis, Characterization, and Electron-Transport Property of Perfluorinated Phenylene Dendrimers, (2000), pp. 1832-1833, vol. 122, No. 8, American Chemical Society.

Shigehiro Yamaguchi, Tomonori Endo, Manabu Uchida, Takenori Izumizawa, Kenji Furukawa, and Kohei Tamao, Diphenylamino-Substituted 2,5-Diarylsiloles for Single-Layer Organic Electroluminescent Devices, Letters, (2001) pp. 98-99, The Chemical Society of Japan.

Nicklas Johansson, Josef Salbeck, Jacqueline Bauer, Frank Weissörtel, Per Bröms, Annica Andersson, and William R. Salaneck, Solid-State Amplified Spontaneous Emission in Some Spiro-Type Molecules: A New Concept for the Design of Solid-State Lasing Molecules, Communications, (1998), pp. 1136-1141, vol. 10, No. 14, Advanced Materials.

C.W. Tang and S.A. Vanslyke, Organic electroluminescent diodes, Applied Physical Letters, (Sep. 21, 1987), pp. 913-915, vol. 51, No. 12, American Institute of Physics.

Chihaya Adachi, Tetsuo Tsutsui and Shogo Saito, Confinement of charge carriers and molecular excitons within 5-nm-thick emitter layer in organic electroluminescent devices with a double heterostructure, Applied Physical Letters, (Aug. 6, 1990), pp. 531-533, vol. 57 No. 6, American Institute of Physics.

Extended European Search Report dated Apr. 29, 2013, issued in connection with European Patent Application No. 13154326.6, in 6 pages.

Lee, K.H., et al. "Synthesis and Electroluminescent Properties of Blue Fluorescent Triphenylamine Substituted Anthracene Derivatives for OLEDs," *Molecular Crystals and Liquid Crystals* 530: 48/[204]55/[211].

Korean Office Action dated Mar. 31, 2014, issued in connection with corresponding Korean Patent Application No. 10-2012-0061676.

Chinese Office Action dated Jul. 27, 2015, issued in corresponding Application No. 201310049362.5.

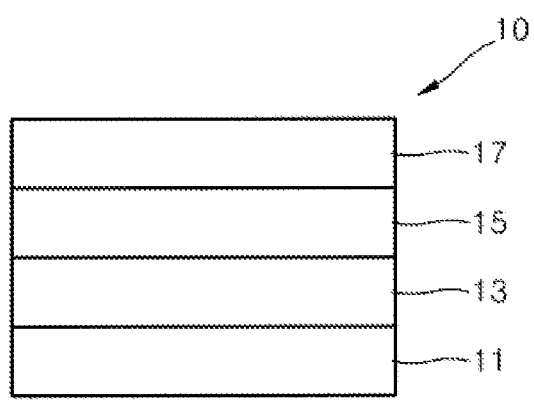

AMINE-BASED COMPOUND AND ORGANIC LIGHT-EMITTING DIODE INCLUDING THE SAME

CROSS-REFERENCE TO RELATED APPLICATIONS

This application is a continuation-in-part of U.S. patent application Ser. No. 13/598,489 filed Aug. 29, 2012, which claims priority to and the benefit of Korean Patent Application Nos. 10-2012-0012532, filed on Feb. 7, 2012, and 10-2012-0061676, filed on Jun. 8, 2012, in the Korean Intellectual Property Office, the entire contents of all of which are incorporated herein by reference.

BACKGROUND

Field

The present embodiments relate to a compound for organic light-emitting diodes, and an organic light-emitting diode including the compound.

Description of the Related Technology

Organic light-emitting diodes (OLEDs), which are self-emitting diodes, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films comprising organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

The present embodiments provide an amine-based compound having a novel structure and an organic light-emitting diode including the amine-based compound.

According to an aspect of the present embodiments, there is provided an amine-based compound represented by Formula 1 below:

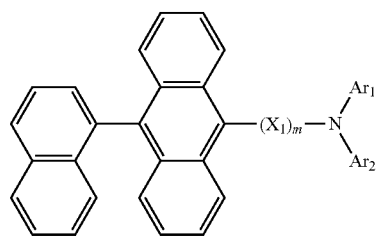

Formula 1 wherein, in Formula 1, $Ar_1$ and $Ar_2$ are each independently a substituted or unsubstituted $C_6$-$C_{60}$ aryl group or a substituted or unsubstituted $C_2$-$C_{60}$ heteroaryl group;

$X_1$ is a substituted or unsubstituted $C_6$-$C_{60}$ arylene group or a substituted or unsubstituted $C_2$-$C_{60}$ heteroarylene group;

m is an integer from 1 to 5; and at least one substituent of each of the substituted $C_6$-$C_{60}$ aryl group, the substituted $C_2$-$C_{60}$ heteroaryl group, the substituted $C_6$-$C_{60}$arylene group, and the substituted $C_2$-$C_{60}$ heteroarylene group is one of a deuterium atom; —F; —Cl; —Br; —I; —CN; a hydroxyl group; —$NO_2$; an amino group; an amidino group; hydrazine; hydrazone; a carboxyl group or a salt thereof; a sulfonic acid group or a salt thereof; a phosphoric acid or a salt thereof; a tri($C_6$-$C_{60}$aryl)silyl group; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group and a $C_2$-$C_{60}$ alkynyl group that is substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, a phosphoric acid or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, a $C_6$-$C_{60}$ arylthiol group; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group that is substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one fluorine (F), a $C_1$-$C_{60}$ alkoxy group, a $C_2$-$C_{60}$ alkenyl group, a $C_2$-$C_{60}$ alkynyl group, a $C_6$-$C_{60}$ aryl group and a $C_2$-$C_{60}$ heteroaryl group, wherein at least one of $Ar_1$ and $Ar_2$ is a $C_6$-$C_{60}$ aryl group substituted with at least one electron withdrawing group selected from the group consisting of —F; —CN; —$NO_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

According to another aspect of the present embodiments, there is provided an organic light-emitting diode comprising a first electrode, a second electrode disposed opposite to the first electrode, and an organic layer disposed between the first electrode and the second electrode, the organic layer comprising at least one of the amine-based compounds.

BRIEF DESCRIPTION OF THE DRAWING

The above and other features and advantages of the present embodiments will become more apparent by describing in detail example embodiments thereof with reference to the attached drawings in which:

FIG. 1 schematically illustrates the structure of an organic light-emitting diode according to an embodiment.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present embodiments, there is provided an amine-based compound represented by Formula 1:

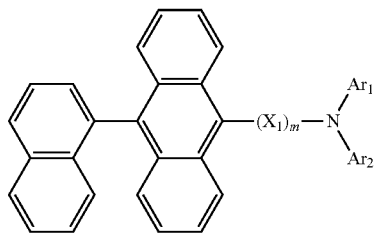

Formula 1

In Formula 1 above, $Ar_1$ and $Ar_2$ are each independently a substituted or unsubstituted $C_6$-$C_{60}$ aryl group, or a substituted or unsubstituted $C_2$-$C_{60}$ heteroaryl group; and $X_1$ is a substituted or unsubstituted $C_6$-$C_{60}$ arylene group, or a substituted or unsubstituted $C_2$-$C_{60}$ heteroarylene group and m is an integer from 1 to 5.

At least one substituent of each of the substituted $C_6$-$C_{60}$ aryl group, the substituted $C_2$-$C_{60}$ heteroaryl group, the substituted $C_6$-$C_{60}$ arylene group, and the substituted $C_2$-$C_{60}$ heteroarylene group may be one of a deuterium atom; —F; —Cl; —Br; —I; —CN; a hydroxyl group; —NO$_2$; an amino group; an amidino group; hydrazine; hydrazone; a carboxyl group or a salt thereof; a sulfonic acid group or a salt thereof; a phosphoric acid or a salt thereof; a tri($C_6$-$C_{60}$aryl)silyl group; a $C_1$-$C_{60}$ alkyl group, a $C_1$-$C_{60}$ alkoxy group, a $C_2$-$C_{60}$ alkenyl group, and a $C_2$-$C_{60}$ alkynyl group; a $C_1$-$C_{60}$ alkyl group, a $C_1$-$C_{60}$ alkoxy group, a $C_2$-$C_{60}$ alkenyl group and a $C_2$-$C_{60}$ alkynyl group that is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, a $C_6$-$C_{60}$ arylthiol group; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group that is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one fluorine (F), a $C_1$-$C_{60}$ alkoxy group, a $C_2$-$C_{60}$ alkenyl group, a $C_2$-$C_{60}$ alkynyl group, a $C_6$-$C_{60}$ aryl group and a $C_2$-$C_{60}$ heteroaryl group, In Formula 1 above, at least one of $Ar_1$ and $Ar_2$ is a $C_6$-$C_{60}$ aryl group substituted with at least one electron withdrawing group selected from the group consisting of —F; —CN; —NO$_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

For example, the at least one electron withdrawing group may be selected from the group consisting of: —F; —CN; —NO$_2$; a $C_1$-$C_{20}$ alkyl group substituted with at least one —F; a $C_2$-$C_{20}$ heteroaryl group including a ring-forming N atom; and a $C_2$-$C_{20}$ heteroaryl group that includes a ring-forming N atom and is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a $C_6$-$C_{20}$ aryl group, and a $C_2$-$C_{20}$ heteroaryl group.

In some embodiments, the at least one electron withdrawing group in Formula 1 may be selected from the group consisting of —F; —CN; a $C_1$-$C_{20}$ alkyl group substituted with at least one —F; a pyrrolyl group, a pyrazolyl group, an imidazolyl group, an imidazolinyl group, an imidazopyridinyl group, an imidazopyrimidinyl group, a pyridinyl group, a pyrazinyl group, a pyrimidinyl group, a benzoimidazolyl group, an indolyl group, a purinyl group, a quinolinyl group, an isoquinolinyl group, a phthalazinyl group, an indolizinyl group, a quinazolinyl group, a cinnolinyl group, an indazolyl group, a carbazolyl group, a phenazinyl group, a phenanthridinyl group, a triazinyl group, a pyridazinyl group, a triazoly group, and a tetrazoly; and a pyrrolyl group, a pyrazolyl group, an imidazolyl group, an imidazolinyl group, an imidazopyridinyl group, imidazopyrimidinyl, pyridinyl, pyrazinyl, pyrimidinyl, benzoimidazolyl, indolyl, purinyl, quinolinyl, isoquinolinyl, phthalazinyl, indolizinyl, quinazolinyl, cinolinyl, indazolyl, carbazolyl, phenazinyl, phenanthridinyl, triazinyl, pyridazinyl, triazolyl, and a tetrazolyl group that is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group and a carbazolyl group.

For example, the at least one electron withdrawing group in Formula 1 above may be selected from, but are not limited to, the group consisting of: —F; —CN; a $C_1$-$C_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group that is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group.

In some embodiments, the at least one electron withdrawing group in Formula 1 above may be selected from the group consisting of —F; —CN; —CH$_2$F; —CHF$_2$; —CF$_3$; and groups represented by Formulae 2(1) to 2(14) below:

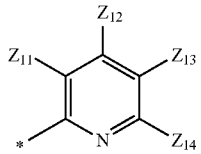
Formula 2(1)

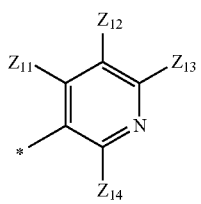
Formula 2(2)

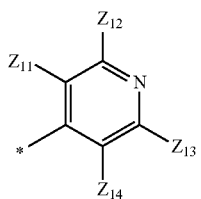
Formula 2(3)

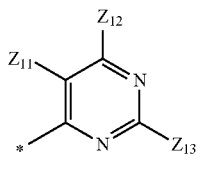
Formula 2(4)

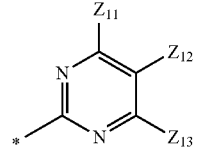
Formula 2(5)

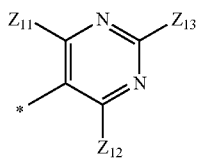
Formula 2(6)

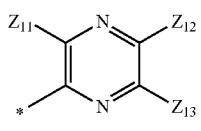
Formula 2(7)

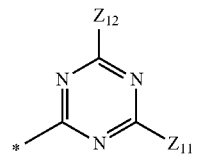
Formula 2(8)

-continued

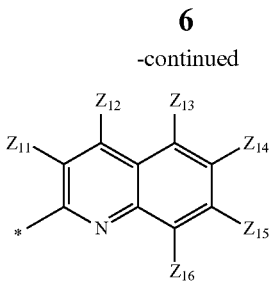
Formula 2(9)

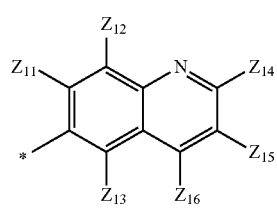
Formula 2(10)

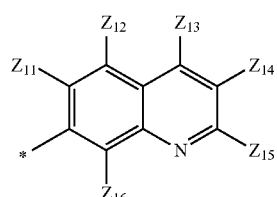
Formula 2(11)

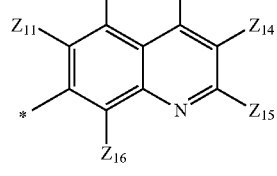
Formula 2(12)

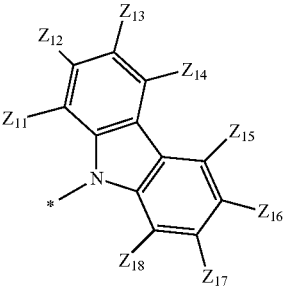
Formula 2(13)

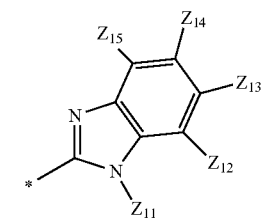
Formula 2(14)

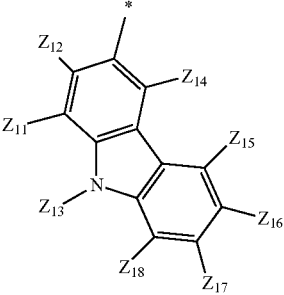

In Formulae 2(1) to 2(14) above, $Z_{11}$ to $Z_{18}$ may be each independently a hydrogen atom, a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a C$_1$-C$_{20}$ alkyl group, a C$_1$-C$_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, or a carbazolyl group.

For example, $Z_{11}$ to $Z_{18}$ in Formulae 2(1) to 2(14) above may be each independently a hydrogen atom, a deuterium atom, —F, —Cl, —Br, —I, —CN, a hydroxyl group, —$NO_2$, an amino group, an amidino group, hydrazine, hydrazone, a carboxyl group or a salt thereof, a sulfonate group or a salt thereof, a phosphoric acid or a salt thereof, a methyl group, an ethyl group, a propyl group, a butyl group, a pentyl group, a methoxy group, an ethoxy group, a propoxy group, a butoxy group, a pentoxy group, a phenyl group, a naphthyl group, an anthryl group, a phenanthrenyl group, a pyrenyl group, a pyridinyl group, a triazinyl group, or a carbazolyl group, but are not limited thereto.

In Formula 1 above, the at least one of $Ar_1$ and $Ar_2$ may be a $C_6$-$C_{60}$ aryl group substituted with at least two electron withdrawing groups. In some embodiments, the at least one of $Ar_1$ and $Ar_2$ may be a phenyl group, a biphenyl group, a naphthyl group, an anthryl group, a phenanthrenyl group, a pyrenyl group, or a fluorenyl group that are substituted with at least two electron withdrawing groups. The electron withdrawing groups may be each independently selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group.

At least one of $Ar_1$ and $Ar_2$ in the amine-based compound of Formula 1 above is a $C_6$-$C_{60}$ aryl group substituted with at least one of the above electron withdrawing groups. Accordingly, the amine-based compound may be represented by Formula 1(1) or Formula 1(2) below:

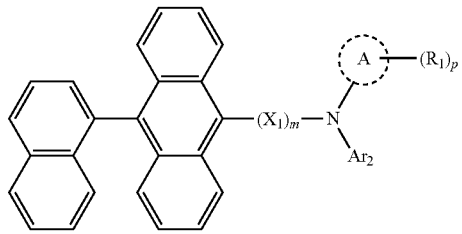

Formula 1(1)

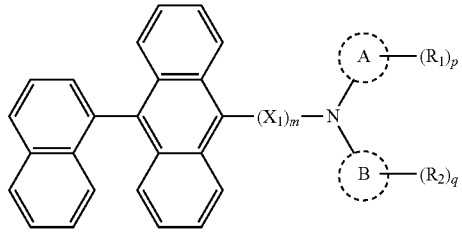

Formula 1(2)

In Formula 1(1) above, $Ar_2$ is a substituted or unsubstituted $C_6$-$C_{20}$ aryl group, or a substituted or unsubstituted $C_2$-$C_{20}$ heteroaryl group. In Formulas 1(1) and 1(2) above, the A and B rings are each independently a substituted $C_6$-$C_{20}$ aryl group; $R_1$ and $R_2$ are each independently an electron withdrawing group selected from the group consisting of: —F; —CN; —$NO_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group; and p and q are each independently an integer from 1 to 9.

The electron withdrawing group in Formulae 1(1) and 1(2) are as described above, and thus a detailed description thereof will not be repeatedly herein.

For example, the amine-based compound may be represented by Formula 1(1) above, wherein at least one of p number of $R_1$ in Formula 1(1) may be —CN.

In some embodiments, the amine-based compound may be represented by Formula 1(2) above, wherein at least one among p number of $R_1$ and q number of $R_2$ in Formula 1(2) may be —CN.

In some embodiments, the amine-based compound may be represented by Formula 1(1) above, wherein the A ring in Formula 1(1) may be a substituted phenyl group, a substituted biphenyl group, a substituted naphthyl group, a substituted anthryl group, a substituted phenanthrenyl group, a substituted pyrenyl group, or a substituted fluorenyl group, but is not limited thereto.

In some embodiments, the amine-based compound may be represented by Formula 1(2) above, wherein the A and B rings in Formula 1(2) may be each independently a substituted phenyl group, a substituted biphenyl group, a substituted naphthyl group, a substituted anthryl group, a substituted phenanthrenyl group, a substituted pyrenyl group, or a substituted fluorenyl group.

In some other embodiments, the amine-based compound may be represented by Formula 1(1), wherein the A ring may be a substituted phenyl group, a substituted biphenyl group, a substituted naphthyl group, a substituted anthryl group, a substituted phenanthrenyl group, a substituted pyrenyl group, or a substituted fluorenyl group; $R_1$ may be at least one electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group; and p may be 2, 3, or 4, for example, may be 2.

In some other embodiments, the amine-based compound may be represented by Formula 1(2), wherein the A ring and the B ring may be each independently is a substituted phenyl group, a substituted biphenyl group, a substituted naphthyl group, a substituted anthryl group, a substituted phenanthrenyl group, a substituted pyrenyl group, or a substituted fluorenyl group; $R_1$ and $R_2$ may be each independently at least one electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group; and p and q may be each independently an integer of 2, 3, or 4, for example, may be both an integer of 2.

At least one of $Ar_1$ and $Ar_2$ in Formula 1 above may be a phenyl group, a biphenyl group, a naphthyl group, a anthryl group, a phenanthrenyl group, a pyrenyl group, or a fluorenyl group that are substituted with at least one of the above-listed electron withdrawing groups.

In Formula 1 above, $Ar_1$ and $Ar_2$ may be each independently a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinylene group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, or a substituted or unsubstituted phenanthrolinyl group. At least one of $Ar_1$ and $Ar_2$ may be a phenyl group, a biphenyl group, a naphthyl group, an anthryl group, a phenanthrenyl group, a pyrenyl group, or a fluorenyl group that are substituted with at least one of the above-listed electron withdrawing groups.

For example, $Ar_1$ and $Ar_2$ in Formula 1 above may be each independently a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted chrysenyl group, a substituted or unsubstituted pyridinyl group, a substituted or unsubstituted pyrazinyl group, a substituted or unsubstituted pyrimidinyl group, a substituted or unsubstituted quinolinyl group, a substituted or unsubstituted carbazolyl group, a substituted or unsubstituted triazinyl group, a substituted or unsubstituted dibenzothiophenyl group, a substituted or unsubstituted dibenzofuranyl group, or a substituted or unsubstituted phenanthrolinyl group. At least one of $Ar_1$ and $Ar_2$ may be a phenyl group, a biphenyl group, a naphthyl group, an anthryl group, a phenanthrenyl group, a pyrenyl group, or a fluorenyl group that is substituted with at least one electron withdrawing group selected from the group consisting of —F; —CN; a $C_1$-$C_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group.

In some embodiments, in Formula 1, $Ar_1$ and $Ar_2$ may be linked together by a single bond.

In some embodiments the amine-based compound may be represented by any one of Formulae 1A to 1J below:

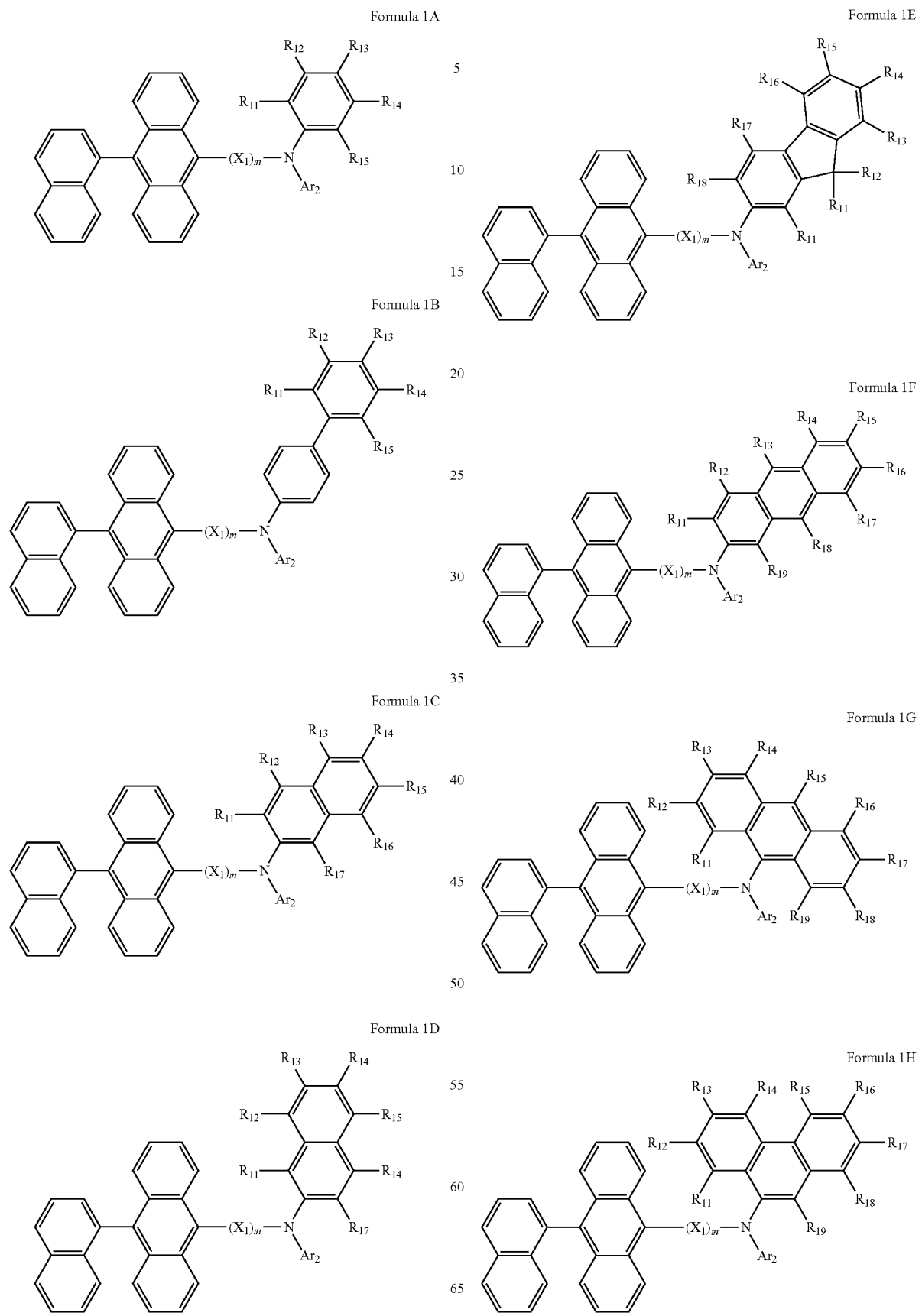

-continued

Formula 1I

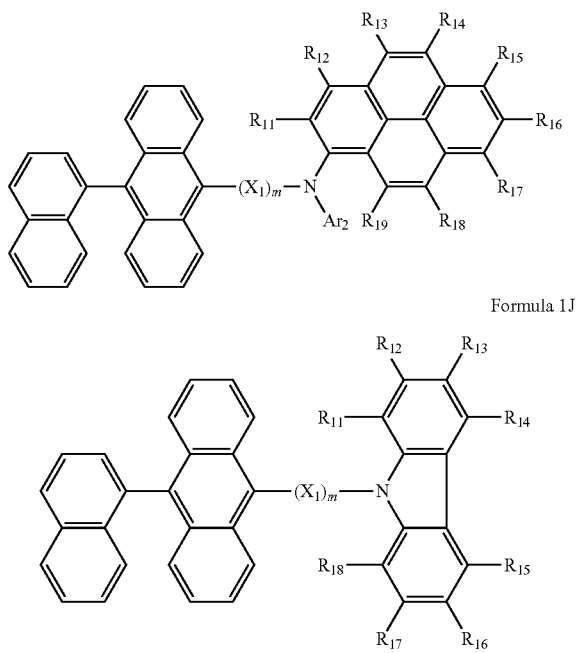

Formula 1J

Ar$_2$ in Formulae 1A to 1I may be the same as described above in conjunction with other formulae.

At least one of R$_{11}$ to R$_{15}$ in Formulae 1A and 1B, at least one of R$_{11}$ to R$_{17}$ in Formulae 1C and 1D, at least one of R$_{11}$ to R$_{18}$ in Formulae 1E and 1J, and at least one of R$_{11}$ to R$_{19}$ in Formula 1F, 1G, 1H and 1I may be each independently an electron withdrawing group selected from the group consisting of —F; —CN; —NO$_2$; a C$_1$-C$_{60}$ alkyl group substituted with at least one —F; a C$_2$-C$_{60}$ heteroaryl group; and a C$_2$-C$_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a C$_1$-C$_{60}$ alkyl group, a C$_1$-C$_{60}$ alkyl group substituted with at least one —F, a C$_1$-C$_{60}$ alkoxy group, a C$_2$-C$_{60}$ alkenyl group, a C$_2$-C$_{60}$ alkynyl group, a C$_6$-C$_{60}$ aryl group, and a C$_2$-C$_{60}$ heteroaryl group.

For example, at least one of R$_{11}$ to R$_{15}$ of Formulae 1A and 1B, at least one of R$_{11}$ to R$_{17}$ in Formulae 1C and 1D, at least one of R$_{11}$ to R$_{18}$ of Formulae 1E and 1J, and at least one of R$_{11}$ to R$_{19}$ of Formulae 1F, 1G, 1H and 1I may be each independently, but are not limited to, an electron withdrawing group selected from the group consisting of: —F; —CN; a C$_1$-C$_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; a pyridinyl group, a pyrazinyl group, a pyrimidinyl group, a quinolinyl group, an isoquinolinyl group, a quinazolinyl group, a phthalazinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a C$_1$-C$_{20}$ alkyl group, a C$_1$-C$_{20}$ alkyl group substituted with at least one —F, a C$_1$-C$_{20}$ alkoxy group, a phenyl group, a naphthyl group, an anthryl group, a phenanthrenyl group, a pyrenyl group, a pyridinyl group, a triazinyl group, and a carbazolyl group.

In some embodiments, Ar$_2$ in Formulae 1A to 1I may be, but are not limited thereto, a phenyl group, a biphenyl group, a naphthyl group, an anthryl group, a phenanthrenyl group, a pyrenyl group, or a fluorenyl group that are substituted with at least one electron withdrawing group selected from the group consisting of —F; —CN; a C$_1$-C$_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a C$_1$-C$_{20}$ alkyl group, a C$_1$-C$_{20}$ alkyl group substituted with at least one —F, a C$_1$-C$_{20}$ alkoxy group, a phenyl group, a naphthyl group, an anthryl group, a phenanthrenyl group, a pyrenyl group, a pyridinyl group, a triazinyl group, and a carbazolyl group.

In some embodiments the amine-based compound may be represented by Formula 1A-(1) or 1A-(2) below:

Formula 1A-(1)

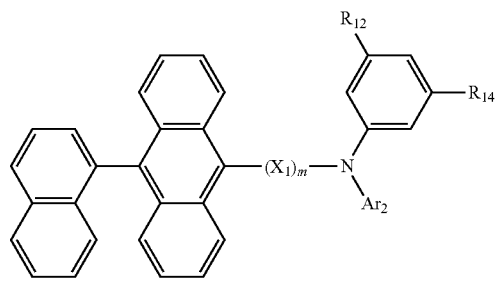

Formula 1A-(2)

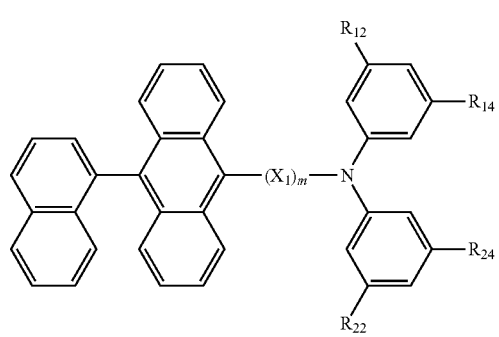

In Formulae 1A-(1) and 1A-(2), R$_{12}$, R$_{14}$, R$_{22}$, and R$_{24}$ may each independently be an electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO₂, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group; and $Ar_2$ may be a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, or a substituted or unsubstituted fluorenyl group.

In some embodiments, in Formulae 1A-(1) and 1A-(2), $R_{12}$, $R_{14}$, $R_{22}$ and $R_{24}$ may be each independently selected from the group consisting of —F; —CN; —CH₂F; —CHF₂; —CF₃; and groups represented by Formulae 2(1) to 2(14) above.

In some other embodiments, in Formulae 1A-(1) and 1A-(2) above, $R_{12}$, $R_{14}$, $R_{22}$ and $R_{24}$ may be each independently one of the groups represented by Formulae 2(1) to 2(8) above.

In some other embodiments, in Formulae 1A-(1) and 1A-(2) above, $R_{12}$, $R_{14}$, $R_{22}$ and $R_{24}$ may be each independently the group represented by Formula 2(2) above, but are not limited thereto.

In Formula 1A-(1), $Ar_2$ may be a phenyl group, a biphenyl group, a naphthyl group, an anthryl group, a phenanthrenyl group, a pyrenyl group, or a fluorenyl group, but are not limited thereto.

In Formula 1, $X_1$ may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, a substituted or unsubstituted oxadiazolylene group, a substituted or unsubstituted pyridazinylene group, a substituted or unsubstituted triazolylene group, or a substituted or unsubstituted tetrazolylene group. $X_1$ in Formula 1 may have at least one substituent, which may be selected from among the substituents described above.

In some embodiments, $X_1$ in Formula 1 may be, but is not limited to, a substituted or unsubstituted phenylene group, a substituted or unsubstituted naphthylene group, a substituted or unsubstituted fluorenylene group, a substituted or unsubstituted phenanthrenylene group, a substituted or unsubstituted anthrylene group, a substituted or unsubstituted triphenylenylene group, a substituted or unsubstituted pyrenylene group, a substituted or unsubstituted chrysenylene group, a substituted or unsubstituted pyridinylene group, a substituted or unsubstituted pyrazinylene group, a substituted or unsubstituted pyrimidinylene group, a substituted or unsubstituted quinolinylene group, a substituted or unsubstituted quinazolinylene group, a substituted or unsubstituted carbazolylene group, a substituted or unsubstituted dibenzothiophenylene group, a substituted or unsubstituted dibenzofuranylene group, a substituted or unsubstituted triazinylene group, a substituted or unsubstituted pyridazinylene group, a substituted or unsubstituted triazolylene group, or a substituted or unsubstituted tetrazolylene group.

For example, $X_1$ in Formula 1 above may be a group represented by one of Formulae 5(1) to 5(16) below:

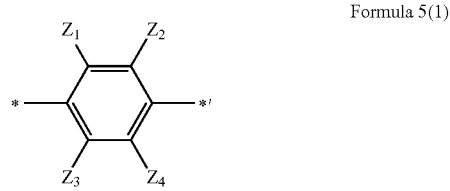

Formula 5(1)

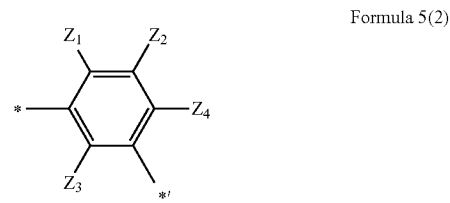

Formula 5(2)

Formula 5(3)
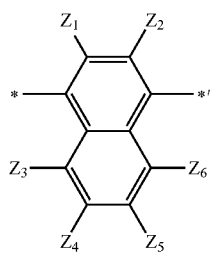
Formula 5(4)
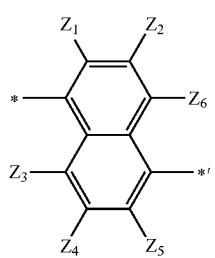
Formula 5(5)
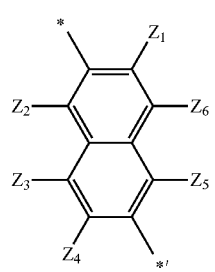
Formula 5(6)
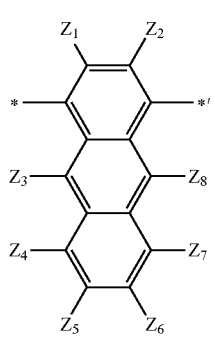
Formula 5(7)
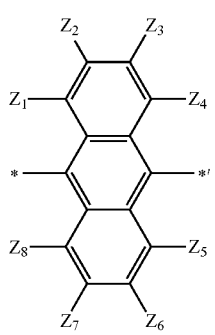
Formula 5(8)
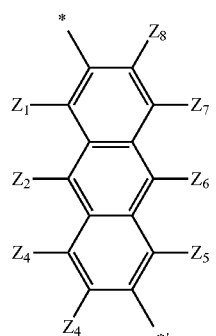
Formula 5(9)
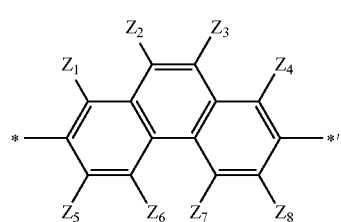
Formula 5(10)
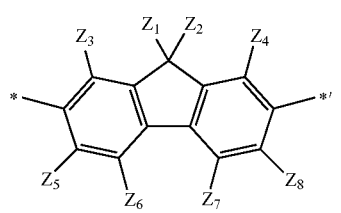
Formula 5(11)
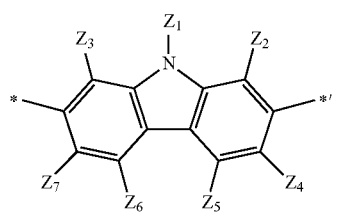
Formula 5(12)
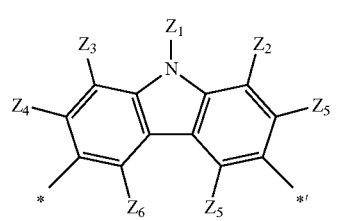
Formula 5(13)
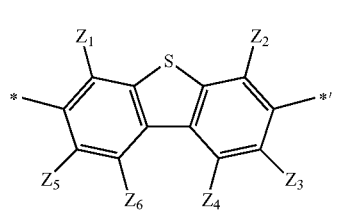
Formula 5(14)
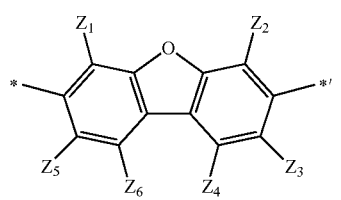

19

-continued

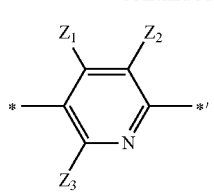

Formula 5(15)

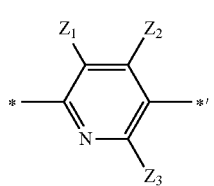

Formula 5(16)

In Formulae 5(1) to 5(16), $Z_1$ to $Z_8$ may be each independently one of a hydrogen atom; a deuterium atom; —F; —Cl; —Br; —I; —CN; a hydroxyl group; —$NO_2$; an amino group; an amidino group; hydrazine; hydrazone; a carboxyl group or a salt thereof; a sulfonic acid group or a salt thereof; phosphoric acid or a salt thereof; a $C_1$-$C_{20}$ alkyl group; a $C_1$-$C_{20}$ alkoxy group; a $C_1$-$C_{20}$ alkyl group and a $C_1$-$C_{20}$ alkoxy groups that are substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, sulfonic acid group or a salt thereof, and phosphoric acid or a salt thereof; a $C_6$-$C_{20}$ aryl group; a $C_2$-$C_{20}$ heteroaryl group; and a $C_6$-$C_{20}$ aryl group and a $C_2$-$C_{20}$ heteroaryl group that are substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkoxy group, a $C_6$-$C_{20}$ aryl group and a $C_2$-$C_{20}$ heteroaryl group.

In Formulae 5(1) to 5(16), * indicates a binding site to anthracene in Formula 1, and *' indicates a binding site to N in Formula 1.

For example, $Z_1$ to $Z_8$ in Formulae 5(1) to 5(16) may be each independently, but are not limited to, a hydrogen atom; a deuterium atom; —F; —Cl; —Br; —I; —CN; a hydroxyl group; —$NO_2$; an amino group; an amidino group; hydrazine; hydrazone; a carboxyl group or a salt thereof; a sulfonic acid group or a salt thereof; a phosphoric acid or a salt thereof; a methyl group, an ethyl group, a propyl group, a butyl group, and a pentyl group; a methoxy group, an ethoxy group, a propoxy group, a butoxy group, and a pentoxy group; a methyl group, an ethyl group, a propyl group, a butyl group, a pentyl group, a methoxy group, an ethoxy group, a propoxy group, a butoxy group, and a pentoxy group that are substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, and a phosphoric acid or a salt thereof; a phenyl group, a naphthyl group, an anthryl group, a phenanthrenyl group, a pyrenyl group, and a fluorenyl group; pyridinyl group, a pyrimidinyl group, a triazinyl group, a quinolyl group, and a carbazolyl group; a phenyl group, a naphthyl group, an anthryl group, a phenanthrenyl group, a pyrenyl group, a fluorenyl group, a pyridinyl group, a pyrimidinyl group, a triazinyl group, a quinolyl group, and a carbazolyl group that are substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, and a $C_1$-$C_{20}$ alkoxy group.

In Formula 1, m is an integer from 1 to 5, and in some embodiments, may be 1, 2, or 3, but is not limited thereto.

The amine-based compound of Formula 1 may be, for example, one of Compounds 1 to 109 below, but is not limited thereto:

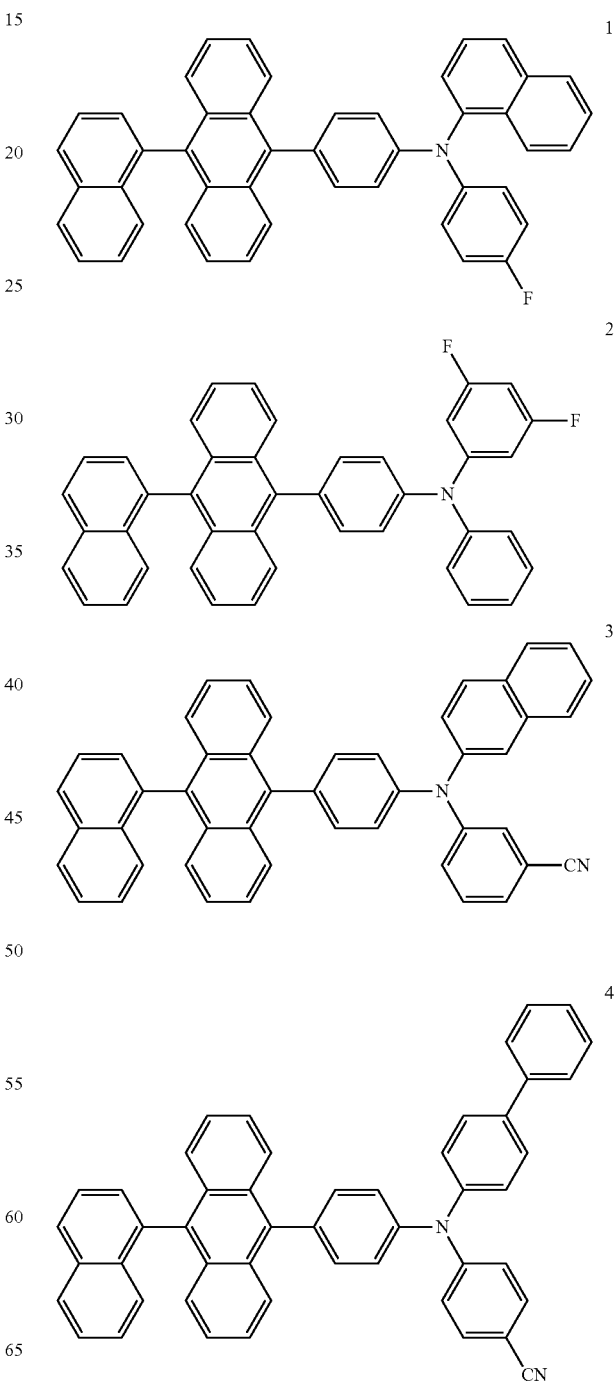

-continued
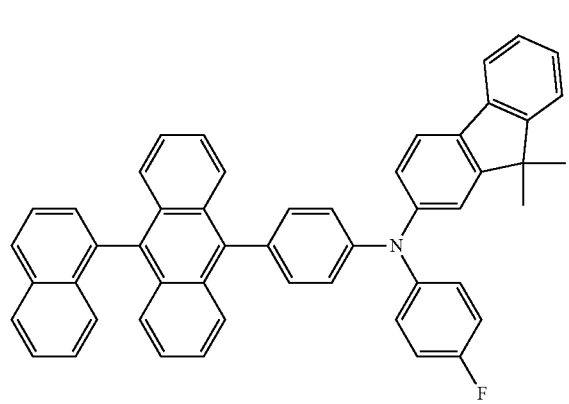
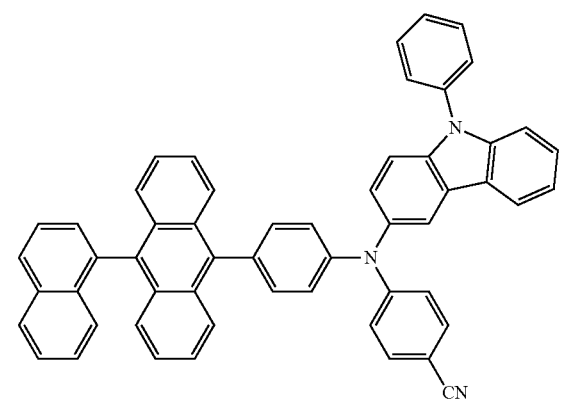
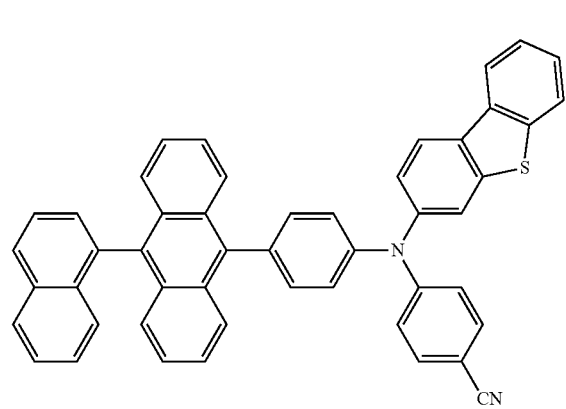
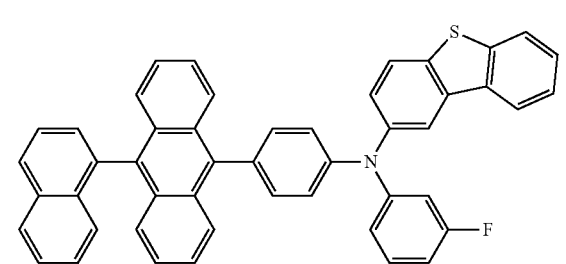
-continued
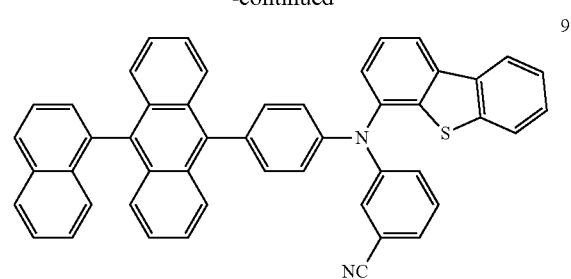
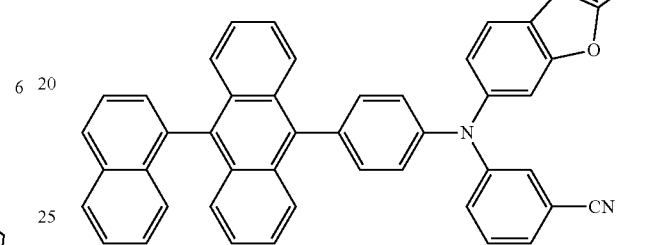
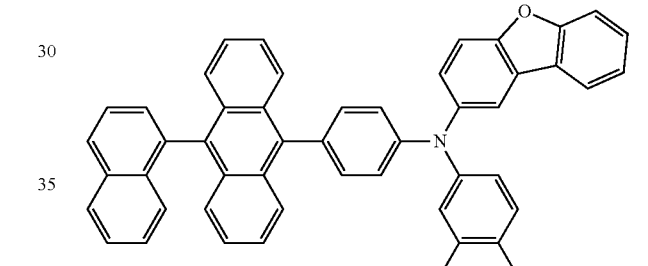
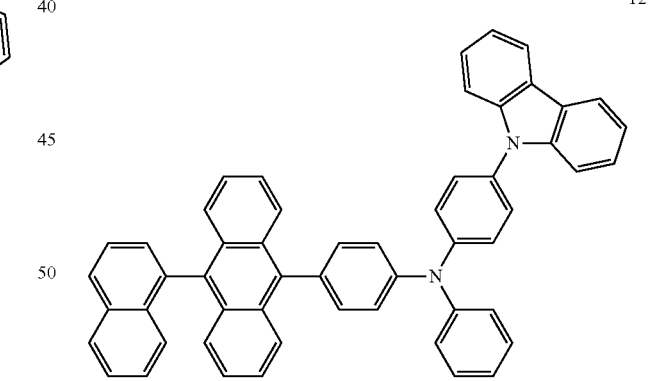
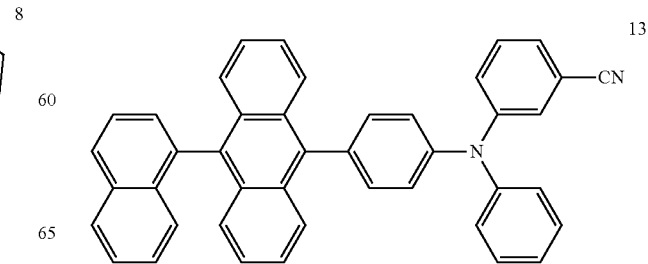

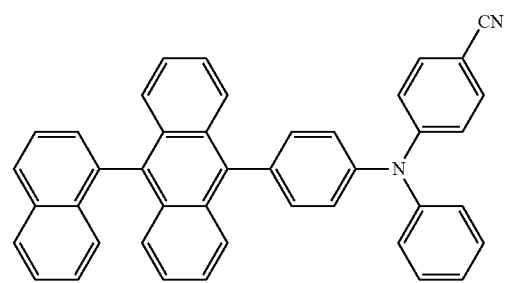
14
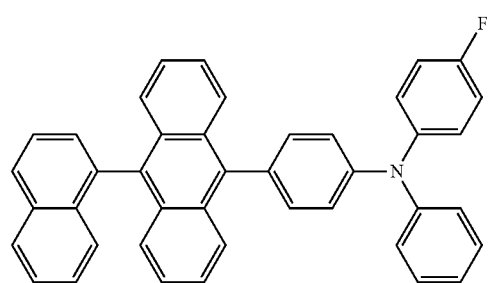
15
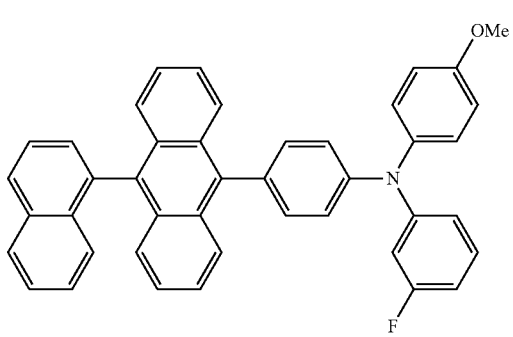
16
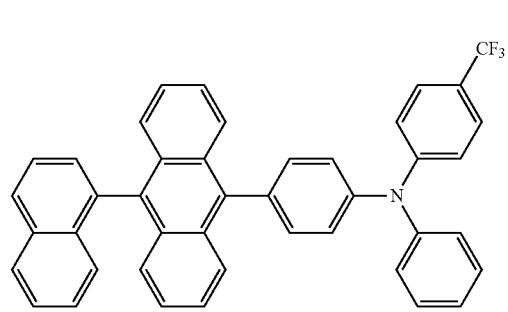
17
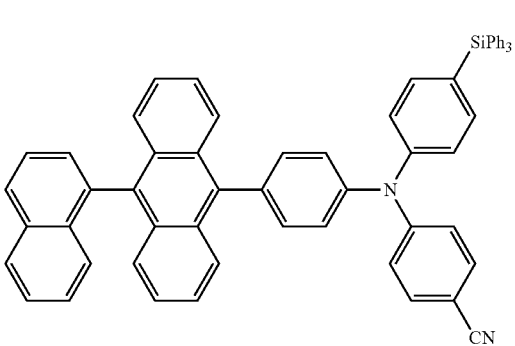
18
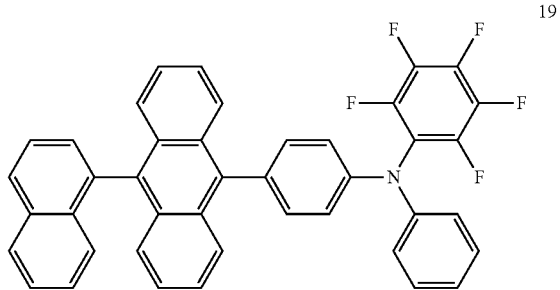
19
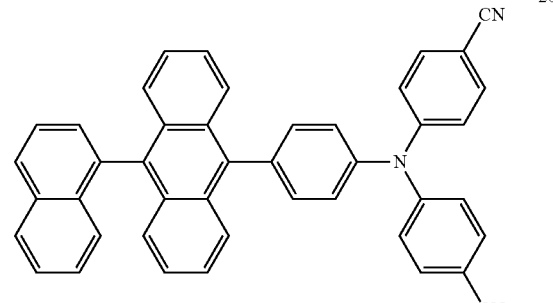
20
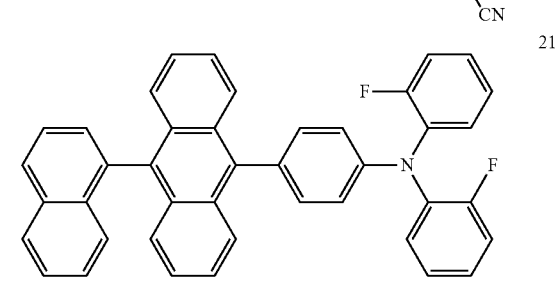
21
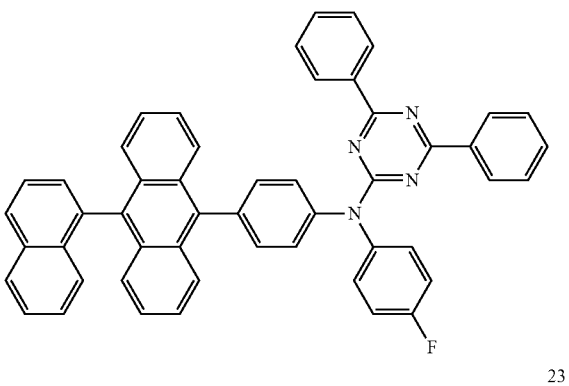
22
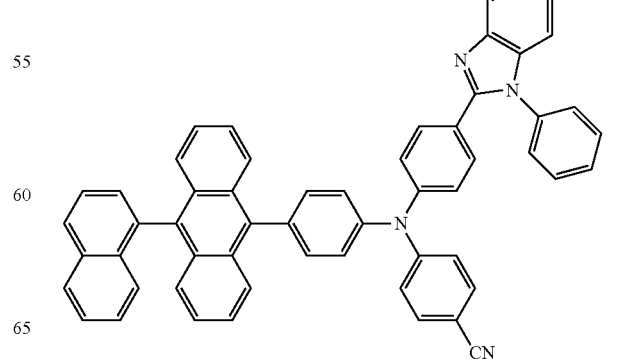
23

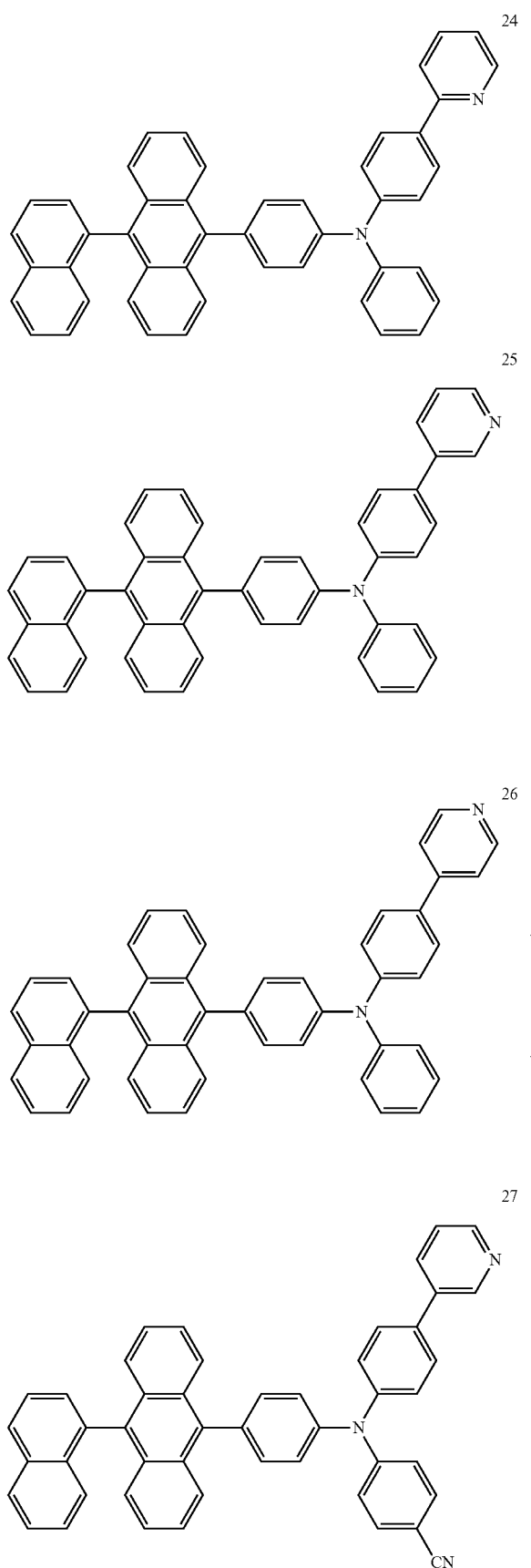
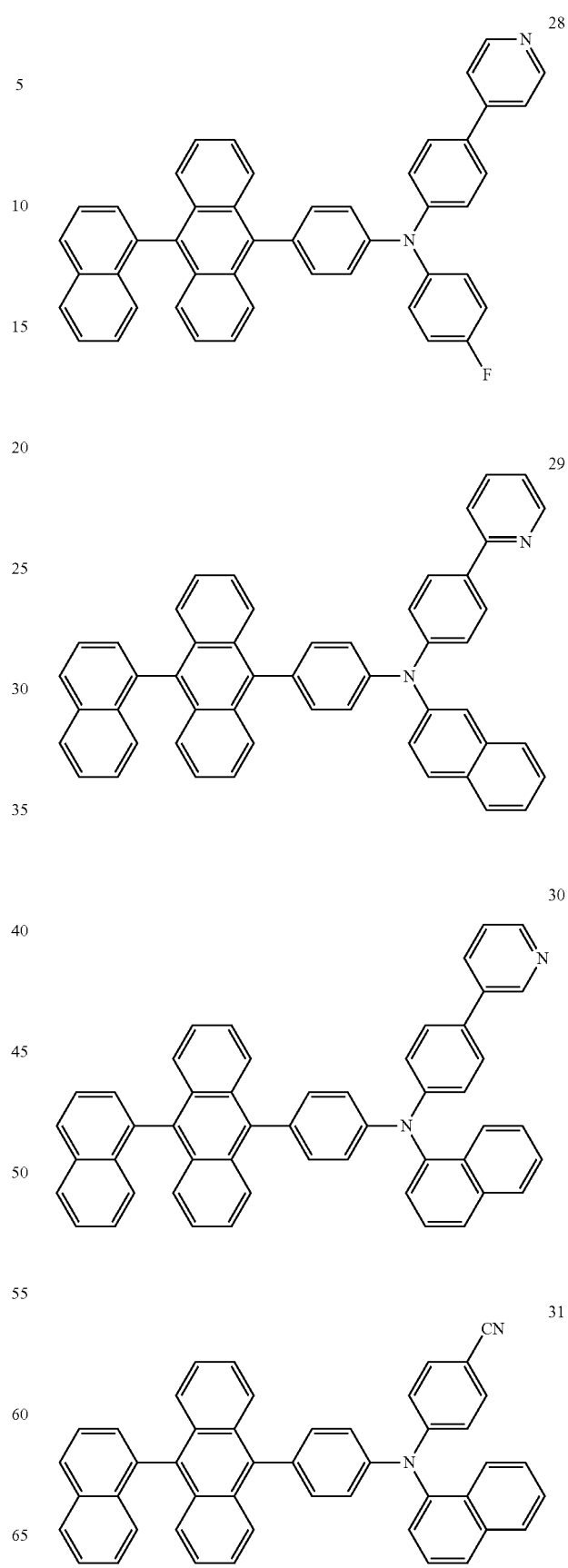

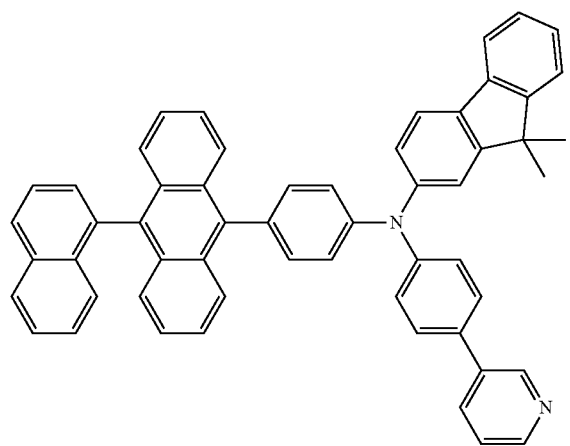
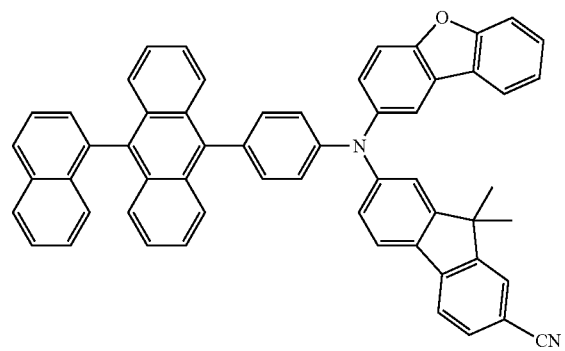
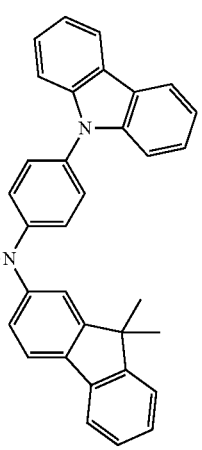
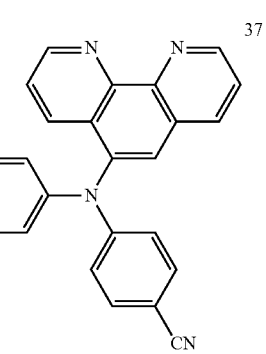
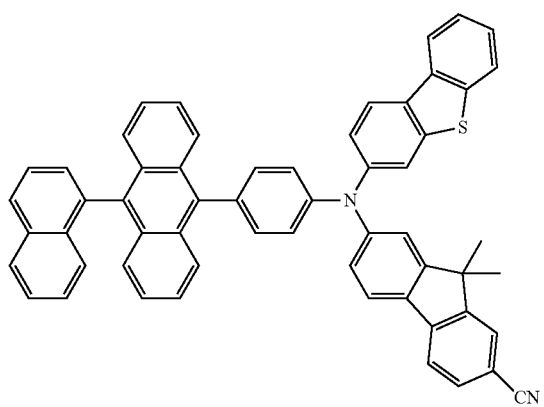
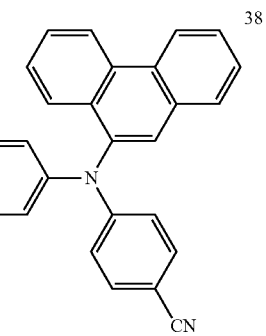

29
-continued
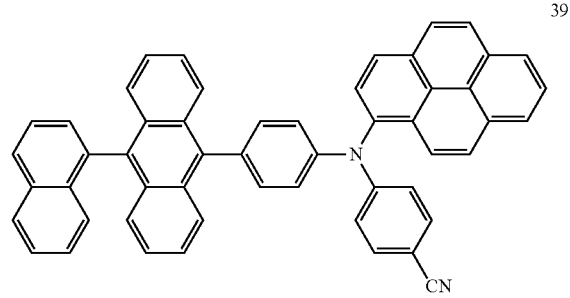
39
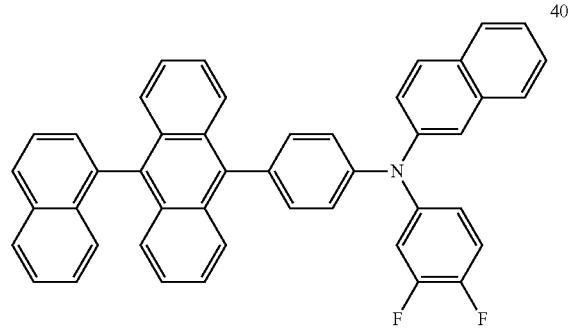
40
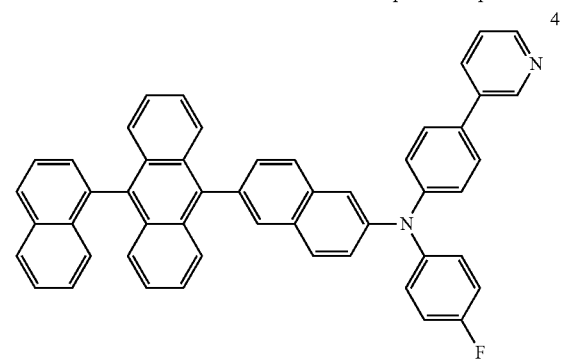
41
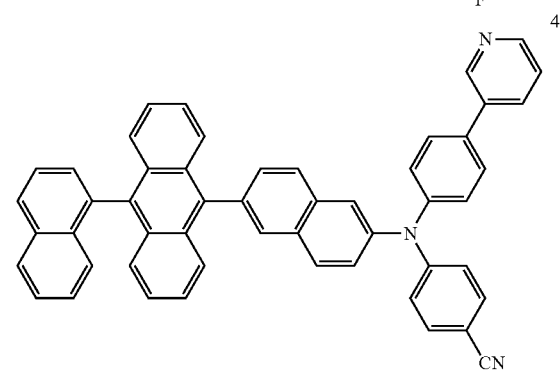
42
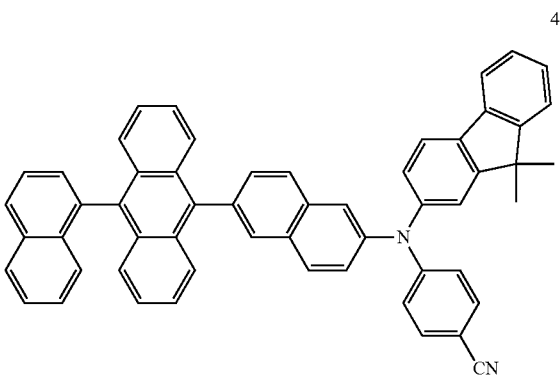
43
30
-continued
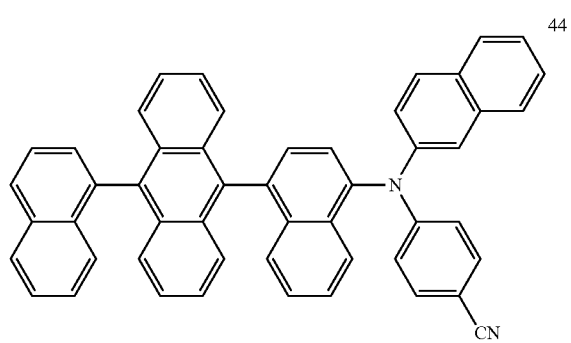
44
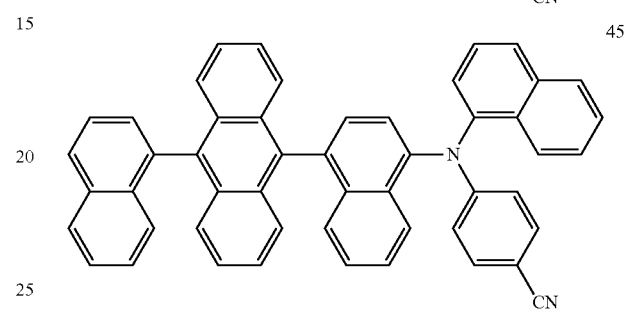
45
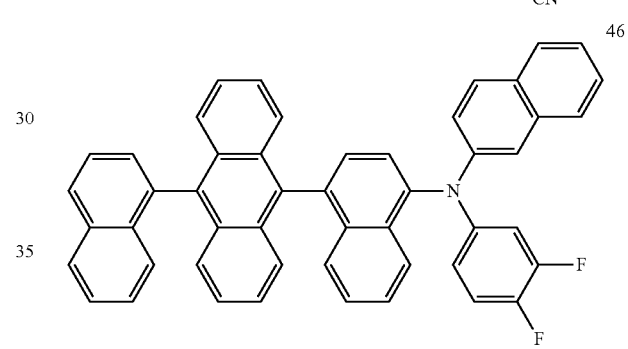
46
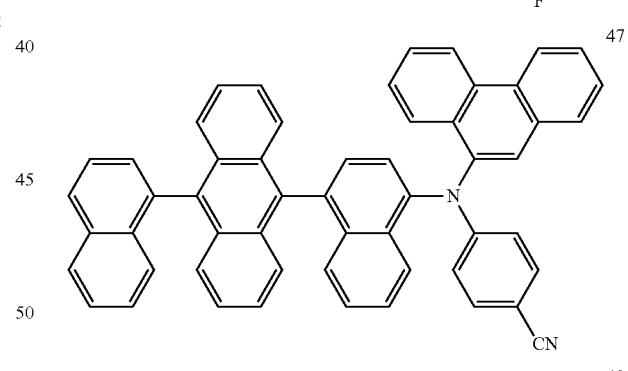
47
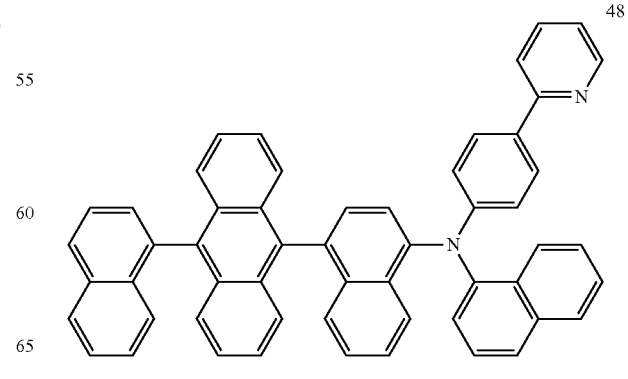
48

49
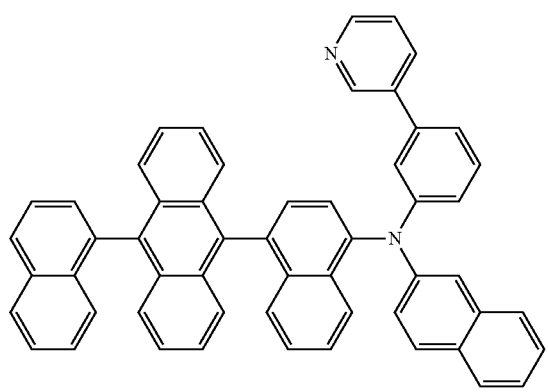
50
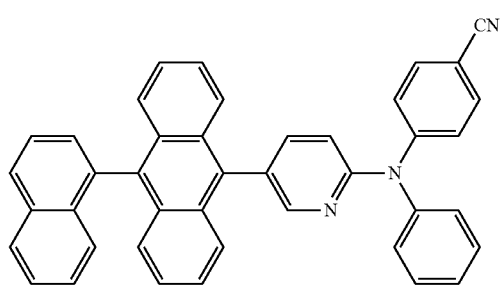
51
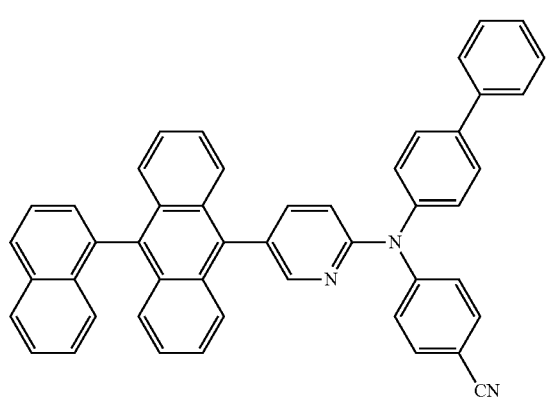
52
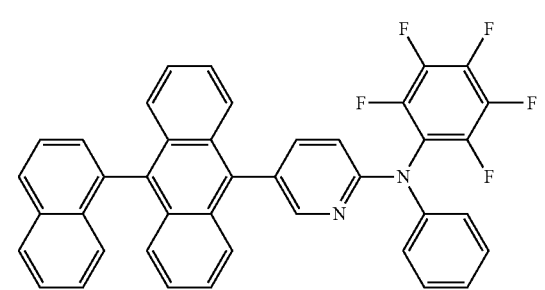
53
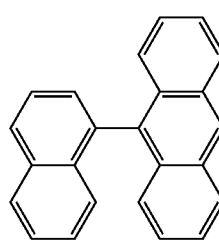
54
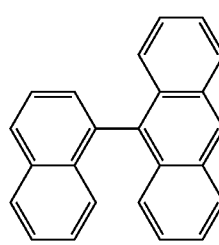
55
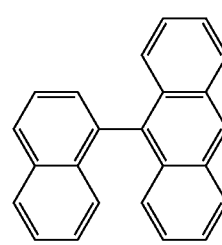
56
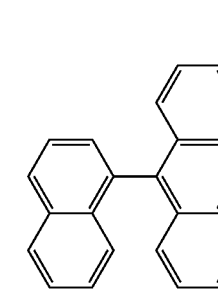

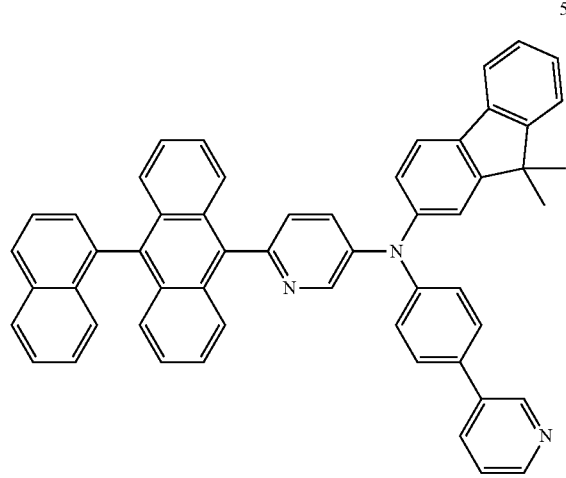
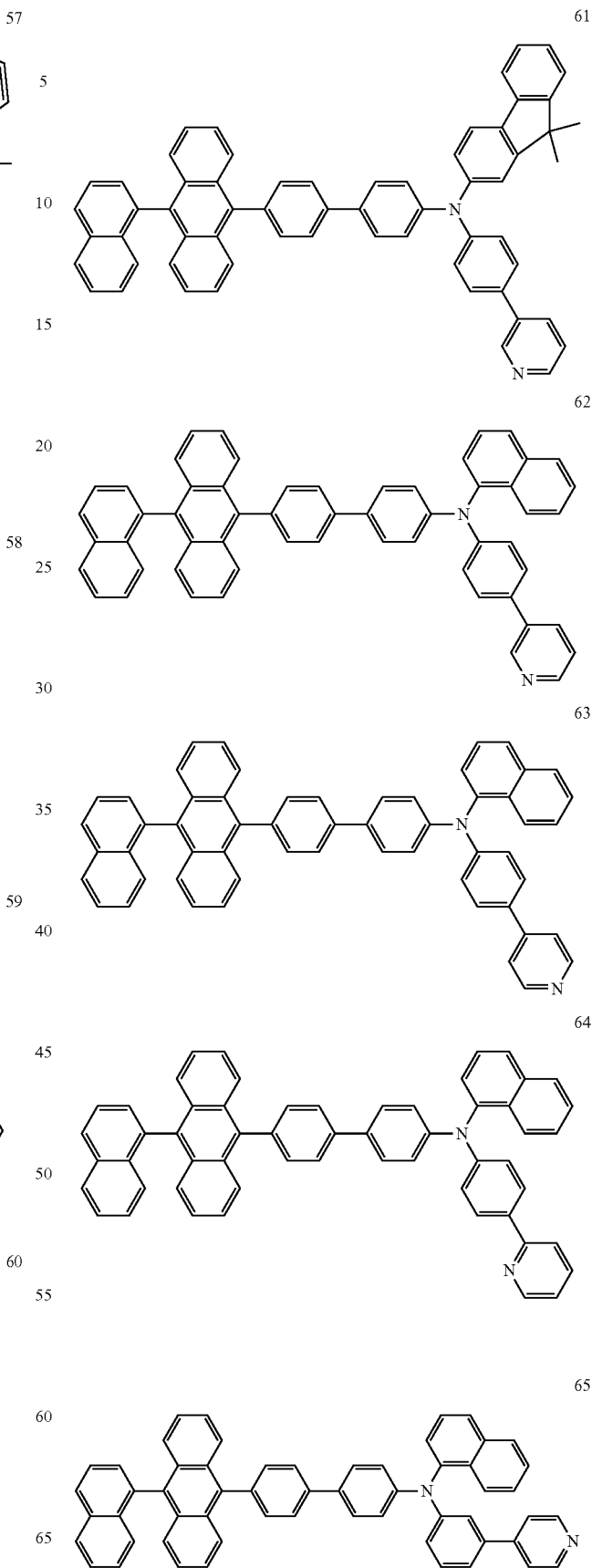

66
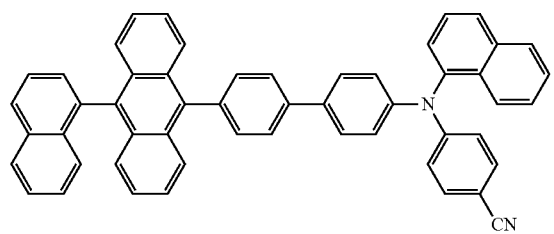
67
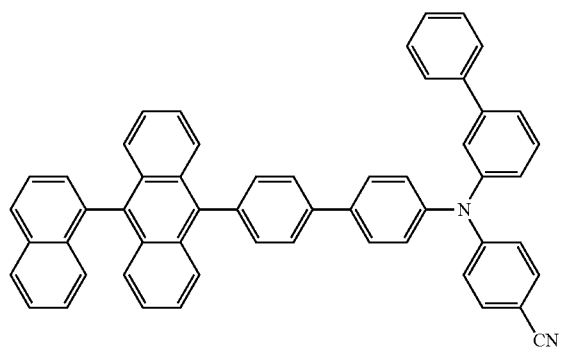
68
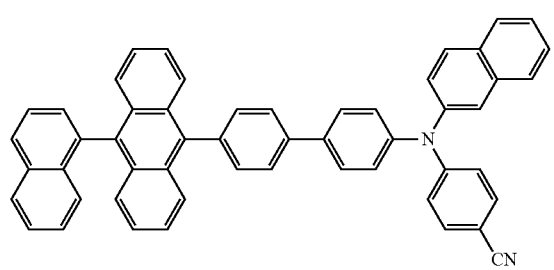
69
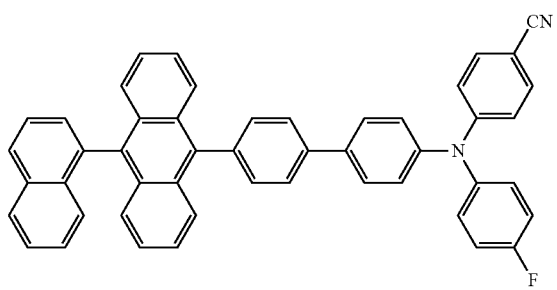
70
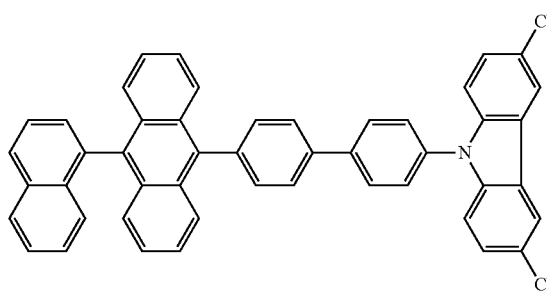
71
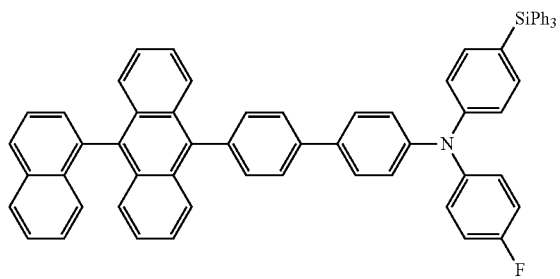
72
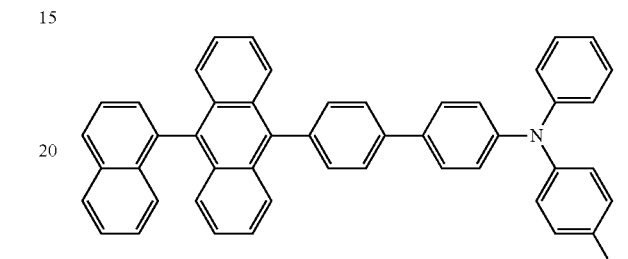
73
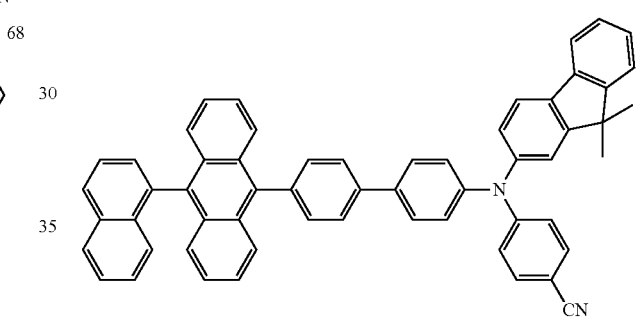
74
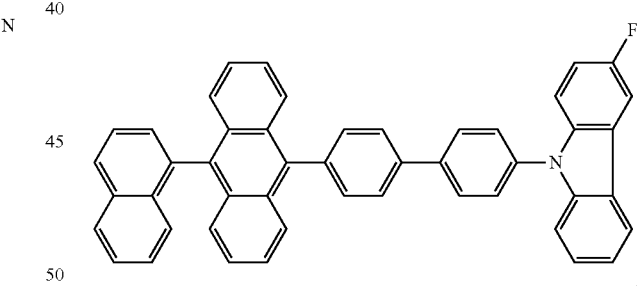
75
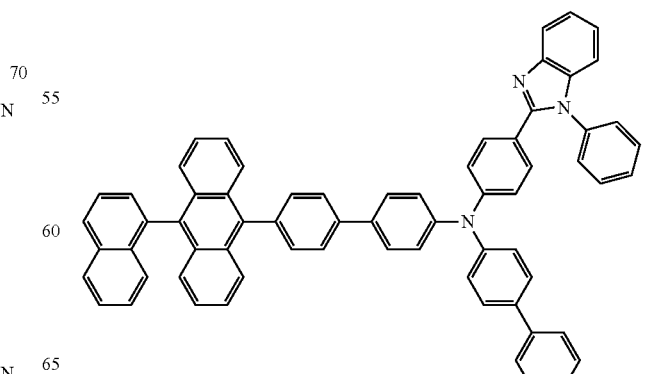

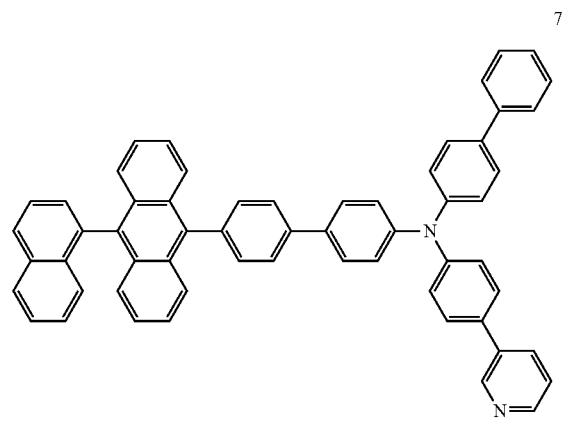
76
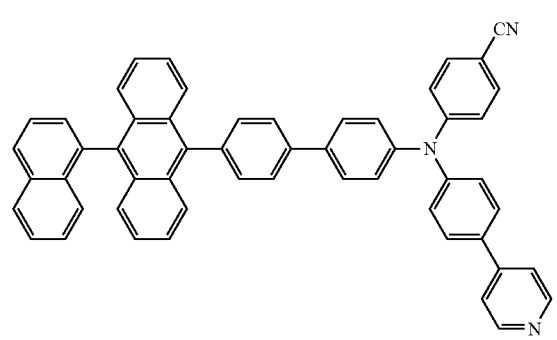
77
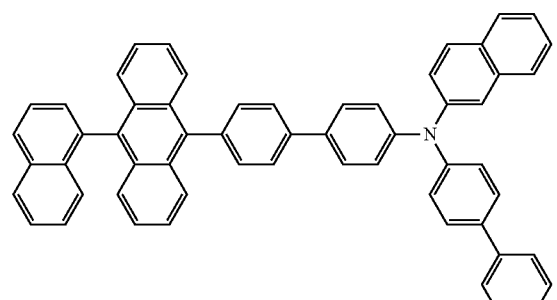
78
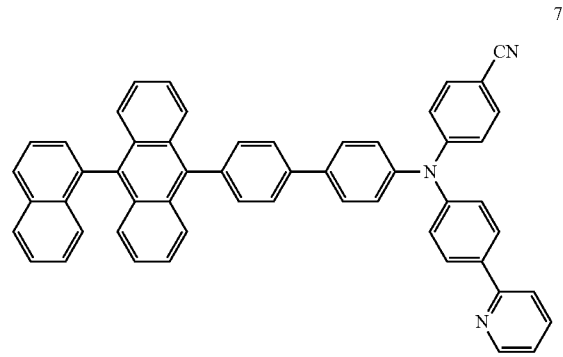
79
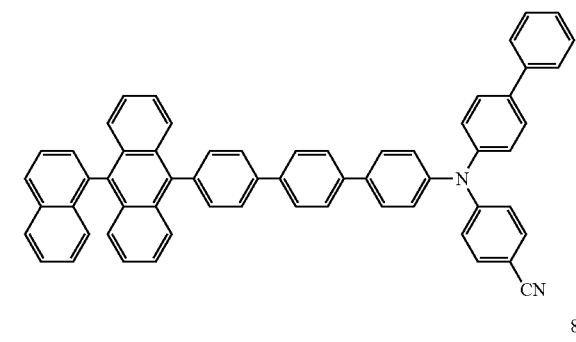
80
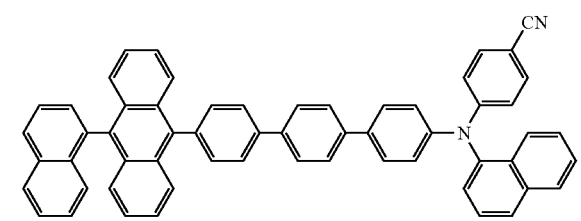
81
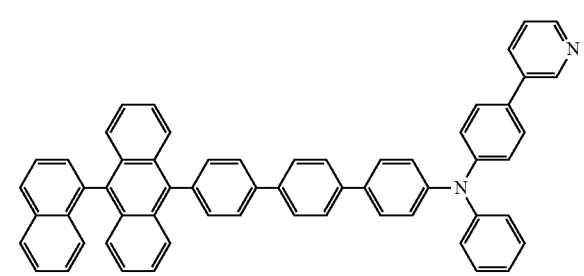
82
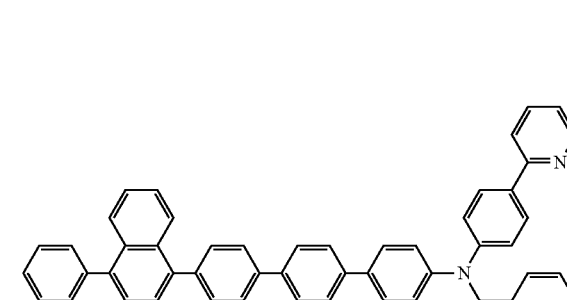
83
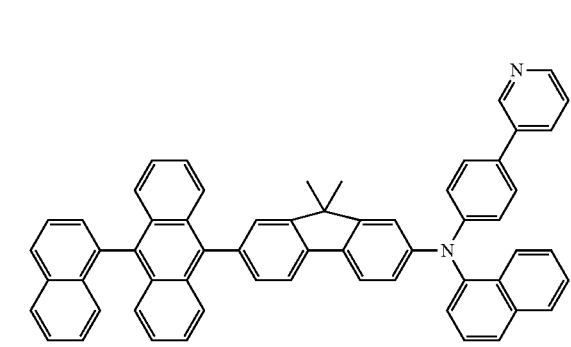
84

85
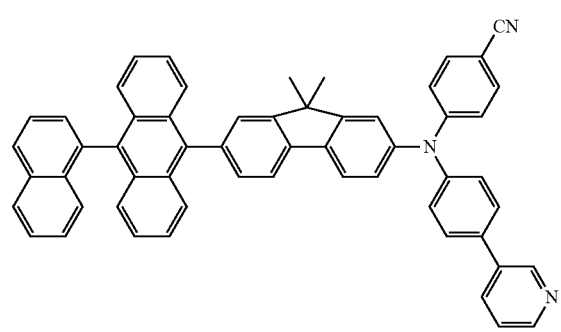
90
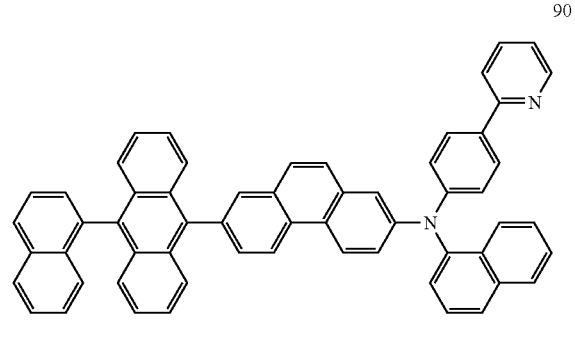
86
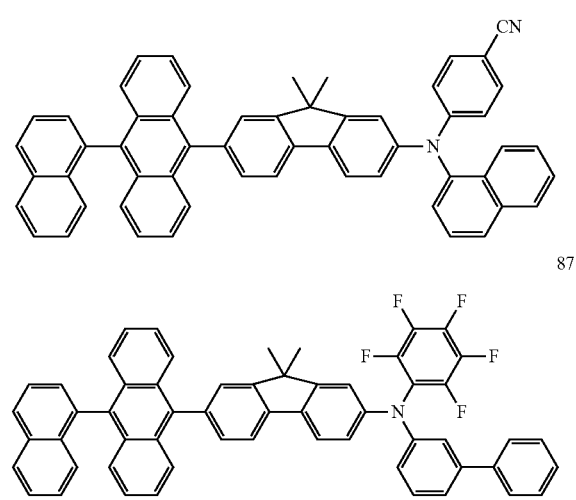
87
88
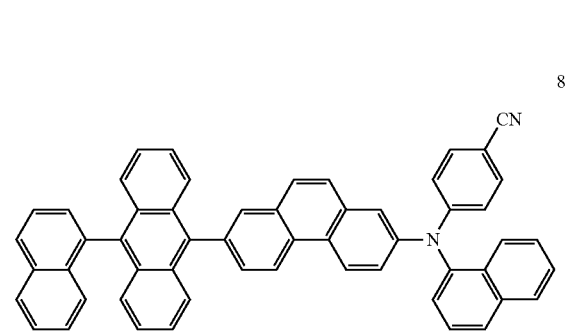
91
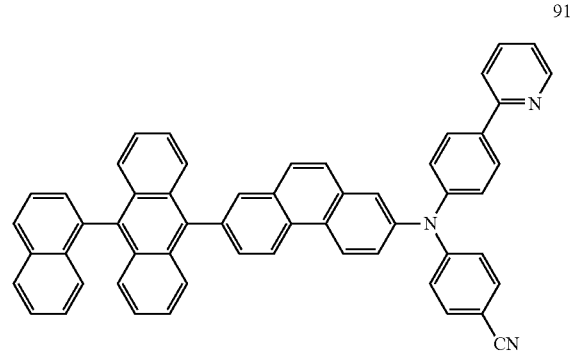
92
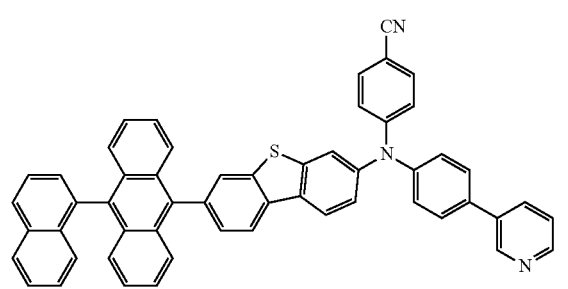
89
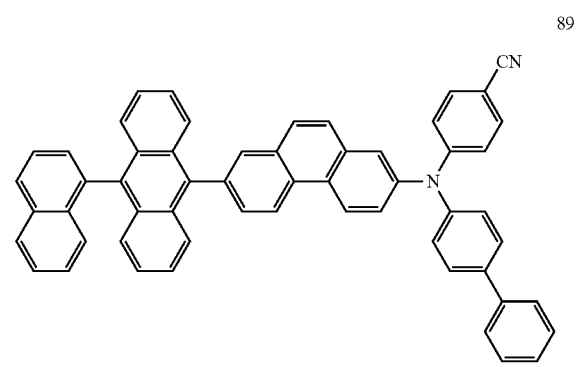
93
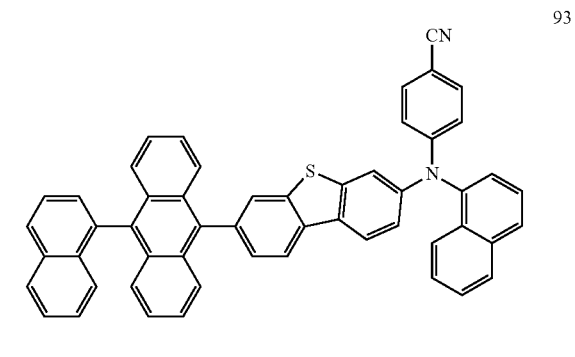

94
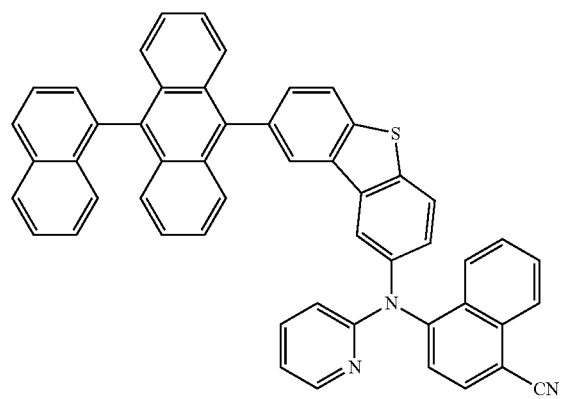
95
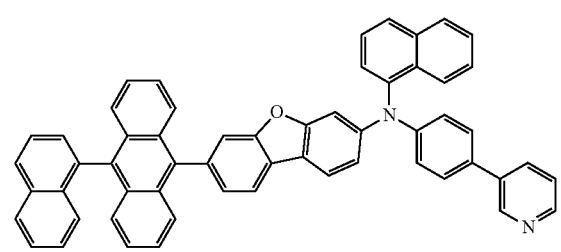
96
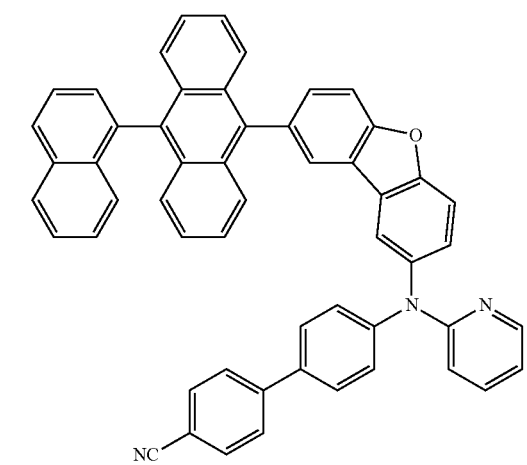
97
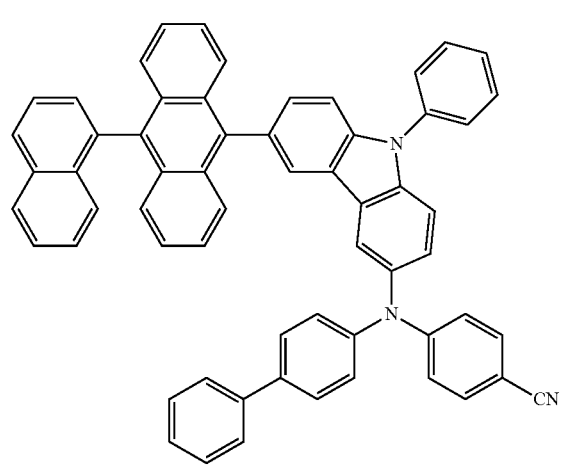
98
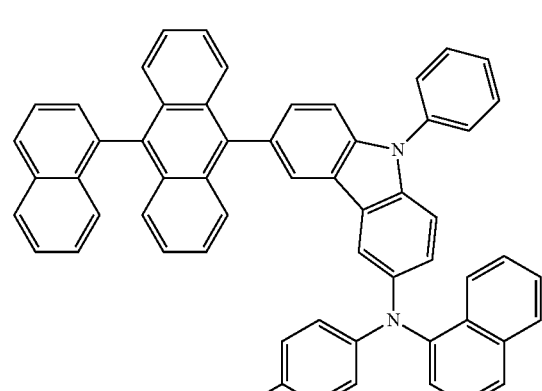
99
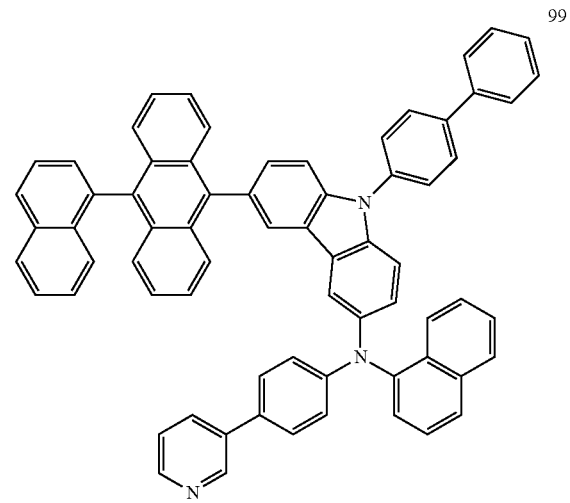
100
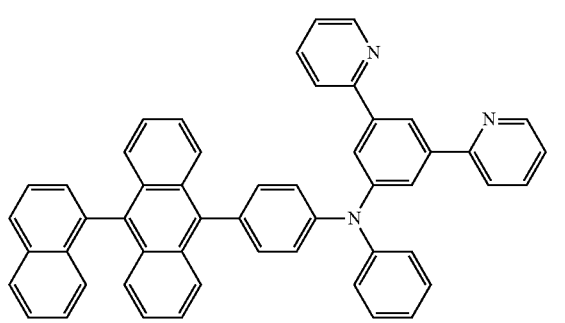
101
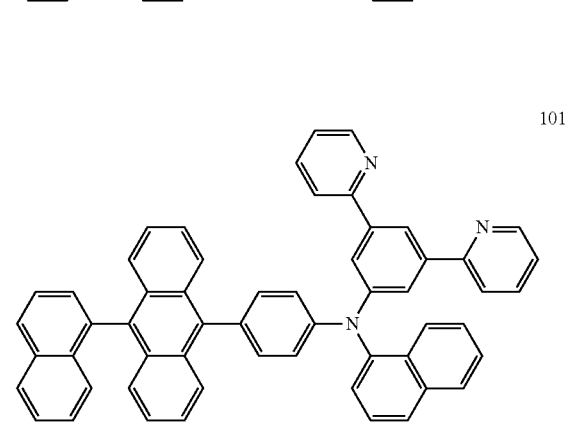

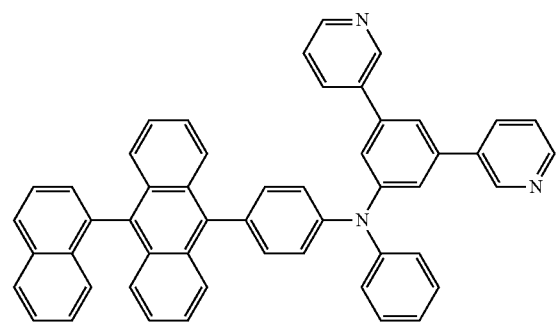
102
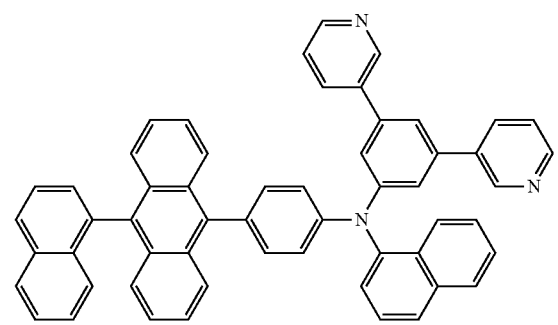
103
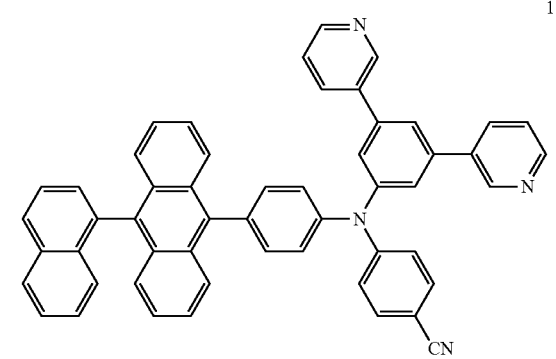
104
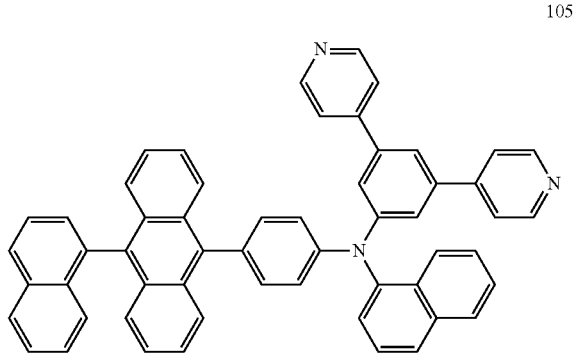
105
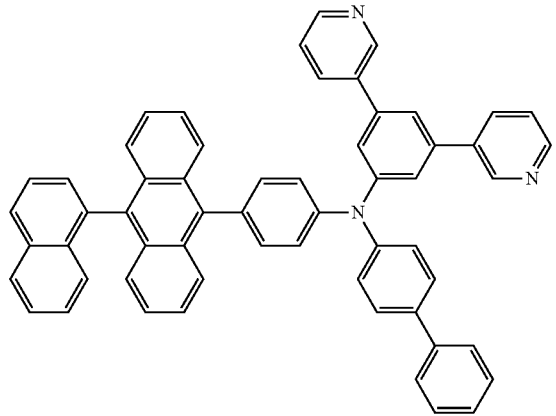
106
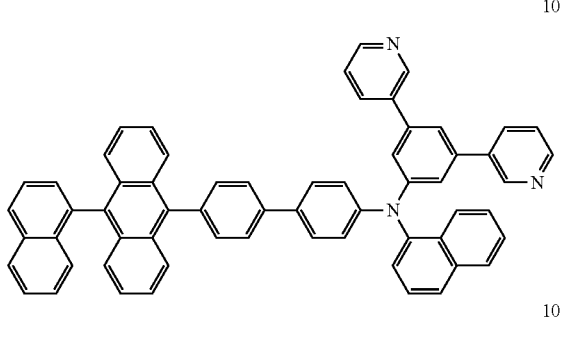
107
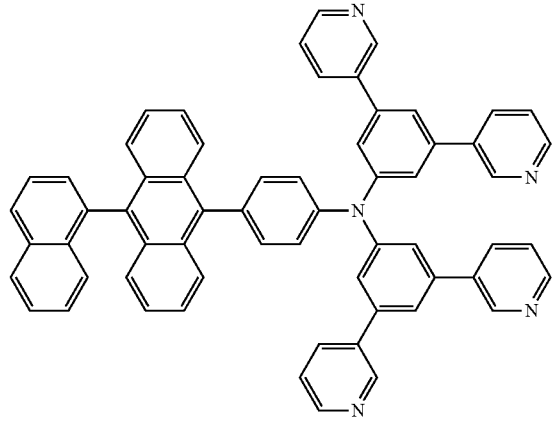
108
109
Since at least one of $Ar_1$ and $Ar_2$ in the amine-based compound of Formula 1 above is a $C_6$-$C_{60}$ aryl group substituted with at least one electron withdrawing group selected from the group consisting of —F; —CN; —NO$_2$; a C$_1$-C$_{60}$ alkyl group substituted with at least one —F; a C$_2$-C$_{60}$ heteroaryl group; and a C$_2$-C$_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a C$_1$-C$_{60}$ alkyl group, a C$_1$-C$_{60}$ alkoxy group, a C$_2$-C$_{60}$ alkenyl group, a C$_2$-C$_{60}$ alkynyl group, a C$_6$-C$_{60}$ aryl group, and a C$_2$-C$_{60}$ heteroaryl group, a moiety represented by "A" in Formula 1' below may be able to withdraw electrons.

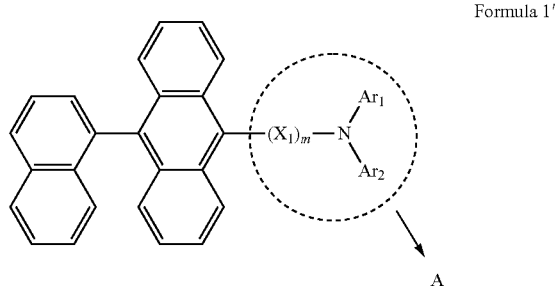

Formula 1'

The amine-based compound of Formula 1 has a naphthyl-anthracene core abundant in electrons and the moiety A with electron withdrawing ability, and thus may have good electron transport characteristics. When the electron withdrawing group is a substituted or unsubstituted C$_2$-C$_{60}$ heteroaryl group, the substituted or unsubstituted C$_2$-C$_{60}$ heteroaryl group is linked to N of Formula 1, not directly, via a C$_6$-C$_{60}$ aryl group. Therefore, an organic light-emitting diode including the amine-based compound of Formula 1 may have improved efficiency characteristics. When the electron withdrawing group is —CN, an organic light-emitting diode including the amine-based compound of Formula 1 may have improved lifetime characteristics.

Not wishing to be bound by a particular theory, in either of i) an amine-based compound including a naphthyl-anthracene core that lacks the above-described electron withdrawing group or ii) an amine-based compound including a naphthyl-anthracene core with pyridine directly linked to N, the highest occupied molecular orbital (HOMO) an electron density may be focused near the anthracene moiety. However, in the amine-based compound of Formula 1 above, the HOMO electron density may be dispersed near the amine moiety, so that the lowest unoccupied molecular orbital (LUMO) electron density may be relatively fixed near anthracene. This may render the amine-based compound of Formula 1 improved dipole characteristics. Thus, the electron transport characteristics of the amine-based compound of Formula 1 may have improved.

Therefore, an organic light-emitting diode including any of the amine-based compounds represented by Formula 1 above may have a low driving voltage, a high luminance, a high efficiency, and a long lifetime.

The amine-based compound of Formula 1 may be synthesized by a known organic synthesis method. A synthesis method of the amine-based compound of Formula 1 may be understood by those of ordinary skill in the art from the examples that will be described below.

At least one of the amine-based compounds of Formula 1 may be used between a pair of electrodes of an organic light-emitting diode. For example, at least one of the amine-based compounds may be in an EML and/or between a cathode and the EML (for example, an ETL, an EIL, or a functional layer having both electron transport and electron injection capabilities).

According to another aspect of the present embodiments, an organic light-emitting diode includes a first electrode, a second electrode disposed opposite to the first electrode, and an organic layer disposed between the first electrode and the second electrode, wherein the first layer includes at least one of the amine-based compounds of Formula 1 described above.

As used herein, "(for example, the organic layer) including at least one amine-based compound" means "(the organic layer) including one of the amine-based compounds of Formula 1 above, or at least two different amine-based compounds of Formula 1 above".

In some embodiments, the organic layer may include only Compound 1 as the amine-based compound. Compound 1 may be in the EML or ETL layer of the organic light-emitting diode. In some embodiments, the organic layer may include Compounds 1 and 3 as the amine-based compound. Compounds 1 and 3 may be in the same layer (for example, in the ETL) or may be in different layers (for example, in the EML and ETL, respectively).

The organic layer may include at least one layer selected from among a hole injection layer (HIL), a hole transport layer (HTL), a functional layer having both hole injection and hole transport capabilities (hereinafter, "H-functional layer"), a buffer layer, an electron blocking layer (EBL), an emission layer (EML), a hole blocking layer (HBL), an electron transport layer (ETL), an electron injection layer (EIL), and a functional layer having both electron injection and electron transport capabilities (hereinafter, "E-functional layer").

The term "organic layer" as used herein refers to a single layer and/or a plurality of layers disposed between the first and second electrodes of the organic light-emitting diode.

The organic layer may include an EML, wherein at least one of the amine-based compounds may be included in the EML.

The amine-based compound in the EML may serve as a host. When the amine-based compound in the EML serves as a host, the EML may further include a fluorescent dopant. The fluorescent dopant may be a blue fluorescent dopant. In some embodiments, the amine-based compound in the EML may serve as a dopant. When the amine-based compound in the EML serves as a dopant, the amine-based compound may be a blue fluorescent dopant.

In some embodiments, the organic layer may include an ETL, wherein at least one of the amine-based compounds may be included in the ETL.

FIG. 1 is a schematic sectional view of an organic light-emitting diode 10 according to an embodiment. Hereinafter, a structure of an organic light-emitting diode according to an embodiment and a method of manufacturing the same will now be described with reference to FIG. 1.

The substrate 11 may be any substrate that is used in existing organic light-emitting diodes. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 constitutes an anode, a material having a high work function may be used as the first electrode-forming material to facilitate hole injection. The first electrode 13 may be a reflective electrode or a transmission electrode. Suitable first electrode-forming materials include transparent and conductive materials such as ITO, IZO, SnO$_2$, and ZnO. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a HIL, a HTL, a buffer layer, an EML, an ETL, and an EIL.

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL 130 may comprise any material that is commonly used to form a HIL. Examples of the material that can be used to form the HIL are, but are not limited to, N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and polyaniline)/poly(4-styrenesulfonate (PANI/PSS).

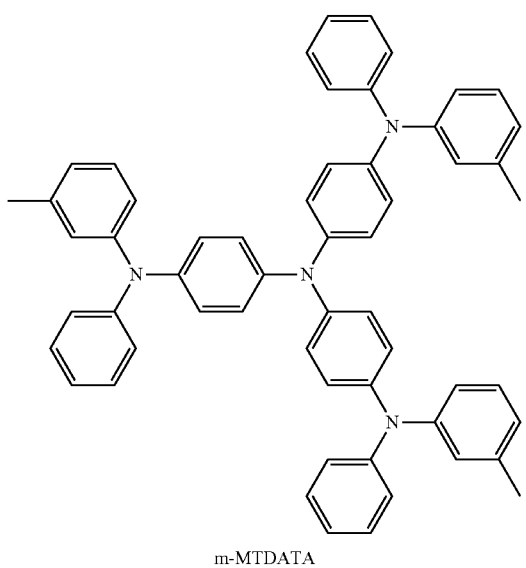

m-MTDATA

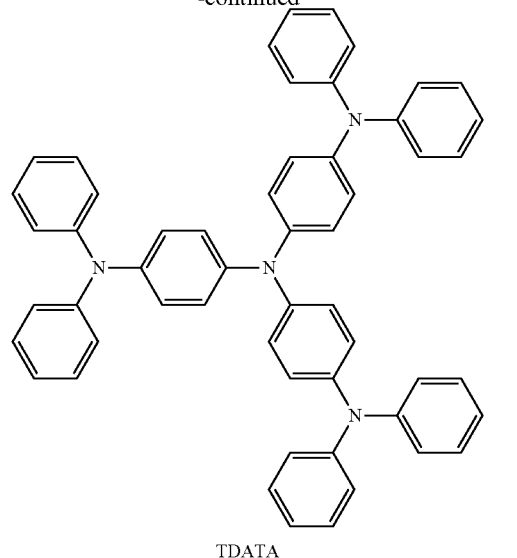

TDATA

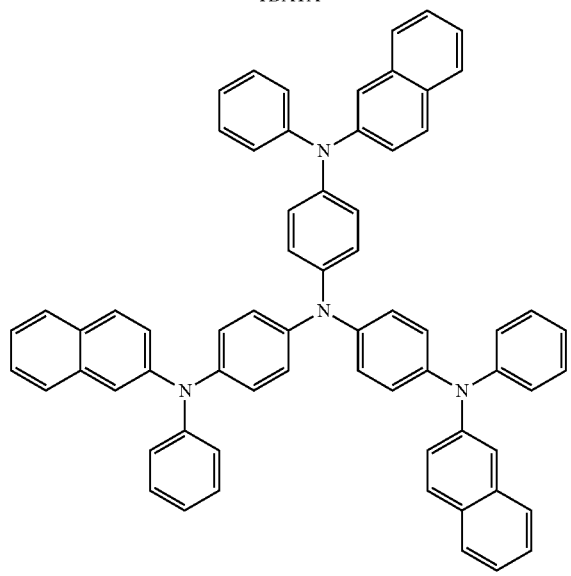

2-TNATA

The thickness of the HIL may be about 100 Å to about 10000 Å, and in some embodiments, may be about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable known hole transport materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

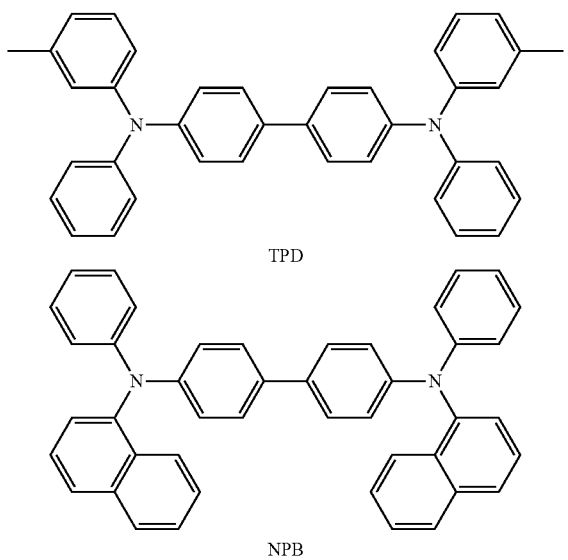

TPD

NPB

The thickness of the HTL may be about 50 Å to about 2000 Å, and in some embodiments, may be about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

Formula 300

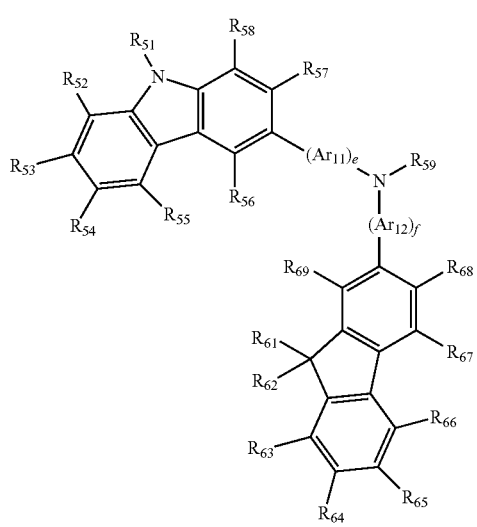

Formula 350

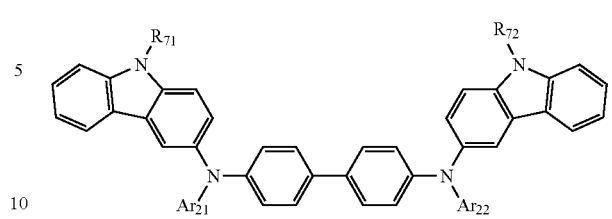

In Formulae 300 and 350, $Ar_{11}$ and $Ar_{12}$ may be each independently a substituted or unsubstituted $C_6$-$C_{60}$ arylene group and $Ar_{21}$ and $Ar_{22}$ may be each independently a substituted or unsubstituted $C_6$-$C_{60}$ aryl group. $Ar_{11}$ and $Ar_{12}$ may be each independently one of a phenylene group, a naphthylene group, a phenanthrenylene group, and a pyrenylene group; and a phenylene group, a naphthylene group, a phenanthrenylene group, a fluorenylene group, and a pyrenylene group that are substituted with at least one of a phenyl group, a naphthyl group, and an anthryl group. $Ar_{21}$ and $Ar_{22}$ may be each independently one of a phenyl group, a naphthyl group, a phenanthrenyl group, and a pyrenyl group; and a phenyl group, a naphthyl group, a phenanthrenyl group, a fluorenyl group, and a pyrenyl group that are substituted with at least one of a phenyl group, a naphthyl group, and an anthryl group.

In Formula 300, e and f may be each independently an integer from 0 to 5, for example, may be 0, 1, or 2. In a non-limiting embodiment, e may be 1, and f may be 0.

In Formulae 300 and 350, $R_{51}$ to $R_{58}$, $R_{61}$ to $R_{69}$, $R_{71}$, and $R_{72}$ may be each independently a hydrogen atom, a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60a}$ aryl group, a substituted or unsubstituted $C_6$-$C_{60}$ aryloxy group, or a substituted or unsubstituted $C_6$-$C_{60}$ arylthiol group. In some non-limiting embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; —$NO_2$; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, and a phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group.

In Formula 300, $R_{59}$ may be one of a phenyl group; a naphthyl group; an anthryl group; a biphenyl group; a pyridyl group; and a phenyl group, a naphthyl group, an anthryl group, a biphenyl group, and a pyridyl group that are substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$alkoxy group.

In an embodiment the compound of Formula 300 may be a compound represented by Formula 300A below:

Formula 300A

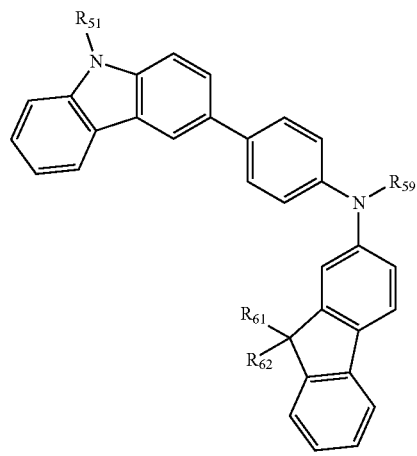

$R_{51}$, $R_{60}$, $R_{61}$ and $R_{59}$ in Formula 300A are as defined above, and thus a detailed description thereof will not be provided here.

In some non-limiting embodiments, at least one of the HIL, HTL, and H-functional layer may include at least one of compounds represented by Formulae 301 to 320 below:

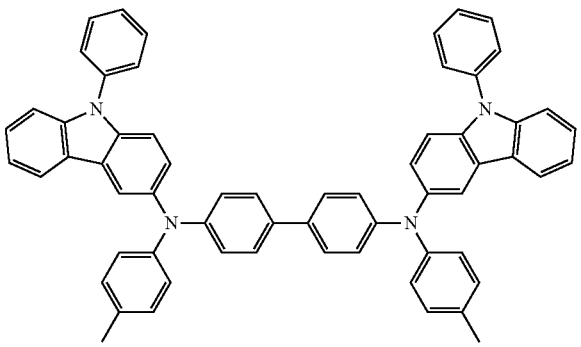

302

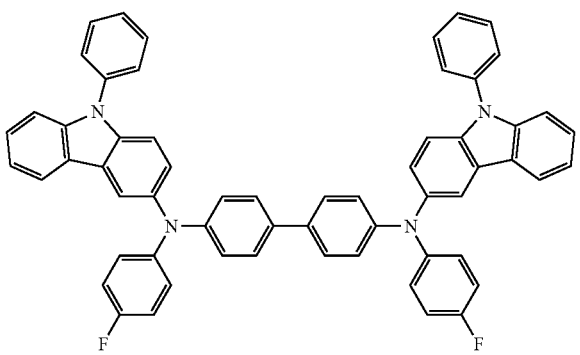

303

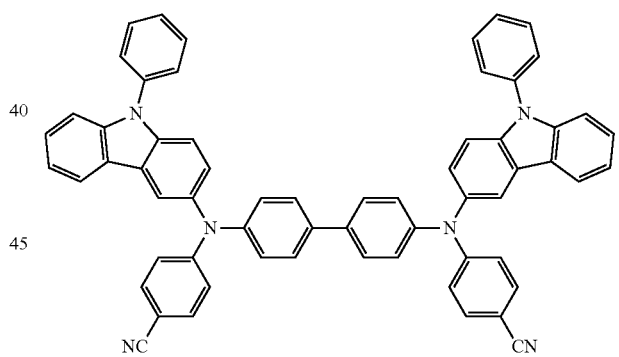

304

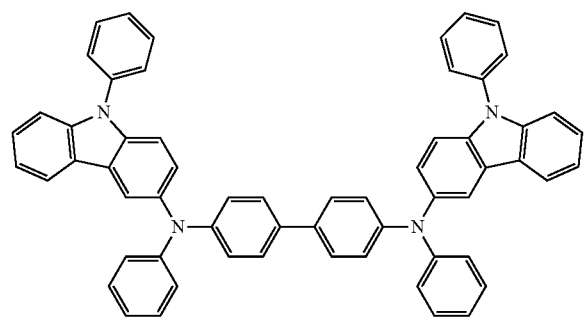

301

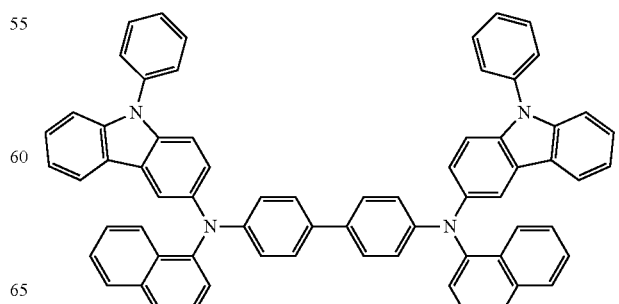

305

306
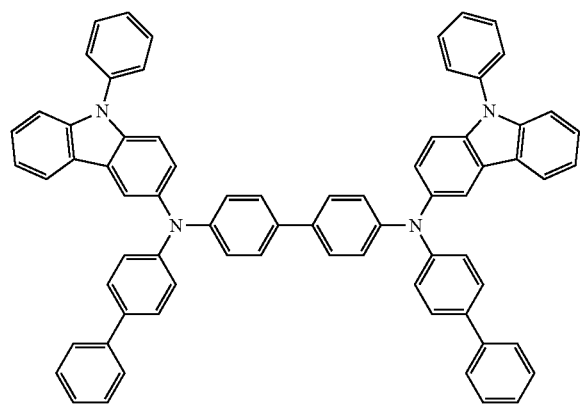
307
308
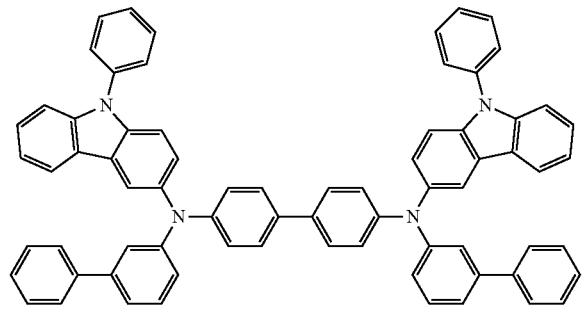
309
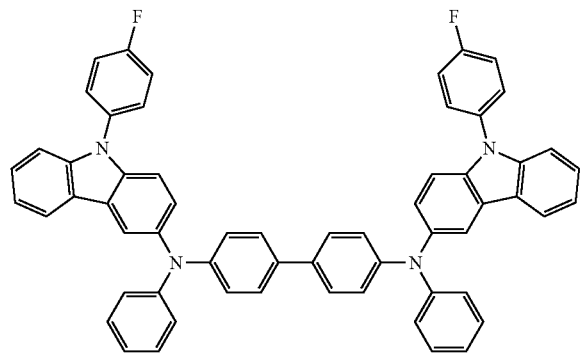
310
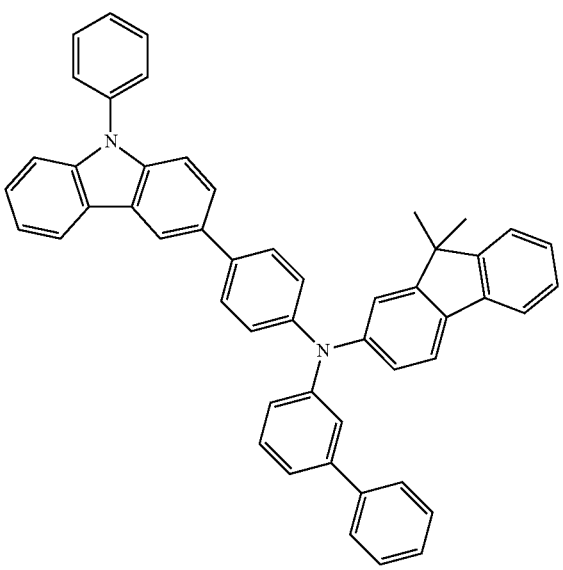
311
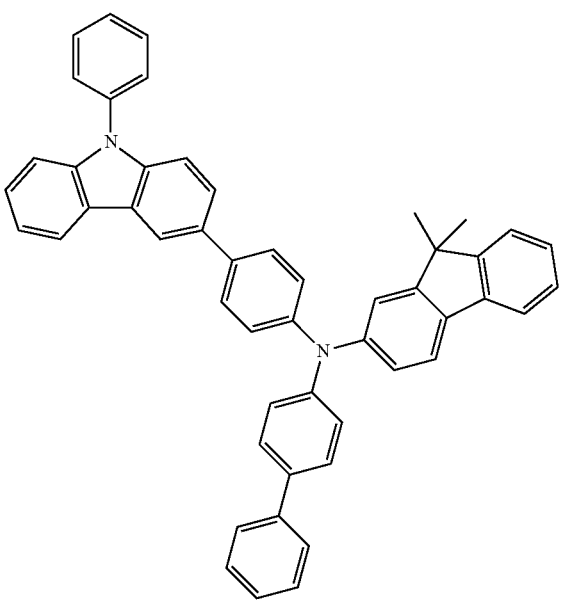

312
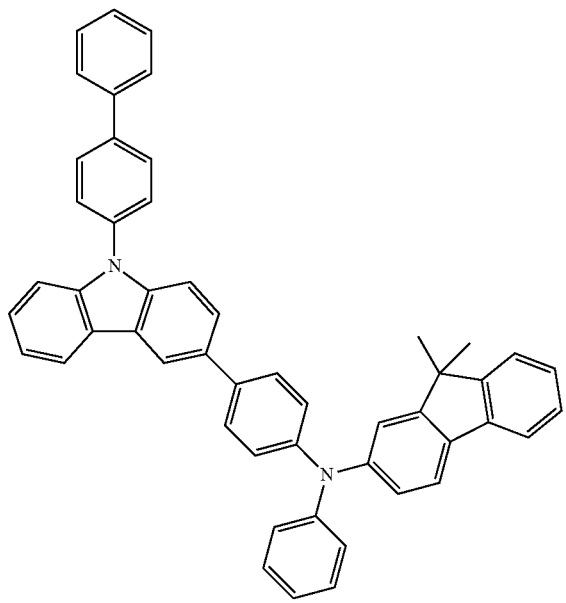
313
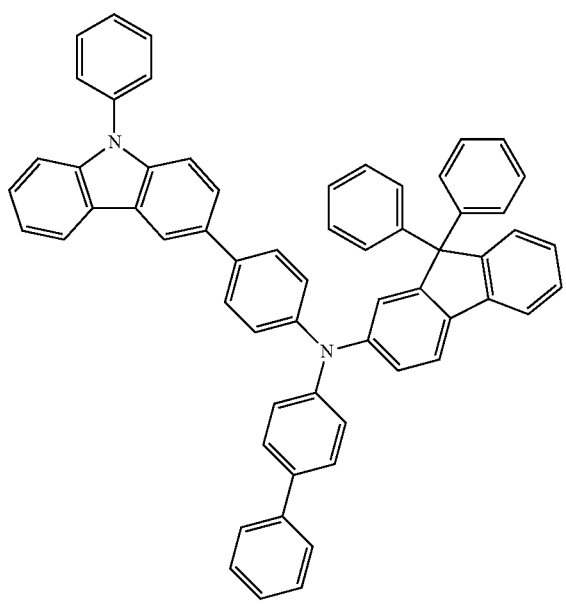
314
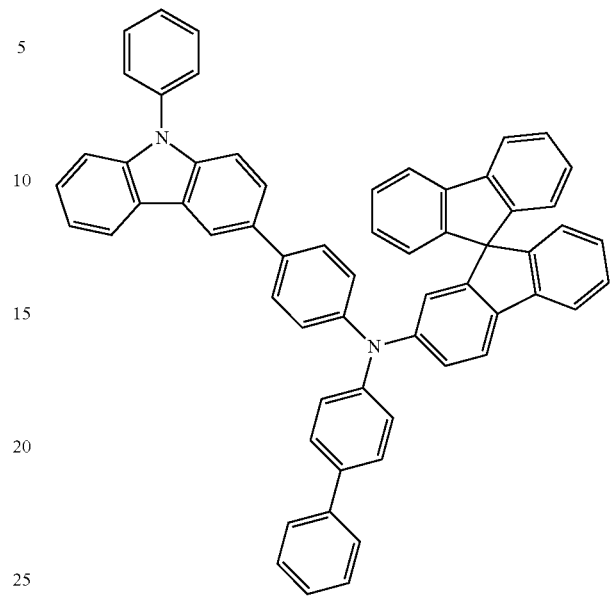
315
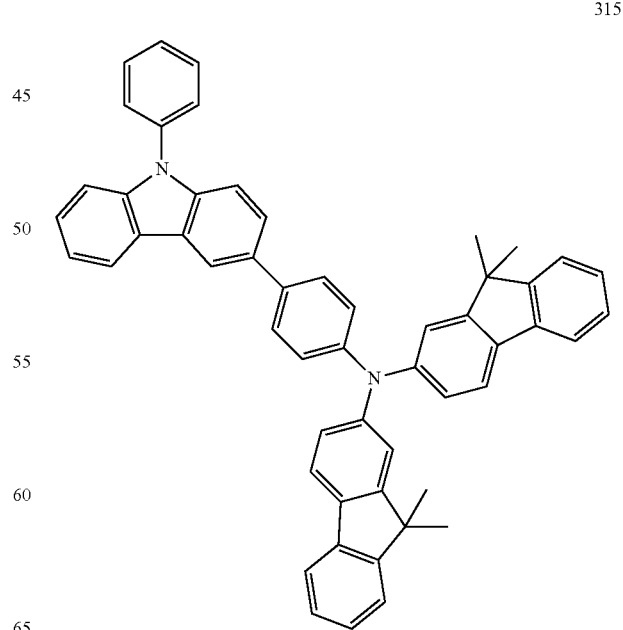

316

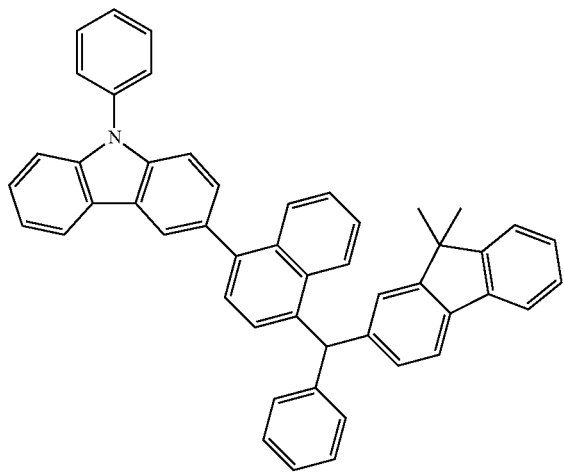

317

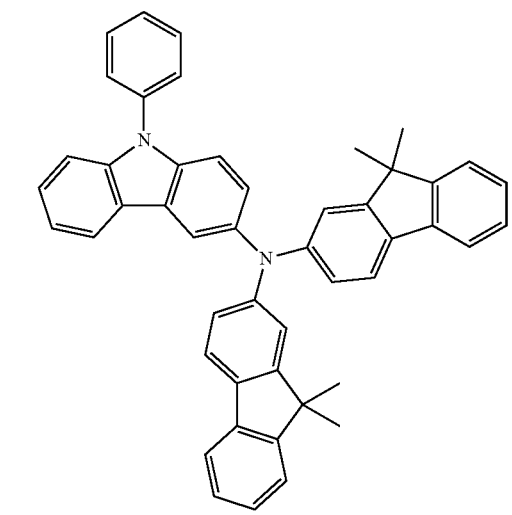

318

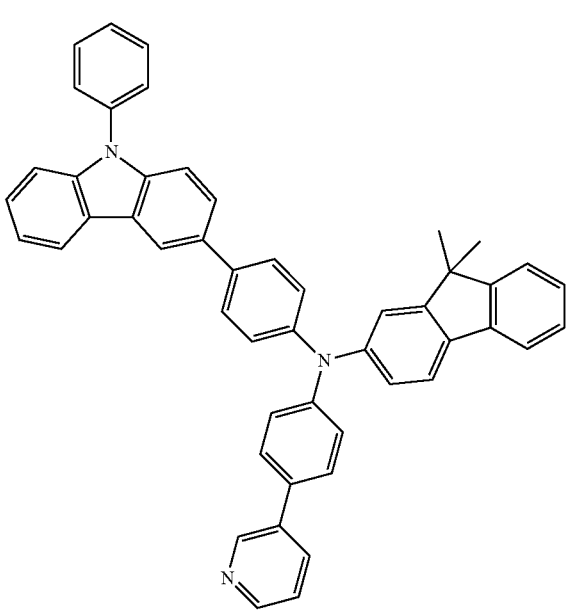

319

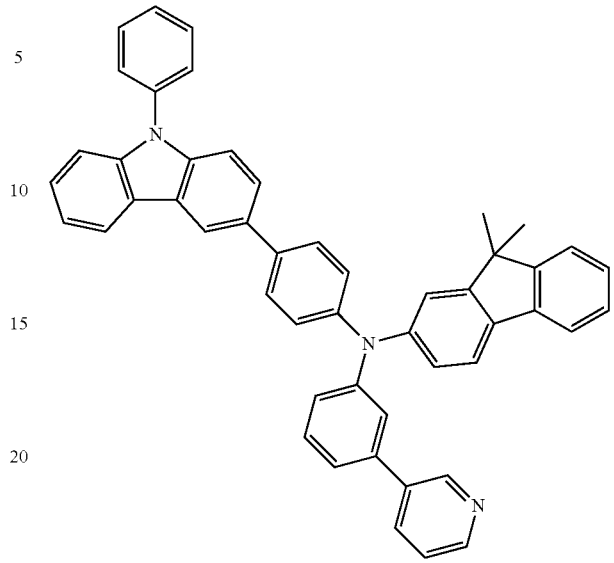

320

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

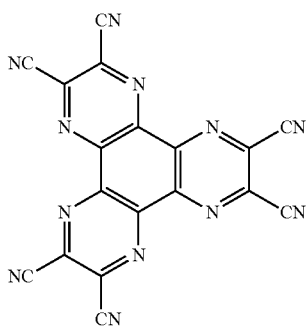

Compound 200

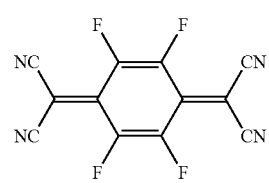

<F4-TCNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In some other embodiments, the buffer layer may include the same material as one of the materials included in the HIL, HTL, and H-functional layer that underly the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include at least one of the amine-based compounds of Formula 1.

The amine-based compound in the EML may serve as a dopant, for example, as a blue fluorescent dopant. The EML may further include a host, in addition to the amine-based compound.

Example of the host are $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below, but are not limited thereto.

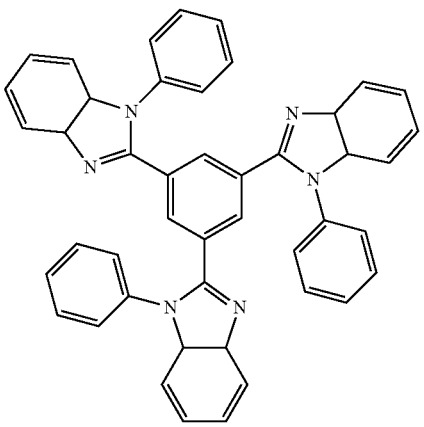

TPBI

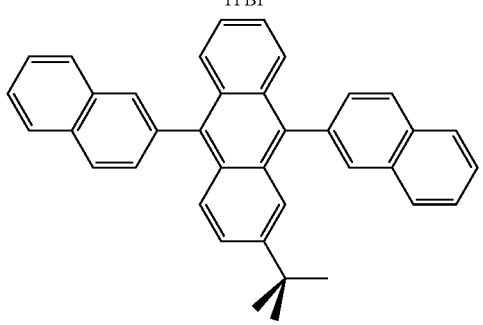

TBADN

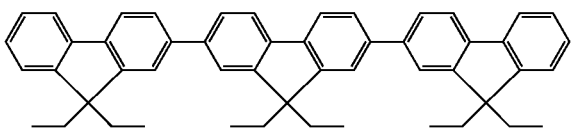

E3

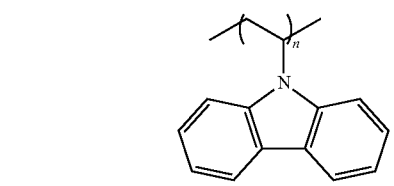

PVK

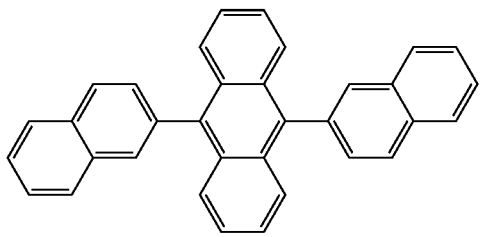

ADN

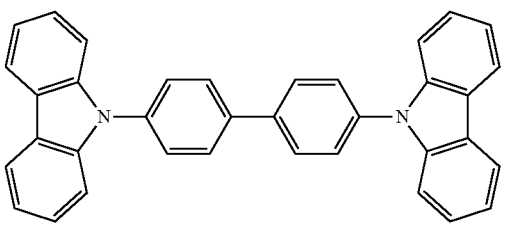

CBP

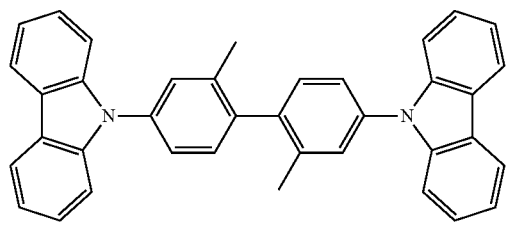
dmCBP
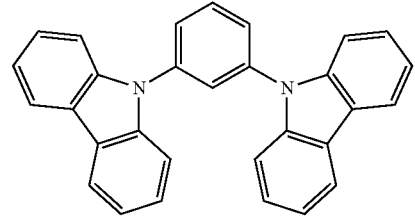
501
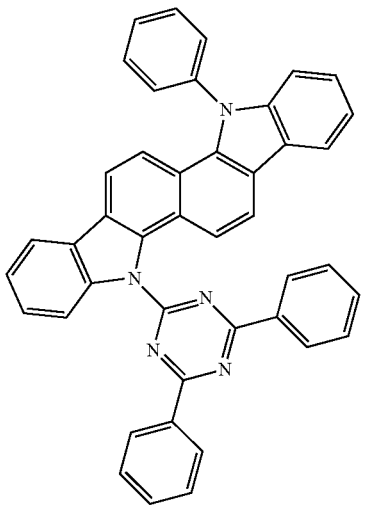
504
502
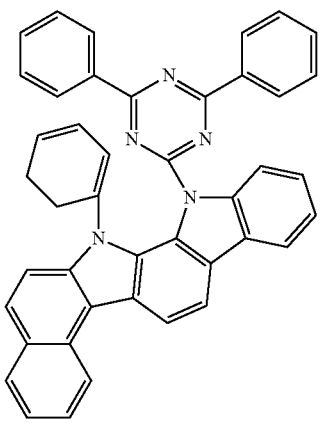
505
503
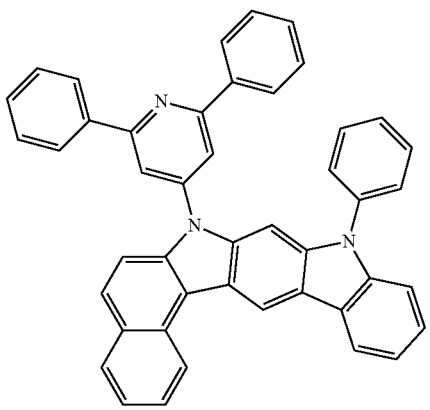
506

507

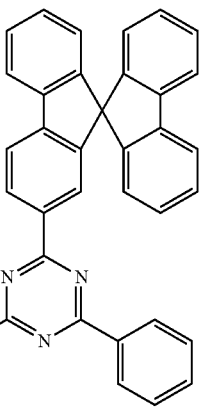

508

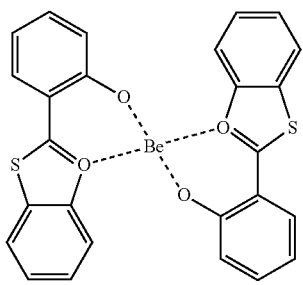

509

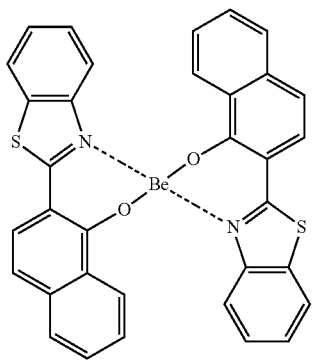

In some embodiments, an anthracene-based compound represented by Formula 400 below may be used as the host.

Formula 400

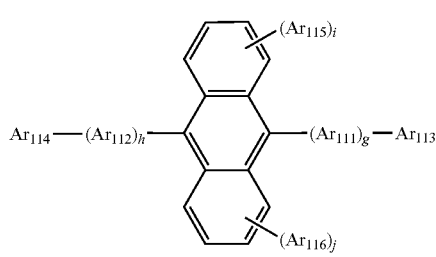

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group or a substituted or unsubstituted $C_6$-$C_{60}$ aryl group; and g, h, I, and j are each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In some non-limiting embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

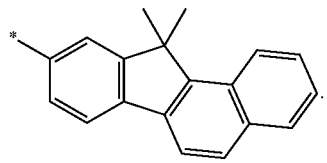 [SMILES: *c1ccc2c(c1)C(C)(C)c1c-2ccc2ccccc12]

For example, the anthracene compound of Formula 400 above may be one of the compounds represented by the following formulae, but is not limited thereto:

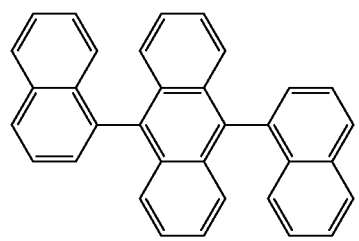

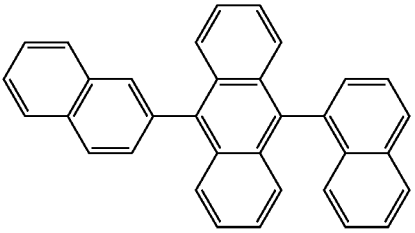

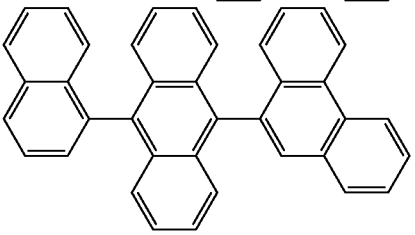

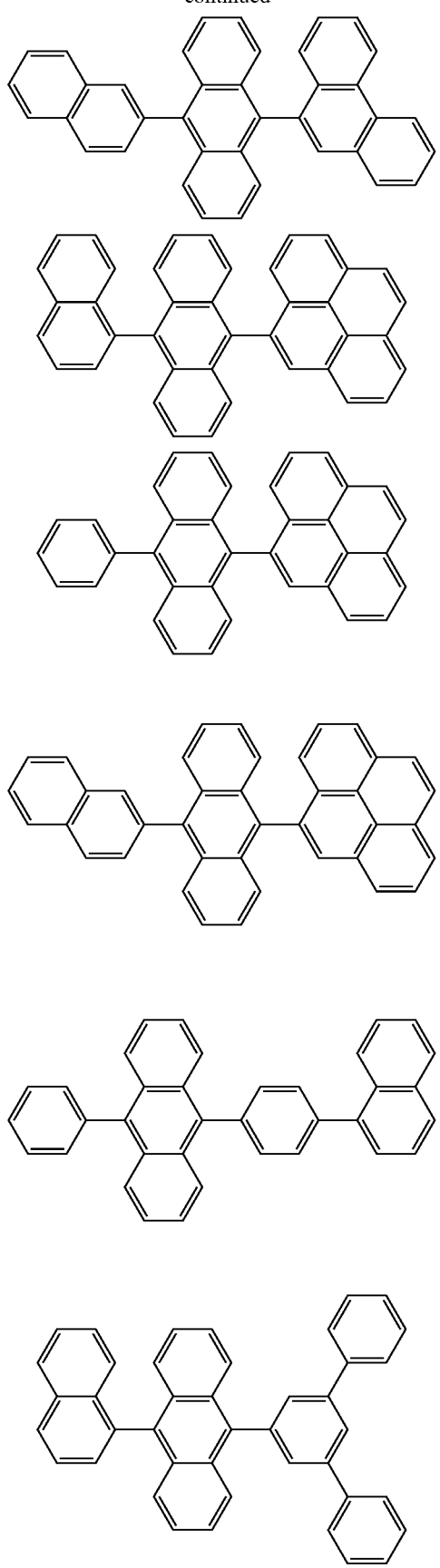
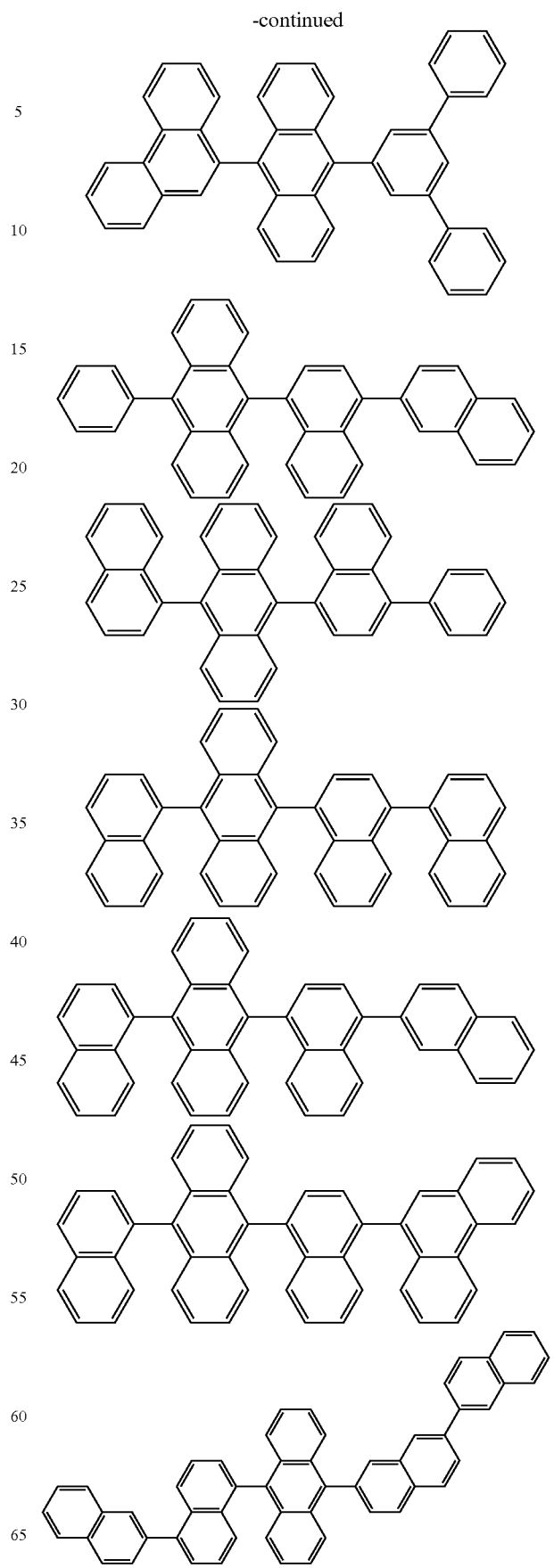

-continued
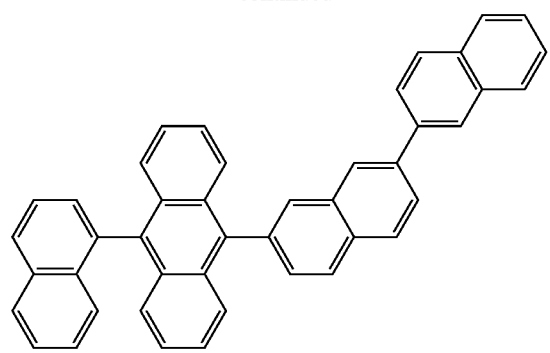
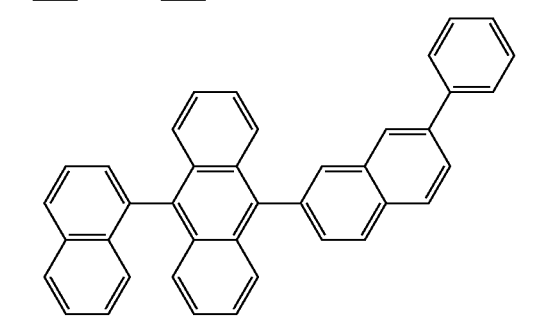
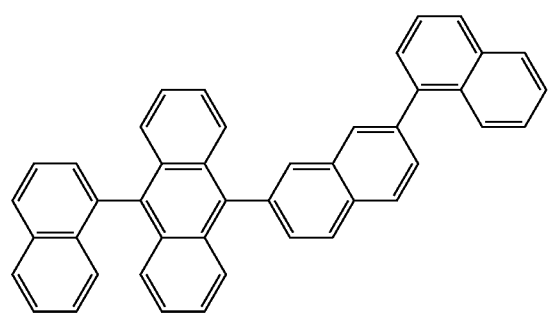
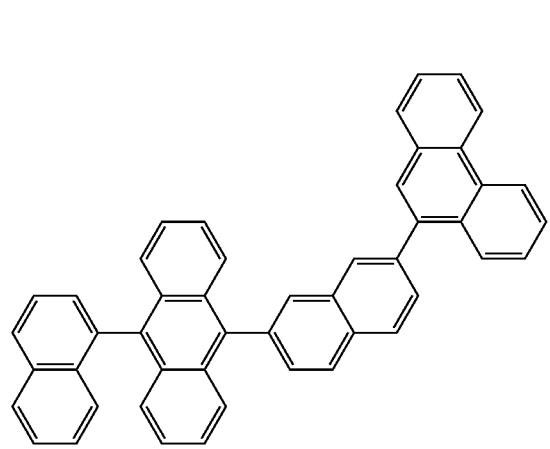
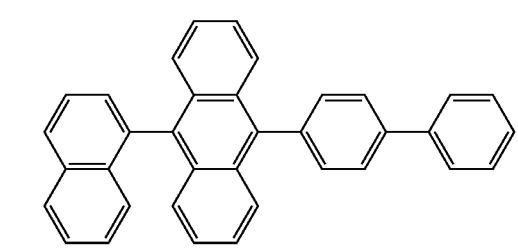
-continued
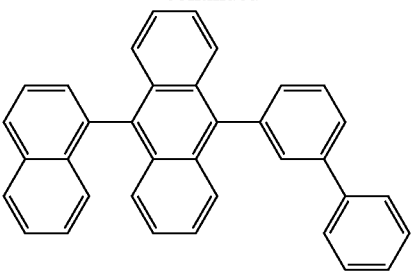
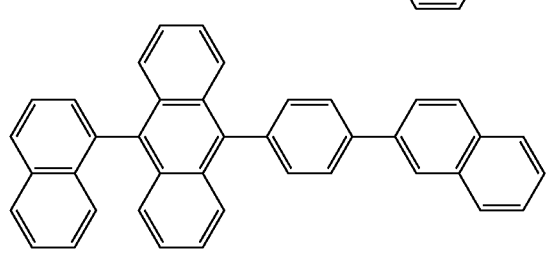
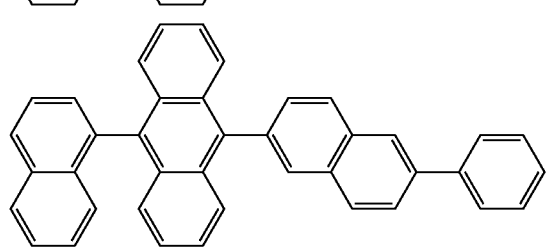
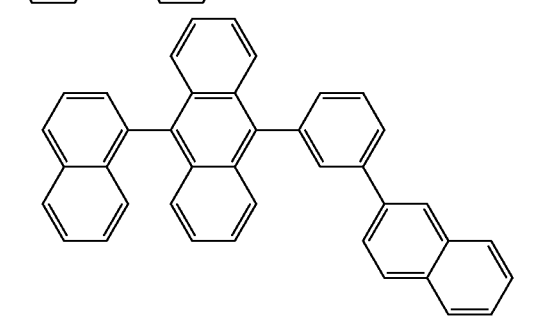
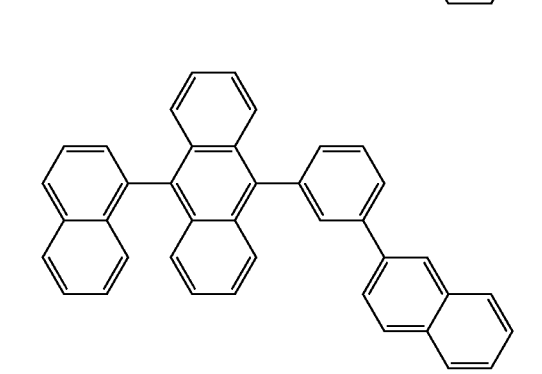
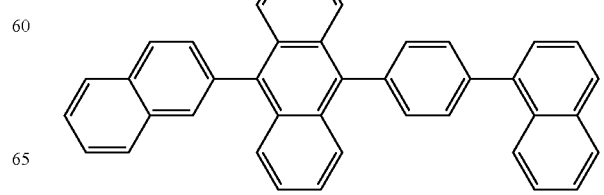

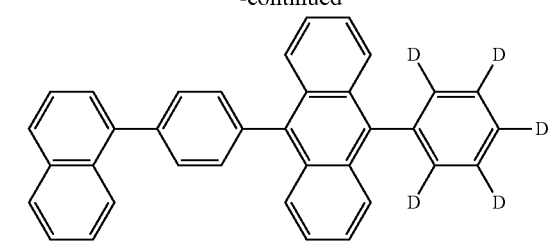
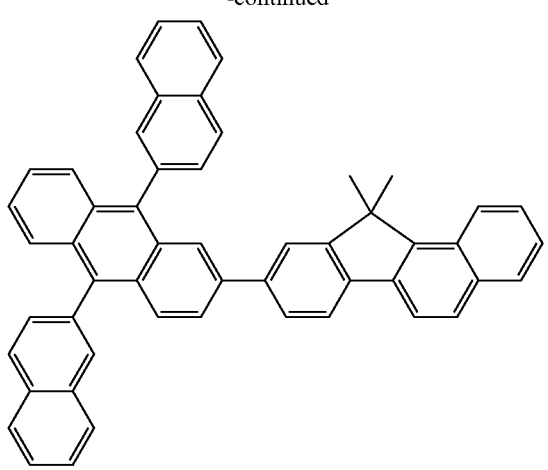
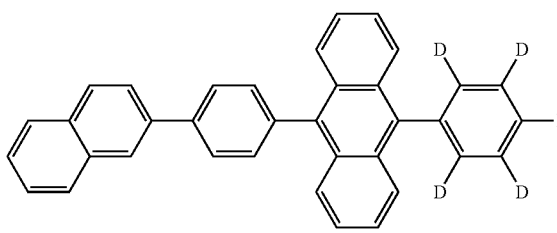
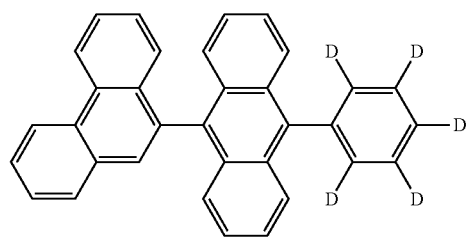
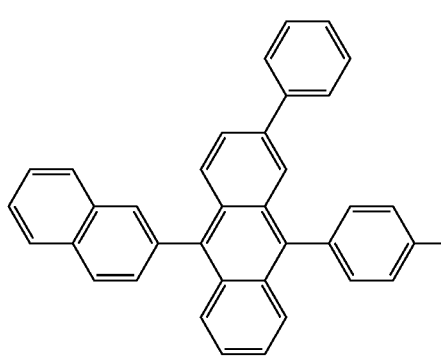
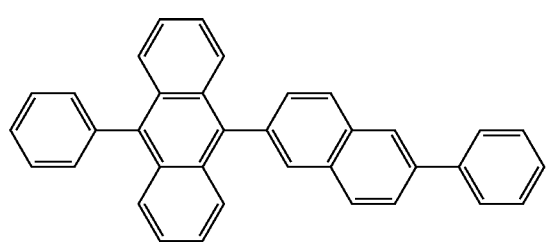
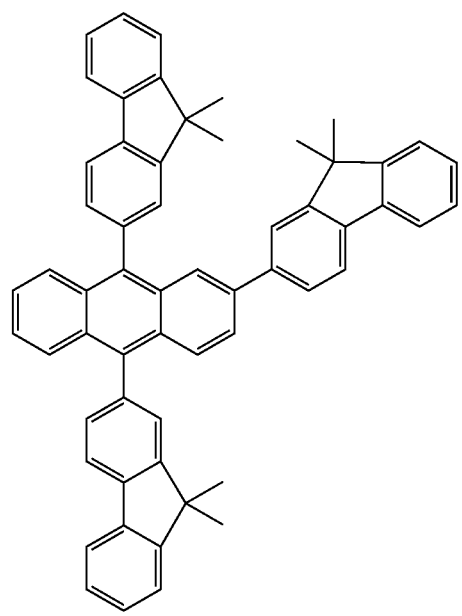

-continued

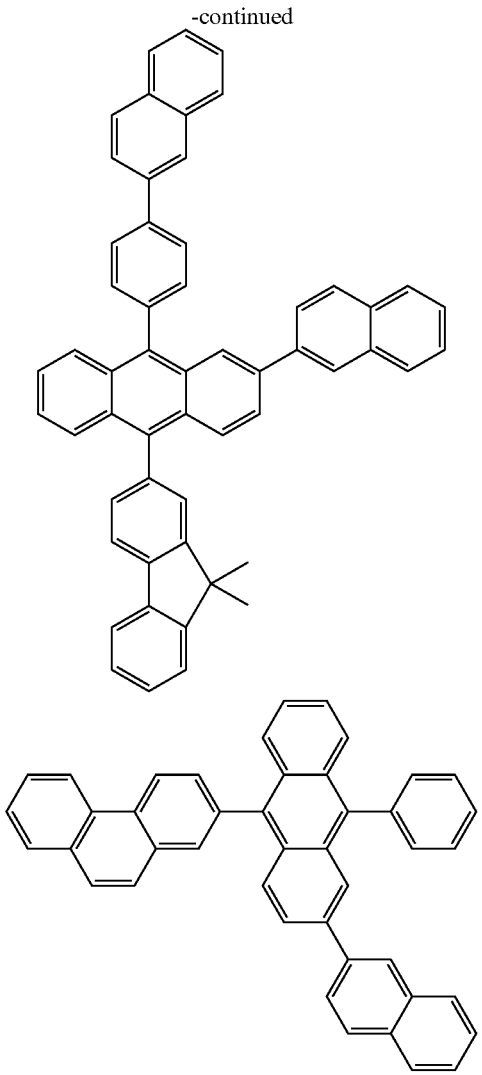

In some embodiments, an anthracene-based compound represented by Formula 401 below may be used as the host.

Formula 401

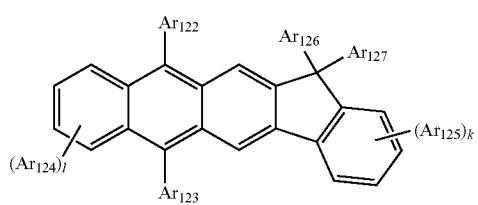

$Ar_{122}$ to $Ar_{125}$ in Formula 401 above may be defined as described above in conjunction with $Ar_{113}$ of Formula 400, and thus a detailed description thereof will not be provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

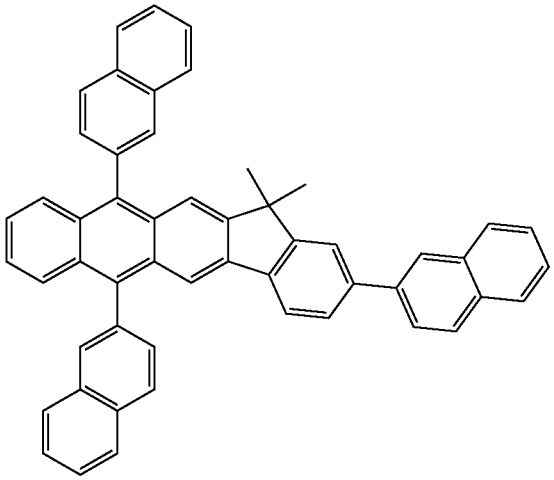

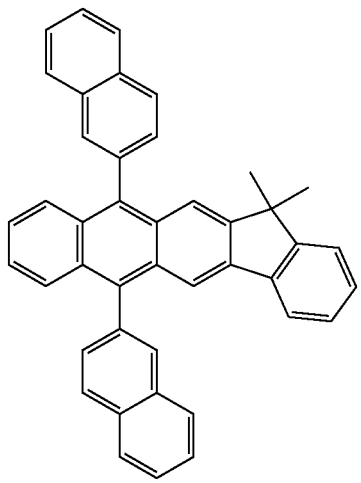

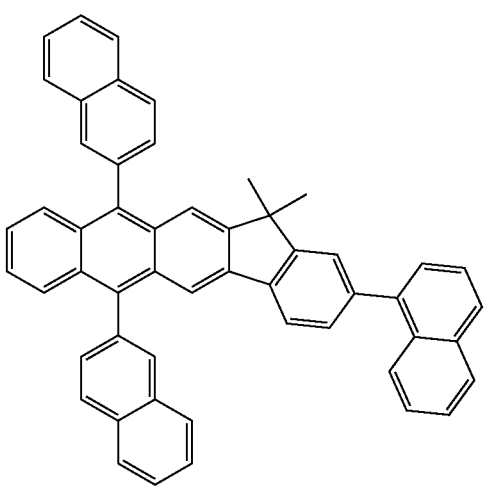

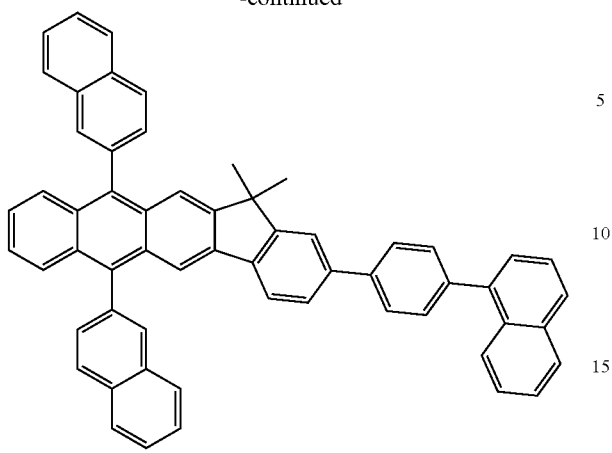
The amine-based compound in the EML may serve as a host. The EML may further include a dopant, for example, a blue dopant, a green dopant, or a red dopant, in addition to the amine-based compound.
Non-limiting examples of the blue dopant are compounds represented by the following formulae.
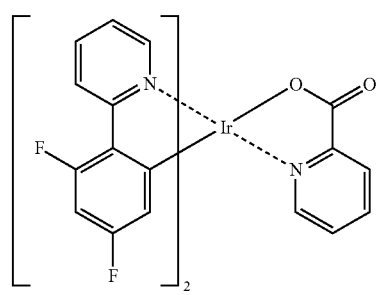
F₂Irpic
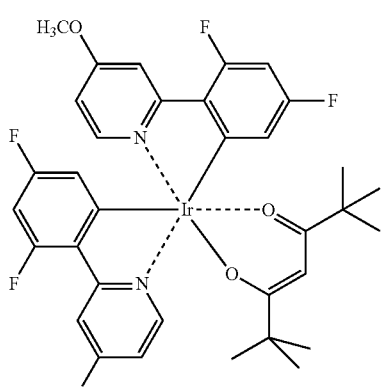
(F2ppy)2Ir(tmd)
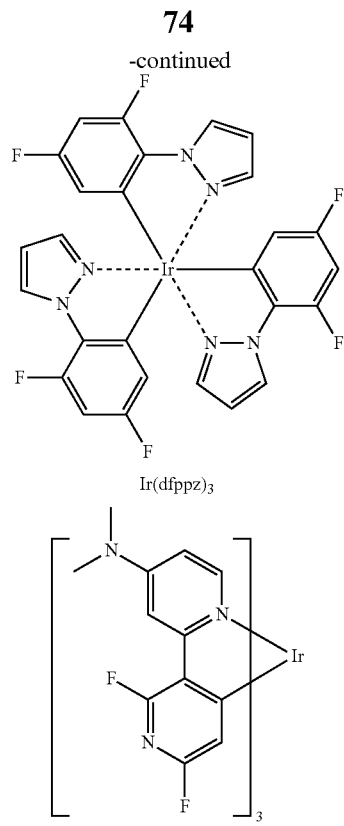
Ir(dfppz)₃
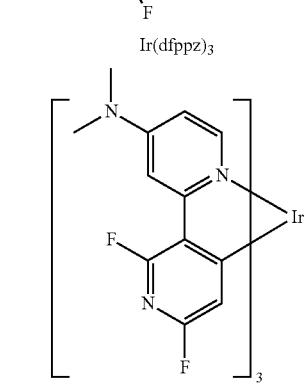
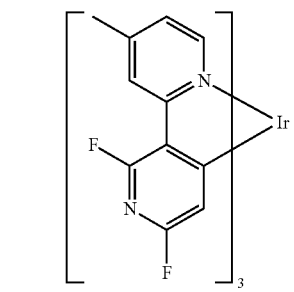
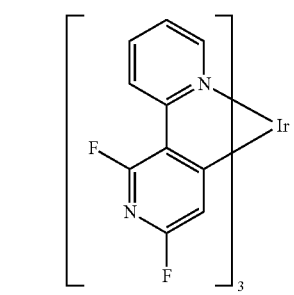
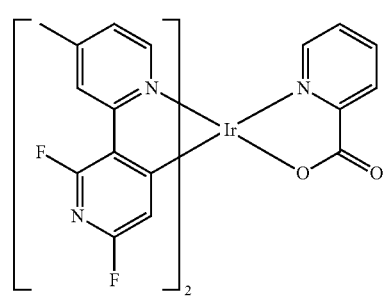

-continued
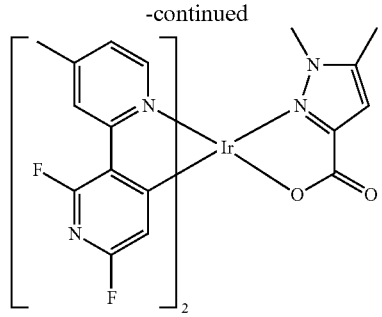
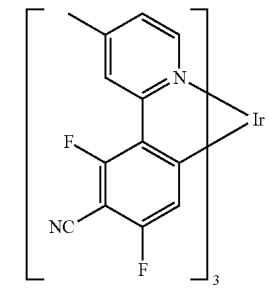
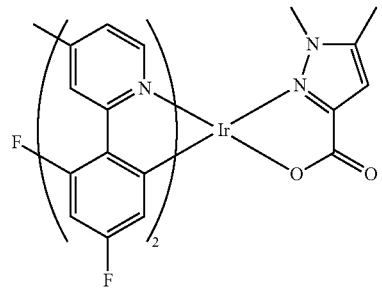
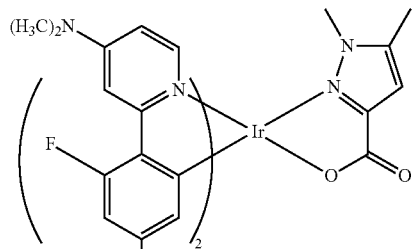
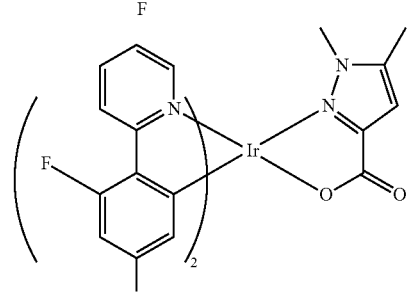
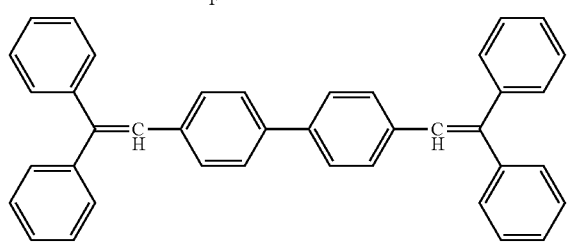
DPVBi
-continued
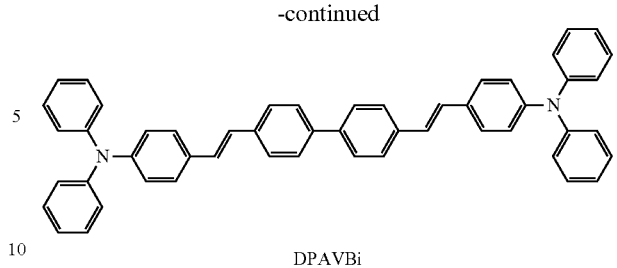
DPAVBi
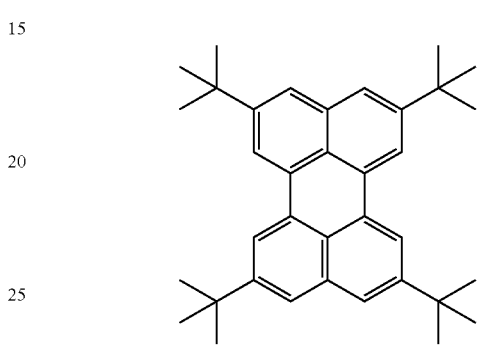
TBPe
Non-limiting examples of the red dopant are compounds represented by the following formulae. In some embodiments, the red dopant may be DCM or DCJTB, which will be described later.
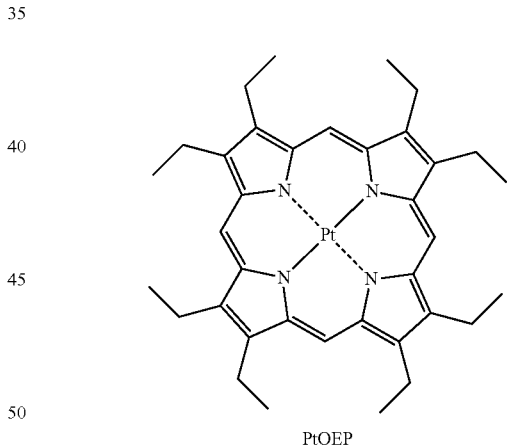
PtOEP
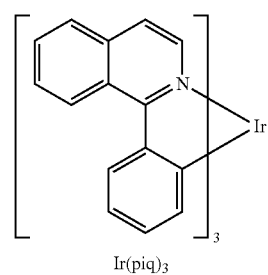
Ir(piq)$_3$ -continued
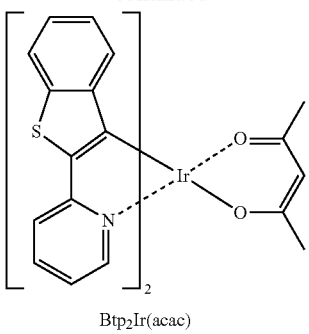
Btp₂Ir(acac)
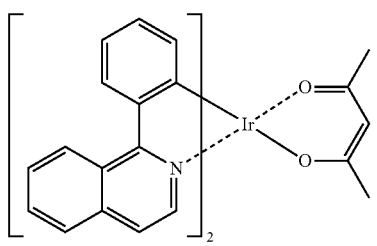
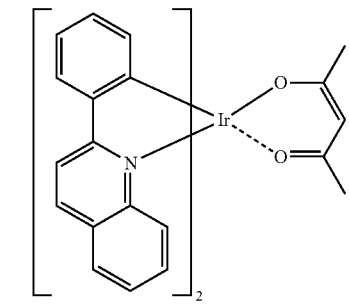
Ir(pq)₂(acac)
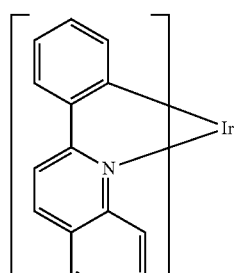
Ir(2-phq)₃
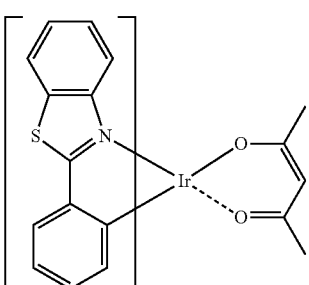
Ir(BT)₂(acac)
-continued
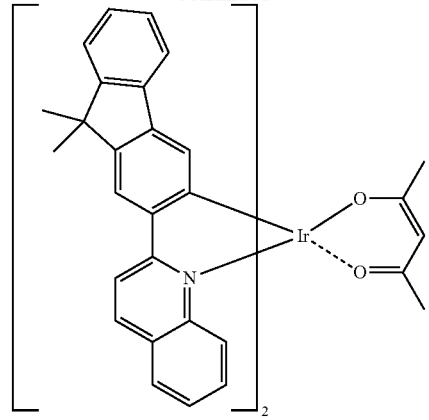
Ir(flq)₂(acac)
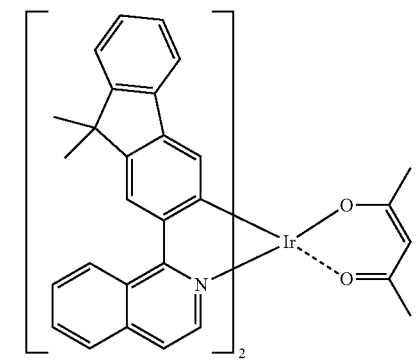
Ir(fliq)₂(acac)
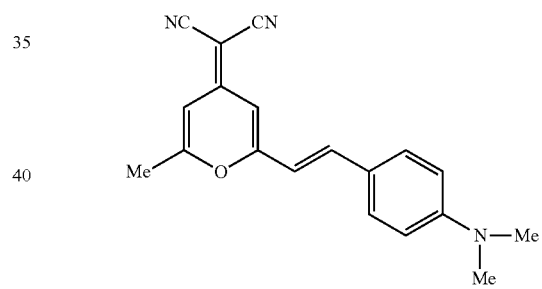
DCM
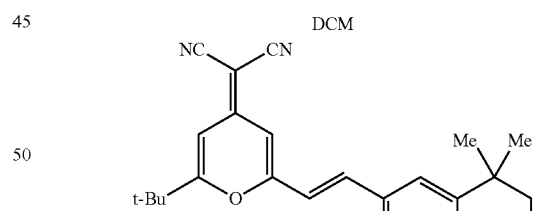
DCJTB
Non-limiting examples of the green dopant are compounds represented by the following formulae. In an embodiment, the green dopant may be C545T represented below.

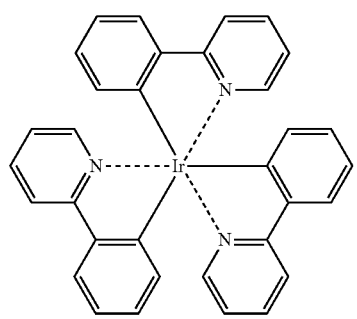
Ir(ppy)₃
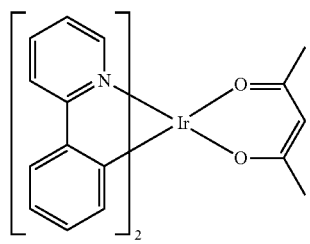
Ir(ppy)₂(acac)
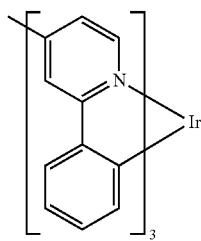
Ir(mpyp)₃
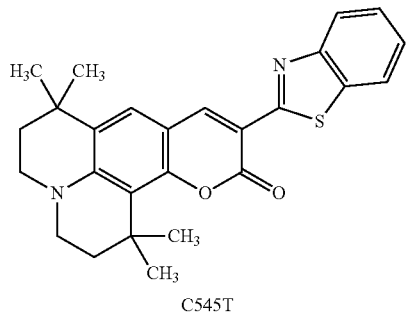
C545T
Non-limiting examples of the dopant that may be used in the EML are Pt complexes represented by the following formulae.
D1
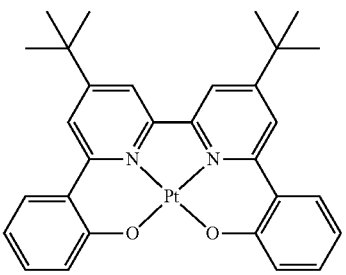
D2
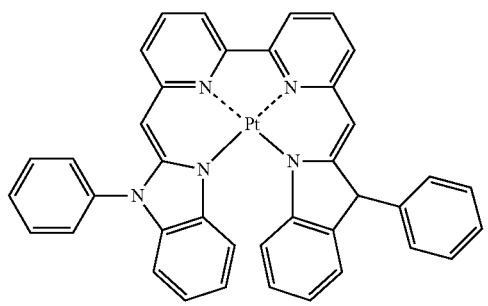
D3
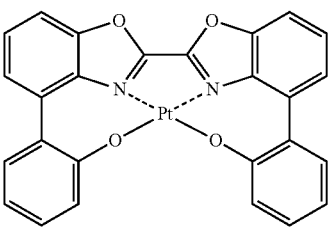
D4
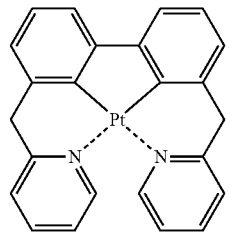
D5
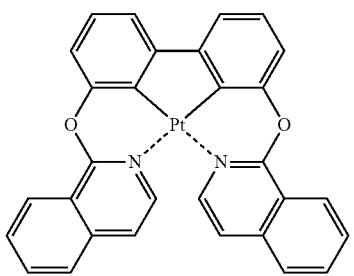
D6
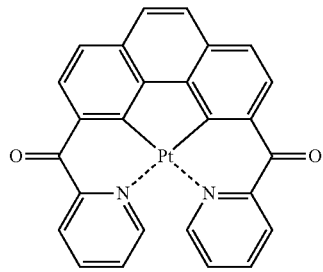
D7

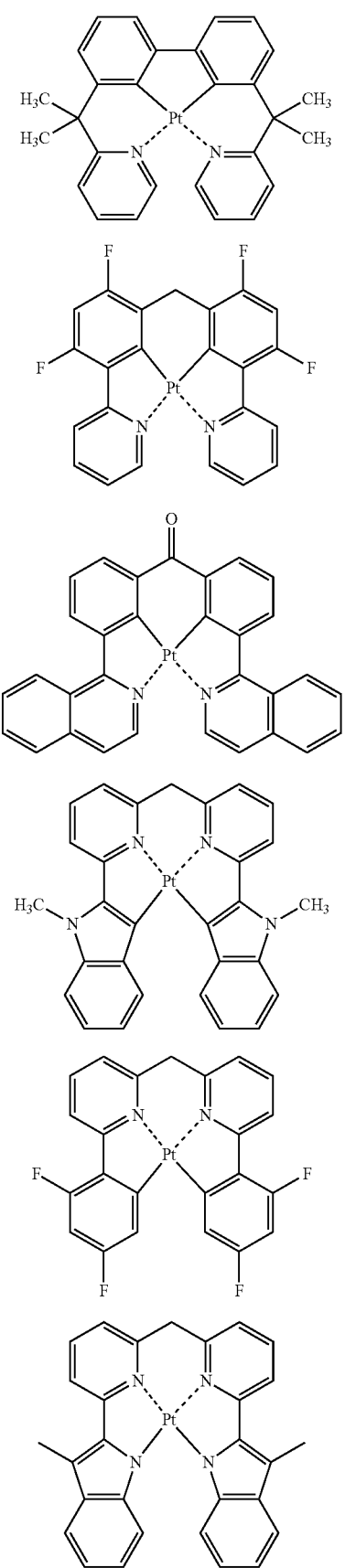
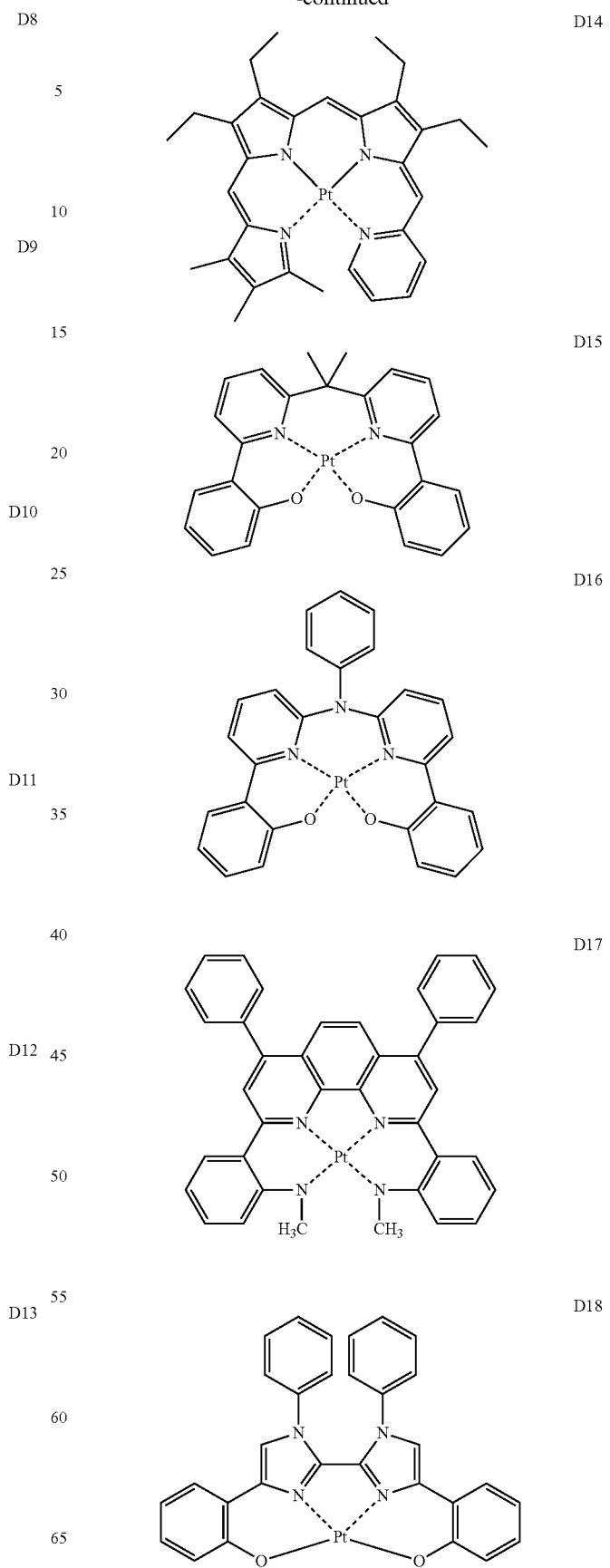

-continued
D19
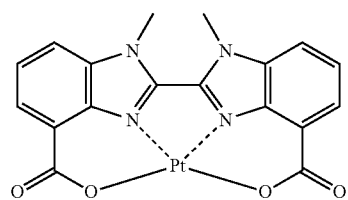
D20
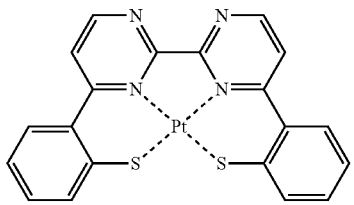
D21
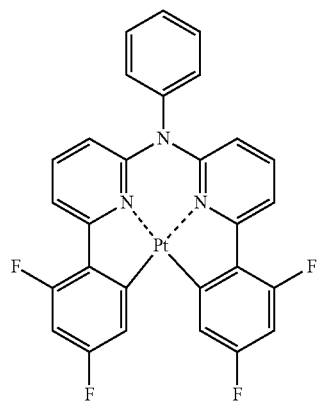
D22
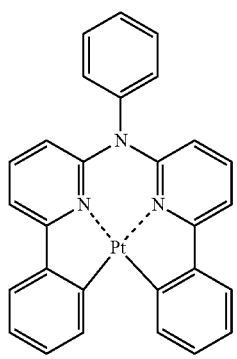
D23
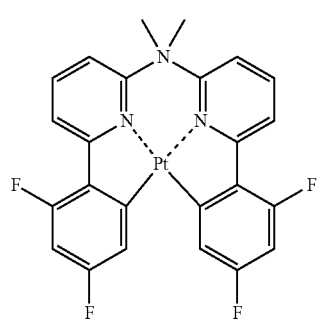
-continued
D24
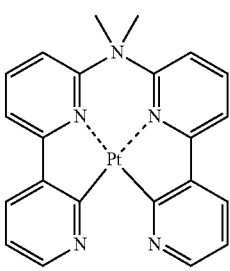
D25
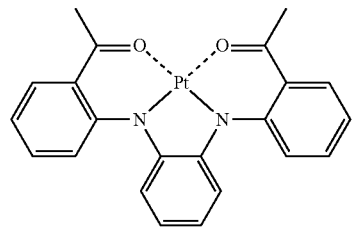
D26
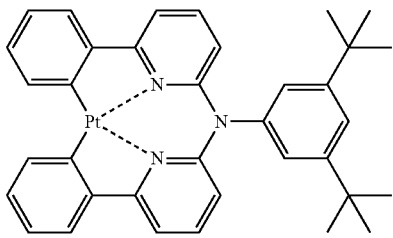
D27
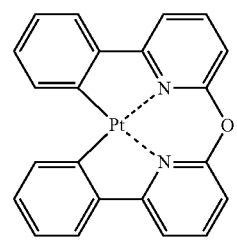
D28
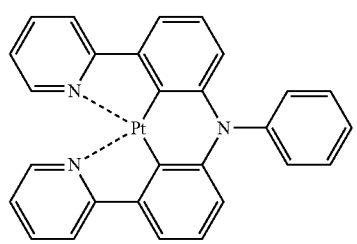
D29
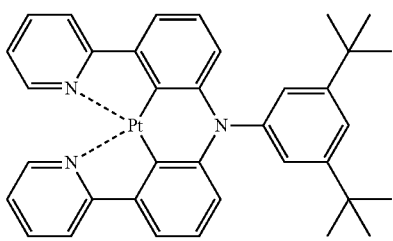

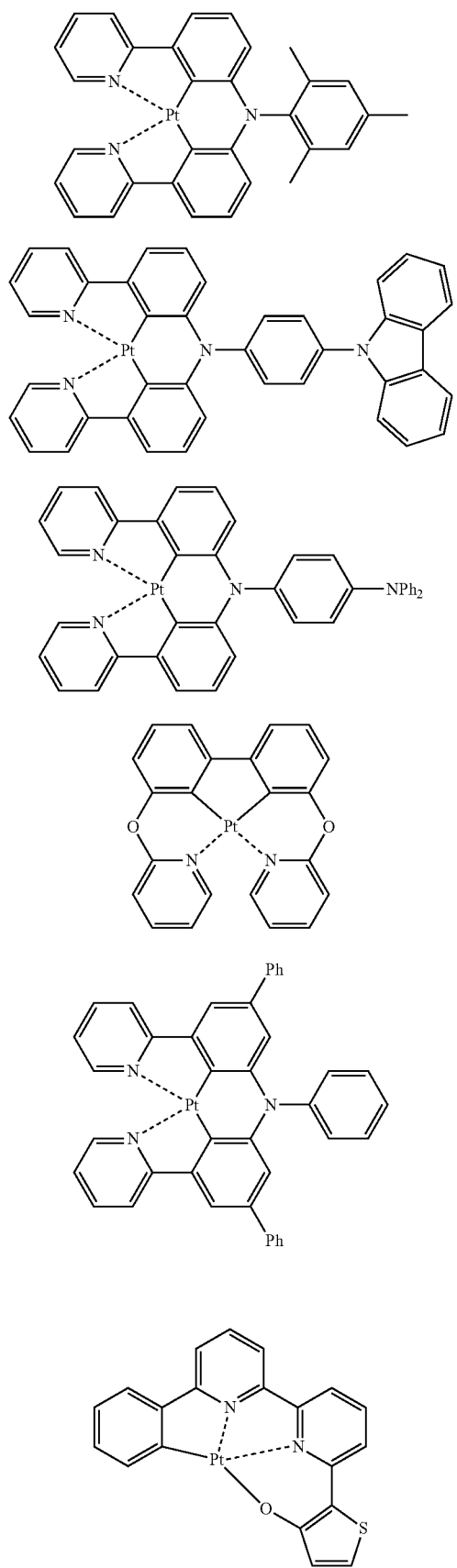
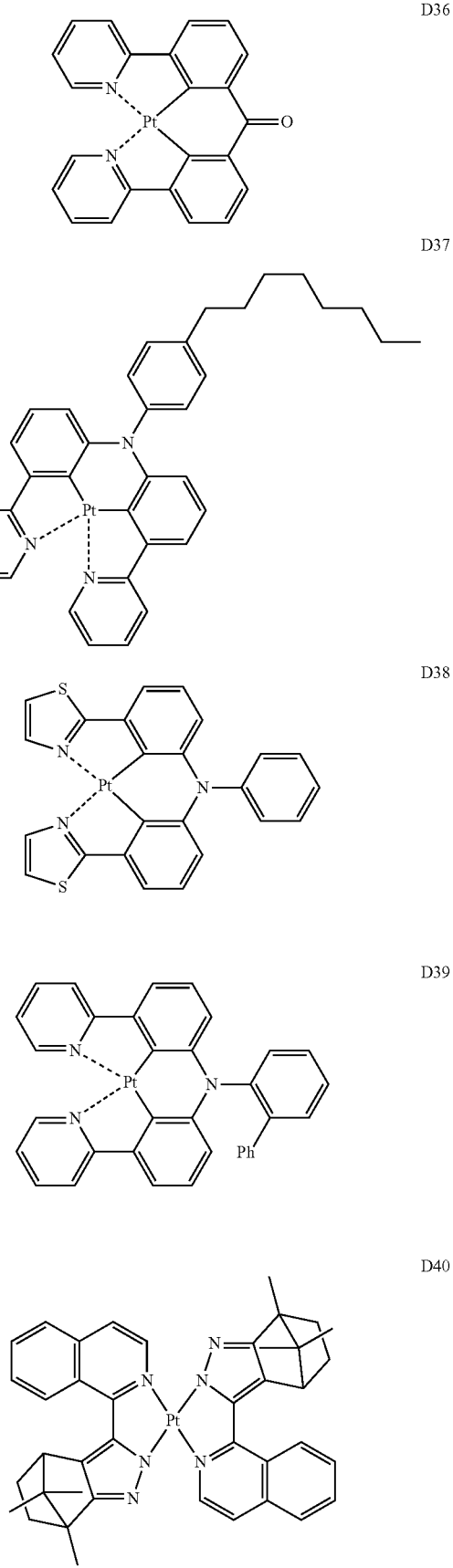

-continued
D41
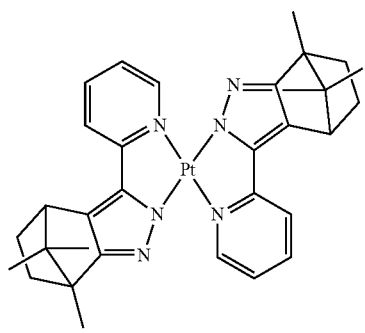
D42
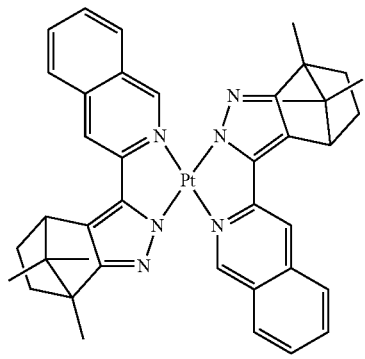
D43
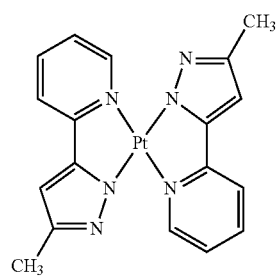
D44
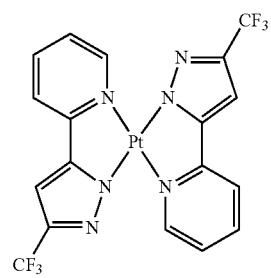
D45
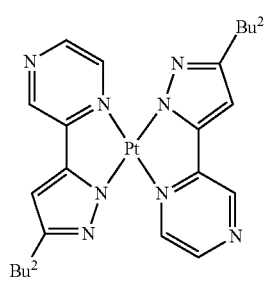
-continued
D46
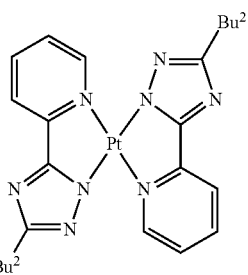
D47
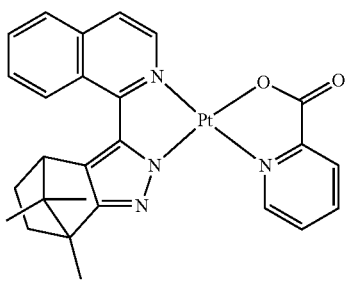
D48
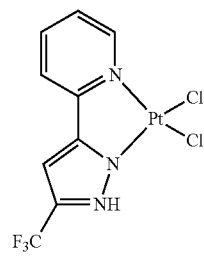
D49
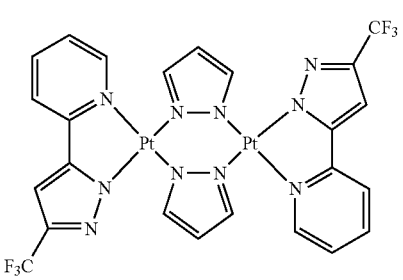
D50
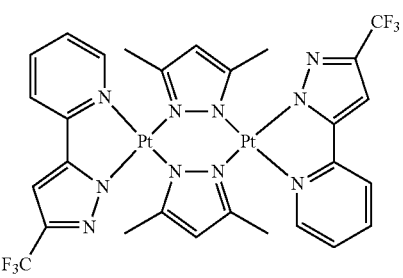
Non-limiting examples of the dopant that may be used in the EML are Os complexes represented by the following formulae.

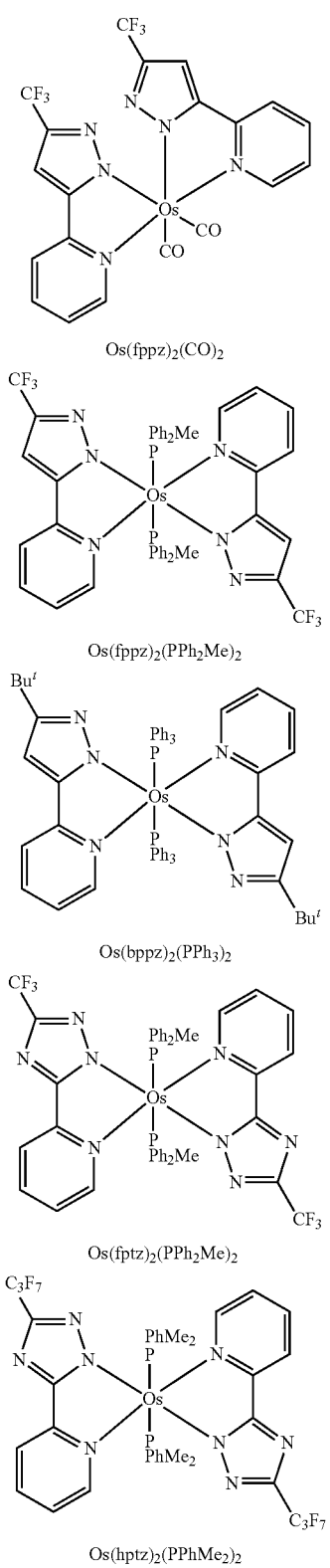

Os(fppz)₂(CO)₂

Os(fppz)₂(PPh₂Me)₂

Os(bppz)₂(PPh₃)₂

Os(fptz)₂(PPh₂Me)₂

Os(hptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any known material that can stably transport electrons injected from an electron injecting electrode (cathode). Examples of materials for forming the ETL are a quinoline derivative, such as tris(8-quinolinorate)aluminum (Alq₃), TAZ, BAlq, beryllium bis(benzoquinolin-10-olate) (Bebq₂), 9,10-di(naphthalene-2-yl)anthracene (ADN), Compound 201, and Compound 202, but are not limited thereto.

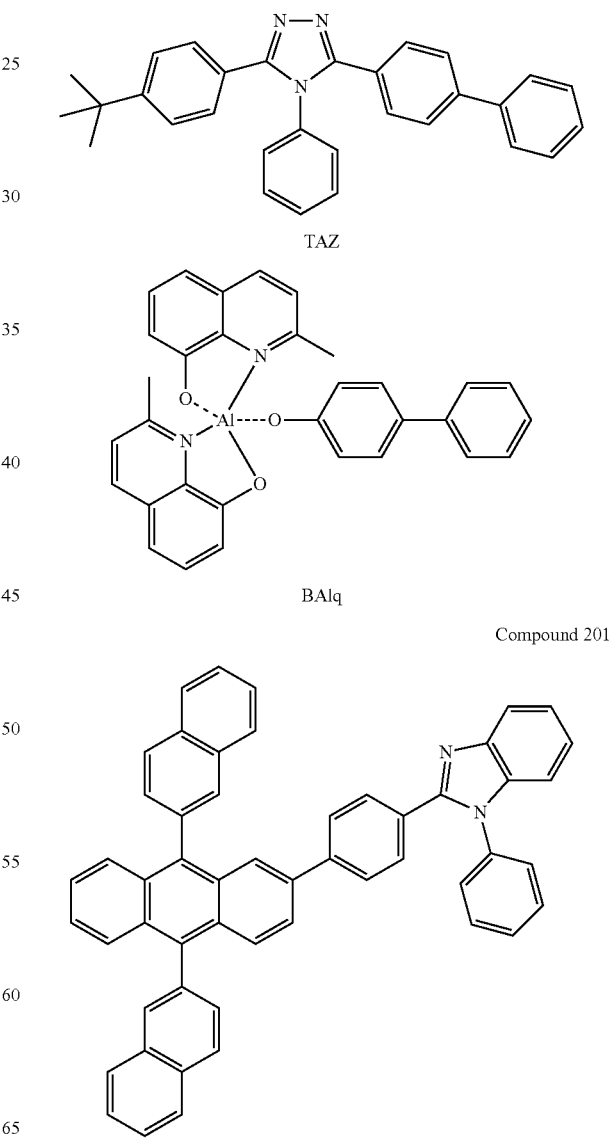

TAZ

BAlq

Compound 201

Compound 202

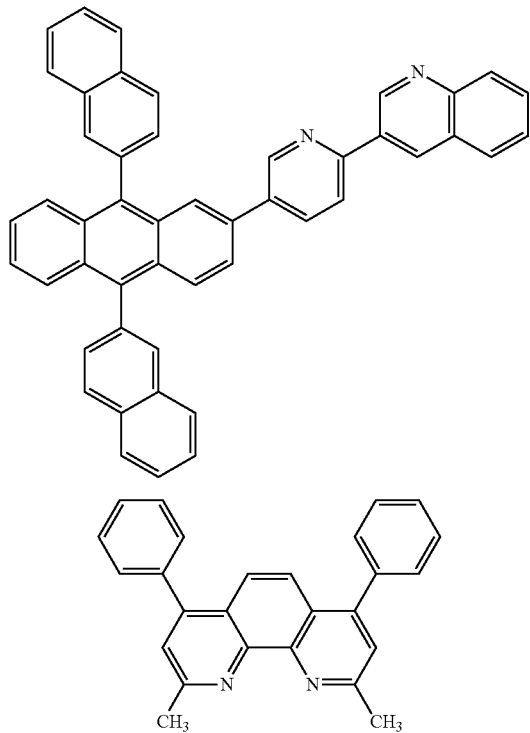

BCP

Compound 203

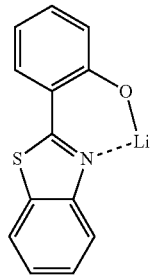

The ETL may include at least one of the amine-based compounds described above.

When the amine-based material of Formula 1 is used as a material for forming the ETL, efficiency and/or lifetime of the organic light-emitting diode may be improved. The ETL including the amine-based compound of Formula 1 may further include a metal complex, for example, lithium quinolate.

The thickness of the ETL may be in a range of about 100 Å to about 1,000 Å, and in some embodiments, may be about 150 Å to about 500 Å. When the thickness of the ETL is within these ranges, the ETL may have satisfactory electron transporting ability without a substantial increase in driving voltage.

In some embodiments the ETL may include further include a metal-containing material, in addition to any known electron-transporting organic compound.

The metal-containing material may be a lithium (Li) complex. Non-limiting examples of the Li complex are lithium quinolate (Liq) and Compound 203 below:

Liq

Then, an EIL, which facilitates injection of electrons from the cathode, may be formed on the ETL. Any suitable electron-injecting material may be used to form the EIL.

Examples of materials for forming the EIL are LiF, NaCl, CsF, $Li_2O$, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be about 1 Å to about 100 Å, and in some embodiments, may be about 3 Å to about 90 Å. When the thickness of the EIL is within these ranges, the EIL may have satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In this regard, the second electrode 17 may comprise lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting diode, the transmission electrode may comprise indium tin oxide (ITO) or indium zinc oxide (IZO).

Although the organic light-emitting device of FIG. 1 is described above, the present embodiments are not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, BCP represented by the following formula may be used as a material for forming the HBL.

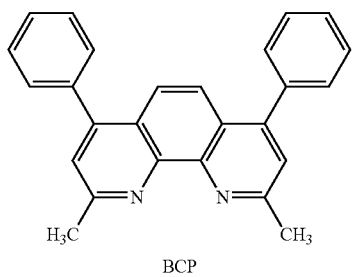

BCP

The thickness of the HBL may be from about 20 Å to about 1000 Å, and in some embodiments, may be from about 30 Å to about 300 Å. When the thickness of the HBL is within these ranges, the HBL may have a good hole blocking ability without a substantial increase in driving voltage.

Examples of the unsubstituted $C_1$-$C_{60}$ alkyl group (or $C_1$-$C_{60}$ alkyl group) as used herein are $C_1$-$C_{60}$ linear or branched alkyl groups, such as methyl, ethyl group, propyl, ethyl, propyl, isobutyl, sec-butyl, pentyl, iso-amyl, and hexyl. Examples of the substituted $C_1$-$C_{60}$ alkyl group are a $C_1$-$C_{60}$ alkyl group of which at least one hydrogen atom is substituted with at least one of a deuterium atom; —F; —Cl; —Br; —I; —CN; a hydroxyl group; —NO$_2$; an amino group; an amidino group; hydrazine; hydrazone; a carboxyl group or a salt thereof; a sulfonic acid group or a salt thereof; a phosphoric acid or a salt thereof; a tri($C_6$-$C_{60}$aryl)silyl group; a $C_1$-$C_{60}$ alkyl group, a $C_1$-$C_{60}$ alkoxy group, a $C_2$-$C_{60}$ alkenyl group, and a $C_2$-$C_{60}$ alkynyl group; an a $C_1$-$C_{60}$ alkyl group, a $C_1$-$C_{60}$ alkoxy group, a $C_2$-$C_{60}$ alkenyl group, and a $C_2$-$C_{60}$ alkynyl group of which at least one hydrogen atom are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, and a phosphoric acid or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group; and a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

The unsubstituted $C_1$-$C_{60}$ alkoxy group (or $C_1$-$C_{60}$ alkoxy group) may be a group represented by —OA, wherein A is an unsubstituted $C_1$-$C_{60}$ alkyl group described above. Examples of the unsubstituted $C_1$-$C_{60}$ alkoxy group are a methoxy group, an ethoxy group, and an isopropyloxy group. At least one of the hydrogen atoms in the alkoxy group may be substituted with the substituents described above in conjunction with the substituted $C_1$-$C_{60}$ alkyl group.

The unsubstituted $C_2$-$C_{60}$ alkenyl group (or $C_2$-$C_{60}$ alkenyl group) is a hydrocarbon chain having a carbon-carbon double bond in the center or at a terminal of the unsubstituted $C_2$-$C_{60}$ alkyl group. Examples of the alkenyl group are an ethenyl group, a propenyl group, a butenyl group, and the like. At least one hydrogen atom in the unsubstituted $C_2$-$C_{60}$ alkenyl group may be substituted with those substituents described in conjunction with the substituted $C_1$-$C_{60}$ alkyl group.

The unsubstituted $C_2$-$C_{60}$ alkynyl group ($C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group (or $C_2$-$C_{60}$ alkynyl group) are an ethenyl group, a propynyl group, and the like. At least one hydrogen atom in the alkynyl group may be substituted with the substituents described above in conjunction with the $C_1$-$C_{60}$ alkyl group.

As used herein, the unsubstituted $C_3$-$C_{60}$ cycloalkyl group indicates a cyclic, monovalent $C_3$-$C_{60}$ saturated hydrocarbon group. Non-limiting examples of the unsubstituted $C_3$-$C_{60}$ cycloalkyl group are cyclopropyl, cyclobutyl, cyclopentyl, cyclohexyl, and cyclooctyl. At least one hydrogen atom in the cyclo alkynyl group may be substituted with those substituents described above in conjunction with the $C_1$-$C_{60}$ alkyl group.

As used herein, the unsubstituted $C_3$-$C_{60}$ cycloalkenyl group indicates a nonaromatic, cyclic unsaturated hydrocarbon group with at least one carbon-carbon double bond. Examples of the unsubstituted $C_3$-$C_{60}$ cycloalkenyl group are cyclopropenyl, cyclobutenyl, cyclopentenyl, cyclohexcenyl, cycloheptenyl, 1,3-cyclohexadienyl, 1,4-cyclohexadienyl, 2,4-cycloheptadienyl, and 1,5-cyclooctadienyl. At least one hydrogen atom in the cycloalkynyl group may be substituted with those substituents described above in conjunction with the substituted $C_1$-$C_{60}$ alkyl group.

The unsubstituted $C_6$-$C_{60}$ aryl group is a monovalent group having a carbocyclic system having 6 to 60 carbon atoms including at least one aromatic ring. The unsubstituted $C_6$-$C_{60}$ arylene group is a bivalent group having a carbocyclic system having 6 to 60 carbon atoms including at least one aromatic ring. When the aryl group and the arylene group have at least two rings, they may be fused to each other via a single bond. At least one hydrogen atom in the aryl group and the arylene group may be substituted with the substituents described above in conjunction with the $C_1$-$C_{60}$ alkyl group.

Examples of the substituted or unsubstituted $C_6$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be inferred based on those of the unsubstituted $C_6$-$C_{60}$ aryl group and the substituted $C_1$-$C_{60}$ alkyl group described above. Examples of the substituted or unsubstituted $C_6$-$C_{60}$ arylene group may be inferred based on those examples of the substituted or unsubstituted $C_6$-$C_{60}$ aryl group described above.

The unsubstituted $C_2$-$C_{60}$ heteroaryl group is a monovalent group having at least one aromatic ring having at least one heteroatom selected from among N, O, P, and S as a ring-forming atom. The unsubstituted $C_2$-$C_{60}$ heteroarylene group is a bivalent group having at least one aromatic ring having at least one heteroatom selected from among N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described above in conjunction with the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the unsubstituted $C_2$-$C_{60}$ heteroarylene group may be inferred based on those examples of the substituted or unsubstituted $C_2$-$C_{60}$ arylene group described above.

The substituted or unsubstituted $C_6$-$C_{60}$ aryloxy group indicates —$OA_2$ (wherein $A_2$ is a substituted or unsubstituted $C_6$-$C_{60}$ aryl group described above). The substituted or unsubstituted $C_6$-$C_{60}$ arylthiol group indicates —$SA_3$ (wherein $A_3$ is a substituted or unsubstituted $C_6$-$C_{60}$ aryl group described above).

Hereinafter, the present embodiments will be described in detail with reference to the following synthesis examples and other examples. However, these examples are for illustrative purposes only and are not intended to limit the scope of the present embodiments.

EXAMPLES

Synthesis Example 1: Synthesis of Compound 1

Compound 1 was synthesized according to Reaction Scheme 1 below:

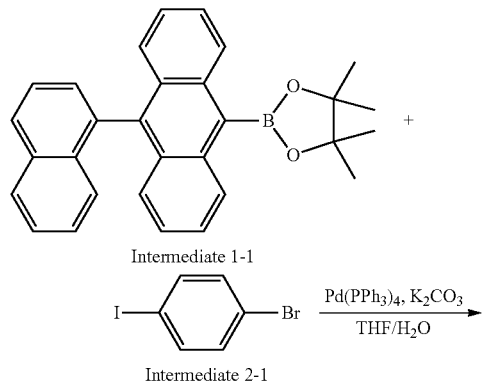

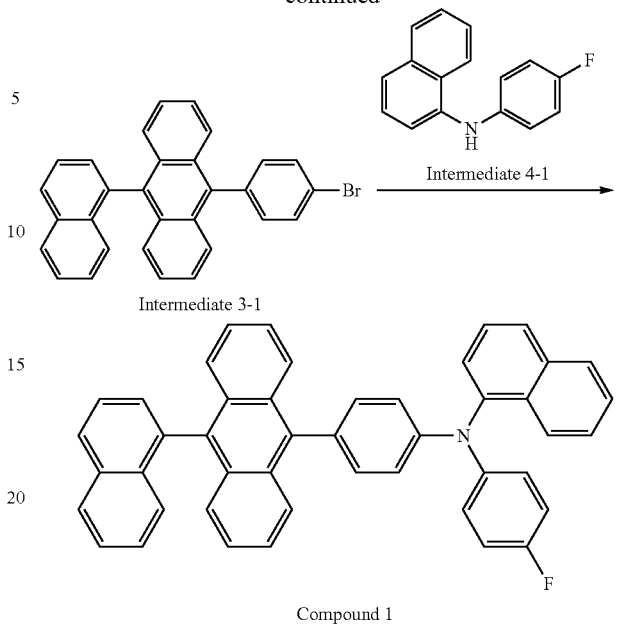

Synthesis of Intermediate 3-1

8.60 g (20.0 mmol) of Intermediate 1-1, 5.66 g (20.0 mmol) of Intermediate 2-1, 1.15 g (1.0 mmol) of tetrakis(triphenylphosphine)palladium(0) (Pd(PPh$_3$)$_4$), and 8.29 g (60.0 mmol) of K$_2$CO$_3$ were dissolved in 50 mL of a mixed solution of THF/H$_2$O (2:1), and then the resultant solution was stirred at about 70° C. for about 5 hours. The resultant mixture was cooled to room temperature, followed by three times of extraction with 50 mL of water and 50 mL of diethylether. An organic layer was collected and was dried using magnesium sulfate to evaporate the solvent. The residue was separated and purified by silica gel column chromatography to obtain 7.33 g (80% Yield) of Intermediate 3-1.

Synthesis of Compound 1

4.58 g (10.0 mmol) of Intermediate 3-1, 2.85 g (12.0 mmol) of Intermediate 4-1, 0.18 g (0.2 mmol) of Pd$_2$(dba)$_3$ [(tris(dibenzylidine acetone)dipalladium(0))], 0.04 g (0.4 mmol) of tri-tert-butylphosphine (P(t-Bu)$_3$), and 1.44 g (15.0 mmol) of NaOtBu were dissolved in 50 mL of toluene, and the resultant solution was then refluxed for about 3 hours. The resultant mixture was cooled to room temperature, followed by three times of extraction with 40 mL of water and 40 mL of diethylether. An organic layer was collected and was dried using magnesium sulfate to evaporate the solvent. The residue was separated and purified by silica gel column chromatography to obtain 4.80 g (78% Yield) of Compound 1. This compound was identified using mass spectroscopy/fast atom bombardment (MS/FAB) and $^1$H NMR.

$C_{46}H_{30}FN$: calc. 615.24, and found; 615.22. $^1$H NMR (CDCl$_3$, 400 MHz) δ (ppm) 8.13-8.11 (dd, 1H), 7.87-7.85 (m, 1H), 7.84-7.80 (m, 3H), 7.72-7.69 (m, 2H), 7.67 (d, 1H), 7.65 (d, 1H), 7.59-7.56 (m, 2H), 7.54-7.51 (dd, 1H), 7.48-7.41 (m, 4H), 7.37-7.23 (m, 6H), 7.18-7.14 (m, 2H), 7.09-7.06 (m, 1H), 6.98-6.94 (m, 2H), 6.85-6.83 (dd, 1H), 6.79-6.75 (m, 2H)

Synthesis Example 2: Synthesis of Compound 3

4.98 g of Compound 3 (Yield 80%) was prepared in the same manner as in the method of preparing Compound 1 of Synthesis Example 1, except that Intermediate 4-3 instead of Intermediate 4-1 was used. Compound 3 was identified using MS/FAB and $^1$H NMR.

$C_{47}H_{30}N_2$: calc. 622.24, and found; 622.23. $^1$H NMR (CDCl$_3$, 400 MHz) δ (ppm) 7.84-7.82 (m, 2H), 7.81 (d, 1H), 7.78-7.76 (m, 1H), 7.72-7.68 (m, 3H), 7.66 (d, 1H), 7.65 (d, 1H), 7.63-7.59 (m, 2H), 7.57-7.52 (m, 3H), 7.47-7.43 (m, 3H), 7.41-7.38 (m, 2H), 7.37-7.27 (m, 6H), 7.17 (dd, 1H), 7.13-7.09 (m, 2H), 6.99-6.95 (m, 1H), 6.88-6.85 (m, 1H)

Synthesis Example 3: Synthesis of Compound 4

4.86 g of Compound 4 (Yield 75%) was prepared in the same manner as in the method of preparing Compound 1 of Synthesis Example 1, except that Intermediate 4-4 instead of Intermediate 4-1 was used. Compound 4 was identified using MS/FAB and $^1$H NMR.

$C_{49}H_{32}N_2$: calc. 648.26, and found; 648.27. $^1$H NMR (CDCl$_3$, 400 MHz) δ (ppm) 7.86-7.82 (m, 2H), 7.81 (d, 1H), 7.73-7.68 (m, 2H), 7.66 (d, 1H), 7.65-7.52 (m, 3H), 7.60-7.58 (m, 2H) 7.54-7.49 (m, 3H), 7.46-7.42 (m, 3H), 7.40-7.28 (m, 8H), 6.99-6.95 (m, 1H), 6.90-6.84 (m, 4H), 6.74-6.70 (m, 2H)

Synthesis Example 4: Synthesis of Compound 5

4.77 g of Compound 5 (Yield 70%) was prepared in the same manner as in the method of preparing Compound 1 of Synthesis Example 1, except that Intermediate 4-5 instead of Intermediate 4-1 was used. Compound 5 was identified using MS/FAB and $^1$H NMR.

$C_{51}H_{36}FN$: calc. 681.28, and found; 681.27. $^1$H NMR (CDCl$_3$, 400 MHz) δ (ppm) 7.84-7.82 (m, 2H), 7.80 (d, 1H), 7.78-7.75 (m, 1H), 7.72-7.68 (m, 2H), 7.67 (d, 1H), 7.65 (d, 1H), 7.62-7.58 (m, 2H), 7.56-7.52 (m, 2H), 7.47-7.44 (m, 1H), 7.38-7.27 (m, 6H), 7.14-7.08 (m, 2H), 6.98-6.96 (m, 1H), 6.94-6.89 (m, 2H), 6.85-6.83 (dd, 1H), 6.79-6.77 (m, 2H), 6.75 (d, 1H), 6.73-6.70 (m, 2H), 1.66 (s, 6H)

Synthesis Example 5: Synthesis of Compound 6

4.87 g of Compound 6 (Yield 66%) was prepared in the same manner as in the method of preparing Compound 1 of Synthesis Example 1, except that Intermediate 4-6 instead of Intermediate 4-1 was used. Compound 6 was identified using MS/FAB and $^1$H NMR.

$C_{55}H_{35}N_3$: calc. 737.28, and found; 737.29. $^1$H NMR (CDCl$_3$, 400 MHz) δ (ppm) 8.07-8.05 (m, 1H), 7.86-7.83 (m, 2H), 7.81 (d, 1H), 7.73-7.69 (m, 2H), 7.68-7.64 (m, 2H), 7.62-7.58 (m, 2H), 7.50-7.44 (m, 6H), 7.42-7.28 (m, 11H), 7.26-7.23 (m, 2H), 6.99-6.96 (m, 1H), 6.90-6.86 (m, 2H), 6.81-6.78 (dd, 1H), 6.73-6.69 (m, 2H)

Synthesis Example 6: Synthesis of Compound 7

4.82 g of Compound 7 (Yield 71%) was prepared in the same manner as in the method of preparing Compound 1 of Synthesis Example 1, except that Intermediate 4-7 instead of Intermediate 4-1 was used. Compound 7 was identified using MS/FAB and $^1$H NMR.

$C_{49}H_{30}N_2S$: calc. 678.21; and found 678.22. $^1$H NMR (CDCl$_3$, 400 MHz) δ (ppm) 8.15-8.13 (m, 1H), 8.09-8.06 (m, 1H), 7.84-7.80 (m, 4H), 7.72-7.69 (m, 2H), 7.68-7.64 (m, 2H), 7.61-7.58 (m, 2H), 7.54-7.51 (m, 1H), 7.47-7.41 (m, 2H), 7.39-7.27 (m, 8H), 7.16 (d, 1H), 7.13-7.10 (dd, 1H), 7.04-7.01 (m, 1H), 6.93-6.90 (m, 2H), 6.88-6.84 (m, 2H)

Synthesis Example 7: Synthesis of Compound 11

4.17 g of Compound 11 (Yield 62%) was prepared in the same manner as in the method of preparing Compound 1 of Synthesis Example 1, except that Intermediate 4-11 instead of Intermediate 4-1 was used. Compound 11 was identified using MS/FAB and $^1$H NMR.

$C_{48}H_{29}F_2NO$: calc. 673.22, and found; 673.21. $^1$H NMR (CDCl$_3$, 400 MHz) δ (ppm) 7.87-7.85 (m, 1H), 7.84-7.81 (m, 3H), 7.76-7.70 (m, 3H), 7.68-7.66 (dd, 1H), 7.65-7.64 (m, 1H), 7.62-7.58 (m, 3H), 7.55-7.50 (m, 3H), 7.46-7.40 (m, 2H), 7.37-7.29 (m, 5H), 7.16-7.13 (dd, 1H), 7.10-7.03 (m, 2H), 6.98-6.93 (m, 2H), 6.86-6.82 (m, 2H)

Synthesis Example 8: Synthesis of Compound 13

4.52 g of Compound 13 (Yield 79%) was prepared in the same manner as in the method of preparing Compound 1 of Synthesis Example 1, except that Intermediate 4-13 instead of Intermediate 4-1 was used. Compound 13 was identified using MS/FAB and $^1$H NMR.

$C_{43}H_{28}N_2$: calc. 572.23, and found; 572.23. $^1$H NMR (CDCl$_3$, 400 MHz) δ (ppm) 7.84-7.82 (m, 2H), 7.80 (d, 1H), 7.73-7.70 (m, 2H), 7.67 (d, 1H), 7.65 (d, 1H), 7.62-7.58 (m, 2H), 7.54-7.52 (dd, 1H), 7.47-7.43 (m, 2H), 7.38-7.29 (m, 7H), 7.22-7.14 (m, 4H), 7.11-7.06 (m, 1H), 6.97-6.95 (m, 1H), 6.89-6.86 (m, 1H), 6.84-6.81 (m, 2H)

Synthesis Example 9: Synthesis of Compound 14

4.29 g of Compound 14 (Yield 75%) was prepared in the same manner as in the method of preparing Compound 1 of Synthesis Example 1, except that Intermediate 4-14 instead of Intermediate 4-1 was used. Compound 14 was identified using MS/FAB and $^1$H NMR.

$C_{43}H_{28}N_2$: calc. 572.23, and found; 572.24. $^1$H NMR (CDCl$_3$, 400 MHz) δ (ppm) 7.86-7.82 (m, 2H), 7.81 (d, 1H), 7.73-7.68 (m, 2H), 7.66 (d, 1H), 7.65 (d, 1H), 7.61-7.57 (m, 2H), 7.54-7.49 (m, 1H), 7.46-7.42 (m, 1H), 7.40-7.28 (m, 7H), 7.22-7.17 (m, 4H), 7.10-7.06 (m, 1H), 6.98-6.95 (m, 2H), 6.88-6.84 (m, 1H), 6.80-6.76 (m, 2H)

Synthesis Example 10: Synthesis of Compound 17

4.49 g of Compound 17 (Yield 73%) was prepared in the same manner as in the method of preparing Compound 1 of Synthesis Example 1, except that Intermediate 4-17 instead of Intermediate 4-1 was used. Compound 17 was identified using MS/FAB and $^1$H NMR.

$C_{43}H_{28}F_3N$: calc. 615.22, and found; 615.23. $^1$H NMR (CDCl$_3$, 400 MHz) δ (ppm) 7.85-7.81 (m, 2H), 7.79 (d, 1H), 7.74-7.69 (m, 2H), 7.67 (d, 1H), 7.66 (d, 1H), 7.62-7.59 (m, 2H), 7.56-7.48 (m, 3H), 7.43-7.41 (m, 1H), 7.34-7.23 (m, 5H), 7.18-7.15 (m, 4H), 7.06-7.03 (m, 1H), 6.97-6.95 (m, 2H), 6.86-6.83 (m, 1H), 6.78-6.74 (m, 2H)

Synthesis Example 11: Synthesis of Compound 18

5.81 g of Compound 18 (Yield 70%) was prepared in the same manner as in the method of preparing Compound 1 of Synthesis Example 1, except that Intermediate 4-18 instead of Intermediate 4-1 was used. Compound 18 was identified using MS/FAB and $^1$H NMR.

$C_{61}H_{42}N_2Si$: calc. 830.31, and found; 830.30. $^1$H NMR (CDCl$_3$, 400 MHz) δ (ppm) 7.82-7.80 (m, 2H), 7.79 (d, 1H), 7.73-7.68 (m, 2H), 7.66 (d, 1H), 7.65 (d, 1H), 7.60-7.55 (m, 8H), 7.52-7.49 (m, 1H), 7.45-7.42 (m, 1H), 7.37-7.26 (m, 15H), 7.24-7.20 (m, 3H), 7.16-7.14 (m, 1H), 7.06-7.02 (m, 2H), 6.96-6.94 (m, 2H), 6.80-6.76 (m, 2H)

Synthesis Example 12: Synthesis of Compound 19

3.70 g of Compound 19 (Yield 58%) was prepared in the same manner as in the method of preparing Compound 1 of Synthesis Example 1, except that Intermediate 4-19 instead of Intermediate 4-1 was used. Compound 19 was identified using MS/FAB and $^1$H NMR.

$C_{42}H_{24}F_5N$: calc. 637.18, and found; 637.19. $^1$H NMR (CDCl$_3$, 400 MHz) δ (ppm) 7.85-7.83 (m, 2H), 7.81 (d, 1H), 7.75-7.71 (m, 2H), 7.68 (d, 1H), 7.66-62 (m, 3H), 7.56-7.54 (dd, 1H), 7.50-7.46 (m, 1H), 7.40-7.31 (m, 5H), 7.25-7.20 (m, 2H), 7.12-7.09 (m, 1H), 7.02-6.99 (m, 1H), 6.92-6.88 (m, 4H)

Synthesis Example 13: Synthesis of Compound 20

4.54 g of Compound 20 (Yield 76%) was prepared in the same manner as in the method of preparing Compound 1 of Synthesis Example 1, except that Intermediate 4-20 instead of Intermediate 4-1 was used. Compound 20 was identified using MS/FAB and $^1$H NMR.

$C_{44}H_{27}N_3$: calc. 597.22, and found; 597.23. $^1$H NMR (CDCl$_3$, 400 MHz) δ (ppm) 7.83-7.81 (m, 2H), 7.80 (d, 1H), 7.72-7.69 (m, 2H), 7.67 (d, 1H), 7.66 (d, 1H), 7.62-7.58 (m, 2H), 7.54-7.51 (m, 1H), 7.47-7.43 (m, 1H), 7.40-7.28 (m, 9H), 7.13-7.10 (m, 1H), 7.02-6.99 (m, 4H), 6.89-6.85 (m, 2H)

Synthesis Example 14: Synthesis of Compound 21

3.44 g of Compound 21 (Yield 59%) was prepared in the same manner as in the method of preparing Compound 1 of Synthesis Example 1, except that Intermediate 4-21 instead of Intermediate 4-1 was used. Compound 21 was identified using MS/FAB and $^1$H NMR.

$C_{42}H_{27}F_2N$: calc. 583.21, and found; 583.22. $^1$H NMR (CDCl$_3$, 400 MHz) δ (ppm) 7.84-7.82 (m, 2H), 7.81 (d, 1H), 7.74-7.70 (m, 2H), 7.68 (d, 1H), 7.67 (d, 1H), 7.64-7.61 (m, 2H), 7.55-7.52 (dd, 1H), 7.48-7.44 (m, 1H), 7.37-7.30 (m, 5H), 7.23-7.20 (m, 4H), 7.15-7.09 (m, 5H), 7.04-7.00 (m, 2H)

Synthesis Example 15: Synthesis of Compound 22

4.03 g of Compound 22 (Yield 56%) was prepared in the same manner as in the method of preparing Compound 1 of Synthesis Example 1, except that Intermediate 4-22 instead of Intermediate 4-1 was used. Compound 22 was identified using MS/FAB and $^1$H NMR.

$C_{51}H_{33}FN_4$: calc. 720.27, and found; 720.28. $^1$H NMR (CDCl$_3$, 400 MHz) δ (ppm) 8.52-8.47 (m, 4H), 7.87-7.82 (m, 5H), 7.76-7.73 (m, 2H), 7.70 (d, 1H), 7.68 (d, 1H), 7.62-7.56 (m, 5H), 7.50-7.46 (m, 1H), 7.44-7.31 (m, 7H), 7.24-7.18 (m, 2H), 7.13-7.09 (m, 2H), 7.00-6.98 (m, 1H), 6.85-6.82 (m, 2H)

Synthesis Example 16: Synthesis of Compound 23

5.35 g of Compound 23 (Yield 70%) was prepared in the same manner as in the method of preparing Compound 1 of Synthesis Example 1, except that Intermediate 4-23 instead of Intermediate 4-1 was used. Compound 23 was identified using MS/FAB and $^1$H NMR.

$C_{56}H_{36}N_4$: calc. 764.29, and found; 764.28. $^1$H NMR (CDCl$_3$, 400 MHz) δ (ppm) 7.85-7.82 (m, 3H), 7.81-7.77 (m, 3H), 7.74-7.70 (m, 2H), 7.69-7.67 (m, 1H), 7.66-7.65 (m, 2H), 7.61-7.52 (m, 5H), 7.47-7.30 (m, 12H), 7.27-7.23 (m, 1H), 7.12-7.10 (m, 1H), 7.02-6.98 (m, 4H), 6.93-6.91 (m, 2H)

Synthesis Example 17: Synthesis of Compound 24

4.74 g of Compound 24 (Yield 76%) was prepared in the same manner as in the method of preparing Compound 1 of Synthesis Example 1, except that Intermediate 4-24 instead of Intermediate 4-1 was used. Compound 24 was identified using MS/FAB and $^1$H NMR.

$C_{47}H_{32}N_2$: calc. 624.26, and found; 624.25. $^1$H NMR (CDCl$_3$, 400 MHz) δ (ppm) 8.49-8.46 (m, 1H), 7.84-7.78 (m, 5H), 7.76-7.68 (m, 3H), 7.67-7.64 (m, 3H), 7.62-7.59 (m, 2H), 7.55-7.53 (m, 1H), 7.48-7.45 (m, 1H), 7.39-7.28 (m, 6H), 7.23-7.19 (m, 4H), 7.11-7.09 (m, 1H), 7.02-6.98 (m, 3H), 6.90-6.86 (m, 2H)

Synthesis Example 18: Synthesis of Compound 25

4.93 g of Compound 25 (Yield 79%) was prepared in the same manner as in the method of preparing Compound 1 of Synthesis Example 1, except that Intermediate 4-25 instead of Intermediate 4-1 was used. Compound 25 was identified using MS/FAB and $^1$H NMR.

$C_{47}H_{32}N_2$: calc. 624.26, and found; 624.25. $^1$H NMR (CDCl$_3$, 400 MHz) δ (ppm) 8.69 (d, 1H), 8.46-8.42 (m, 1H), 7.91-7.97 (m, 1H), 7.86-7.81 (m, 3H), 7.75-7.70 (m, 2H), 7.69-7.66 (m, 2H), 7.63-7.60 (m, 2H), 7.57-7.54 (m, 1H), 7.51-7.47 (m, 2H), 7.40-7.29 (m, 7H), 7.15-7.10 (m, 4H), 6.98-6.91 (m, 3H), 6.87-6.85 (m, 1H), 6.82-6.78 (m, 2H)

Synthesis Example 19: Synthesis of Compound 26

4.99 g of Compound 26 (Yield 80%) was prepared in the same manner as in the method of preparing Compound 1 of Synthesis Example 1, except that Intermediate 4-26 instead of Intermediate 4-1 was used. Compound 26 was identified using MS/FAB and $^1$H NMR.

$C_{47}H_{32}N_2$: calc. 624.26, and found; 624.25. $^1$H NMR (CDCl$_3$, 400 MHz) δ (ppm) 8.56-8.53 (m, 2H), 7.85-7.82 (m, 2H), 7.80 (d, 1H), 7.73-7.69 (m, 2H), 7.68-7.66 (m, 1H), 7.65 (d, 1H), 7.61-7.51 (m, 7H), 7.47-7.44 (m, 1H), 7.38-7.26 (m, 5H), 7.18-7.13 (m, 4H), 7.09-7.04 (m, 1H), 6.93-6.88 (m, 3H), 6.84-6.80 (m, 2H)

Synthesis Example 20: Synthesis of Compound 27

4.29 g of Compound 27 (Yield 66%) was prepared in the same manner as in the method of preparing Compound 1 of Synthesis Example 1, except that Intermediate 4-27 instead of Intermediate 4-1 was used. Compound 27 was identified using MS/FAB and $^1$H NMR.

$C_{48}H_{31}N_3$: calc. 649.25, and found; 649.26. $^1$H NMR (CDCl$_3$, 400 MHz) δ (ppm) 8.72 (d, 1H), 8.42-8.39 (m, 1H), 7.95-7.92 (m, 1H), 7.84-7.81 (m, 2H), 7.79 (d, 1H), 7.71-7.68 (m, 2H), 7.66 (d, 1H), 7.64 (d, 1H), 7.62-7.57 (m, 2H), 7.55-7.52 (m, 1H), 7.49-7.44 (m, 2H), 7.40-7.26 (m, 9H), 7.11-7.06 (m, 1H), 7.02-7.00 (m, 2H), 6.93-6.89 (m, 2H), 6.79-6.77 (m, 2H)

Synthesis Example 21: Synthesis of Compound 30

4.99 g of Compound 30 (Yield 74%) was prepared in the same manner as in the method of preparing Compound 1 of Synthesis Example 1, except that Intermediate 4-30 instead of Intermediate 4-1 was used. Compound 30 was identified using MS/FAB and $^1$H NMR.

$C_{51}H_{34}N_2$: calc. 674.27, and found; 674.26. $^1$H NMR (CDCl$_3$, 400 MHz) δ (ppm) 8.74 (d, 1H), 8.44-8.31 (m, 1H), 8.12-8.08 (dd, 1H), 7.94-7.90 (m, 1H), 7.87-7.80 (m, 4H), 7.75-7.71 (m, 2H), 7.68 (d, 1H), 7.65 (d, 1H), 7.60-7.56 (m, 2H), 7.54-7.52 (m, 1H), 7.49-7.41 (m, 5H), 7.38-7.21 (m, 8H), 7.11-7.07 (m, 2H), 7.03-7.00 (m, 3H), 6.87-6.85 (dd, 1H)

Synthesis Example 22: Synthesis of Compound 31

4.98 g of Compound 31 (Yield 80%) was prepared in the same manner as in the method of preparing Compound 1 of Synthesis Example 1, except that Intermediate 4-31 instead of Intermediate 4-1 was used. Compound 31 was identified using MS/FAB and $^1$H NMR.

$C_{47}H_{30}N_2$: calc. 622.24, and found; 622.23. $^1$H NMR (CDCl$_3$, 400 MHz) δ (ppm) 8.05-8.01 (dd, 1H), 7.89-7.86 (m, 1H), 7.84-7.80 (m, 3H), 7.74-7.69 (m, 2H), 7.67 (d, 1H), 7.65 (d, 1H), 7.59-7.56 (m, 2H), 7.53-7.50 (m, 1H), 7.48-7.41 (m, 4H), 7.40-7.22 (m, 8H), 7.13-7.09 (m, 2H), 7.05-7.03 (m, 1H), 6.96-6.93 (dd, 1H), 6.88-6.84 (m, 2H)

Synthesis Example 23: Synthesis of Compound 32

5.40 g of Compound 32 (Yield 73%) was prepared in the same manner as in the method of preparing Compound 1 of Synthesis Example 1, except that Intermediate 4-32 instead of Intermediate 4-1 was used. Compound 32 was identified using MS/FAB and $^1$H NMR.

$C_{56}H_{40}N_2$: calc. 740.32, and found; 740.31. $^1$H NMR (CDCl$_3$, 400 MHz) δ (ppm) 8.76 (d, 1H), 8.51-8.47 (dd, 1H), 7.91-7.88 (m, 1H), 7.83-7.79 (m, 3H), 7.78-7.76 (m, 1H), 7.73-7.69 (m, 2H), 7.68 (d, 1H), 7.66 (d, 1H), 7.62-7.58 (m, 2H), 7.56-7.51 (m, 2H), 7.47-7.43 (m, 2H), 7.39-7.26 (m, 8H), 7.15-7.10 (m, 2H), 7.06-7.04 (m, 1H), 6.94-6.90 (m, 3H), 6.87 (d, 1H), 6.83-6.81 (m, 2H), 1.67 (s, 6H)

Synthesis Example 24: Synthesis of Compound 35

5.05 g of Compound 35 (Yield 67%) was prepared in the same manner as in the method of preparing Compound 1 of Synthesis Example 1, except that Intermediate 4-35 instead of Intermediate 4-1 was used. Compound 35 was identified using MS/FAB and $^1$H NMR.

$C_{58}H_{38}N_2O$: calc. 778.30, and found; 778.29. $^1$H NMR (CDCl$_3$, 400 MHz) δ (ppm) 7.84-7.80 (m, 4H), 7.78-7.76 (m, 1H), 7.74-7.65 (m, 6H), 7.62-7.59 (m, 3H), 7.55-7.49 (m, 4H), 7.46-7.40 (m, 3H), 7.38-7.27 (m, 5H), 7.19-7.11 (m, 2H), 7.05 (d, 1H), 6.87 (d, 1H), 6.79-6.74 (m, 2H), 1.64 (s, 6H)

Synthesis Example 25: Synthesis of Compound 36

5.80 g of Compound 36 (Yield 70%) was prepared in the same manner as in the method of preparing Compound 1 of Synthesis Example 1, except that Intermediate 4-36 instead of Intermediate 4-1 was used. Compound 36 was identified using MS/FAB and $^1$H NMR.

$C_{63}H_{44}N_2$: calc. 828.35, and found; 828.34. $^1$H NMR (CDCl$_3$, 400 MHz) δ (ppm) 8.08-8.04 (m, 2H), 7.85-7.82 (m, 2H), 7.81 (d, 1H), 7.77-7.75 (m, 1H), 7.72-7.68 (m, 2H), 7.68 (d, 1H), 7.66 (d, 1H), 7.62-7.58 (m, 2H), 7.56-7.52 (m, 2H), 7.47-7.43 (m, 1H), 7.36-7.26 (m, 12H), 7.15-7.10 (m, 4H), 7.04-7.02 (m, 1H), 6.99-6.91 (m, 3H), 6.89 (d, 1H), 6.85-6.81 (m, 2H), 1.65 (s, 6H)

Synthesis Example 26: Synthesis of Compound 38

5.04 g of Compound 38 (Yield 75%) was prepared in the same manner as in the method of preparing Compound 1 of Synthesis Example 1, except that Intermediate 4-38 instead of Intermediate 4-1 was used. Compound 38 was identified using MS/FAB and $^1$H NMR.

$C_{51}H_{32}N_2$: calc. 672.26, and found; 672.25. $^1$H NMR (CDCl$_3$, 400 MHz) δ (ppm) 8.50-8.47 (m, 1H), 8.16-8.12 (m, 1H), 7.96-7.92 (m, 1H), 7.86-7.82 (m, 2H), 7.80 (d, 1H), 7.73-7.69 (m, 4H), 7.67 (d, 1H), 7.65 (d, 1H), 7.60-7.52 (m, 5H), 7.47-7.41 (m, 2H), 7.39-7.28 (m, 8H), 7.22-7.18 (m, 2H), 7.07-7.03 (m, 1H), 6.97-6.95 (m, 2H)

Synthesis Example 27: Synthesis of Compound 42

Synthesis of Intermediate 3-42

Intermediate 3-42 was prepared in the same manner as in the method of preparing Intermediate 3-1 of Synthesis Example 1, except that Intermediate 2-42 instead of Intermediate 2-1 was used.

Synthesis of Compound 42

4.54 g of Compound 42 (Yield 65%) was prepared in the same manner as in the method of preparing Compound 1 of Synthesis Example 1, except that Intermediates 3-42 and 4-27, instead of Intermediates 3-1 and 4-1, were used. Compound 42 was identified using MS/FAB and $^1$H NMR.

$C_{52}H_{33}N_3$: calc. 699.27, and found; 699.28. $^1$H NMR (CDCl$_3$, 400 MHz) δ (ppm) 8.78 (d, 1H), 8.45-8.42 (m, 1H), 8.11-8.08 (m, 1H), 7.94-7.91 (m, 1H), 7.89-7.86 (m, 1H), 7.83-7.80 (m, 2H), 7.78 (d, 1H), 7.72-7.67 (m, 3H), 7.65-7.62 (dd, 1H), 7.58-7.55 (m, 3H), 7.54-7.52 (m, 1H), 7.48-7.43 (m, 2H), 7.40-7.33 (m, 5H), 7.31-7.27 (m, 4H), 7.18-7.15 (dd, 1H), 6.99-6.95 (m, 1H), 6.82-6.79 (m, 2H), 6.77-6.73 (m, 2H)

Synthesis Example 28: Synthesis of Compound 43

5.24 g of Compound 43 (Yield 71%) was prepared in the same manner as in the method of preparing Compound 42 of Synthesis Example 27, except that Intermediate 4-43 instead of Intermediate 4-27 was used. Compound 43 was identified using MS/FAB and $^1$H NMR.

$C_{56}H_{38}N_2$: calc. 738.30, and found; 738.31. $^1$H NMR (CDCl$_3$, 400 MHz) δ (ppm) 8.10-8.08 (m, 1H), 7.90-7.87 (m, 1H), 7.85-7.82 (m, 2H), 7.80 (d, 1H), 7.78-7.75 (m, 1H), 7.71-7.65 (m, 4H), 7.59-7.57 (m, 1H), 7.55-7.51 (m, 4H), 7.46-7.42 (m, 1H), 7.39-7.27 (m, 8H), 7.16-7.10 (m, 3H), 6.97-6.93 (m, 1H), 6.89-6.86 (m, 2H), 6.83-6.81 (dd, 1H), 6.79 (d, 1H), 1.66 (s, 6H)

Synthesis Example 29: Synthesis of Compound 45

Synthesis of Intermediate 3-45

Intermediate 3-45 was prepared in the same manner as in the method of preparing Intermediate 3-1 of Synthesis Example 1, except that Intermediate 2-45 instead of Intermediate 2-1 was used.

Synthesis of Compound 45

5.38 g of Compound 45 (Yield 80%) was prepared in the same manner as in the method of preparing Compound 1 of Synthesis Example 1, except that Intermediates 3-45 and 4-31, instead of Intermediates 3-1 and 4-1, were used. Compound 45 was identified using MS/FAB and $^1$H NMR.

$C_{51}H_{32}N_2$: calc. 672.26, and found; 672.27. $^1$H NMR (CDCl$_3$, 400 MHz) δ (ppm) 8.03-8.00 (m, 1H), 7.88-7.85 (m, 1H), 7.84-7.79 (m, 5H), 7.73-7.68 (m, 2H), 7.65-7.63 (m, 1H), 7.60 (d, 1H), 7.55-7.37 (m, 9H), 7.35-7.28 (m, 5H), 7.20-7.15 (m, 2H), 7.10-7.06 (m, 1H), 6.97-6.92 (m, 1H), 6.86-6.85 (dd, 1H), 6.80-6.77 (m, 2H)

Synthesis Example 30: Synthesis of Compound 48

5.50 g of Compound 48 (Yield 76%) was prepared in the same manner as in the method of preparing Compound 45 of Synthesis Example 29, except that Intermediate 4-48 instead of Intermediate 4-31 was used. Compound 48 was identified using MS/FAB and $^1$H NMR.

$C_{55}H_{36}N_2$: calc. 724.29, and found; 724.30. $^1$H NMR (CDCl$_3$, 400 MHz) δ (ppm) 8.56-8.53 (dd, 1H), 8.06-8.03 (m, 1H), 7.85-7.78 (m, 6H), 7.76-7.69 (m, 5H), 7.66-7.60 (m, 3H), 7.55-7.40 (m, 7H), 7.36-7.32 (m, 5H), 7.29-7.25 (m, 1H), 7.21-7.17 (m, 2H), 7.11-7.07 (m, 1H), 6.99-6.94 (m, 1H), 6.87-6.85 (dd, 1H), 6.82-6.79 (m, 2H)

Synthesis Example 31: Synthesis of Compound 51

Synthesis of Intermediate 3-51

Intermediate 3-51 was prepared in the same manner as in the method of preparing Intermediate 3-1 of Synthesis Example 1, except that Intermediate 2-51 instead of Intermediate 2-1 was used.

Synthesis of Compound 51

4.29 g of Compound 51 (Yield 66%) was prepared in the same manner as in the method of preparing Compound 1 of Synthesis Example 1, except that Intermediates 3-51 and 4-4, instead of Intermediates 3-1 and 4-1, were used. Compound 51 was identified using MS/FAB and $^1$H NMR.

$C_{48}H_{31}N_3$: calc. 649.25, and found; 649.26. $^1$H NMR (CDCl$_3$, 400 MHz) δ (ppm) 8.50 (d, 1H), 7.93-7.90 (m, 2H), 7.89-7.87 (m, 2H), 7.85 (d, 1H), 7.84-7.81 (m, 1H), 7.74-7.69 (m, 2H), 7.65-7.61 (m, 2H), 7.56-7.49 (m, 5H), 7.46-7.37 (m, 6H), 7.36-7.34 (m, 1H), 7.32-7.27 (m, 2H), 7.14-7.10 (m, 2H), 6.99-6.94 (m, 2H), 6.83-6.79 (m, 2H)

Synthesis Example 32: Synthesis of Compound 54

4.23 g of Compound 54 (Yield 65%) was prepared in the same manner as in the method of preparing Compound 51 of Synthesis Example 31, except that Intermediate 4-27 instead of Intermediate 4-4 was used. Compound 54 was identified using MS/FAB and $^1$H NMR.

$C_{47}H_{30}N_4$: calc. 650.25, and found; 650.24. $^1$H NMR (CDCl$_3$, 400 MHz) δ (ppm) 8.73 (m, 1H), 8.55 (d, 1H), 8.52-8.47 (m, 1H), 7.96-7.88 (m, 5H), 7.86 (d, 1H), 7.84-7.81 (m, 1H), 7.73-7.68 (m, 2H), 7.56-7.53 (m, 1H), 7.49-7.38 (m, 6H), 7.36-7.28 (m, 5H), 7.16-7.13 (m, 2H), 7.00-6.95 (m, 2H), 6.89-6.85 (m, 2H)

Synthesis Example 33: Synthesis of Compound 57

Synthesis of Intermediate 3-57

Intermediate 3-57 was prepared in the same manner as in the method of preparing Intermediate 3-1 of Synthesis Example 1, except that Intermediate 2-57 instead of Intermediate 2-1 was used.

Synthesis of Compound 57

4.97 g of Compound 57 (Yield 67%) was prepared in the same manner as in the method of preparing Compound 1 of Synthesis Example 1, except that Intermediates 3-57 and 4-32, instead of Intermediates 3-1 and 4-1, were used. Compound 57 was identified using MS/FAB and $^1$H NMR.

$C_{55}H_{39}N_3$: calc. 741.31, and found; 741.32. $^1$H NMR (CDCl$_3$, 400 MHz) δ (ppm) 8.77 (dd, 1H), 8.52 (d, 1H), 8.23-8.20 (m, 1H), 7.93-7.90 (m, 1H), 7.89 (d, 1H), 7.87 (d, 1H), 7.85-7.82 (m, 1H), 7.78-7.75 (m, 1H), 7.72-7.68 (m, 2H), 7.53-7.44 (m, 6H), 7.42-7.23 (m, 9H), 7.14-7.09 (m, 2H), 6.99-6.95 (m, 1H), 6.87-6.83 (m, 4H), 6.78 (d, 1H), 1.63 (s, 6H)

Synthesis Example 34: Synthesis of Compound 58

Synthesis of Intermediate 3-58

Intermediate 3-58 was prepared in the same manner as in the method of preparing Intermediate 3-1 of Synthesis Example 1, except that Intermediate 2-58 instead of Intermediate 2-1 was used.

Synthesis of Compound 58

5.67 g of Compound 58 (Yield 81%) was prepared in the same manner as in the method of preparing Compound 1 of Synthesis Example 1, except that Intermediates 3-58 and 4-25, instead of Intermediates 3-1 and 4-1, were used. Compound 58 was identified using MS/FAB and $^1$H NMR.

$C_{53}H_{36}N_2$: calc. 700.29, and found; 700.30. $^1$H NMR (CDCl$_3$, 400 MHz) δ (ppm) 8.74 (dd, 1H), 8.51-8.48 (m, 1H), 7.94-7.90 (m, 1H), 7.83-7.77 (m, 5H), 7.74-7.65 (m, 6H), 7.55-7.52 (m, 1H), 7.48-7.44 (m, 4H), 7.38-7.25 (m, 7H), 7.19-7.15 (m, 2H), 7.08-7.03 (m, 3H), 6.96-6.92 (m, 2H), 6.86-6.83 (m, 1H), 6.80-6.79 (m, 2H)

Synthesis Example 35: Synthesis of Compound 59

5.46 g of Compound 59 (Yield 78%) was prepared in the same manner as in the method of preparing Compound 58 of Synthesis Example 34, except that Intermediate 4-24 instead of Intermediate 4-25 was used. Compound 59 was identified using MS/FAB and $^1$H NMR.

$C_{53}H_{36}N_2$: calc. 700.29, and found; 700.29. $^1$H NMR (CDCl$_3$, 400 MHz) δ (ppm) 8.58-8.54 (m, 1H), 7.86-7.80 (m, 7H), 7.78-7.70 (m, 5H), 7.68-7.65 (m, 3H), 7.54-7.51 (m, 1H), 7.47-7.44 (m, 3H), 7.37-7.26 (m, 6H), 7.17-7.13 (m, 2H), 7.09-7.07 (m, 1H), 7.01-6.97 (m, 2H), 6.98-6.93 (m, 3H), 6.84-6.81 (m, 2H)

Synthesis Example 36: Synthesis of Compound 60

5.08 g of Compound 60 (Yield 70%) was prepared in the same manner as in the method of preparing Compound 58 of Synthesis Example 34, except that Intermediate 4-27 instead of Intermediate 4-25 was used. Compound 60 was identified using MS/FAB and $^1$H NMR.

$C_{54}H_{35}N_3$: calc. 725.28, and found; 725.27. $^1$H NMR (CDCl$_3$, 400 MHz) δ (ppm) 8.71-8.69 (m, 1H), 8.44-8.41 (m, 1H), 7.93-7.91 (m, 1H), 7.84-7.78 (m, 5H), 7.74-7.69 (m, 4H), 7.68-7.65 (m, 2H), 7.55-7.52 (m, 1H), 7.48-7.43 (m, 4H), 7.39-7.24 (m, 9H), 7.12-7.11 (m, 1H), 7.03-6.99 (m, 2H), 6.93-6.89 (m, 2H), 6.82-6.80 (m, 2H)

Synthesis Example 37: Synthesis of Compound 61

6.04 g of Compound 61 (Yield 74%) was prepared in the same manner as in the method of preparing Compound 58 of Synthesis Example 34, except that Intermediate 4-32 instead of Intermediate 4-25 was used. Compound 61 was identified using MS/FAB and $^1$H NMR.

$C_{62}H_{44}N_2$: calc. 816.35, and found; 816.34. $^1$H NMR (CDCl$_3$, 400 MHz) δ (ppm) 8.69-8.67 (dd, 1H), 8.41-8.38 (m, 1H), 7.91-7.88 (m, 1H), 7.83-7.76 (m, 6H), 7.74-7.68 (m, 4H), 7.67-7.64 (m, 2H), 7.56-7.51 (m, 2H), 7.47-7.44 (m, 4H), 7.37-7.25 (m, 8H), 7.15-7.09 (m, 2H), 6.99-6.94 (m, 1H), 6.90-6.86 (m, 3H), 6.83-6.79 (m, 2H), 6.77-6.76 (m, 1H), 1.64 (s, 6H)

Synthesis Example 38: Synthesis of Compound 62

5.93 g of Compound 62 (Yield 79%) was prepared in the same manner as in the method of preparing Compound 58 of Synthesis Example 34, except that Intermediate 4-30 instead of Intermediate 4-25 was used. Compound 62 was identified using MS/FAB and $^1$H NMR.

$C_{57}H_{38}N_2$: calc. 750.30, and found; 750.29. $^1$H NMR (CDCl$_3$, 400 MHz) δ (ppm) 8.51-8.48 (m, 2H), 8.17-8.15 (dd, 1H), 7.87-7.78 (m, 6H), 7.74-7.65 (m, 6H), 7.55-7.51 (m, 5H), 7.48-7.40 (m, 6H), 7.38-7.28 (m, 5H), 7.23 (t, 1H), 7.14-7.13 (m, 1H), 7.06-7.02 (m, 2H), 6.95-6.93 (dd, 1H), 6.88-6.85 (m, 2H)

Synthesis Example 39: Synthesis of Compound 63

5.85 g of Compound 63 (Yield 78%) was prepared in the same manner as in the method of preparing Compound 58 of Synthesis Example 34, except that Intermediate 4-63 instead of Intermediate 4-25 was used. Compound 63 was identified using MS/FAB and $^1$H NMR.

$C_{57}H_{38}N_2$: calc. 750.30, and found; 750.31. $^1$H NMR (CDCl$_3$, 400 MHz) δ (ppm) 8.50-8.47 (m, 2H), 8.15-8.13 (dd, 1H), 7.86-7.77 (m, 6H), 7.73-7.69 (m, 4H), 7.68-7.65 (m, 2H), 7.56-7.52 (m, 5H), 7.49-7.39 (m, 6H), 7.37-7.29 (m, 5H), 7.22 (t, 1H), 7.18-7.16 (m, 1H), 7.11-7.07 (m, 2H), 6.96-6.94 (dd, 1H), 6.89-6.86 (m, 2H)

Synthesis Example 40: Synthesis of Compound 64

5.40 g of Compound 64 (Yield 72%) was prepared in the same manner as in the method of preparing Compound 58 of Synthesis Example 34, except that Intermediate 4-48 instead of Intermediate 4-25 was used. Compound 64 was identified using MS/FAB and $^1$H NMR.

$C_{57}H_{38}N_2$: calc. 750.30, and found; 750.31. $^1$H NMR (CDCl$_3$, 400 MHz) δ (ppm) 8.48-8.45 (m, 1H), 8.16-8.14 (dd, 1H), 7.87-7.82 (m, 3H), 7.81-7.68 (m, 10H), 7.67-7.64 (m, 3H), 7.54-7.51 (m, 1H), 7.48-7.40 (m, 6H), 7.38-7.21 (m, 7H), 7.09-7.07 (m, 1H), 7.01-6.99 (m, 2H), 6.95-6.94 (dd, 1H), 6.87-6.83 (m, 2H)

Synthesis Example 41: Synthesis of Compound 66

5.38 g of Compound 66 (Yield 77%) was prepared in the same manner as in the method of preparing Compound 58 of Synthesis Example 34, except that Intermediate 4-31 instead of Intermediate 4-25 was used. Compound 66 was identified using MS/FAB and $^1$H NMR.

$C_{53}H_{34}N_2$: calc. 698.27, and found; 698.28. $^1$H NMR (CDCl$_3$, 400 MHz) δ (ppm) 8.06-8.04 (dd, 1H), 7.88-7.85 (m, 1H), 7.84-7.79 (m, 4H), 7.78-7.76 (m, 1H), 7.74-7.69 (m, 4H), 7.67-7.64 (m, 2H), 7.56-7.52 (m, 1H), 7.48-7.29 (m, 13H), 7.22 (t, 1H), 7.13-7.11 (m, 1H), 7.05-7.01 (m, 2H), 6.96-6.94 (dd, 1H), 6.87-6.84 (m, 2H)

Synthesis Example 42: Synthesis of Compound 67

5.36 g of Compound 67 (Yield 74%) was prepared in the same manner as in the method of preparing Compound 58 of Synthesis Example 34, except that Intermediate 4-67 instead of Intermediate 4-25 was used. Compound 67 was identified using MS/FAB and $^1$H NMR.

$C_{55}H_{36}N_2$: calc. 724.29, and found; 724.30. $^1$H NMR (CDCl$_3$, 400 MHz) δ (ppm) 7.85-7.82 (m, 2H), 7.81-7.79 (m, 2H), 7.78-7.76 (m, 1H), 7.73-7.68 (m, 4H), 7.67 (d, 1H), 7.65 (d, 1H), 7.60-7.57 (m, 2H), 7.54-7.52 (dd, 1H), 7.48-7.28 (m, 13H), 7.26-7.22 (m, 2H), 7.16-7.15 (m, 1H), 7.06-7.01 (m, 2H), 6.94-6.90 (m, 2H), 6.87-6.84 (m, 2H)

Synthesis Example 43: Synthesis of Compound 68

5.45 g of Compound 68 (Yield 78%) was prepared in the same manner as in the method of preparing Compound 58 of Synthesis Example 34, except that Intermediate 4-68 instead of Intermediate 4-25 was used. Compound 68 was identified using MS/FAB and $^1$H NMR.

$C_{53}H_{34}N_2$: calc. 698.27, and found; 698.28. $^1$H NMR (CDCl$_3$, 400 MHz) δ (ppm) 7.86-7.83 (m, 2H), 7.82-7.79 (m, 2H), 7.78-7.76 (m, 2H), 7.74-7.68 (m, 4H), 7.66-7.63 (m, 3H), 7.57-7.54 (m, 2H), 7.53-7.50 (m, 2H), 7.47-7.43 (m, 3H), 7.41-7.28 (m, 8H), 7.18-7.16 (m, 1H), 7.06-7.05 (dd, 1H), 6.92-6.88 (m, 2H), 6.85-6.82 (m, 2H)

Synthesis Example 44: Synthesis of Compound 70

3.56 g of Compound 70 (Yield 53%) was prepared in the same manner as in the method of preparing Compound 58 of Synthesis Example 34, except that Intermediate 4-70 instead of Intermediate 4-25 was used. Compound 70 was identified using MS/FAB and $^1$H NMR.

$C_{50}H_{29}N_3$: calc. 671.24, and found; 671.23. $^1$H NMR (CDCl$_3$, 400 MHz) δ (ppm) 8.22-8.20 (m, 2H), 7.92-7.88 (m, 2H), 7.85-7.82 (m, 2H), 7.80 (d, 1H), 7.75-7.69 (m, 4H), 7.67-7.66 (dd, 1H), 7.65-7.63 (m, 2H), 7.61 (d, 1H), 7.55-7.53 (dd, 1H), 7.49-7.42 (m, 7H), 7.38-7.29 (m, 5H), 7.02-6.97 (m, 1H)

Synthesis Example 45: Synthesis of Compound 73

4.97 g of Compound 73 (Yield 65%) was prepared in the same manner as in the method of preparing Compound 58 of Synthesis Example 34, except that Intermediate 4-43 instead of Intermediate 4-25 was used. Compound 73 was identified using MS/FAB and $^1$H NMR.

$C_{58}H_{40}N_2$: calc. 764.32, and found; 764.33. $^1$H NMR (CDCl$_3$, 400 MHz) δ (ppm) 7.85-7.82 (m, 2H), 7.81-7.79 (m, 2H), 7.78-7.75 (m, 2H), 7.73-7.68 (m, 4H), 7.67-7.64 (m, 2H), 7.56-7.52 (m, 2H), 7.47-7.44 (m, 3H), 7.39-7.27

(m, 8H), 7.13-7.09 (m, 2H), 7.02-7.00 (m, 1H), 6.96-6.92 (m, 2H), 6.86-6.84 (dd, 1H), 6.82-6.79 (m, 2H), 6.77 (d, 1H), 1.65 (s, 6H)

Synthesis Example 46: Synthesis of Compound 76

6.06 g of Compound 76 (Yield 78%) was prepared in the same manner as in the method of preparing Compound 58 of Synthesis Example 34, except that Intermediate 4-76 instead of Intermediate 4-25 was used. Compound 76 was identified using MS/FAB and $^1$H NMR.

$C_{59}H_{40}N_2$: calc. 776.32, and found; 776.32. $^1$H NMR (CDCl$_3$, 400 MHz) δ (ppm) 8.68-8.67 (m, 1H), 8.39-8.36 (m, 1H), 7.94-7.91 (m, 1H), 7.84-7.80 (m, 3H), 7.79-7.78 (m, 1H), 7.73-7.69 (m, 4H), 7.67-7.61 (m, 4H), 7.55-7.38 (m, 10H), 7.37-7.24 (m, 7H), 7.18-7.16 (m, 1H), 7.06-7.02 (m, 2H), 6.91-6.88 (m, 2H), 6.82-6.78 (m, 2H)

Synthesis Example 47: Synthesis of Compound 77

5.22 g of Compound 77 (Yield 72%) was prepared in the same manner as in the method of preparing Compound 58 of Synthesis Example 34, except that Intermediate 4-77 instead of Intermediate 4-25 was used. Compound 77 was identified using MS/FAB and $^1$H NMR.

$C_{54}H_{35}N_3$: calc. 725.28, and found; 725.27. $^1$H NMR (CDCl$_3$, 400 MHz) δ (ppm) 8.55-8.52 (m, 2H), 7.85-7.82 (m, 2H), 7.81-7.77 (m, 3H), 7.74-7.70 (m, 4H), 7.67 (d, 1H), 7.65 (d, 1H), 7.58-7.52 (m, 5H), 7.47-7.44 (m, 3H), 7.39-7.28 (m, 7H), 7.11-7.09 (m, 1H), 7.02-6.99 (m, 2H), 6.93-6.89 (m, 2H), 6.81-6.77 (m, 2H)

Synthesis Example 48: Synthesis of Compound 78

5.63 g of Compound 78 (Yield 75%) was prepared in the same manner as in the method of preparing Compound 58 of Synthesis Example 34, except that Intermediate 4-78 instead of Intermediate 4-25 was used. Compound 78 was identified using MS/FAB and $^1$H NMR.

$C_{57}H_{38}N_2$: calc. 750.30, and found; 750.29. $^1$H NMR (CDCl$_3$, 400 MHz) δ (ppm) 8.67-8.65 (dd, 1H), 8.40-8.37 (m, 1H), 7.95-7.92 (m, 1H), 7.85-7.82 (m, 2H), 7.81-7.79 (m, 2H), 7.78-7.76 (m, 2H), 7.74-7.68 (m, 4H), 7.66-7.63 (m, 3H), 7.58-7.52 (m, 4H), 7.48-7.44 (m, 4H), 7.37-7.25 (m, 8H), 7.16-7.15 (m, 1H), 7.02-7.00 (dd, 1H), 6.95-6.91 (m, 2H), 6.84-6.81 (m, 2H)

Synthesis Example 49: Synthesis of Compound 79

5.00 g of Compound 79 (Yield 69%) was prepared in the same manner as in the method of preparing Compound 58 of Synthesis Example 34, except that Intermediate 4-79 instead of Intermediate 4-25 was used. Compound 79 was identified using MS/FAB and $^1$H NMR.

$C_{54}H_{35}N_3$: calc. 725.28, and found; 725.27. $^1$H NMR (CDCl$_3$, 400 MHz) δ (ppm) 8.49-8.46 (m, 1H), 7.84-7.77 (m, 7H), 7.74-7.68 (m, 5H), 7.67-7.63 (m, 3H), 7.56-7.54 (dd, 1H), 7.47-7.43 (m, 3H), 7.39-7.26 (m, 8H), 7.19-7.17 (m, 1H), 7.03-6.99 (m, 2H), 6.92-6.88 (m, 2H), 6.81-6.78 (m, 2H)

Synthesis Example 50: Synthesis of Compound 82

Synthesis of Intermediate 3-82

Intermediate 3-82 was prepared in the same manner as in the method of preparing Intermediate 3-1 of Synthesis Example 1, except that Intermediate 2-82 instead of Intermediate 2-1 was used.

Synthesis of Compound 82

5.20 g of Compound 82 (Yield 67%) was prepared in the same manner as in the method of preparing Compound 1 of Synthesis Example 1, except that Intermediates 3-82 and 4-25, instead of Intermediates 3-1 and 4-1, were used. Compound 82 was identified using MS/FAB and $^1$H NMR.

$C_{59}H_{40}N_2$: calc. 776.32, and found; 776.33. $^1$H NMR (CDCl$_3$, 400 MHz) δ (ppm) 8.68 (d, 1H), 8.41-8.38 (m, 1H), 7.94-7.91 (m, 1H), 7.86-7.80 (m, 5H), 7.74-7.64 (m, 10H), 7.56-7.53 (m, 1H), 7.49-7.44 (m, 4H), 7.38-7.24 (m, 7H), 7.13-7.09 (m, 2H), 7.04-6.99 (m, 3H), 6.96-6.92 (m, 2H), 6.87-6.83 (m, 1H), 6.81-6.78 (m, 2H)

Synthesis Example 51: Synthesis of Compound 83

5.58 g of Compound 83 (Yield 68%) was prepared in the same manner as in the method of preparing Compound 82 of Synthesis Example 50, except that Intermediate 4-48 instead of Intermediate 4-25 was used. Compound 83 was identified using MS/FAB and $^1$H NMR.

$C_{63}H_{42}N_2$: calc. 826.33, and found; 826.32. $^1$H NMR (CDCl$_3$, 400 MHz) δ (ppm) 8.46-8.43 (m, 1H), 8.17-8.14 (m, 1H), 7.87-7.80 (m, 6H), 7.79-7.75 (m, 2H), 7.74-7.63 (m, 12H), 7.56-7.54 (dd, 1H), 7.49-7.40 (m, 6H), 7.38-7.22 (m, 7H), 7.16-7.14 (m, 1H), 7.05-7.00 (m, 2H), 6.95-6.93 (dd, 1H), 6.85-6.82 (m, 2H)

Synthesis Example 52: Synthesis of Compound 84

Synthesis of Intermediate 3-84

Intermediate 3-84 was prepared in the same manner as in the method of preparing Intermediate 3-1 of Synthesis Example 1, except that Intermediate 2-84 instead of Intermediate 2-1 was used.

Synthesis of Compound 84

4.90 g of Compound 84 (Yield 62%) was prepared in the same manner as in the method of preparing Compound 1 of Synthesis Example 1, except that Intermediates 3-84 and 4-30, instead of Intermediates 3-1 and 4-1, were used. Compound 84 was identified using MS/FAB and $^1$H NMR.

$C_{60}H_{42}N_2$: calc. 790.33, and found; 790.32. $^1$H NMR (CDCl$_3$, 400 MHz) δ (ppm) 8.69 (d, 1H), 8.40-8.37 (m, 1H), 8.11-8.08 (m, 1H), 7.93-7.90 (m, 2H), 7.89-7.85 (m, 2H), 7.84-7.79 (m, 4H), 7.72-7.68 (m, 2H), 7.62-7.59 (m, 2H), 7.53-7.51 (m, 1H), 7.49-7.42 (m, 6H), 7.40-7.25 (m, 8H), 7.13-7.11 (m, 1H), 7.07-7.05 (dd, 1H), 6.98-6.96 (dd, 1H), 6.90-6.86 (m, 2H), 6.82 (d, 1H), 1.62 (s, 6H)

Synthesis Example 53: Synthesis of Compound 85

4.90 g of Compound 84 (Yield 64%) was prepared in the same manner as in the method of preparing Compound 84 of Synthesis Example 52, except that Intermediate 4-27 instead of Intermediate 4-30 was used. Compound 85 was identified using MS/FAB and $^1$H NMR.

$C_{57}H_{39}N_3$: calc. 765.31, and found; 765.30. $^1$H NMR (CDCl$_3$, 400 MHz) δ (ppm) 8.68 (d, 1H), 8.38-8.35 (m, 1H), 7.95-7.92 (m, 2H), 7.90-7.88 (m, 1H), 7.85-7.80 (m, 4H), 7.73-7.69 (m, 2H), 7.63-7.60 (m, 2H), 7.55-7.52 (m, 2H), 7.48-7.44 (m, 2H), 7.41-7.33 (m, 5H), 7.32-7.25 (m, 4H), 7.12-7.09 (m, 1H), 7.03-6.96 (m, 2H), 6.93-6.90 (dd, 1H), 6.88-6.84 (m, 2H), 6.80 (d, 1H), 1.61 (s, 6H)

Synthesis Example 54: Synthesis of Compound 86

4.73 g of Compound 86 (Yield 64%) was prepared in the same manner as in the method of preparing Compound 84 of Synthesis Example 52, except that Intermediate 4-31 instead of Intermediate 4-30 was used. Compound 86 was identified using MS/FAB and $^1$H NMR.

$C_{56}H_{38}N_2$: calc. 738.30, and found; 738.31. $^1$H NMR (CDCl$_3$, 400 MHz) δ (ppm) 8.11-8.08 (m, 1H), 7.94-7.91 (m, 1H), 7.89-7.85 (m, 2H), 7.84-7.79 (m, 4H), 7.72-7.69 (m, 2H), 7.62-7.59 (m, 2H), 7.54-7.51 (m, 1H), 7.49-7.41 (m, 5H), 7.40-7.34 (m, 5H), 7.32-7.25 (m, 3H), 7.14-7.12 (m, 1H), 7.01-6.99 (m, 1H), 6.93-6.87 (m, 3H), 6.85 (d, 1H), 1.62 (s, 6H)

Synthesis Example 55: Synthesis of Compound 89

Synthesis of Intermediate 3-89

Intermediate 3-89 was prepared in the same manner as in the method of preparing Intermediate 3-1 of Synthesis Example 1, except that Intermediate 2-89 instead of Intermediate 2-1 was used.

Synthesis of Compound 89

5.61 g of Compound 89 (Yield 75%) was prepared in the same manner as in the method of preparing Compound 1 of Synthesis Example 1, except that Intermediates 3-89 and 4-4, instead of Intermediates 3-1 and 4-1, were used. Compound 89 was identified using MS/FAB and $^1$H NMR.

$C_{57}H_{36}N_2$: calc. 748.29, and found; 748.30. $^1$H NMR (CDCl$_3$, 400 MHz) δ (ppm) 8.25-8.19 (m, 2H), 8.11-8.09 (m, 1H), 8.06-8.04 (m, 1H), 7.85-7.82 (m, 2H), 7.81-7.80 (m, 1H), 7.78-7.77 (m, 1H), 7.72-7.68 (m, 3H), 7.64-7.61 (m, 2H), 7.59-7.55 (m, 3H), 7.54-7.48 (m, 3H), 7.47-7.43 (m, 3H), 7.42-7.35 (m, 5H), 7.34-7.27 (m, 3H), 7.12-7.08 (m, 2H), 7.02-6.98 (m, 2H), 6.90-6.86 (m, 2H)

Synthesis Example 56: Synthesis of Compound 92

Synthesis of Intermediate 3-92

Intermediate 3-92 was prepared in the same manner as in the method of preparing Intermediate 3-1 of Synthesis Example 1, except that Intermediate 2-92 instead of Intermediate 2-1 was used.

Synthesis of Compound 92

4.61 g of Compound 92 (Yield 61%) was prepared in the same manner as in the method of preparing Compound 1 of Synthesis Example 1, except that Intermediates 3-92 and 4-27, instead of Intermediates 3-1 and 4-1, were used. Compound 92 was identified using MS/FAB and $^1$H NMR.

$C_{54}H_{33}N_3S$: calc. 755.24, and found; 755.25. $^1$H NMR (CDCl$_3$, 400 MHz) δ (ppm) 8.70-8.68 (m, 1H), 8.40-8.37 (m, 2H), 8.01 (d, 1H), 7.93-7.91 (m, 1H), 7.88-7.86 (dd, 1H), 7.85-7.82 (m, 2H), 7.81-7.80 (m, 1H), 7.78-7.76 (m, 1H), 7.73-7.69 (m, 2H), 7.64 (d, 1H), 7.63-7.62 (m, 1H), 7.54-7.51 (m, 1H), 7.48-7.43 (m, 2H), 7.40-7.35 (m, 4H), 7.34-7.24 (m, 5H), 7.13-7.12 (m, 1H), 7.06-7.03 (dd, 1H), 6.98-6.93 (m, 1H), 6.92-6.84 (m, 4H)

Synthesis Example 57: Synthesis of Compound 95

Synthesis of Intermediate 3-95

Intermediate 3-95 was prepared in the same manner as in the method of preparing Intermediate 3-1 of Synthesis Example 1, except that Intermediate 2-95 instead of Intermediate 2-1 was used.

Synthesis of Compound 95

4.74 g of Compound 95 (Yield 62%) was prepared in the same manner as in the method of preparing Compound 1 of Synthesis Example 1, except that Intermediates 3-95 and 4-30, instead of Intermediates 3-1 and 4-1, were used. Compound 95 was identified using MS/FAB and $^1$H NMR.

$C_{57}H_{36}N_2O$: calc. 764.28, and found; 764.29. $^1$H NMR (CDCl$_3$, 400 MHz) δ (ppm) 8.69-8.67 (m, 1H), 8.41-8.38 (m, 1H), 8.11-8.08 (m, 1H), 8.04-8.02 (m, 1H), 7.99-7.96 (m, 2H), 7.94-7.91 (m, 1H), 7.87-7.85 (m, 1H), 7.84-7.77 (m, 6H), 7.73-7.69 (m, 2H), 7.55-7.52 (m, 1H), 7.48-7.41 (m, 5H), 7.40-7.36 (m, 3H), 7.35-7.25 (m, 5H), 7.10-7.04 (m, 2H), 6.98-6.96 (m, 1H), 6.94-6.92 (dd, 1H), 6.88-6.85 (m, 2H)

Synthesis Example 58: Synthesis of Compound 97

Synthesis of Intermediate 3-97

Intermediate 3-97 was prepared in the same manner as in the method of preparing Intermediate 3-1 of Synthesis Example 1, except that Intermediate 2-97 instead of Intermediate 2-1 was used.

Synthesis of Compound 97

4.96 g of Compound 97 (Yield 61%) was prepared in the same manner as in the method of preparing Compound 1 of Synthesis Example 1, except that Intermediates 3-97 and 4-4, instead of Intermediates 3-1 and 4-1, were used. Compound 97 was identified using MS/FAB and $^1$H NMR.

$C_{61}H_{39}N_3$: calc. 813.31, and found; 813.32. $^1$H NMR (CDCl$_3$, 400 MHz) δ (ppm) 8.31-8.29 (m, 1H), 7.84-7.82 (m, 2H), 7.81-7.80 (m, 1H), 7.77-7.74 (m, 1H), 7.72-7.68 (m, 4H), 7.64-7.61 (m, 2H), 7.60-7.58 (m, 1H), 7.54-7.47 (m, 7H), 7.46-7.41 (m, 4H), 7.40-7.36 (m, 5H), 7.34-7.28 (m, 4H), 7.24-7.22 (m, 1H), 7.16-7.14 (m, 1H), 7.06-7.00 (m, 2H), 6.86-6.80 (m, 3H)

Synthesis Example 59: Synthesis of Compound 98

4.65 g of Compound 98 (Yield 59%) was prepared in the same manner as in the method of preparing Compound 97 of Synthesis Example 58, except that Intermediate 4-31 instead of Intermediate 4-4 was used. Compound 98 was identified using MS/FAB and $^1$H NMR.

$C_{59}H_{37}N_3$: calc. 787.30, and found; 787.29. $^1$H NMR (CDCl$_3$, 400 MHz) δ (ppm) 8.32-8.30 (m, 1H), 8.10-8.07 (dd, 1H), 7.87-7.85 (m, 1H), 7.84-7.80 (m, 2H), 7.80-7.79 (m, 1H), 7.76-7.74 (m, 1H), 7.73-7.68 (m, 4H), 7.61-7.58 (m, 1H), 7.55-7.51 (m, 7H), 7.50-7.43 (m, 7H), 7.42-7.35 (m, 6H), 7.34-7.23 (m, 6H), 7.13-7.10 (m, 1H), 7.04-7.03 (dd, 1H), 6.94-6.91 (dd, 1H), 6.87-6.84 (m, 2H)

Synthesis Example 60: Synthesis of Compound 99

Synthesis of Intermediate 3-99

Intermediate 3-99 was prepared in the same manner as in the method of preparing Intermediate 3-1 of Synthesis Example 1, except that Intermediate 2-98 instead of Intermediate 2-1 was used.

Synthesis of Compound 99

5.03 g of Compound 99 (Yield 55%) was prepared in the same manner as in the method of preparing Compound 1 of Synthesis Example 1, except that Intermediates 3-99 and 4-30, instead of Intermediates 3-1 and 4-1, were used. Compound 99 was identified using MS/FAB and $^1$H NMR.

$C_{69}H_{45}N_3$: calc. 915.36, and found; 915.35. $^1$H NMR (CDCl$_3$, 400 MHz) δ (ppm) 8.90 (s, 1H), 8.60-8.58 (dd, 1H), 8.45 (s, 1H), 8.13-8.11 (dd, 1H), 7.94-7.91 (m, 1H), 7.87-7.75 (m, 5H), 7.72-7.58 (m, 7H), 7.54-7.21 (m, 23), 7.16-7.14 (m, 1H), 7.03-6.99 (m, 2H), 6.89-6.84 (m, 2H)

Synthesis Example 61: Synthesis of Compound 103

5.71 g of Compound 103 (Yield 76%) was prepared in the same manner as in the method of preparing Compound 1 of Synthesis Example 1, except that Intermediate B37 instead of Intermediate 4-1 was used. Compound 103 was identified using MS/FAB and $^1$H NMR.

$C_{56}H_{37}N_3$: calc. 751.30, found 751.28.
$^1$H NMR (CDCl$_3$, 400 MHz) δ (ppm) 8.76 (s, 2H), 8.57 (d, 2H), 8.12 (d, 1H), 7.93 (d, 2H), 7.87-7.65 (m, 9H), 7.61-7.27 (m, 15H), 7.14-7.10 (m, 2H), 7.08-7.05 (m, 3H), 6.98 (d, 1H)

Synthesis Example 62: Synthesis of Compound 104

5.23 g of Compound 104 (Yield 72%) was prepared in the same manner as in the method of preparing Compound 1 of Synthesis Example 1, except that Intermediate B38 instead of Intermediate 4-1 was used. Compound 104 was identified using MS/FAB and $^1$H NMR.

$C_{53}H_{34}N_4$: calc. 726.28, found 726.27. $^1$H NMR (CDCl$_3$, 400 MHz) δ (ppm) 8.78 (s, 2H), 8.56 (d, 2H), 7.94 (d, 2H), 7.84-7.80 (m, 3H), 7.72-7.60 (m, 7H), 7.54-7.25 (m, 11H), 7.12-7.08 (m, 5H), 7.02-6.99 (m, 2H)

Synthesis Example 63: Synthesis of Compound 107

Synthesis of Intermediate 3-107

Intermediate 3-107 was prepared in the same manner as in the method of preparing Intermediate 3-1 of Synthesis Example 1, except that Intermediate 2-58 instead of Intermediate 2-1 was used.

Synthesis of Compound 107

6.21 g of Compound 107 (Yield 75%) was prepared in the same manner as in the method of preparing Compound 1 of Synthesis Example 1, except that Intermediates 3-107 and B37, instead of Intermediates 3-1 and 4-1, were used. Compound 107 was identified using MS/FAB and $^1$H NMR.

$C_{62}H_{41}N_3$: calc. 827.33, found 827.31. $^1$H NMR (CDCl$_3$, 400 MHz) δ (ppm) 8.76 (s, 2H), 8.57 (d, 2H), 8.11 (d, 1H), 7.94 (d, 2H), 7.87-7.62 (m, 13H), 7.54-7.26 (m, 15H), 7.12-7.10 (m, 3H), 7.06-7.03 (m, 1H), 6.96-6.92 (m, 2H)

2-1

2-42
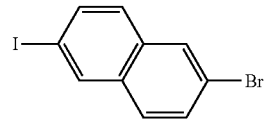

2-45
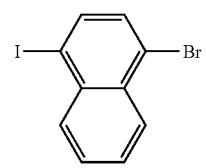

2-51
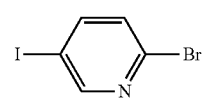

2-57
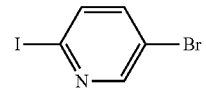

2-58
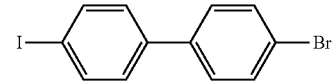

2-82

2-84
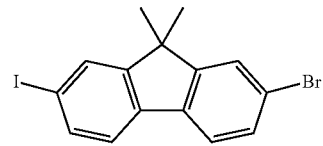

2-89
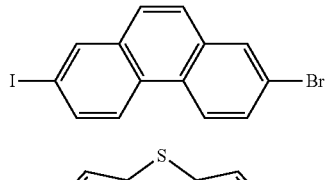

2-92
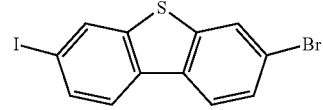

2-95
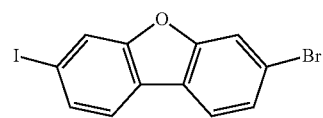

2-97
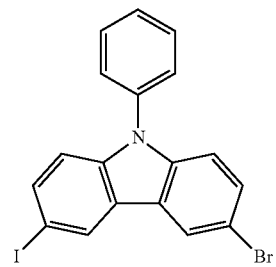

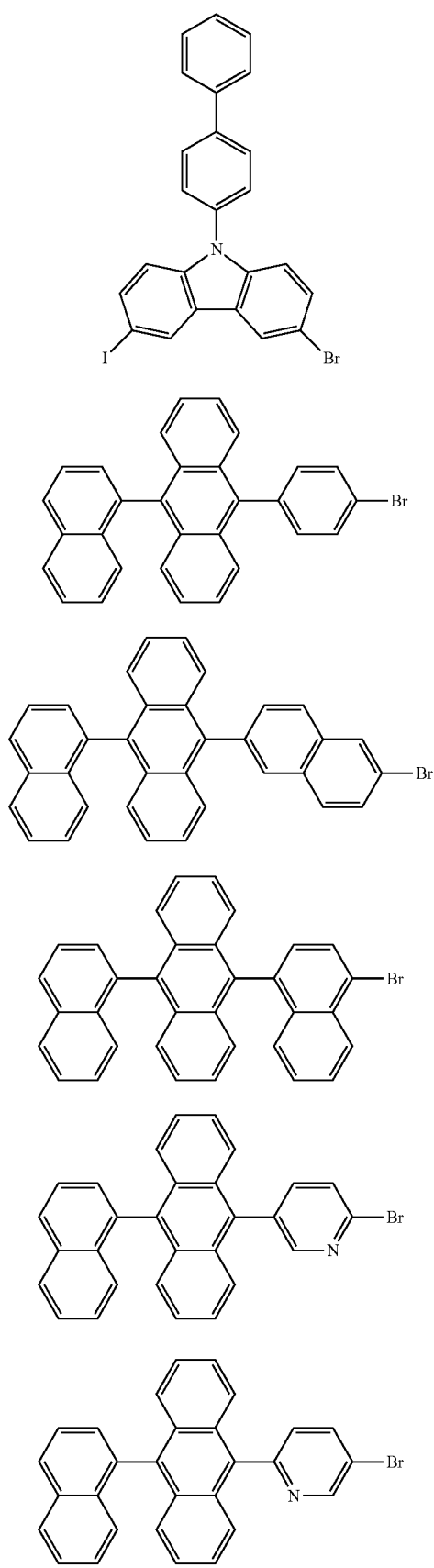
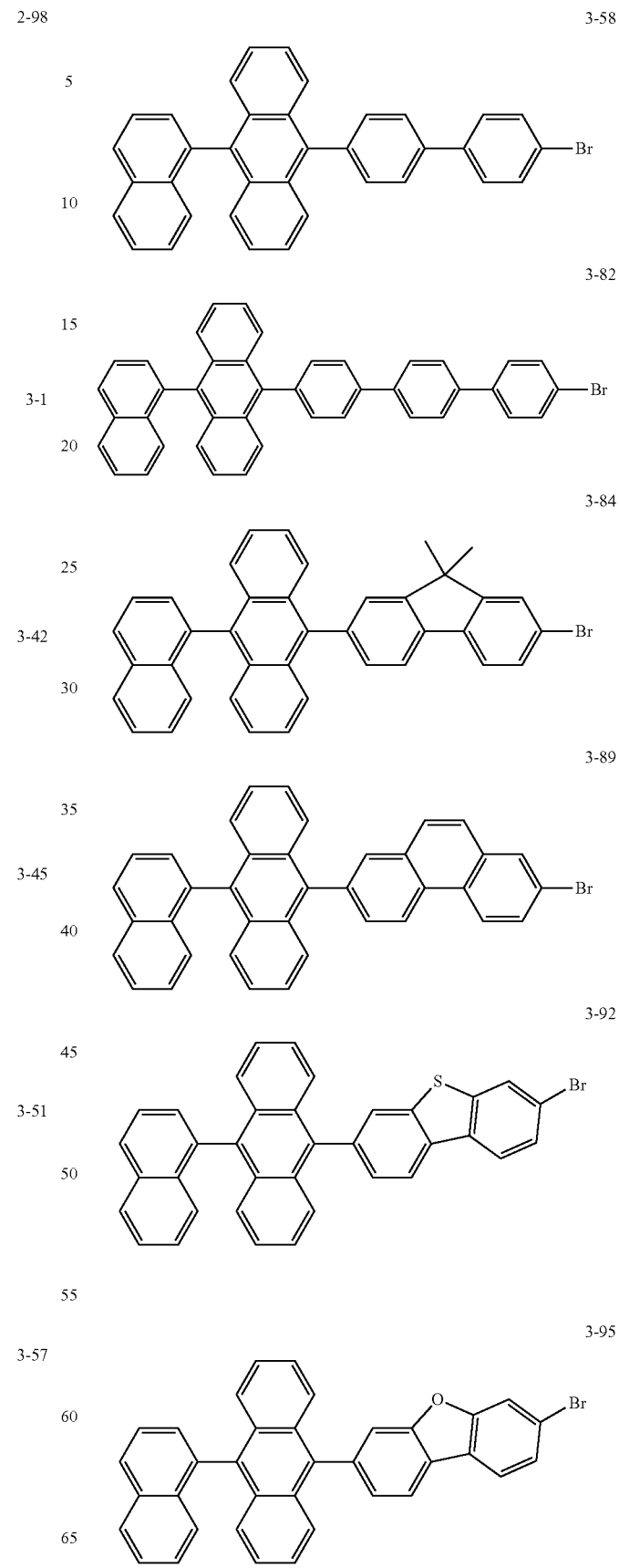

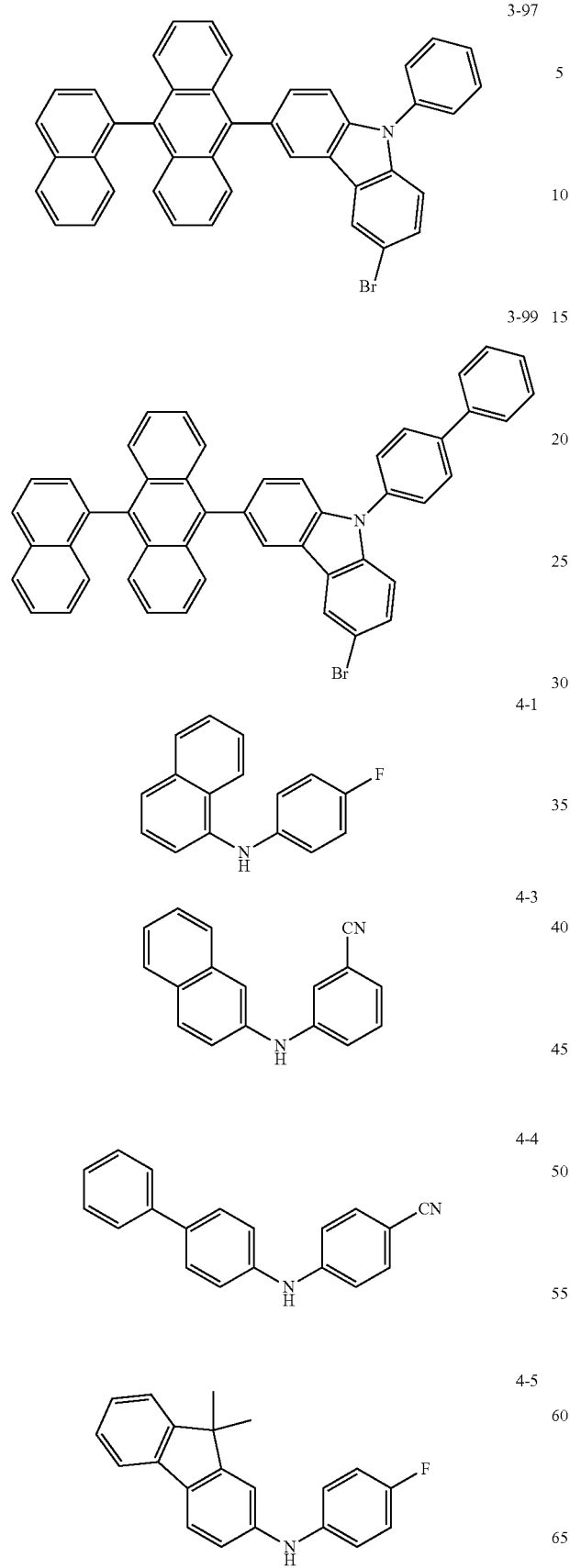
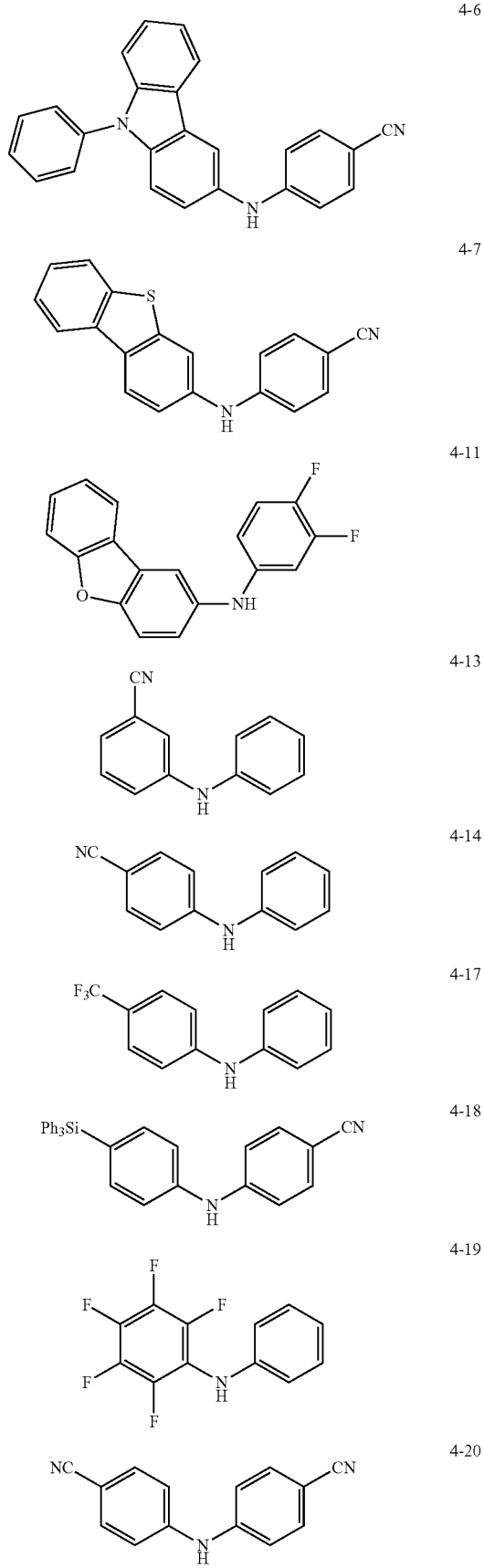

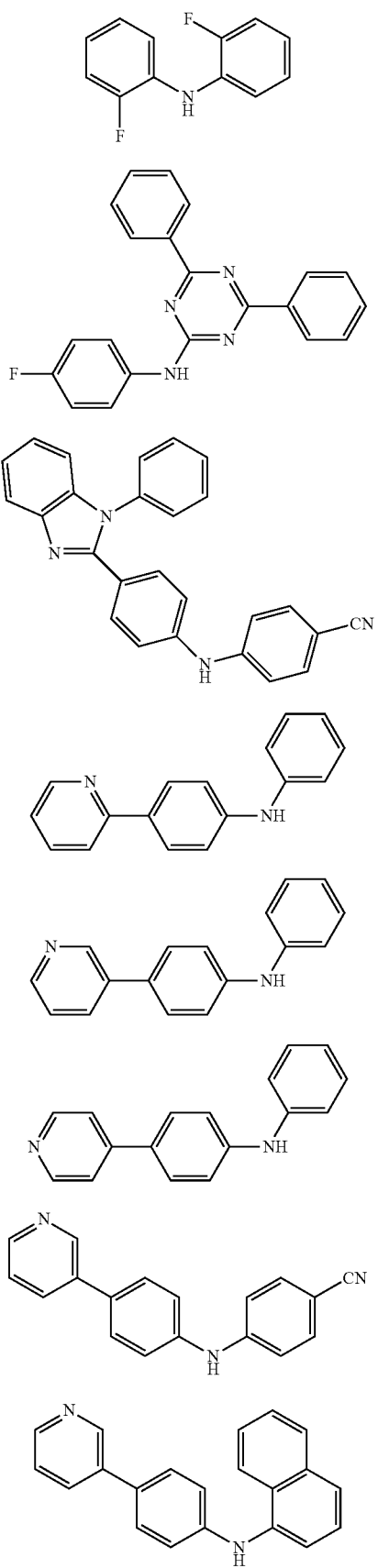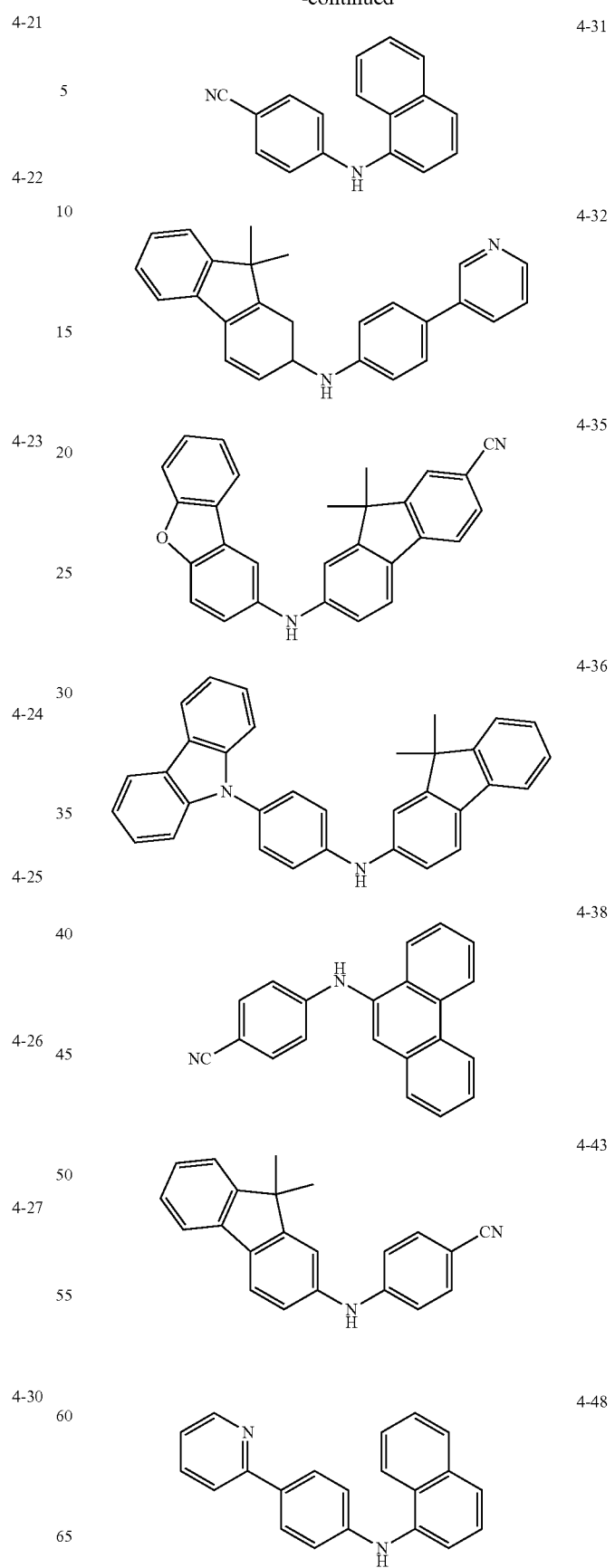

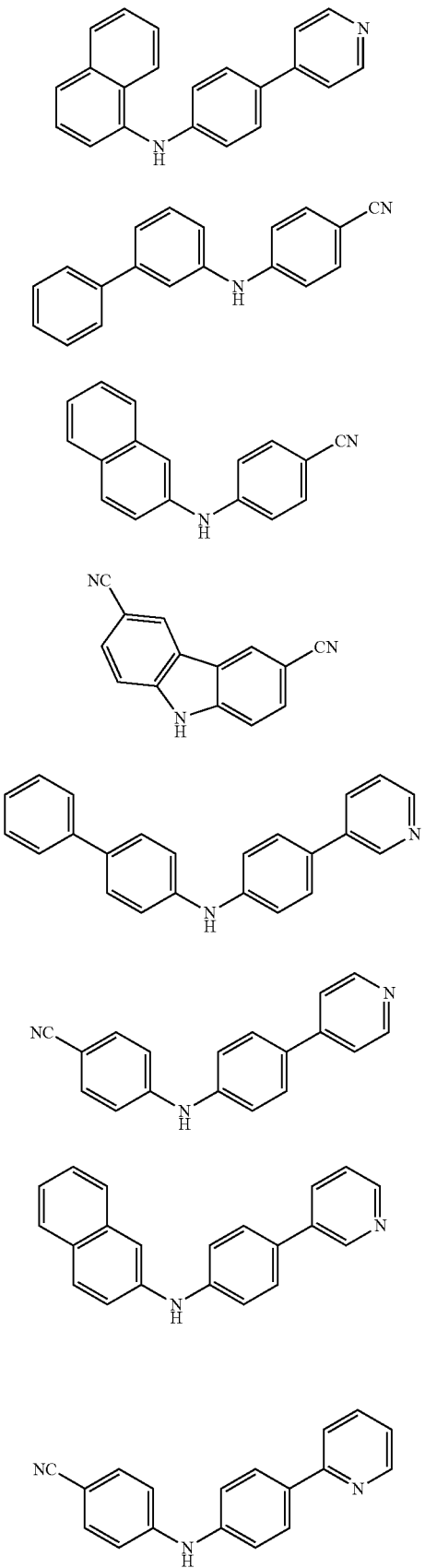
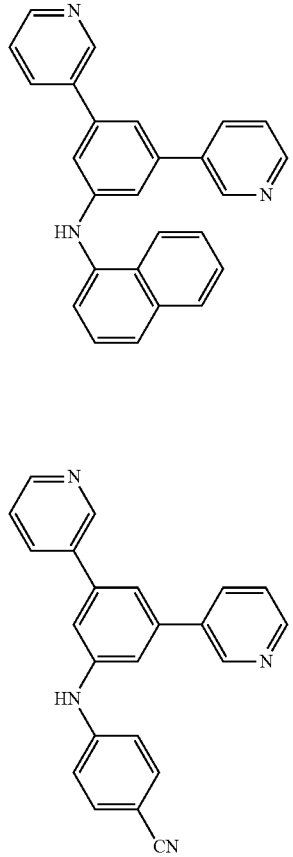

Example 1

To manufacture an anode, a corning 15Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition diode.

2-TNATA was deposited on the ITO glass substrate to form an HIL having a thickness of 600 Å on the anode, and then 4,4'-bis[N-(1-naphthyl)-N-phenylamino]biphenyl (NPS) was deposited on the HIL to form a HTL having a thickness of 300 Å.

Subsequently, 9,10-di-naphthalene-2-yl-anthracene (AND) and 4,4'-bis[2-(4-(N,N-diphenylamino)phenyl)vinyl]biphenyl (DPAVBi) were co-deposited on the HTL in a weight ratio of 98:2 to form an EML having a thickness of about 300 Å.

Then, Compound 1 was deposited on the EML to form an ETL having a thickness of about 300 Å, and then LiF was deposited on the ETL to form an EIL having a thickness of about 10 Å. Then, Al was deposited on the EIL to form a second electrode (cathode) having a thickness of about 3000 Å, thereby completing the manufacture of an organic light-emitting diode.

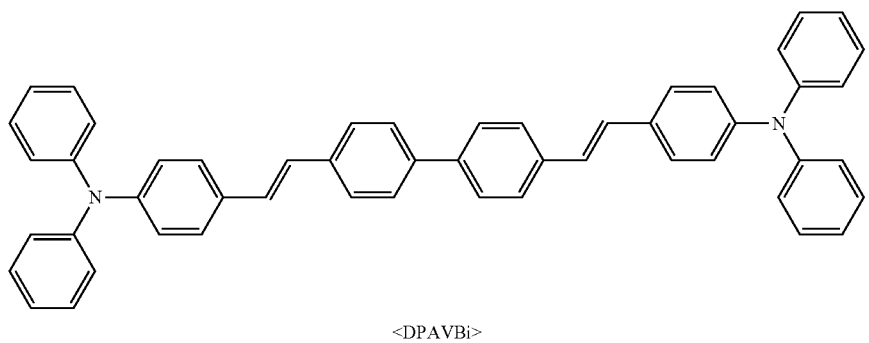 [SMILES: C(=C\c1ccc(N(c2ccccc2)c2ccccc2)cc1)/c1ccc(-c2ccc(/C=C/c3ccc(N(c4ccccc4)c4ccccc4)cc3)cc2)cc1]

<DPAVBi>

Example 2

An organic light-emitting diode was manufactured in the same manner as in Example 1, except that Compound 4, instead of Compound 1, was used to form the ETL.

Example 3

An organic light-emitting diode was manufactured in the same manner as in Example 1, except that Compound 14, instead of Compound 1, was used to form the ETL.

Example 4

An organic light-emitting diode was manufactured in the same manner as in Example 1, except that Compound 23, instead of Compound 1, was used to form the ETL.

Example 5

An organic light-emitting diode was manufactured in the same manner as in Example 1, except that Compound 25, instead of Compound 1, was used to form the ETL.

Example 6

An organic light-emitting diode was manufactured in the same manner as in Example 1, except that Compound 27, instead of Compound 1, was used to form the ETL.

Example 7

An organic light-emitting diode was manufactured in the same manner as in Example 1, except that Compound 31, instead of Compound 1, was used to form the ETL.

Example 8

An organic light-emitting diode was manufactured in the same manner as in Example 1, except that Compound 32, instead of Compound 1, was used to form the ETL.

Example 9

An organic light-emitting diode was manufactured in the same manner as in Example 1, except that Compound 42, instead of Compound 1, was used to form the ETL.

Example 10

An organic light-emitting diode was manufactured in the same manner as in Example 1, except that Compound 48, instead of Compound 1, was used to form the ETL.

Example 11

An organic light-emitting diode was manufactured in the same manner as in Example 1, except that Compound 58, instead of Compound 1, was used to form the ETL.

Example 12

An organic light-emitting diode was manufactured in the same manner as in Example 1, except that Compound 60, instead of Compound 1, was used to form the ETL.

Example 13

An organic light-emitting diode was manufactured in the same manner as in Example 1, except that Compound 62, instead of Compound 1, was used to form the ETL.

Example 14

An organic light-emitting diode was manufactured in the same manner as in Example 1, except that Compound 66, instead of Compound 1, was used to form the ETL.

Example 15

An organic light-emitting diode was manufactured in the same manner as in Example 1, except that Compound 70, instead of Compound 1, was used to form the ETL.

Example 16

An organic light-emitting diode was manufactured in the same manner as in Example 1, except that Compound 77, instead of Compound 1, was used to form the ETL.

Example 17

An organic light-emitting diode was manufactured in the same manner as in Example 1, except that Compound 82, instead of Compound 1, was used to form the EML.

Example 18

An organic light-emitting diode was manufactured in the same manner as in Example 1, except that Compound 86, instead of Compound 1, was used to form the ETL.

Example 19

An organic light-emitting diode was manufactured in the same manner as in Example 1, except that Compound 97, instead of Compound 1, was used to form the EML.

Example 20

An organic light-emitting diode was manufactured in the same manner as in Example 1, except that Compound 25, instead of DPAVBi, was used to form the EML, and Alq₃, instead of Compound 1, was used to form the ETL.

Example 21

An organic light-emitting diode was manufactured in the same manner as in Example 1, except that Compound 86, instead of DPAVBi, was used to form the EML, and Alq₃, instead of Compound 1, was used to form the ETL.

Example 22

An organic light-emitting device was manufactured in the same manner as in Example 1, except that Compound 103, instead of Compound 1, was used to form the ETL.

Example 23

An organic light-emitting device was manufactured in the same manner as in Example 1, except that Compound 104, instead of Compound 1, was used to form the ETL.

Example 24

An organic light-emitting device was manufactured in the same manner as in Example 1, except that Compound 107, instead of Compound 1, was used to form the ETL.

Comparative Example 1

An organic light-emitting diode was manufactured in the same manner as in Example 1, except that Alq₃, instead of Compound 1, was used to form the ETL.

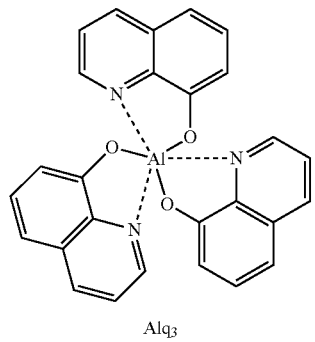

Alq₃

Comparative Example 2

Compound A was synthesized according to Reaction Scheme A below:

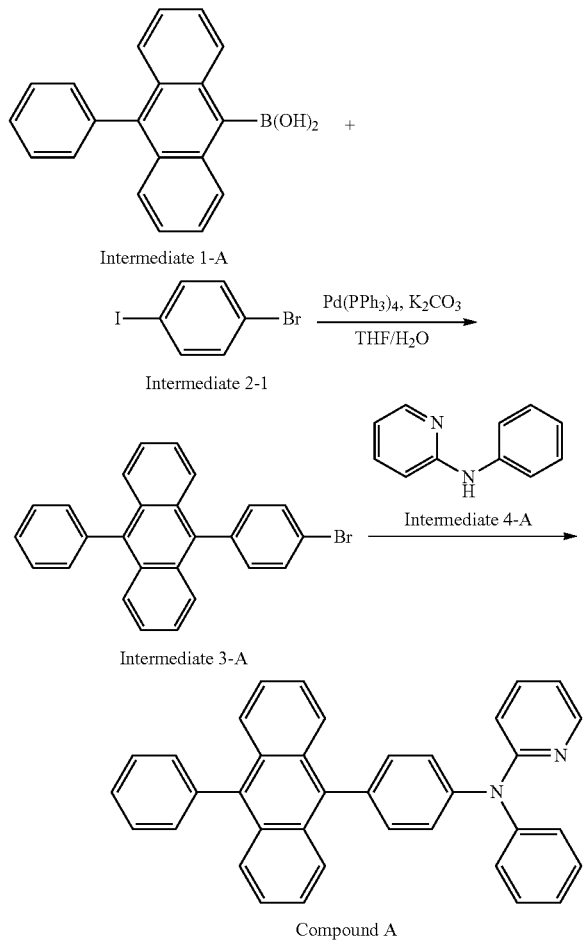

Reaction Scheme A

Synthesis of Intermediate 3-A

Intermediate 3-A was prepared in the same manner as in the method of preparing Intermediate 3-1 of Synthesis Example 1, except that Intermediate 1-A, instead of Intermediate 1, was used.

Synthesis of Compound A 3.23 g of Compound A (Yield 63%) was prepared in the same manner as in the method of preparing Compound 1 of Synthesis Example 1, except that 4.24 g (10 mmol) of Intermediate 3-A and 2.23 g (12.0 mmol) of Intermediate 4-A, instead of Intermediates 3-1 and 4-1, were used.

Manufacture of Organic Light-Emitting Diode

An organic light-emitting diode was manufactured in the same manner as in Example 1, except that Compound A, instead of Compound 1, was used to form the ETL.

125
Comparative Example 3

Compound B was synthesized according to Reaction Scheme B below:

126
Comparative Example 4

Compound C was synthesized according to Reaction Scheme C below:

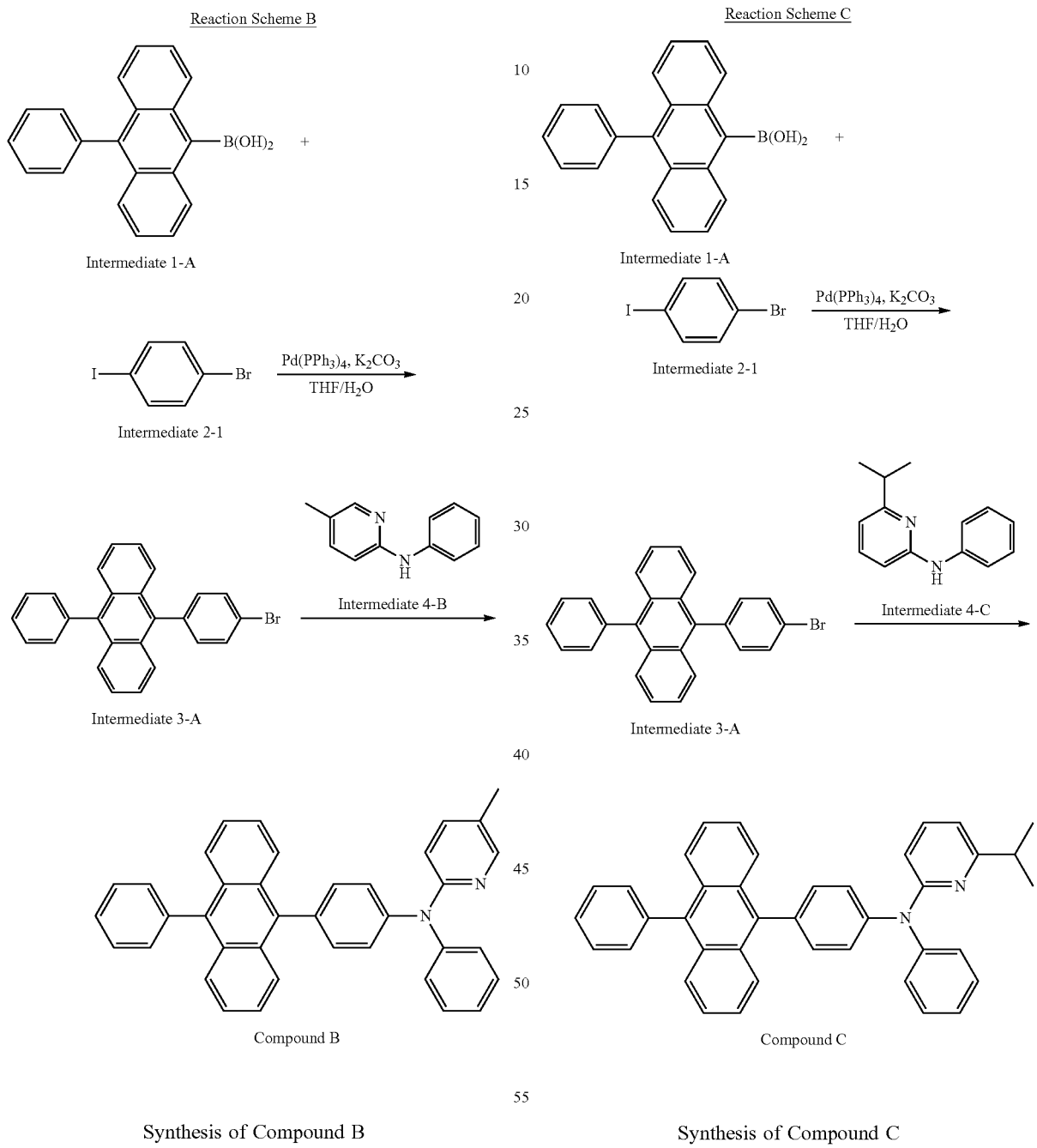

Synthesis of Compound B

Intermediate B was prepared in the same manner as in the method of preparing Compound A of Comparative Example 2, except that Intermediate 4-A, instead of Intermediate 4-B, was used.

Manufacture of Organic Light-Emitting Diode

An organic light-emitting diode was manufactured in the same manner as in Example 1, except that Compound B, instead of Compound 1, was used to form the ETL.

Synthesis of Compound C

Compound C was prepared in the same manner as in the method of preparing Compound A of Comparative Example 2, except that Intermediate 4-C, instead of Intermediate 4-C, was used.

Manufacture of Organic Light-Emitting Diode

An organic light-emitting diode was manufactured in the same manner as in Example 1, except that Compound C, instead of Compound 1, was used to form the ETL.

Comparative Example 5

Compound D was synthesized according to Reaction Scheme D below:

Reaction Scheme D

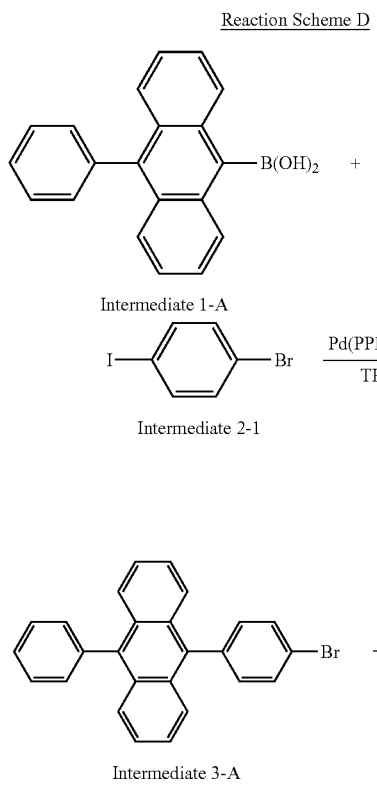

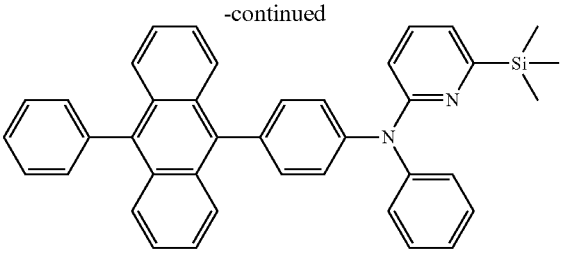

Compound D

Synthesis of Compound D

Compound D was prepared in the same manner as in the method of preparing Compound A of Comparative Example 2, except that Intermediate 4-D, instead of Intermediate 4-D, was used.

Manufacture of Organic Light-Emitting Diode

An organic light-emitting diode was manufactured in the same manner as in Example 1, except that Compound D, instead of Compound 1, was used to form the ETL.

Evaluation Example 1

Driving voltages, luminances, emitting-light colors, efficiencies (@current density of 50 mA/cm$^2$, and half-life spans (@100 mA/cm$^2$) of the organic light-emitting diodes of Examples 1 to 20 and Comparative Examples 1 to 5 were measured using a PR650 (Spectroscan) Source Measurement Unit (available from Photo Research, Inc.). The results are shown in Table 1 below.

TABLE 1

| | EML host | EML dopant | ETL | Driving voltage (V) | Luminance (cd/m$^2$) | Efficiency (cd/A) | Light-emitting color | Half-life span (hr) |
|---|---|---|---|---|---|---|---|---|
| Example 1 | ADN | DPVABi | Compound 1 | 5.36 | 3,335 | 6.67 | blue | 492 |
| Example 2 | ADN | DPVABi | Compound 4 | 5.32 | 3,390 | 6.78 | blue | 596 |
| Example 3 | ADN | DPVABi | Compound 14 | 5.29 | 3,380 | 6.76 | blue | 542 |
| Example 4 | ADN | DPVABi | Compound 23 | 5.24 | 3,470 | 6.94 | blue | 589 |
| Example 5 | ADN | DPVABi | Compound 25 | 5.26 | 3,465 | 6.93 | blue | 536 |
| Example 6 | ADN | DPVABi | Compound 27 | 5.21 | 3,505 | 7.01 | blue | 564 |
| Example 7 | ADN | DPVABi | Compound 31 | 5.26 | 3,280 | 6.56 | blue | 632 |
| Example 8 | ADN | DPVABi | Compound 32 | 5.30 | 3,440 | 6.88 | blue | 559 |
| Example 9 | ADN | DPVABi | Compound 42 | 5.23 | 3,565 | 7.13 | blue | 658 |
| Example 10 | ADN | DPVABi | Compound 48 | 5.31 | 3,435 | 6.87 | blue | 524 |
| Example 11 | ADN | DPVABi | Compound 58 | 5.26 | 3,580 | 7.16 | blue | 532 |
| Example 12 | ADN | DPVABi | Compound 60 | 5.24 | 3,515 | 7.03 | blue | 582 |
| Example 13 | ADN | DPVABi | Compound 62 | 5.31 | 3,605 | 7.21 | blue | 529 |
| Example 14 | ADN | DPVABi | Compound 66 | 5.27 | 3,345 | 6.69 | blue | 608 |
| Example 15 | ADN | DPVABi | Compound 70 | 5.16 | 3,015 | 6.03 | blue | 583 |
| Example 16 | ADN | DPVABi | Compound 77 | 5.21 | 3,560 | 7.12 | blue | 637 |

TABLE 1-continued

| | EML host | EML dopant | ETL | Driving voltage (V) | Luminance (cd/m²) | Efficiency (cd/A) | Light-emitting color | Half-life span (hr) |
|---|---|---|---|---|---|---|---|---|
| Example 17 | ADN | DPVABi | Compound 82 | 5.32 | 3,460 | 6.92 | blue | 543 |
| Example 18 | ADN | DPVABi | Compound 86 | 5.43 | 3,445 | 6.89 | blue | 469 |
| Example 19 | ADN | DPVABi | Compound 97 | 5.62 | 3,070 | 6.14 | blue | 486 |
| Example 20 | ADN | Compound 25 | Alq₃ | 6.86 | 2,190 | 4.38 | blue | 216 |
| Example 21 | ADN | Compound 86 | Alq₃ | 6.97 | 2,260 | 4.52 | blue | 238 |
| Example 22 | ADN | DPVABi | Compound 103 | 5.35 | 3,640 | 7.82 | blue | 659 |
| Example 23 | ADN | DPVABi | Compound 104 | 5.12 | 3,445 | 6.89 | blue | 618 |
| Example 24 | ADN | DPVABi | Compound 107 | 5.63 | 3,590 | 7.18 | blue | 689 |
| Comparative Example 1 | ADN | DPVABi | Alq₃ | 7.35 | 2,065 | 4.13 | blue | 145 |
| Comparative Example 2 | ADN | DPVABi | Compound A | 5.71 | 2,865 | 5.73 | blue | 311 |
| Comparative Example 3 | ADN | DPVABi | Compound B | 5.75 | 2,730 | 5.46 | blue | 320 |
| Comparative Example 4 | ADN | DPVABi | Compound C | 5.73 | 2,845 | 5.69 | blue | 297 |
| Comparative Example 5 | ADN | DPVABi | Compound D | 5.73 | 2,830 | 5.66 | blue | 213 |

Referring to Table 1, the organic light-emitting devices of Examples 1 to 19 are found to have lower driving voltages, higher luminances, higher efficiencies, and better lifetime characteristics as compared to the organic light-emitting diodes of Comparative Examples 1 to 5. The organic light-emitting devices of Examples 20 and 21 are found to have lower driving voltages and better lifetime characteristics as compared to the organic light-emitting diode of Comparative Example 1.

As described above, an organic light-emitting diode including any of the amine-based compounds according to embodiments may have a low driving voltage, a high luminance, a high efficiency, and a long lifetime.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:

1. An amine-based compound represented by Formula 1 below:

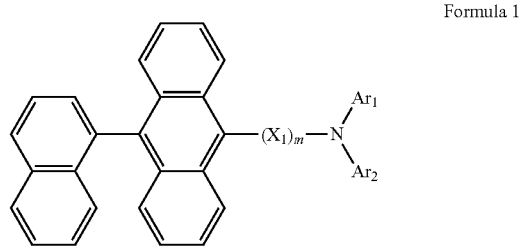

Formula 1 wherein, in Formula 1, $Ar_1$ and $Ar_2$ are each independently a substituted or unsubstituted $C_6$-$C_{60}$ aryl group or a substituted or unsubstituted $C_2$-$C_{60}$ heteroaryl group;

$X_1$ is a substituted or unsubstituted $C_6$-$C_{60}$ arylene group or a substituted or unsubstituted $C_2$-$C_{60}$ heteroarylene group;

m is an integer from 1 to 5; and at least one substituent of each of the substituted $C_6$-$C_{60}$ aryl group, the substituted $C_2$-$C_{60}$ heteroaryl group, the substituted $C_6$-$C_{60}$arylene group, and the substituted $C_2$-$C_{60}$ heteroarylene group is one of a deuterium atom; —F; —Cl; —Br; —I; —CN; a hydroxyl group; —NO₂; an amino group; an amidino group; hydrazine; hydrazone; a carboxyl group or a salt thereof; a sulfonic acid group or a salt thereof; a phosphoric acid or a salt thereof; a tri($C_6$-$C_{60}$aryl)silyl group; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group and a $C_2$-$C_{60}$ alkynyl group that is substituted with at least one of a deuterium atom, —F, —Cl, —Br, —I, —CN, a hydroxyl group, —NO₂, an amino group, an amidino group, hydrazine, hydrazone, a carboxyl group or a salt thereof, a sulfonic acid group or a salt thereof, a phosphoric acid or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, a $C_6$-$C_{60}$ arylthio group; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group that is substituted with at least one of a deuterium atom, —F, —Cl, —Br, —I, —CN, a hydroxyl group, —NO₂, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one fluorine (F), a $C_1$-$C_{60}$ alkoxy group, a $C_2$-$C_{60}$ alkenyl group, a $C_2$-$C_{60}$ alkynyl group, a $C_6$-$C_{60}$ aryl group and a $C_2$-$C_{60}$ heteroaryl group, wherein at least one of $Ar_1$ and $Ar_2$ is a $C_6$-$C_{60}$ aryl group substituted with at least one electron withdrawing group selected from the group consisting of —F; —CN; —NO$_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

2. The amine-based compound of claim 1, wherein the at least one electron withdrawing group is selected from the group consisting of: —F; —CN; —NO$_2$; a $C_1$-$C_{20}$ alkyl group substituted with at least one —F; a $C_2$-$C_{20}$ heteroaryl group including a ring-forming N atom; and a $C_2$-$C_{20}$ heteroaryl group that includes a ring-forming N atom and is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$alkyl group, a $C_1$-$C_{20}$ alkyl group substituted with at least one —F, a $C_1$-$C_{20}$ alkoxy group, a $C_6$-$C_{20}$ aryl group, and a $C_2$-$C_{20}$ heteroaryl group.

3. The amine-based compound of claim 1, wherein the at least one electron withdrawing group is selected from the group consisting of: —F; —CN; a $C_1$-$C_{20}$ alkyl group substituted with at least one —F; a pyrrolyl group, a pyrazolyl group, an imidazolyl group, an imidazolinyl group, an imidazopyridinyl group, an imidazopyrimidinyl group, a pyridinyl group, a pyrazinyl group, a pyrimidinyl group, a benzoimidazolyl group, an indolyl group, a purinyl group, a quinolinyl group, an isoquinolinyl group, a phthalazinyl group, an indolizinyl group, a quinazolinyl group, a cinnolinyl group, an indazolyl group, a carbazolyl group, a phenazinyl group, a phenanthridinyl group, a triazinyl group, a pyridazinyl group, a triazoly group, and a tetrazoly; and a pyrrolyl group, a pyrazolyl group, an imidazolyl group, an imidazolinyl group, an imidazopyridinyl group, imidazopyrimidinyl, pyridinyl, pyrazinyl, pyrimidinyl, benzoimidazolyl, indolyl, purinyl, quinolinyl, isoquinolinyl, phthalazinyl, indolizinyl, quinazolinyl, cinolinyl, indazolyl, carbazolyl, phenazinyl, phenanthridinyl, triazinyl, pyridazinyl, triazolyl, and a tetrazolyl group that is substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group and a carbazolyl group.

4. The amine-based compound of claim 1, wherein the at least one electron withdrawing group in Formula 1 is selected from the group consisting of: —F; —CN; a $C_1$-$C_{20}$ alkyl group substituted with at least one —F; a pyridinyl group, a pyrazinyl group, a pyrimidinyl group, a quinolinyl group, an isoquinolinyl group, a quinazolinyl group, a triazinyl group, and a benzoimidazolyl group; and a pyridinyl group, a pyrazinyl group, a pyrimidinyl group, a quinolinyl group, an isoquinolinyl group, a quinazolinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$alkoxy group, a phenyl group, a naphthyl group, an anthryl group, a phenanthrenyl group, a pyrenyl group, a pyridinyl group, a triazinyl group, and a carbazolyl group.

5. The amine-based compound of claim 1, wherein the at least one electron withdrawing group is selected from the group consisting of —F; —CN; —CH$_2$F; —CHF$_2$; —CF$_3$; and groups represented by Formulae 2(1) to 2(14) below:

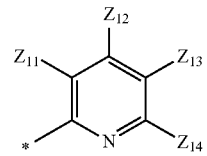

Formula 2(1)

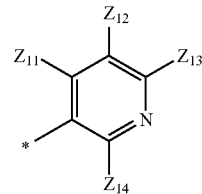

Formula 2(2)

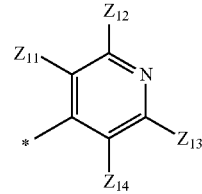

Formula 2(3)

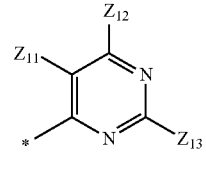

Formula 2(4)

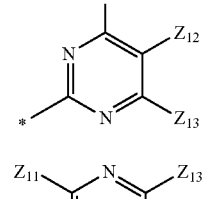

Formula 2(5)

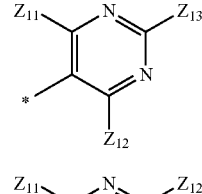

Formula 2(6)

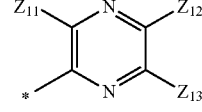

Formula 2(7)

Formula 2(8)

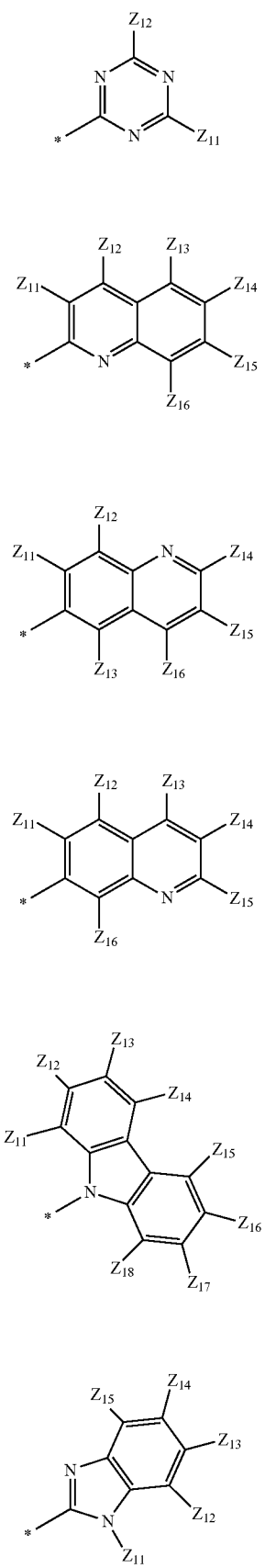

Formula 2(9)

Formula 2(10)

Formula 2(11)

Formula 2(12)

Formula 2(13)

Formula 2(14)

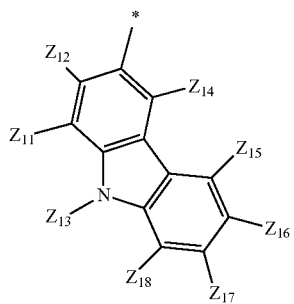

wherein, in Formulae 2(1) to 2(14), $Z_{11}$ to $Z_{18}$ are each independently a hydrogen atom, a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, or a carbazolyl group.

6. The amine-based compound of claim 1, wherein the at least one of Ar$_1$ and Ar$_2$ is a $C_6$-$C_{60}$ aryl group substituted with at least two electron withdrawing groups.

7. The amine-based compound of claim 1, wherein the at least one of Ar$_1$ and Ar$_2$ is a phenyl group, a biphenyl group, a naphthyl group, an anthryl group, a phenanthrenyl group, a pyrenyl group, or a fluorenyl group that are substituted with at least two electron withdrawing groups; and the electron withdrawing groups are each independently selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group.

8. The amine-based compound of claim 1, wherein the amine-based compound is represented by Formula 1(1) or 1(2) below:

Formula 1(1)

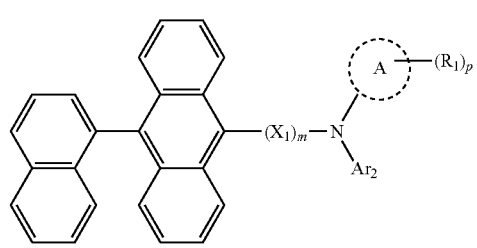

Formula 1(2)

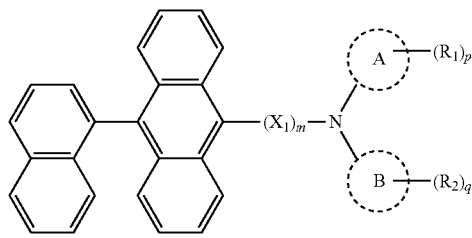

wherein, in Formula 1(1), $Ar_2$ is a substituted or unsubstituted $C_6$-$C_{20}$ aryl group or a substituted or unsubstituted $C_2$-$C_{20}$ heteroaryl group; and in Formulae 1(1) and 1(2), A and B rings are each independently a substituted $C_6$-$C_{20}$ aryl group;

$R_1$ and $R_2$ are each independently an electron withdrawing group selected from the group consisting of —F; —CN; —NO$_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group; and p and q are each independently an integer from 1 to 9.

9. The amine-based compound of claim 8, wherein the amine-based compound is represented by Formula 1(1) in which at least one of p number of $R_1$ is —CN; or is represented by Formula 1(2) in which at least one of p number of $R_1$ and one of q number of $R_2$ is —CN.

10. The amine-based compound of claim 8, wherein the amine-based compound is represented by Formula 1(2) in which at least one of p number of $R_1$ and q number of $R_2$ is —CN.

11. The amine-based compound of claim 8, wherein the amine-based compound is represented by Formula 1(1) in which the A ring is a substituted phenyl group, a substituted biphenyl group, a substituted naphthyl group, a substituted anthryl group, a substituted phenanthrenyl group, a substituted pyrenyl group, or a substituted fluorenyl group; or wherein the amine-based compound is represented by Formula 1(2) in which the A and B ring are each independently a substituted phenyl group, a substituted biphenyl group, a substituted naphthyl group, a substituted anthryl group, a substituted phenanthrenyl group, a substituted pyrenyl group, or a substituted fluorenyl group.

12. The amine-based compound of claim 8, wherein the amine-based compound is represented by Formula 1(1), wherein the A ring is a substituted phenyl group, a substituted biphenyl group, a substituted naphthyl group, a substituted anthryl group, a substituted phenanthrenyl group, a substituted pyrenyl group, or a substituted fluorenyl group;

$R_1$ is at least one electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group; and p is 2, 3, or 4.

13. The amine-based compound of claim 8, wherein the amine-based compound is represented by Formula 1(2), wherein the A ring and the B ring are each independently is a substituted phenyl group, a substituted biphenyl group, a substituted naphthyl group, a substituted anthryl group, a substituted phenanthrenyl group, a substituted pyrenyl group, or a substituted fluorenyl group; $R_1$ and $R_2$ are each independently at least one electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_1$-$C_{20}$ alkyl group substituted with at least one —F, a $C_1$-$C_{20}$alkoxy group, a phenyl group, a naphthyl group, an anthryl group, a phenanthrenyl group, a pyrenyl group, a pyridinyl group, a triazinyl group, and a carbazolyl group; and p and q are each independently 2, 3, or 4.

14. The amine-based compound of claim 4, wherein the at least one of $Ar_1$ and $Ar_2$ is a phenyl group, a biphenyl group, a naphthyl group, a anthryl group, a phenanthrenyl group, a pyrenyl group, or a fluorenyl group that are substituted with at least one of the electron withdrawing groups.

15. The amine-based compound of claim 5, wherein the at least one of $Ar_1$ and $Ar_2$ is a phenyl group, a biphenyl group, a naphthyl group, a anthryl group, a phenanthrenyl group, a pyrenyl group, or a fluorenyl group that are substituted with at least one of the electron withdrawing groups.

16. The amine-based compound of claim 1, wherein $Ar_1$ and $Ar_2$ are each independently a substituted or unsubstituted phenyl group, a substituted or unsubstituted pentalenyl group, a substituted or unsubstituted indenylene group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinylene group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, or a substituted or unsubstituted phenonthrolinyl group, wherein the at least one of $Ar_1$ and $Ar_2$ is a phenyl group, a biphenyl group, a naphthyl group, an anthryl group, a phenanthrenyl group, a pyrenyl group, or a fluorenyl group that are substituted with at least one of the above-listed electron withdrawing groups.

17. The amine-based compound of claim 1, wherein $Ar_1$ and $Ar_2$ are each independently a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted chrysenyl group, a substituted or unsubstituted pyridinyl group, a substituted or unsubstituted pyrazinyl group, a substituted or unsubstituted pyrimidinyl group, a substituted or unsubstituted quinolyl group, a substituted or unsubstituted carbazolyl group, a substituted or unsubstituted triazinyl group, a substituted or unsubstituted dibenzothiophenyl group, a substituted or unsubstituted dibenzofuranyl group, or a substituted or unsubstituted phenanthrolinyl group, wherein at least one of $Ar_1$ and $Ar_2$ is a phenyl group, a biphenyl group, a naphthyl group, an anthryl group, a phenanthrenyl group, a pyrenyl group, or a fluorenyl group that are substituted with at least one electron withdrawing group selected from the group consisting of —F; —CN; a $C_1$-$C_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a triazinyl group, a benzoimidazolyl group, and a carbazolyl group that are substituted with at least one of a deuterium atom, —F, —Cl, —Br, —I, —CN, a hydroxyl group, —$NO_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, and a carbazolyl group.

18. The amine-based compound of claim 1, wherein $Ar_1$ and $Ar_2$ are linked by a single bond.

19. The amine-based compound of claim 1, wherein the amine-based compound is represented by one of Formulae 1A to 1J below:

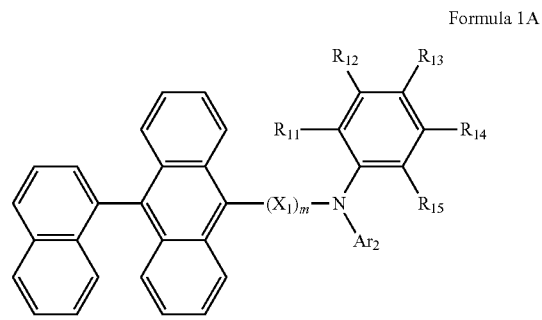

Formula 1A

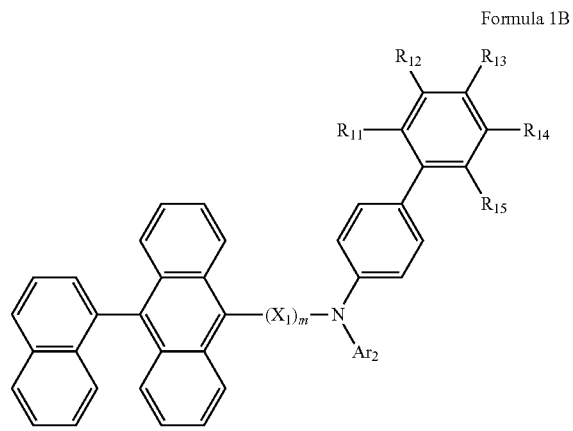

Formula 1B

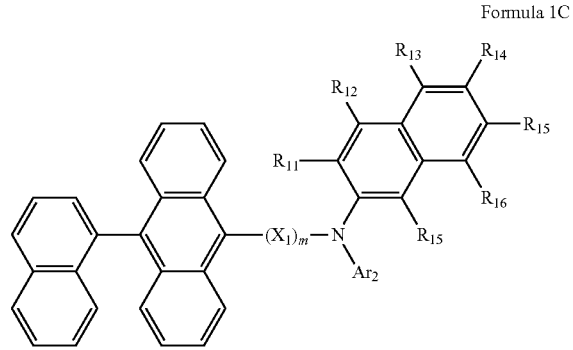

Formula 1C

-continued

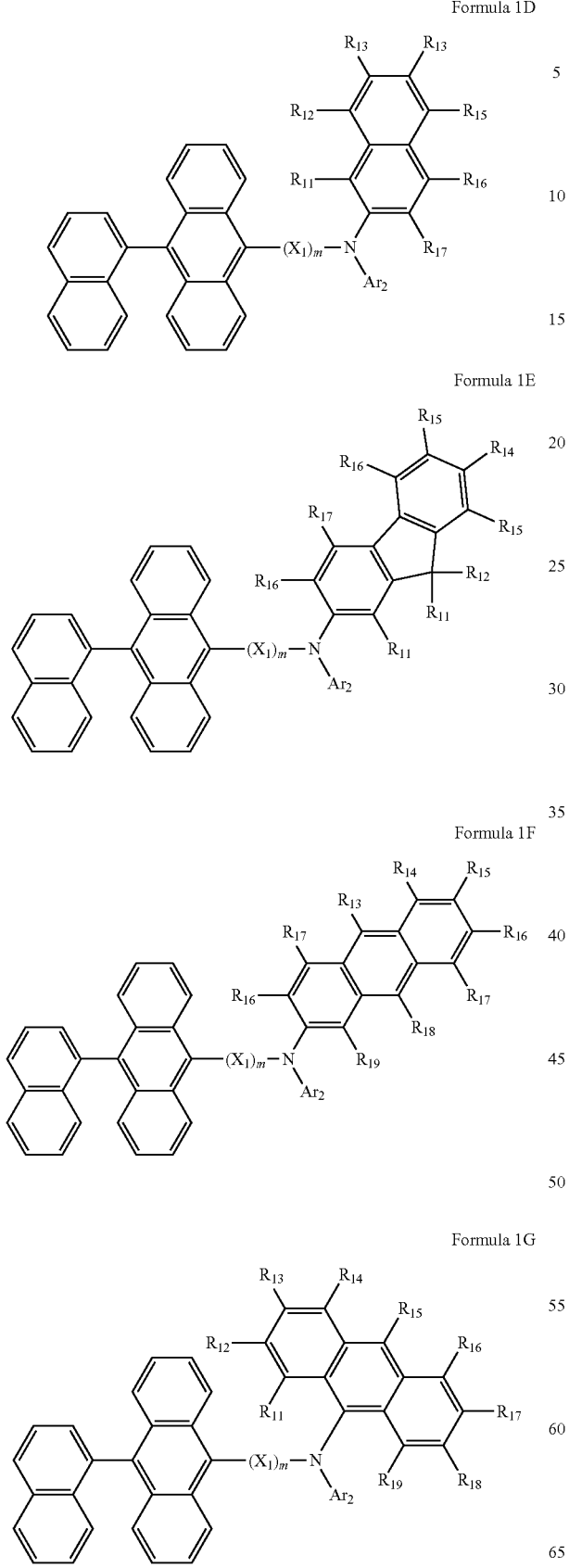

Formula 1D

Formula 1E

Formula 1F

Formula 1G

-continued

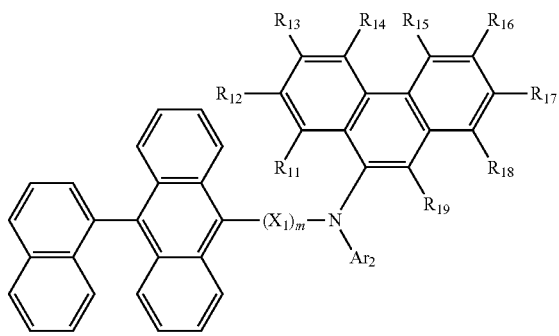

Formula 1H

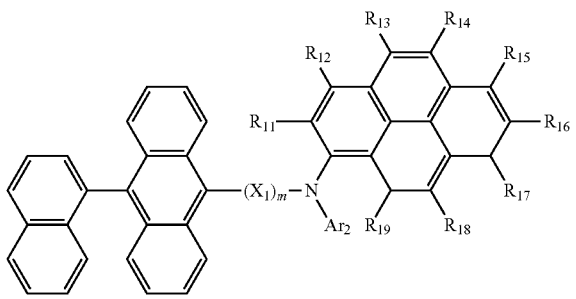

Formula 1I

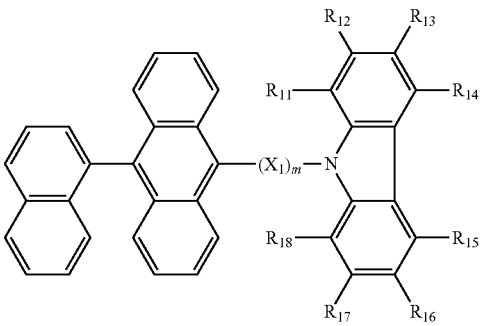

Formula 1J wherein, in Formulae 1A to 1J, $Ar_2$ is a substituted or unsubstituted phenyl group, a substituted or unsubstituted pentalenyl group, a substituted or unsubstituted indenylene group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, or a substituted or unsubstituted phenanthrolinyl group, substituents of the substituted phenyl group, the substituted pentalenyl group, the substituted indenyl group, the substituted naphthyl group, the substituted azulenyl group, the substituted heptalenyl group, the substituted indacenyl group, the substituted acenaphthyl group, the substituted fluorenyl group, the substituted phenalenyl group, the substituted phenanthrenyl group, the substituted anthryl group, the substituted fluoranthenyl group, the substituted triphenylenyl group, the substituted pyrenyl group, the substituted chrysenyl group, the substituted naphthacenyl group, the substituted picenyl, the substituted perylenyl group, the substituted pentaphenyl group, the substituted hexacenyl group, the substituted pyrrolyl group, the substituted pyrazolyl group, the substituted imidazolyl group, the substituted imidazolinyl group, the substituted imidazopyridinyl group, the substituted imidazopyrimidinyl group, the substituted pyridinyl group, the substituted pyrazinyl group, the substituted pyrimidinyl group, the substituted benzoimidazolyl group, the substituted indolyl group, the substituted purinyl group, the substituted quinolinyl group, the substituted phthalazinyl group, the substituted indolizinyl group, the substituted naphthyridinyl group, the substituted quinazolinyl group, the substituted cinolinyl group, the substituted indazolyl group, the substituted carbazolyl group, the substituted phenazinyl group, the substituted phenanthridinyl group, the substituted pyranyl group, the substituted chromenyl group, the substituted furanyl group, the substituted benzofuranyl group, the substituted thiophenyl group, the substituted benzothiophenyl group, the substituted isothiazolyl group, the substituted benzoimidazolyl group, the substituted isoxazolyl group, the substituted dibenzothiophenyl group, the substituted dibenzofuranyl group, the substituted triazinyl group, the substituted oxadiazolyl group, the substituted pyridazinyl group, the substituted triazolyl group, the substituted tetrazolyl group, and the substituted phenanthrolinyl group, and $R_{11}$ to $R_{19}$ are each independently a hydrogen atom; a deuterium atom; —F; —Cl; —Br; —I; —CN; a hydroxyl group; —NO$_2$; an amino group; an amidino group; hydrazine; hydrazone; a carboxyl group or a salt thereof; a sulfonic acid group or a salt thereof; phosphoric acid or a salt thereof; a tri($C_6$-$C_{60}$aryl)silyl group; a $C_1$-$C_{60}$ alkyl group, a $C_1$-$C_{60}$ alkoxy group, a $C_2$-$C_{60}$ alkenyl group, and a $C_2$-$C_{60}$ alkynyl group; a $C_1$-$C_{60}$ alkyl group, a $C_1$-$C_{60}$ alkoxy group, a $C_2$-$C_{60}$ alkenyl group and a $C_2$-$C_{60}$ alkynyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, and phosphoric acid or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group; and a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthiol group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group and a $C_2$-$C_{60}$ heteroaryl group, wherein at least one of $R_{11}$ to $R_{15}$ in Formulae 1A and 1B, at least one of $R_{11}$ to $R_{17}$ in Formulae 1C and 1D, at least one of $R_{11}$ to $R_{18}$ in Formulae 1E and 1J, and at least one of $R_{11}$ to $R_{19}$ in Formula 1F, 1G, 1H and 1I are each independently an electron withdrawing group selected from the group consisting of —F; —CN; —NO$_2$; a $C_1$-$C_{60}$ alkyl group substituted with at least one —F; a $C_2$-$C_{60}$ heteroaryl group; and a $C_2$-$C_{60}$ heteroaryl group substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

20. The amine-based compound of claim 19, wherein $Ar_1$ is a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted chrysenyl group, a substituted or unsubstituted pyridinyl group, a substituted or unsubstituted pyrazinyl group, a substituted or unsubstituted pyrimidinyl group, a substituted or unsubstituted quinolinyl group, a substituted or unsubstituted carbazolyl group, a substituted or unsubstituted triazinyl group, or a substituted or unsubstituted phenanthrolinyl group; and at least one of $R_{11}$ to $R_{15}$ of Formulae 1A and 1B, at least one of $R_{11}$ to $R_{17}$ in Formulae 1C and 1D, at least one of $R_{11}$ to $R_{18}$ of Formulae 1E and 1J, and at least one of $R_{11}$ to $R_{19}$ of Formulae 1F to 1I are each independently an electron withdrawing group selected from the group consisting of: —F; —CN; —NO$_2$; a C$_1$-C$_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; a pyridinyl group, a pyrazinyl group, a pyrimidinyl group, a quinolinyl group, an isoquinolinyl group, a quinazolinyl group, a phthalazinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid or a salt thereof, a C$_1$-C$_{20}$ alkyl group, a C$_1$-C$_{20}$ alkyl group substituted with at least one —F, a C$_1$-C$_{20}$ alkoxy group, a phenyl group, a naphthyl group, an anthryl group, a phenanthrenyl group, a pyrenyl group, a pyridinyl group, a triazinyl group, and a carbazolyl group.

21. The amine-based compound of claim 19, wherein Ar$_2$ is a phenyl group, a biphenyl group, a naphthyl group, an anthryl group, a phenanthrenyl group, a pyrenyl group, or a fluorenyl group that are substituted with at least one electron withdrawing group selected from the group consisting of —F; —CN; —NO$_2$; a C$_1$-C$_{20}$ alkyl group substituted with at least one —F; a pyridinyl group, a pyrazinyl group, a pyrimidinyl group, a quinolinyl group, an isoquinolinyl group, a quinazolinyl group, a triazinyl group, a benzoimidazolyl group, a carbazolyl group; a pyridinyl group, a pyrazinyl group, a pyrimidinyl group, a quinolinyl group, an isoquinolinyl group, a quinazolinyl group, a phthalazinyl group, a triazinyl group, a benzoimidazolyl group, and a carbazolyl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a C$_1$-C$_{20}$ alkyl group, a C$_1$-C$_{20}$ alkyl group substituted with at least one —F, a C$_1$-C$_{20}$ alkoxy group, a phenyl group, a naphthyl group, an anthryl group, a phenanthrenyl group, a pyrenyl group, a pyridinyl group, a triazinyl group, and a carbazolyl group.

22. The amine-based compound of claim 1, wherein the amine-based compound is represented by Formula 1A-(1) or 1A-(2) below:

Formula 1A-(1)

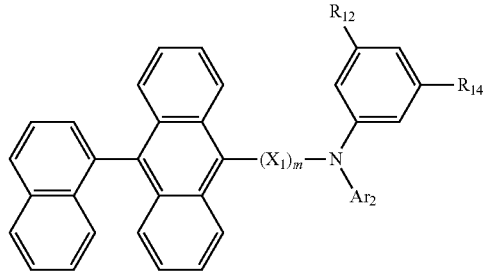

Formula 1A-(2)

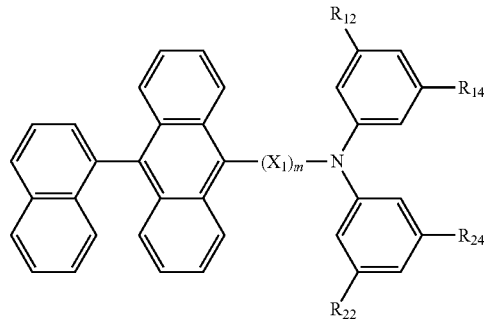

wherein, in Formulae 1A-(1) and 1A-(2), $R_{12}$, $R_{14}$, $R_{22}$, and $R_{24}$ are each independently be an electron withdrawing group selected from the group consisting of a pyridinyl group, a pyrazinyl group, a pyrimidinyl group, a quinolinyl group, an isoquinolinyl group, a quinazolinyl group, a triazinyl group, a benzoimidazolyl group, and a carbazolyl group; and a pyridinyl group, a pyrazinyl group, a pyrimidinyl group, a quinolinyl group, an isoquinolinyl group, a quinazolinyl group, a phthalazinyl group, a benzoimidazolyl group, and a carbazolyl group that are substituted with at least one of a deuterium atom, —F, —Cl, —Br, —I, —CN; a hydroxyl group, —NO$_2$, an amino group, an amidino group, hydrazine, hydrazone, a carboxyl group or a salt thereof, a sulfonic acid group or a salt thereof, a phosphoric acid or a salt thereof, a C$_1$-C$_{20}$ alkyl group, a C$_1$-C$_{20}$ alkyl group substituted with at least one —F, a C$_1$-C$_{20}$ alkoxy group, a phenyl group, a naphthyl group, an anthryl group, a phenanthrenyl group, a pyrenyl group, a pyridinyl group, a triazinyl group, and a carbazolyl group; and Ar$_2$ is a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, or a substituted or unsubstituted fluorenyl group.

23. The amine-based compound of claim 1, wherein $R_{12}$, $R_{14}$, $R_{22}$ and $R_{24}$ are each independently selected from the group consisting of —F; —CN; —CH$_2$F; —CHF$_2$; —CF$_3$; and groups represented by Formulae 2(1) to 2(14) below:

Formula 2(1)

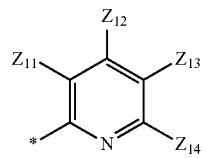

Formula (2)2

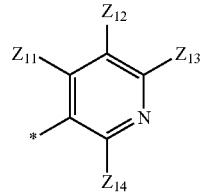

-continued

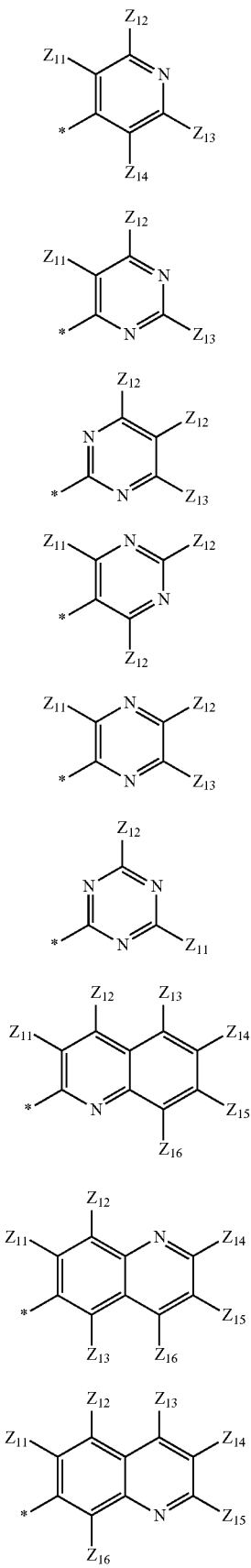

Formula 2(3)
Formula 2(4)
Formula 2(5)
Formula 2(6)
Formula 2(7)
Formula 2(8)
Formula 2(9)
Formula 2(10)
Formula 2(11)

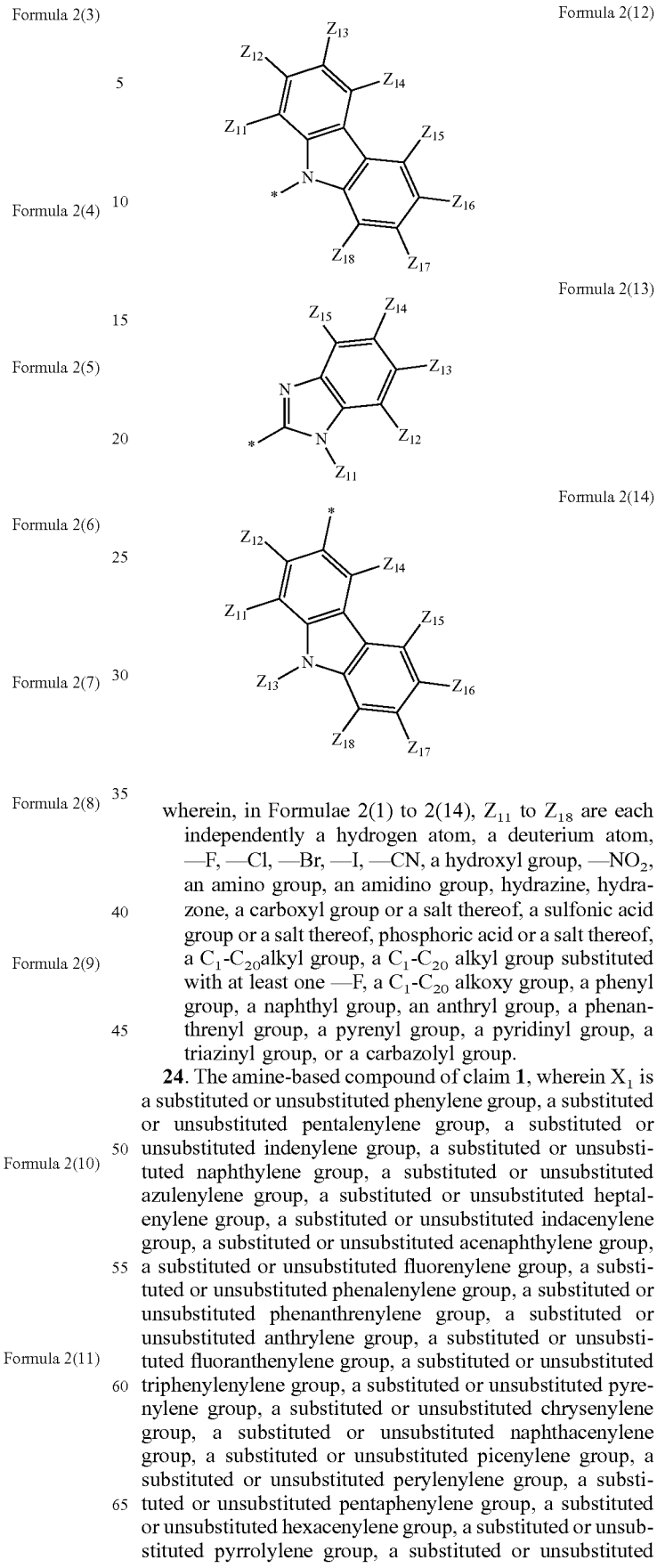

Formula 2(12)
Formula 2(13)
Formula 2(14)

wherein, in Formulae 2(1) to 2(14), $Z_{11}$ to $Z_{18}$ are each independently a hydrogen atom, a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkyl group substituted with at least one —F, a $C_1$-$C_{20}$ alkoxy group, a phenyl group, a naphthyl group, an anthryl group, a phenanthrenyl group, a pyrenyl group, a pyridinyl group, a triazinyl group, or a carbazolyl group.

24. The amine-based compound of claim 1, wherein $X_1$ is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, a substituted or unsubstituted oxadiazolylene group, a substituted or unsubstituted pyridazinylene group, a substituted or unsubstituted triazolylene group, or a substituted or unsubstituted tetrazolylene group.

25. The amine-based compound of claim 1, wherein $X_1$ is a substituted or unsubstituted phenylene group, a substituted or unsubstituted naphthylene group, a substituted or unsubstituted fluorenylene group, a substituted or unsubstituted phenanthrenylene group, a substituted or unsubstituted anthrylene group, a substituted or unsubstituted triphenylenylene group, a substituted or unsubstituted pyrenylene group, a substituted or unsubstituted chrysenylene group, a substituted or unsubstituted pyridinylene group, a substituted or unsubstituted pyrazinylene group, a substituted or unsubstituted pyrimidinylene group, a substituted or unsubstituted quinolinylene group, a substituted or unsubstituted quinazolinylene group, a substituted or unsubstituted carbazolylene group, a substituted or unsubstituted dibenzothiophenylene group, a substituted or unsubstituted dibenzofuranylene group, a substituted or unsubstituted triazinylene group, a substituted or unsubstituted pyridazinylene group, a substituted or unsubstituted triazolylene group, or a substituted or unsubstituted tetrazolylene group.

26. The amine-based compound of claim 1, wherein $X_1$ is a group represented by one of Formulae 5(1) to 5(16) below:

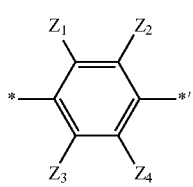

Formula 5(1)

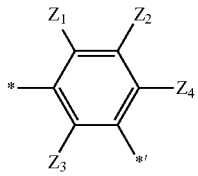

Formula 5(2)

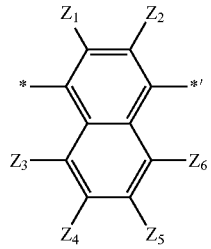

Formula 5(3)

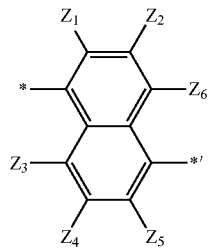

Formula 5(4)

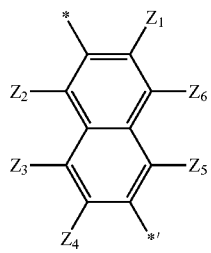

Formula 5(5)

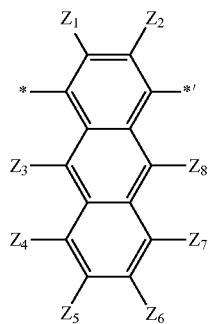

Formula 5(6)

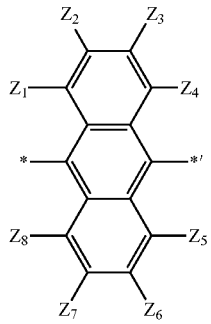

Formula 5(7)

-continued

Formula 5(8)

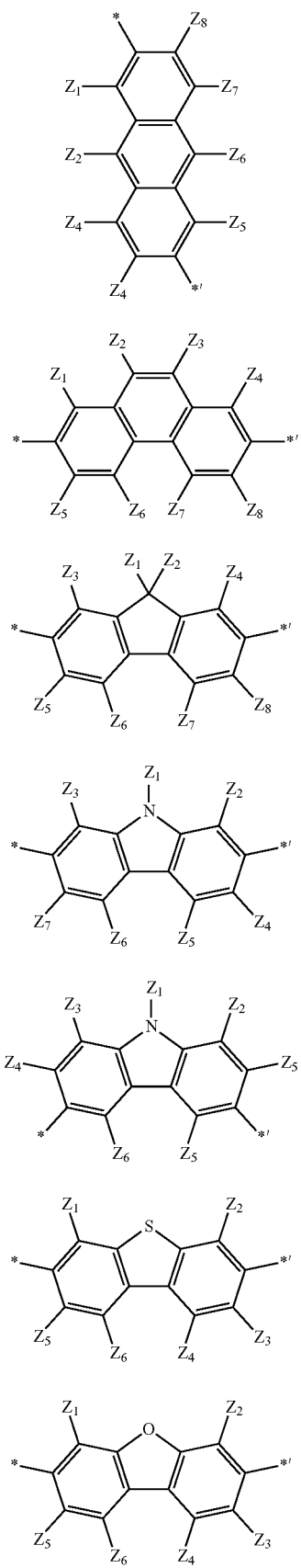

Formula 5(9)

Formula 5(10)

Formula 5(11)

Formula 5(12)

Formula 5(13)

Formula 5(14)

Formula 5(15)

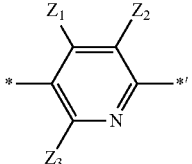

Formula 5(16)

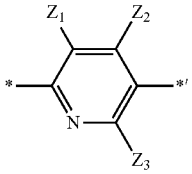

wherein, in Formulae 5(1) to 5(16), $Z_1$ to $Z_8$ are each independently one of a hydrogen atom; a deuterium atom; —F; —Cl; —Br; —I; —CN; a hydroxyl group; —NO$_2$; an amino group; an amidino group; hydrazine; hydrazone; a carboxyl group or a salt thereof; a sulfonic acid group or a salt thereof; phosphoric acid or a salt thereof; a $C_1$-$C_{20}$ alkyl group; a $C_1$-$C_{20}$ alkoxy group; a $C_1$-$C_{20}$ alkyl group and a $C_1$-$C_{20}$ alkoxy groups that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, sulfonic acid group or a salt thereof, and phosphoric acid or a salt thereof; a $C_6$-$C_{20}$ aryl group; a $C_2$-$C_{20}$ heteroaryl group; and a $C_6$-$C_{20}$ aryl group and a $C_2$-$C_{20}$ heteroaryl group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, phosphoric acid or a salt thereof, a $C_1$-$C_{20}$ alkyl group, a $C_1$-$C_{20}$ alkoxy group, a $C_6$-$C_{20}$ aryl group and a $C_2$-$C_{20}$ heteroaryl group;

wherein * indicates a binding site to anthracene in Formula 1; and wherein *' indicates a binding site to N in Formula 1.

27. The amine-based compound of claim 26, wherein $Z_1$ to $Z_8$ are each independently one of a hydrogen atom; a deuterium atom; —F; —Cl; —Br; —I; —CN; a hydroxyl group; —NO$_2$; an amino group; an amidino group; hydrazine; hydrazone; a carboxyl group or a salt thereof; a sulfonic acid group or a salt thereof; a phosphoric acid or a salt thereof; a methyl group, an ethyl group, a propyl group, a butyl group, and a pentyl group; a methoxy group, an ethoxy group, a propoxy group, a butoxy group, and a pentoxy group; a methyl group, an ethyl group, a propyl group, a butyl group, a pentyl group, a methoxy group, an ethoxy group, a propoxy group, a butoxy group, and a pentoxy group that are substituted with at least one of a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, and a phosphoric acid or a salt thereof; a phenyl group, a naphthyl group, an anthryl group, a phenanthrenyl group, a pyrenyl group, and a fluorenyl group; a pyridinyl group, a pyrimidinyl group, a triazinyl group, a quinolyl group, and a carbazolyl group; a phenyl group, a naphthyl group, an anthryl group, a phenanthrenyl group, a pyrenyl group, a fluorenyl group, a pyridinyl group, a pyrimidinyl group, a triazinyl group, a quinolyl group, and a carbazolyl group that are substituted with at least one of a deuterium atom, —F, —Cl, —Br, —I, —CN, a hydroxyl group, —NO₂, an amino group, an amidino group, hydrazine, hydrazone, a carboxyl group or a salt thereof, a sulfonic acid group or a salt thereof, a phosphoric acid or a salt thereof, a $C_1$-$C_{20}$alkyl group, and a $C_1$-$C_{20}$alkoxy group.

28. The amine-based compound of claim 1, wherein m is 1, 2, or 3.

29. The amine-based compound of claim 1, wherein the amine-based compound is one of Compounds 1 to 109 below:

1
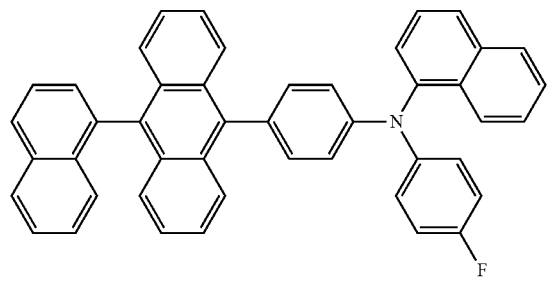

2
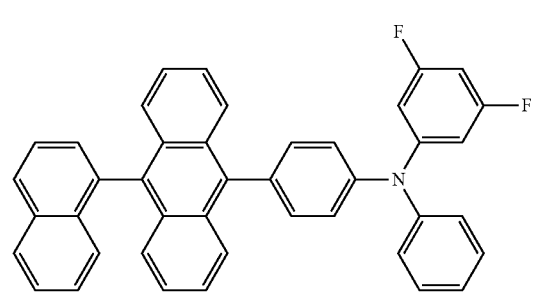

3
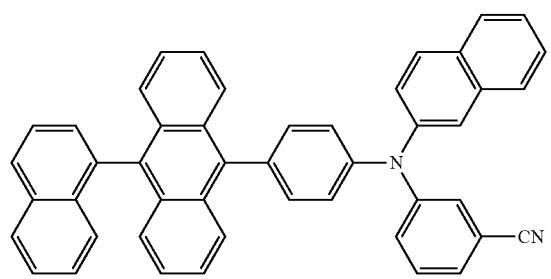

4
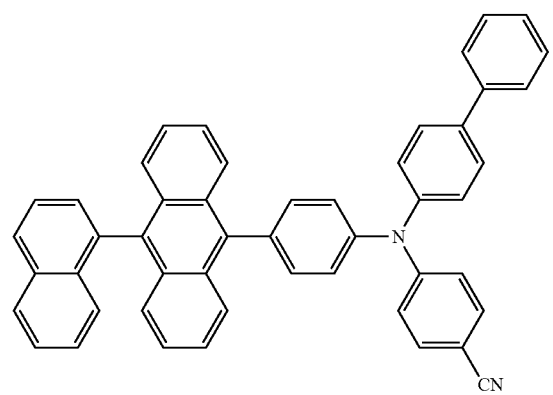

5
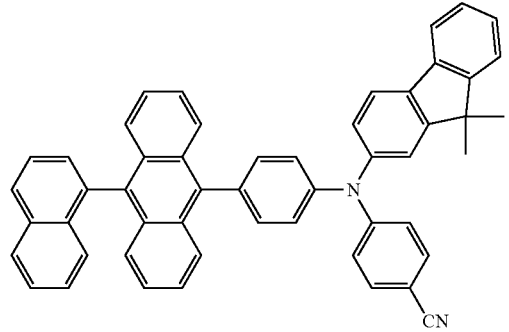

6
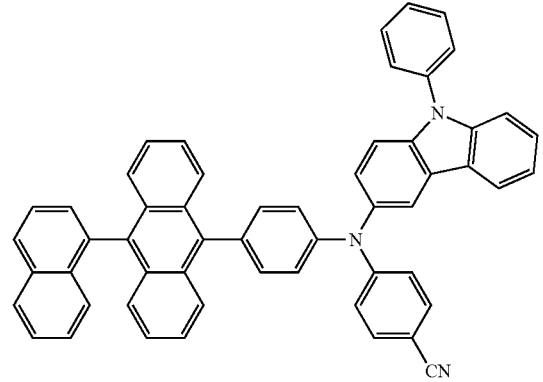

7
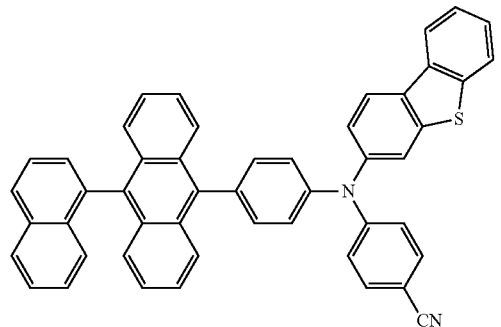

8
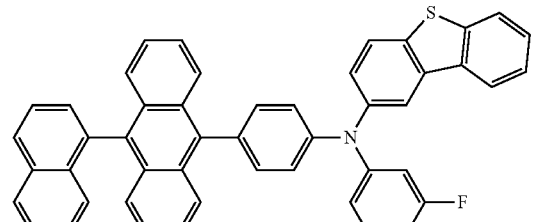

-continued
9
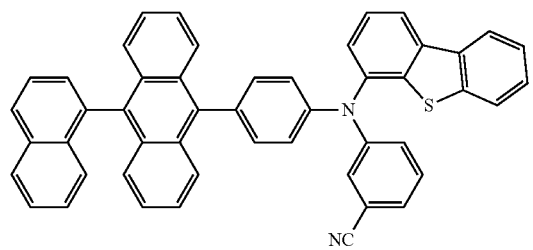
10
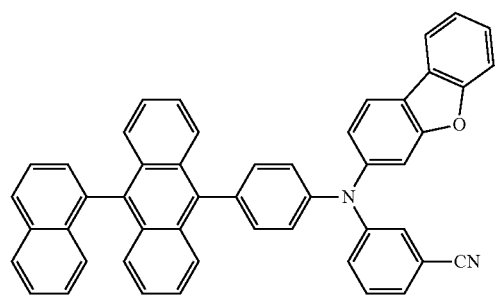
11
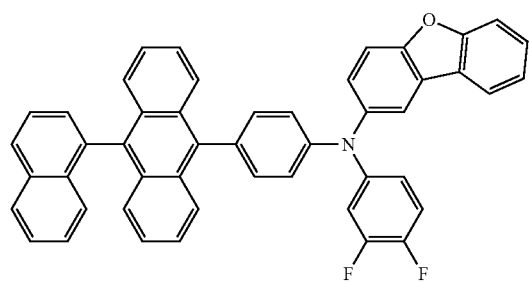
12
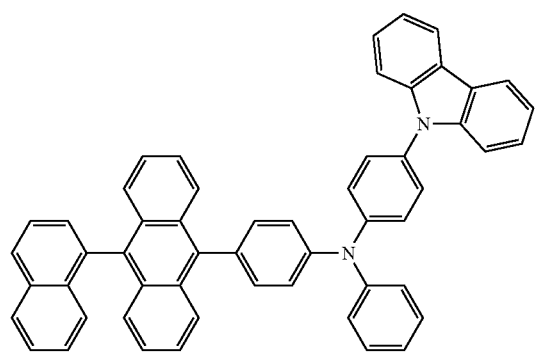
13
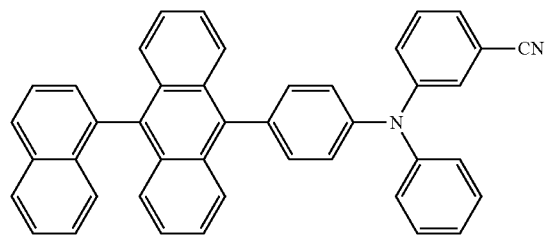
14
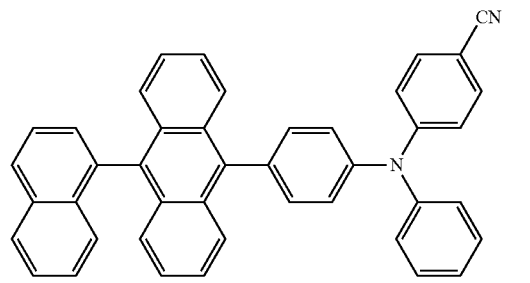
15
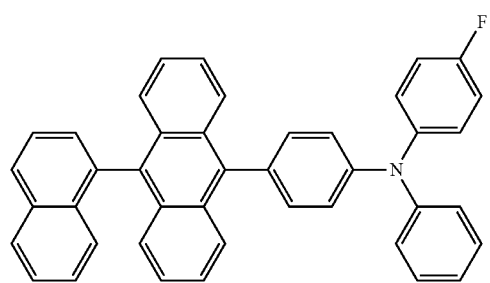
16
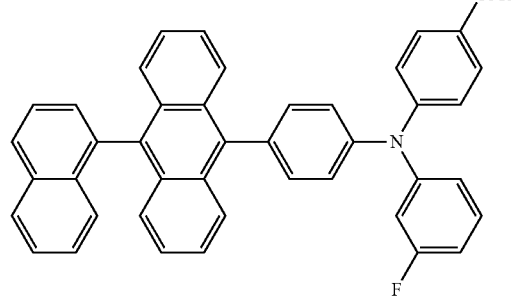
17
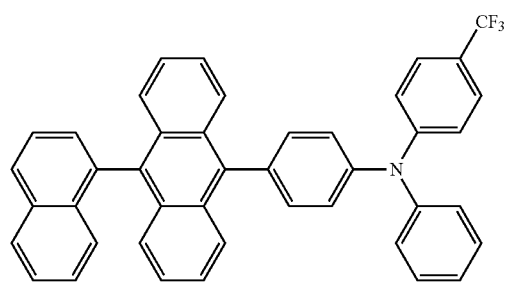
18
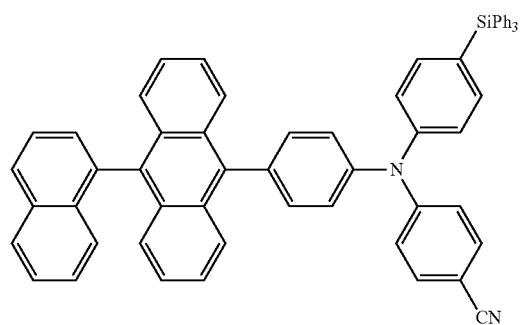

-continued
19
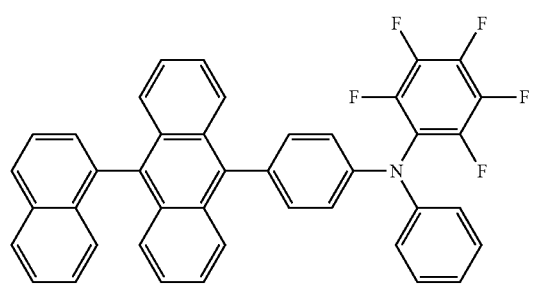
20
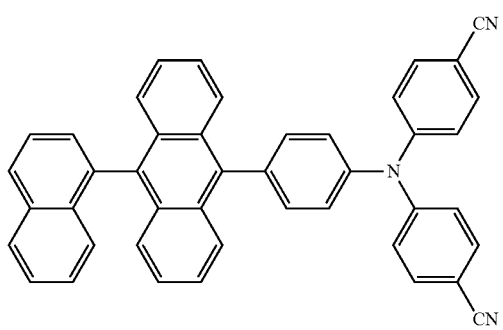
21
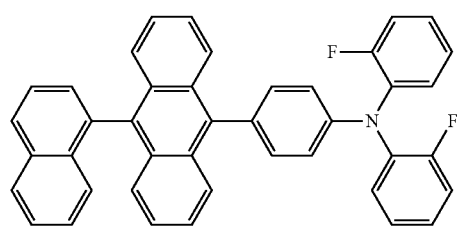
22
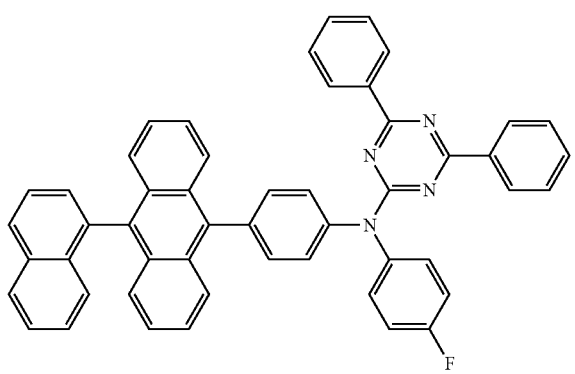
23
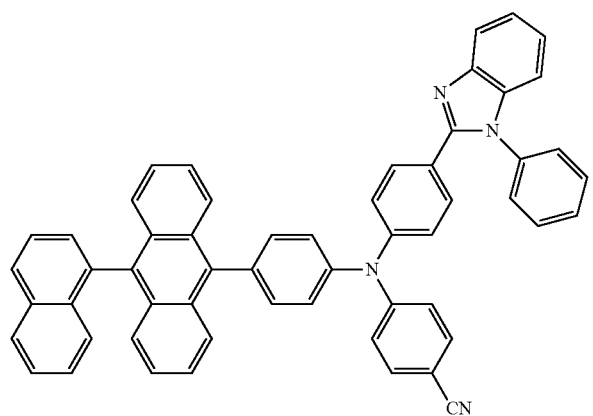
24
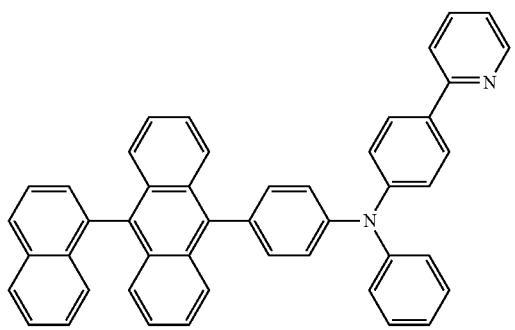
25
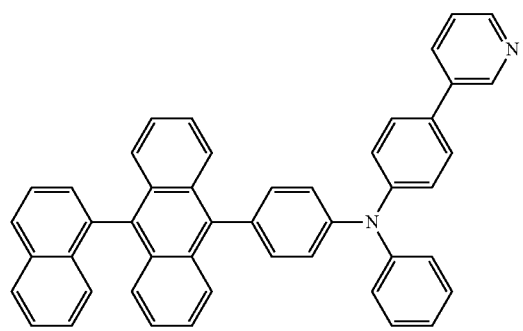
26
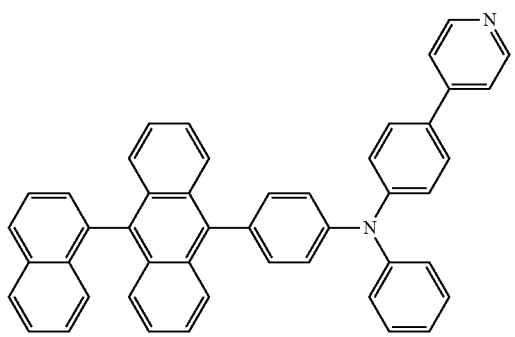

-continued
27
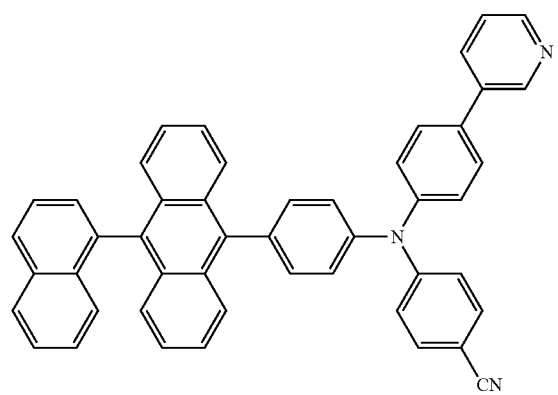
28
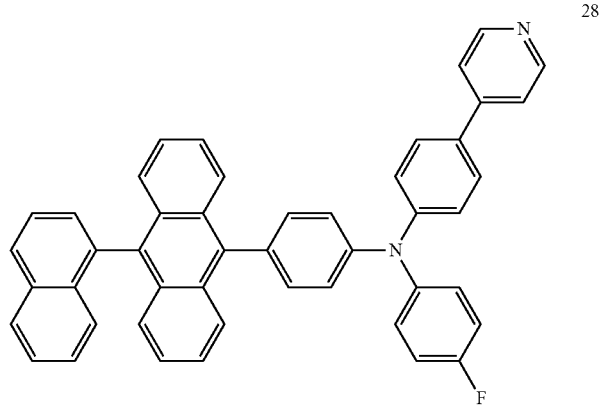
29
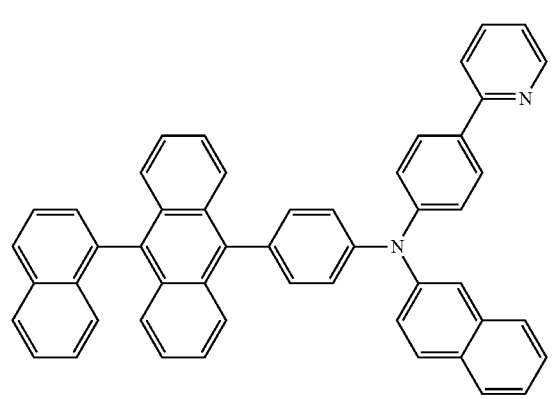
30
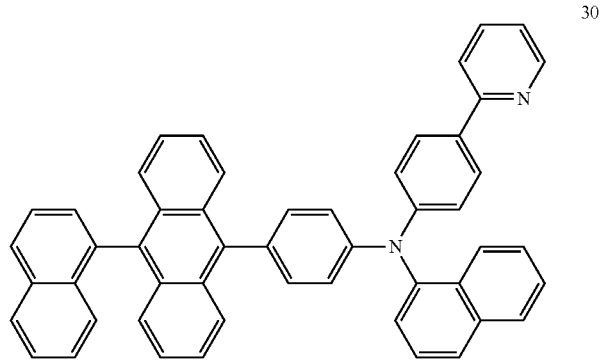
31
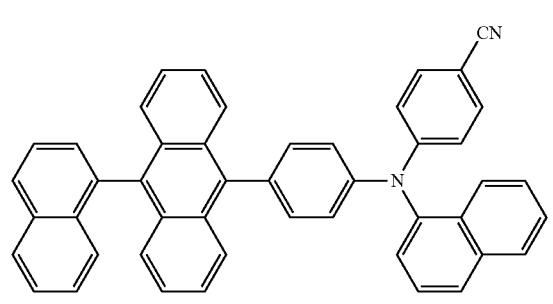
32
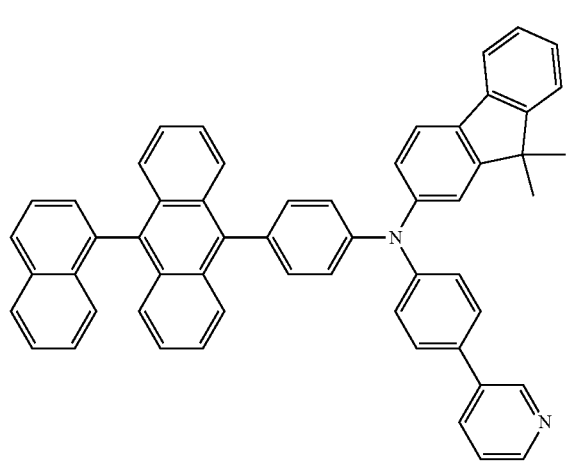

-continued
33
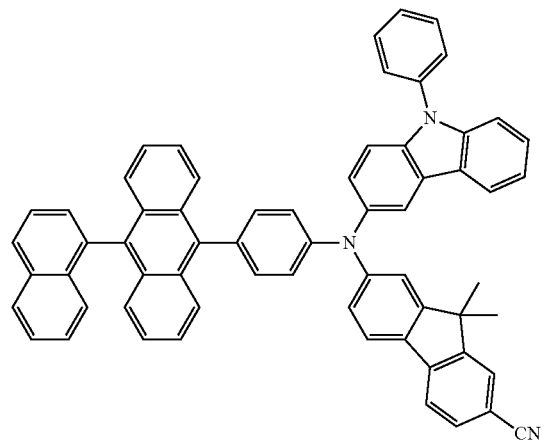
34
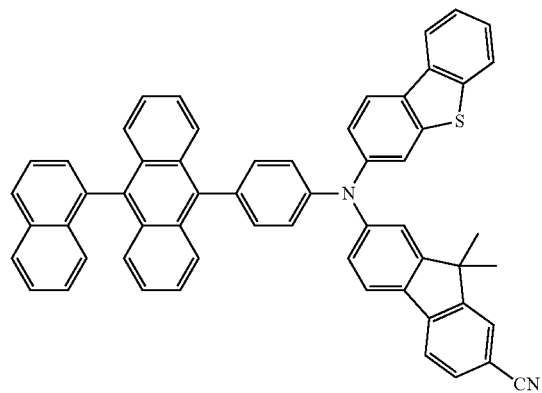
35
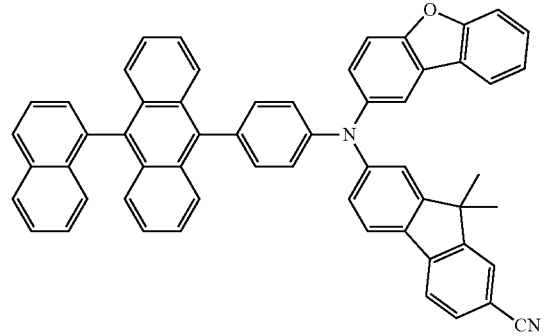
36
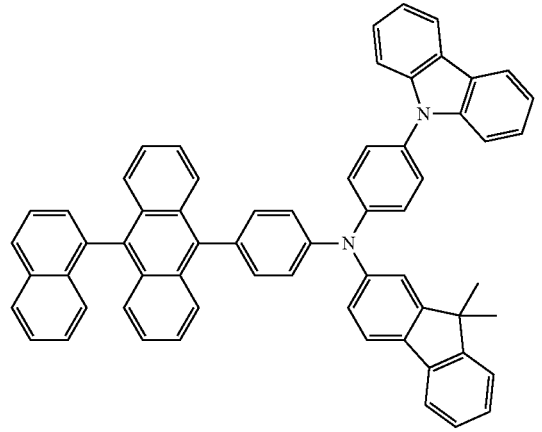
37
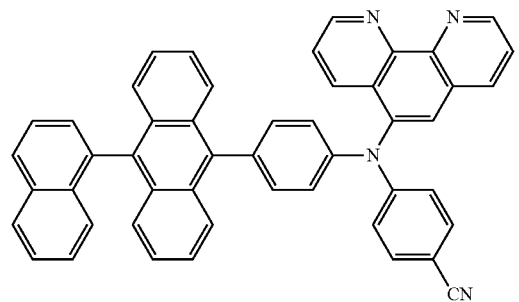
38
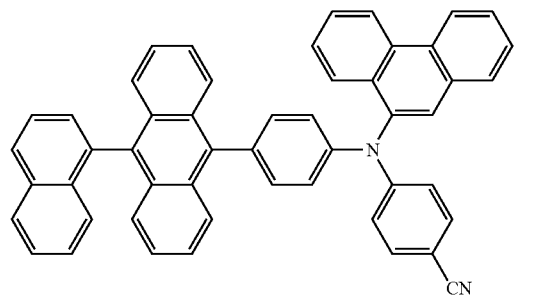
39
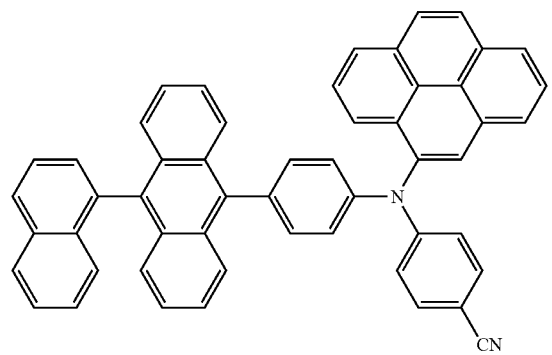
40
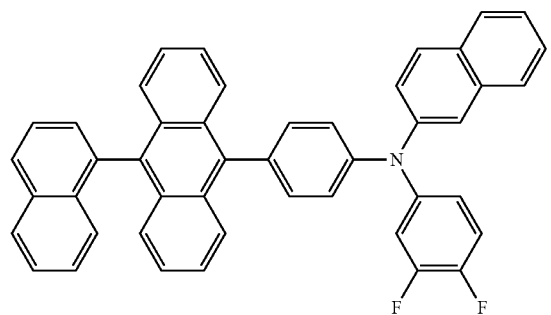

-continued
41
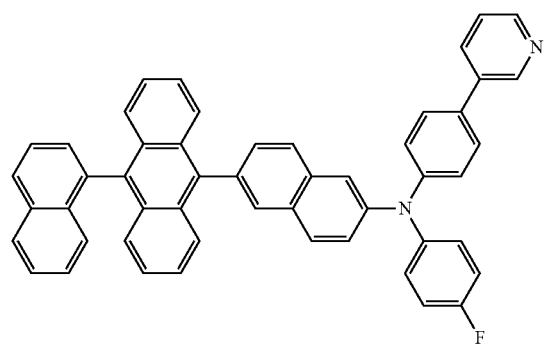
42
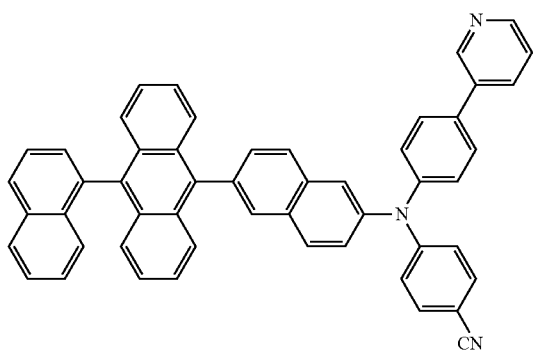
43
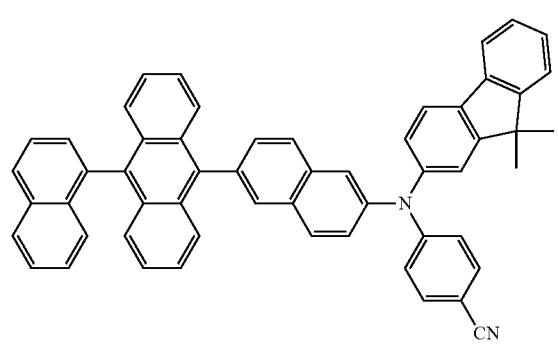
44
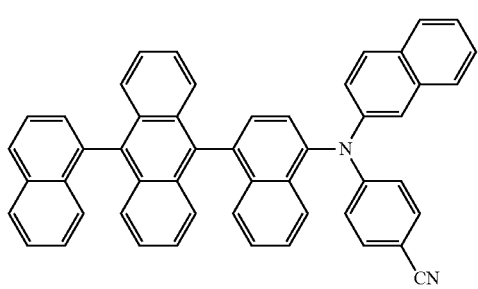
45
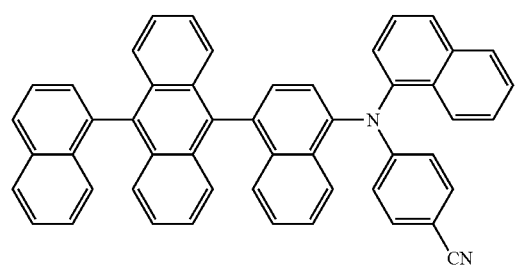
46
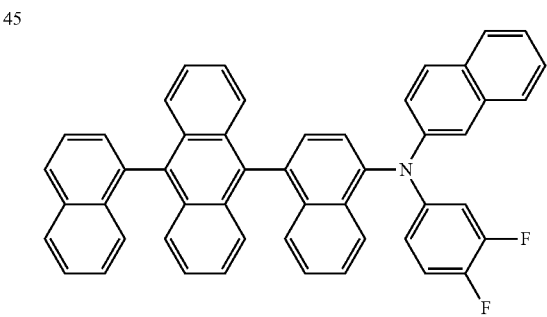
47
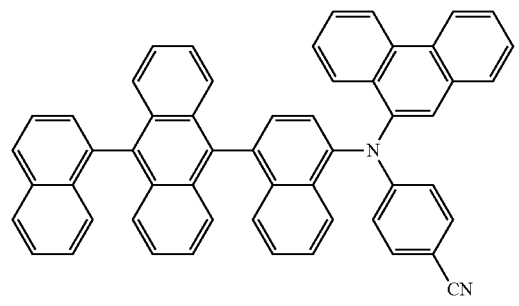
48
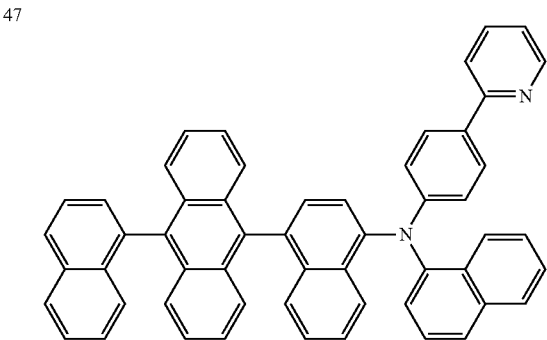

-continued
49
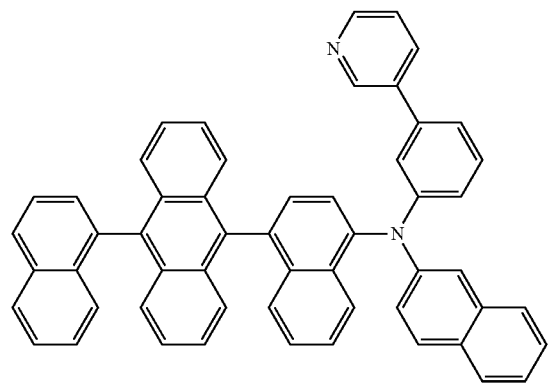
51
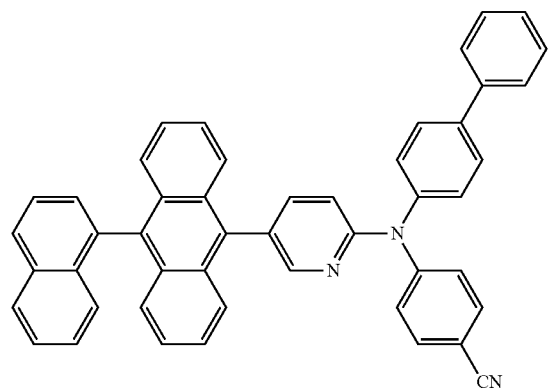
53
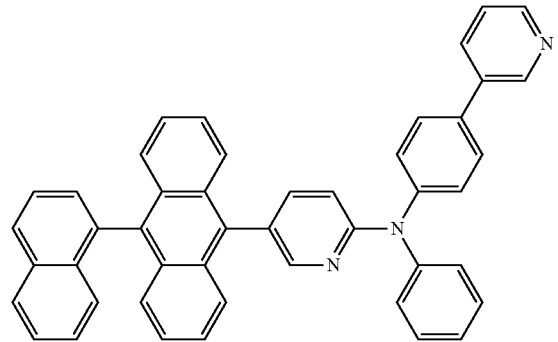
55
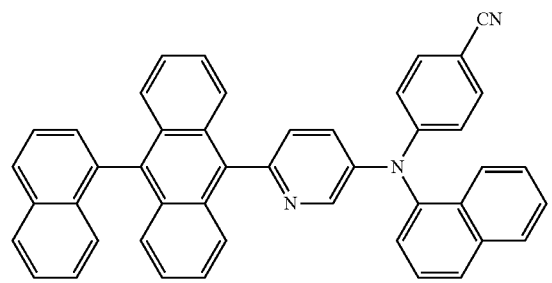
50
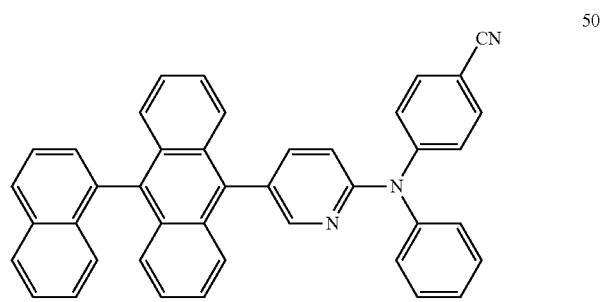
52
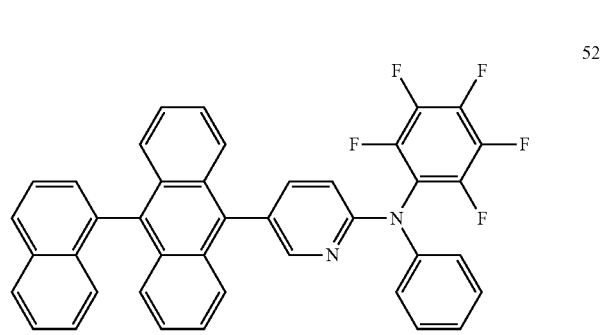
54
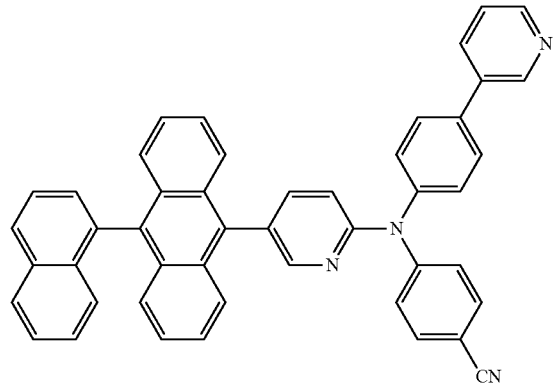
56
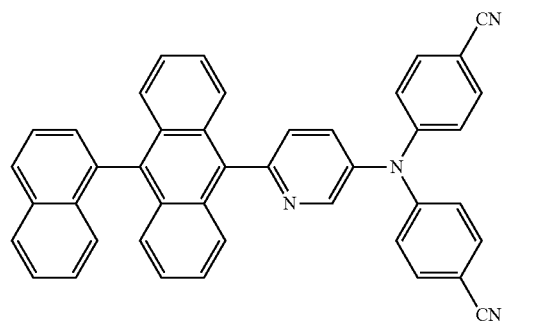

-continued
57
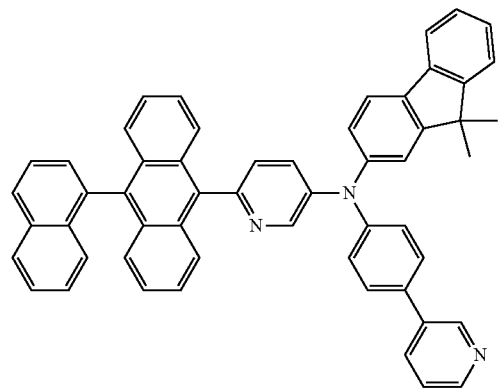
58
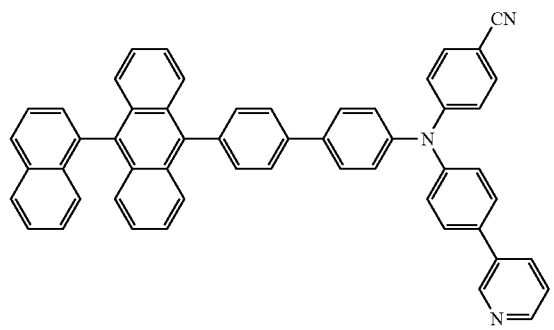
59
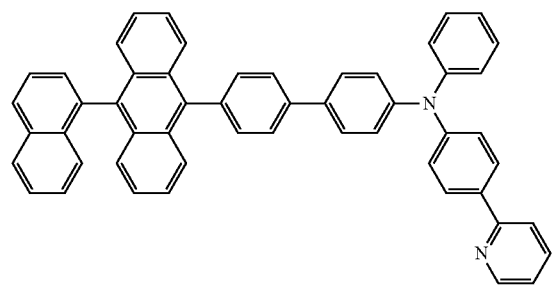
60
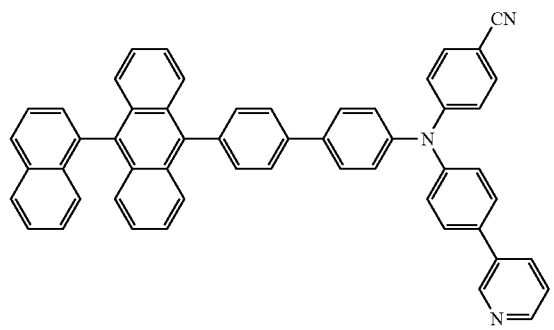
61
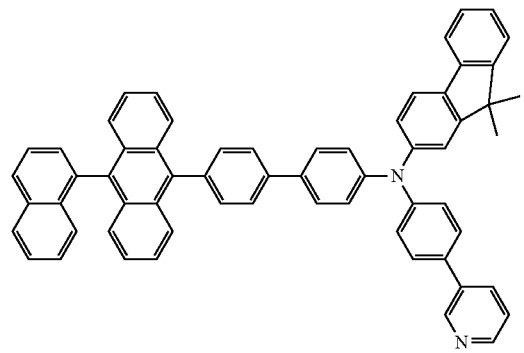
62
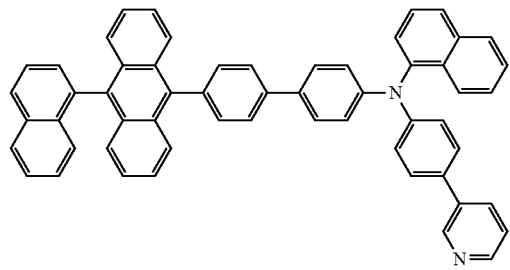
63
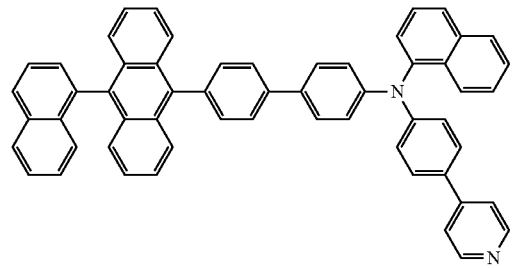
64
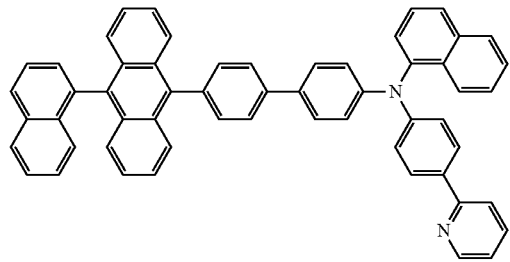
65
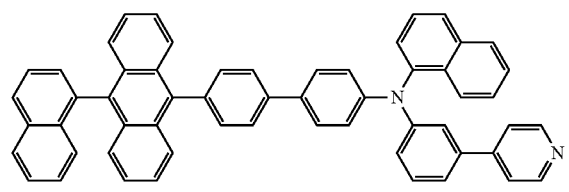
66
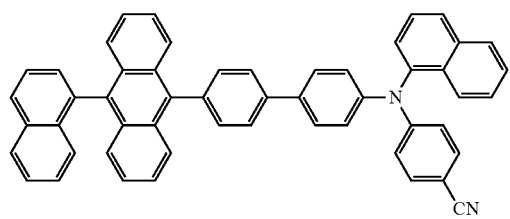

-continued
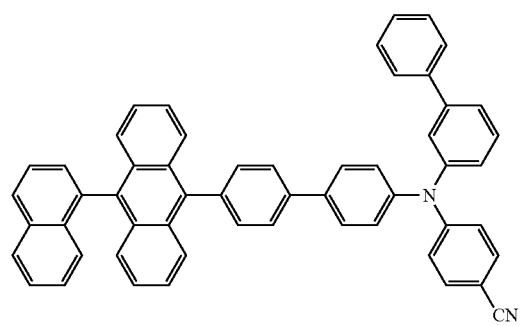
67
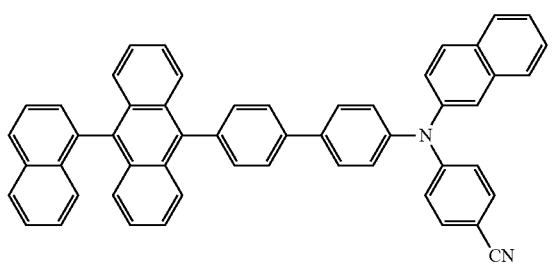
68
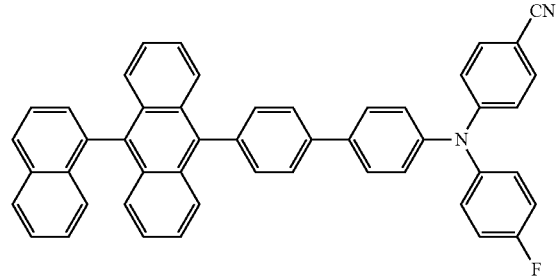
69
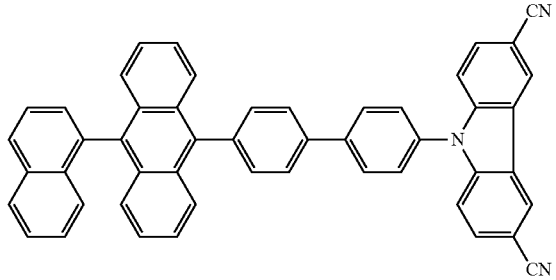
70
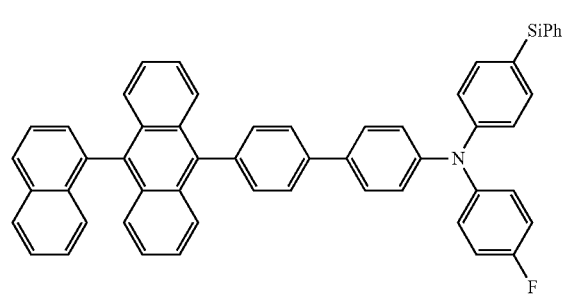
71
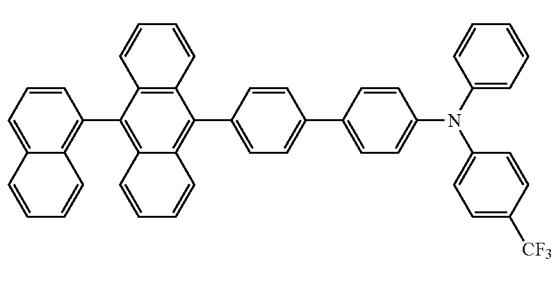
72
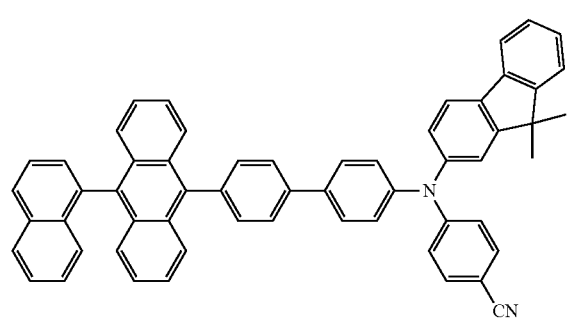
73
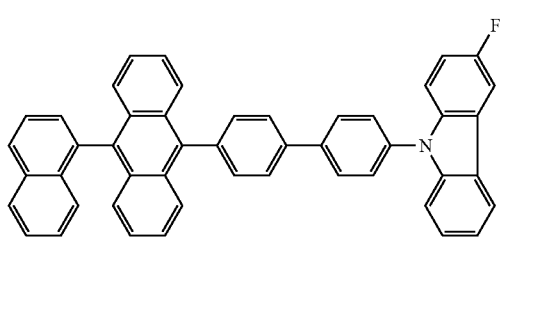
74
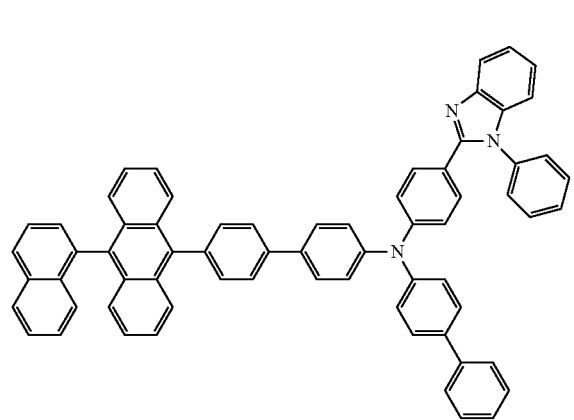
75
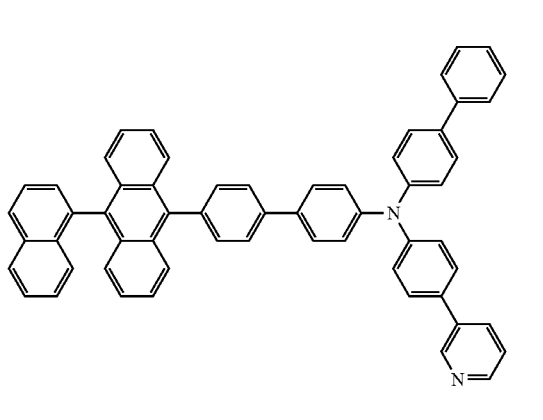
76

-continued
77
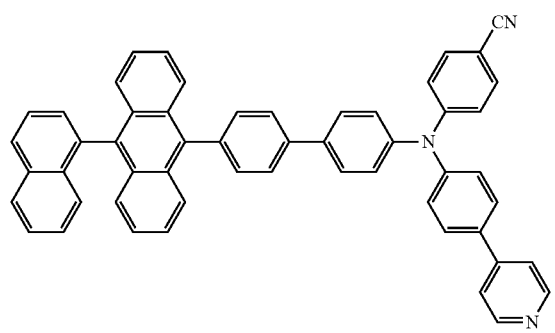
78
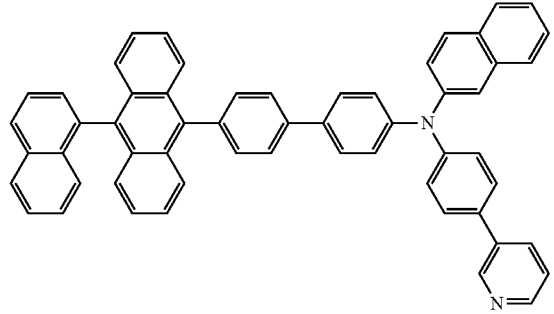
79
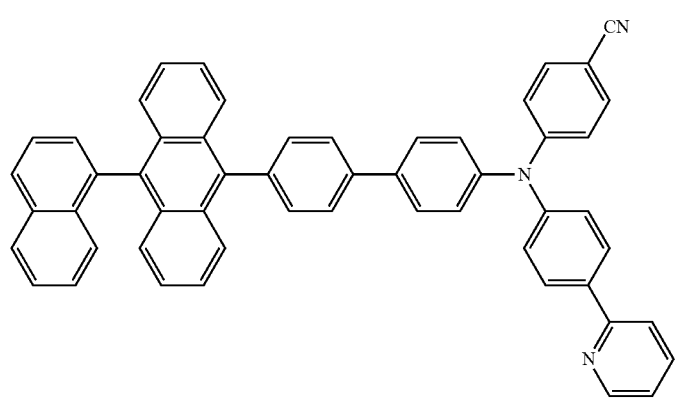
80
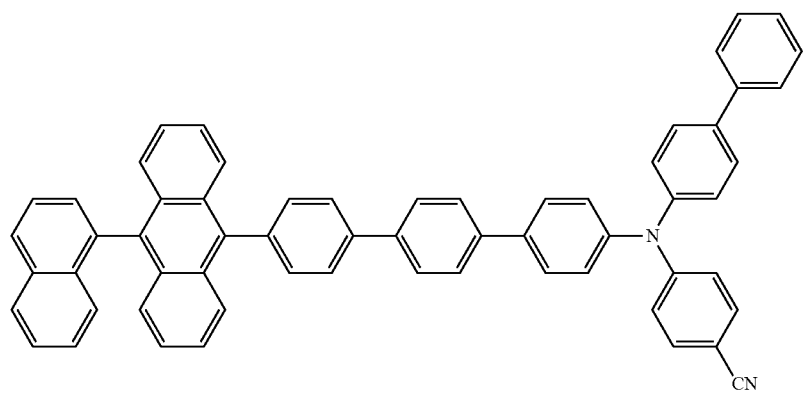
81
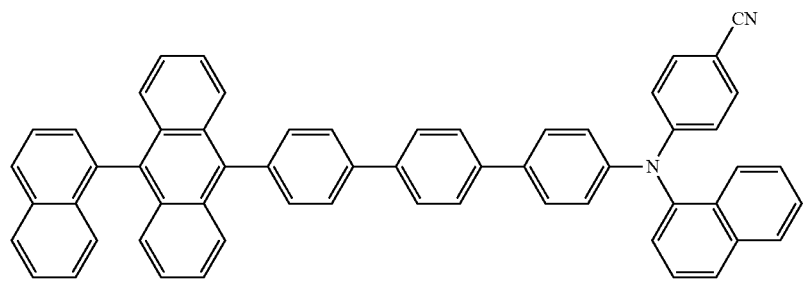

-continued
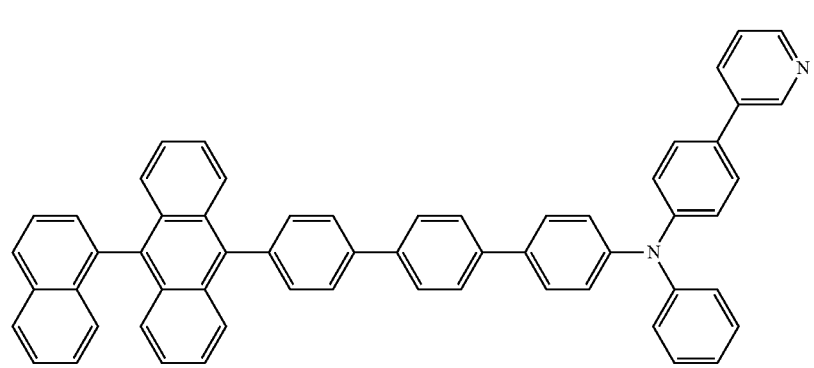
82
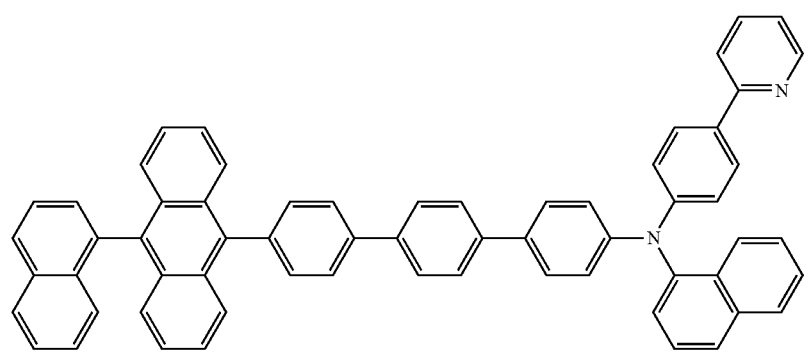
83
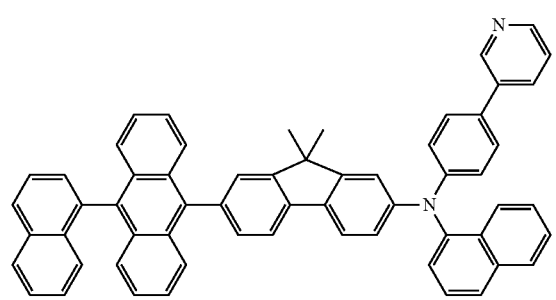
84
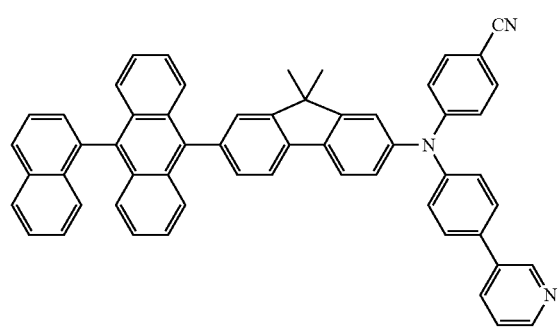
85
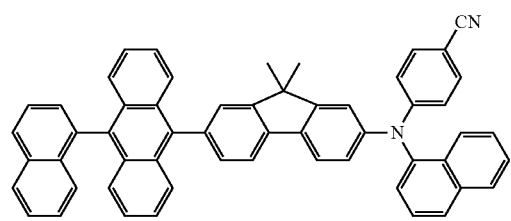
86
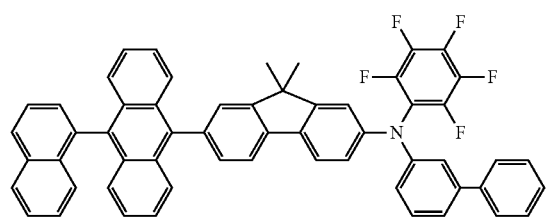
87
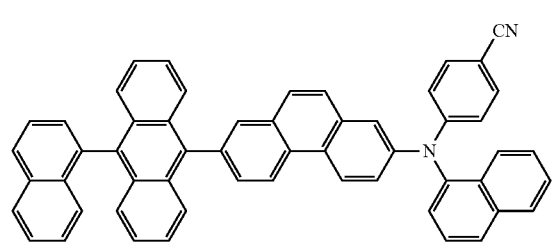
88
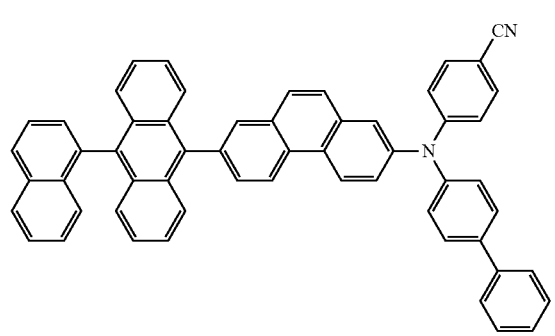
89

-continued
90
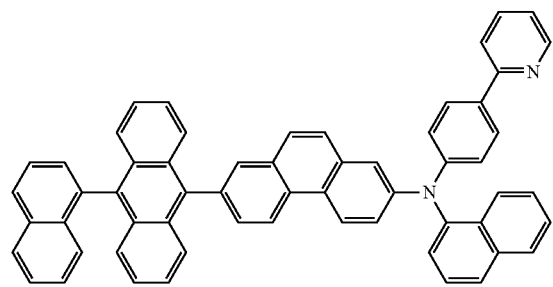
91
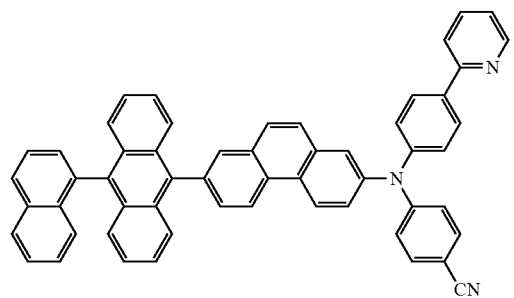
92
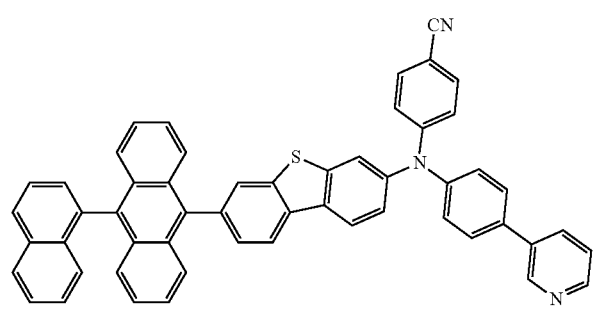
93
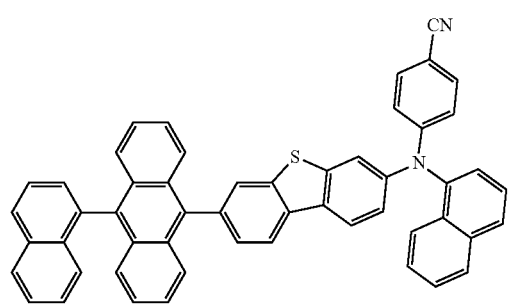
94
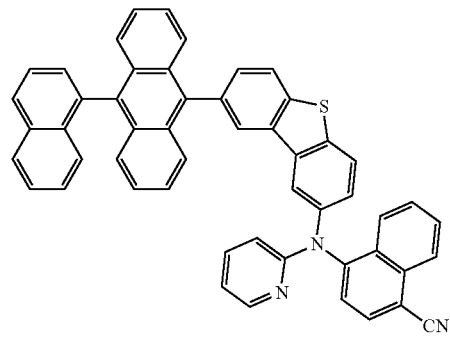
95
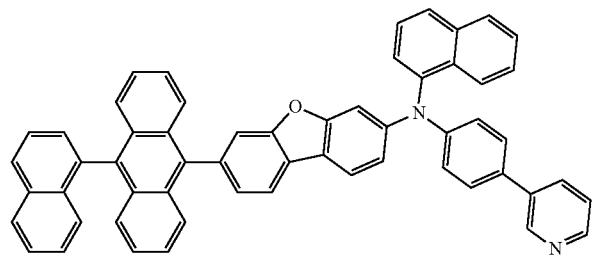
96
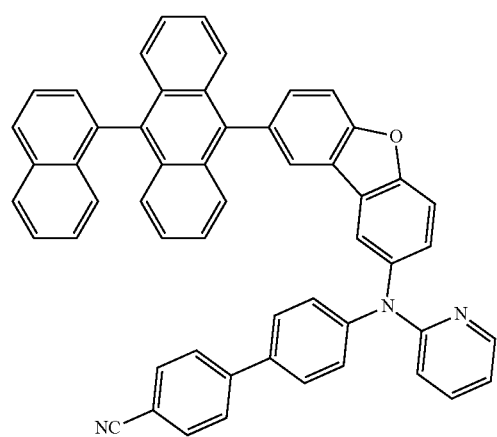
97
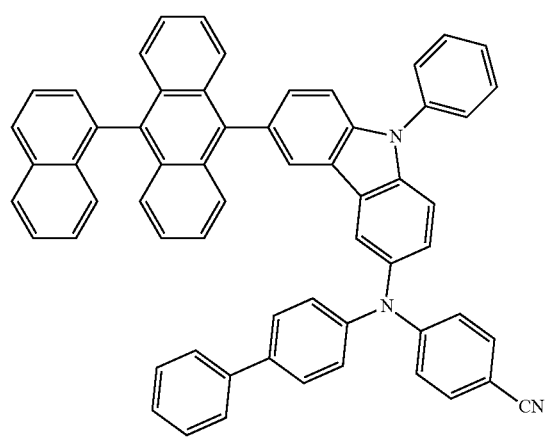

-continued
98
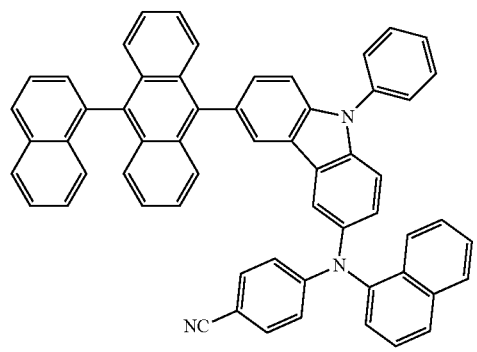
99
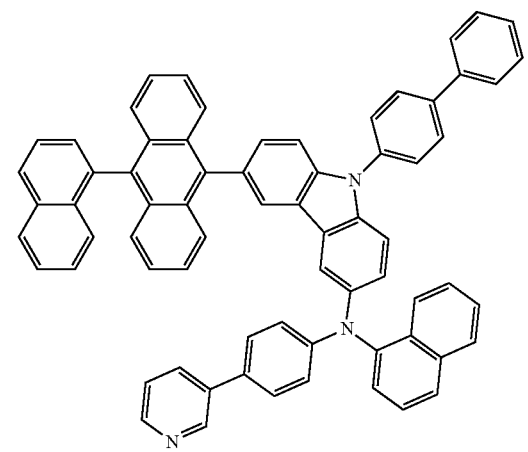
100
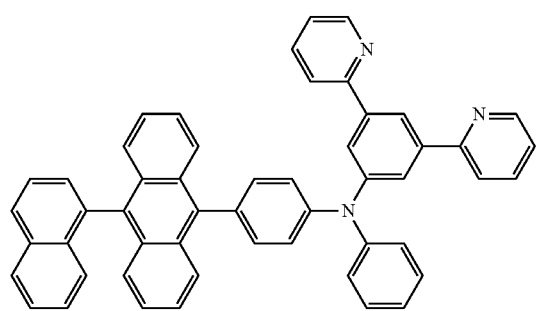
101
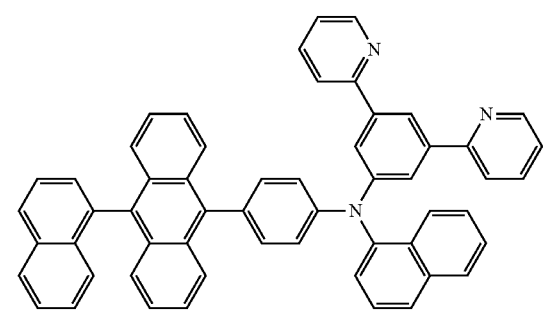
102
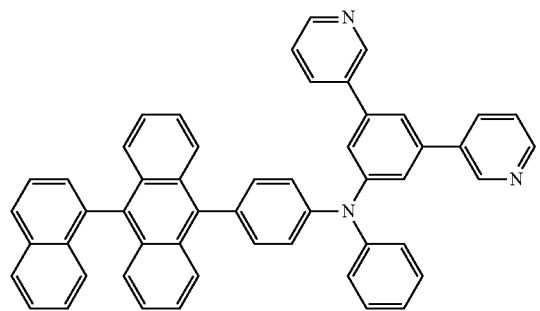
103
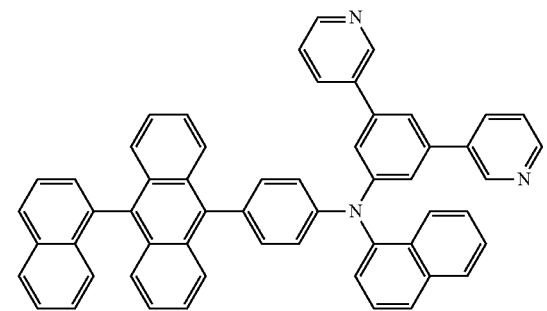
104
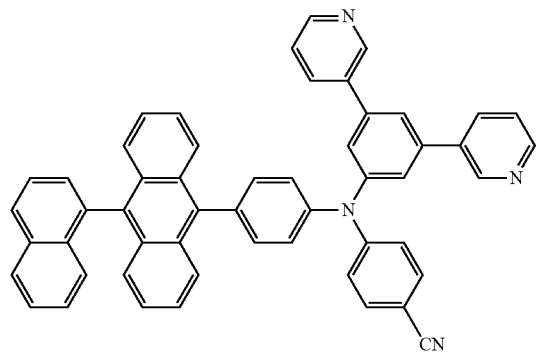
105
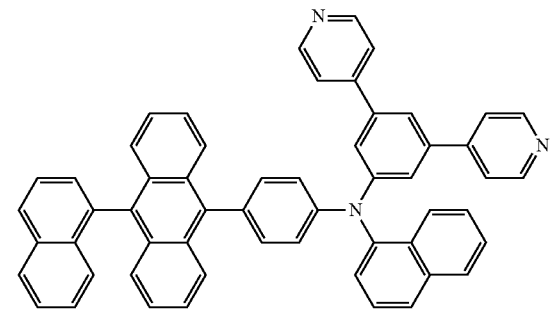

106

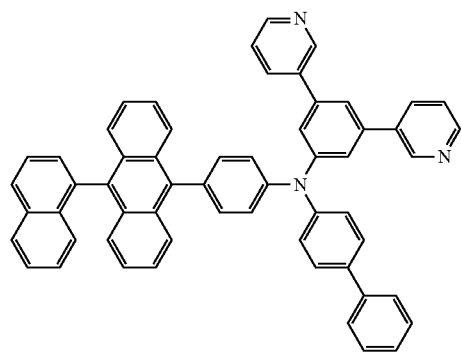

107

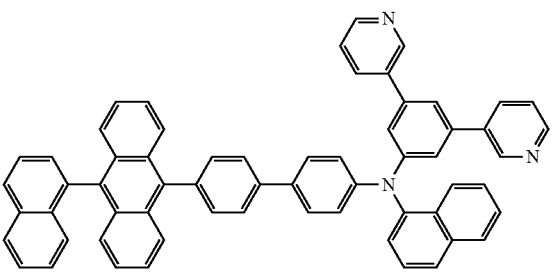

108

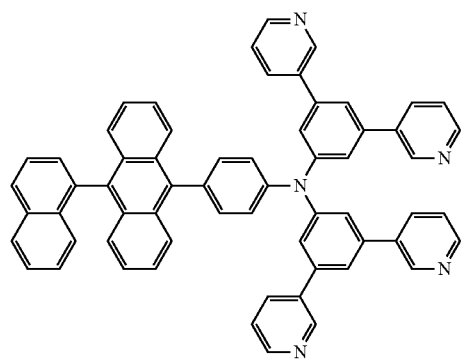

109

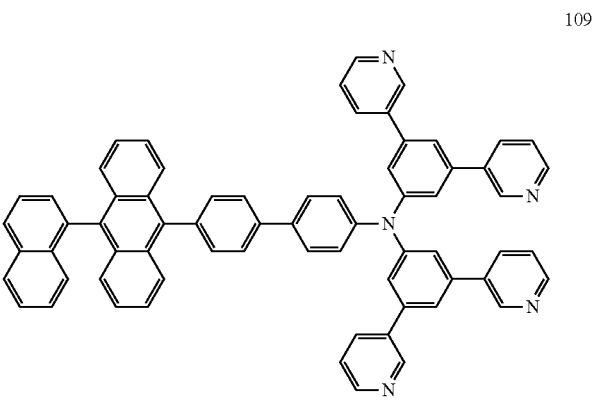

30. An organic light-emitting diode comprising a first electrode, a second electrode disposed opposite to the first electrode, and an organic layer disposed between the first electrode and the second electrode, the organic layer comprising at least one of the amine-based compounds of claim 1.

31. The organic light-emitting diode of claim 30, wherein the organic layer comprises at least one of a hole injection layer, a hole transport layer, a functional layer having both hole injection and hole transport capabilities, a buffer layer, an electro blocking layer, an emission layer, a hole blocking layer, an electron transport layer, an electron injection layer, and a functional layer having both electron injection and electron transport capabilities.

32. The organic light-emitting diode of claim 31, wherein the organic layer comprises an electron transport layer, and the amine-based compound is included in the electron transport layer.

33. The organic light-emitting diode of claim 32, wherein the electron transport layer further comprises a metal complex.

34. The organic light-emitting diode of claim 33, wherein the metal complex comprises lithium quinolate.

35. The organic light-emitting diode of claim 31, wherein the organic layer comprises an emission layer, and the amine-based compound is included in the emission layer.

36. The organic light-emitting diode of claim 35, wherein the amine-based compound in the emission layer serves as a host, and the emission layer further comprises a blue fluorescent dopant.

37. The organic light-emitting diode of claim 35, wherein the amine-based compound in the emission layer serves as a dopant, and the emission layer further comprises at least one of an anthracene-based compound represented by Formula 400 below and an anthracene-based compound represented by Formula 401 below:

Formula 400

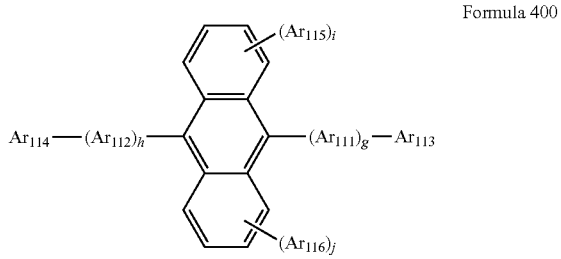

Formula 401

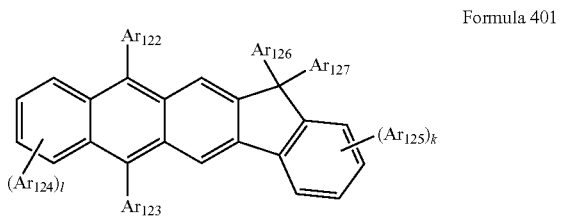

wherein, in Formulae 400 and 401, $Ar_{111}$ and $Ar_{112}$ are each independently a substituted or unsubstituted $C_6$-$C_{60}$ arylene group; $Ar_{113}$ to $Ar_{116}$, and $Ar_{122}$ to $Ar_{125}$ are each independently a substituted or unsubstituted $C_1$-$C_{10}$ alkyl group, or a substituted or unsubstituted $C_6$-$C_{60}$ aryl group; $Ar_{126}$ and $Ar_{127}$ are each independently a $C_1$-$C_{10}$ alkyl group; and g, h, i, j, k, and l are each independently an integer from 0 to 4.

38. The organic light-emitting diode of claim 37, wherein $Ar_{111}$ and $Ar_{112}$ are each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group;

$Ar_{113}$ to $Ar_{116}$, and $Ar_{122}$ to $Ar_{125}$ are each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

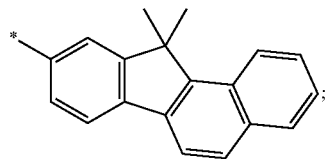 [SMILES: *c1ccc2c(c1)C(C)(C)c1c-2ccc2ccccc12]

$Ar_{126}$ and $Ar_{127}$ are each independently a methyl group, an ethyl group, or a propyl group; and g, h, i, j, k, and l are each independently 0, 1, or 2.

39. The organic light-emitting diode of claim 31, wherein the organic layer comprises at least one of a hole injection layer, a hole transport layer, and a functional layer having both hole injection and hole transport capabilities, and the at least one of the hole injection layer, the hole transport layer, and the functional layer having both hole injection and hole transport capabilities comprises a p-dopant.

* * * * *